«12» United States Patent
Bussat et al.

(10) Patent No.: US 8,466,107 B2
(45) Date of Patent: *Jun. 18, 2013

(54) FIBRIN-BINDING PEPTIDES AND CONJUGATES THEREOF

(75) Inventors: Philippe Bussat, La Roche sur Foron (FR); Bernard Lamy, Saint-Julien-en-Genevois (FR); Edmund R. Marinelli, Tucson, AZ (US); Sibylle Pochon, Troinex (CH); Bo Song, Princeton, NJ (US); Rolf E. Swenson, Princeton, NJ (US)

(73) Assignee: Bracco Imaging SpA, Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/598,811

(22) Filed: Aug. 30, 2012

(65) Prior Publication Data

US 2012/0328512 A1  Dec. 27, 2012

Related U.S. Application Data

(63) Continuation of application No. 12/517,239, filed as application No. PCT/US2007/025403 on Dec. 11, 2007, now Pat. No. 8,278,274.

(60) Provisional application No. 60/869,472, filed on Dec. 11, 2006.

(51) Int. Cl.
*A61K 38/36* (2006.01)

(52) U.S. Cl.
USPC ............................................. 514/13.6

(58) Field of Classification Search
None
See application file for complete search history.

(56) References Cited

U.S. PATENT DOCUMENTS

| 5,910,300 A | 6/1999 | Tournier et al. |
| 2003/0143158 A1 | 7/2003 | Wescott et al. |
| 2006/0034773 A1 | 2/2006 | Giovenzana et al. |
| 2006/0148683 A1 | 7/2006 | McMurry et al. |

FOREIGN PATENT DOCUMENTS

| JP | 2003-508027 A | 3/2003 |
| JP | 2004-523514 A | 8/2004 |
| WO | 01-09188 A1 | 2/2001 |
| WO | 02055544 A2 | 7/2002 |
| WO | 02055544 A3 | 7/2002 |

OTHER PUBLICATIONS

Botnar et al., "Iin vivo molecular imaging of acute and subacute thrombosis using a fibrin-binding magnetic resonance imaging contrast agent", Circulation, Lippincott Williams & Wilkins, vol. 109(16), pp. 2023-2029, Jan. 1, 2004.
Extended European Search Report for EP07862810.4, mail date Mar. 11, 2011.
PCT International Search Report for PCT/EP2007/063659, mail date Apr. 16, 2008.
PCT Written Opinion for PCT/EP2007/063659, mail date Apr. 16, 2008.
PCT International Search Report for PCT/US07/25403, mail date Aug. 5, 2008.
PCT International Preliminary Report on Patentability for PCT/US2007/25403, mail date Aug. 12, 2009.
Moskowitz, Keith A., Biochemistry, vol. 33, No. 44, Nov. 8, 1994, pp. 12937-12944.
Office Action, mail date Oct. 16, 2012 for Japanese application No. 2009-541359.
Office Action, mail date Oct. 16, 2012 for Japanese application No. 2009-540744.

*Primary Examiner* — Christina Bradley
(74) *Attorney, Agent, or Firm* — M. Caragh Noone

(57) ABSTRACT

Fibrin-binding peptides having high binding affinity and excellent physical characteristics compared to previously known fibrin-binding peptides are provided. These fibrin-binding peptides may be conjugated to a detectable label or a therapeutic agent and used to detect and facilitate treatment of pathological conditions associated with the presence of fibrin such as thrombic, angiogenic and neoplastic conditions. These peptides may be used in imaging processes such as MRI, ultrasound and nuclear medicine imaging (e.g. PET, scintigraphic imaging, etc.). The peptides may also be used therapeutically. The present invention also provides processes and methods for making and using such peptides and conjugates thereof.

27 Claims, 11 Drawing Sheets

15

16

17

18

19

20

21a

21b

22

23

24

25

26

27

28

29

30

31

32

33

SEQUENCE LISTING

```
<160> NUMBER OF SEQ ID NOS: 145

<210> SEQ ID NO 1
<211> LENGTH: 15
<212> TYPE: PRT
<213> ORGANISM: Artificial
<220> FEATURE:
<223> OTHER INFORMATION: Description of Artificial Sequence:  Fibrin-
      binding peptide

<400> SEQUENCE: 1

Trp Gln Pro Cys Pro Ala Glu Ser Trp Thr Phe Cys Trp Asp Pro
1               5                   10                  15

<210> SEQ ID NO 2
<211> LENGTH: 19
<212> TYPE: PRT
<213> ORGANISM: Artificial
<220> FEATURE:
<223> OTHER INFORMATION: Description of Artificial Sequence:  Fibrin-
      binding peptide

<400> SEQUENCE: 2

Trp Gln Pro Cys Pro Ala Glu Ser Trp Thr Phe Cys Trp Asp Pro Gly
1               5                   10                  15

Gly Gly Lys

<210> SEQ ID NO 3
<211> LENGTH: 19
<212> TYPE: PRT
<213> ORGANISM: Artificial
<220> FEATURE:
<223> OTHER INFORMATION: Description of Artificial Sequnce:  Fibrin-
      binding peptide

<400> SEQUENCE: 3

Gly Pro Pro Gly Trp Gln Pro Cys Pro Trp Glu Ser Trp Thr Phe Cys
1               5                   10                  15

Trp Asp Pro

<210> SEQ ID NO 4
<211> LENGTH: 23
<212> TYPE: PRT
<213> ORGANISM: Artificial
<220> FEATURE:
<223> OTHER INFORMATION: Description of Artificial Sequence:  Fibrin-
      binding peptide

<400> SEQUENCE: 4

Gly Pro Pro Gly Trp Gln Pro Cys Pro Trp Glu Ser Trp Thr Phe Cys
1               5                   10                  15

Trp Asp Pro Gly Gly Gly Lys
                20

<210> SEQ ID NO 5
<211> LENGTH: 19
<212> TYPE: PRT
<213> ORGANISM: Artificial
```

```
<220> FEATURE:
<223> OTHER INFORMATION: Description of Artificial Sequnce:  Fibrin-
      binding peptide

<400> SEQUENCE: 5

Gly Gly Arg Gly Trp Gln Pro Cys Pro Trp Glu Ser Trp Thr Phe Cys
1               5                   10                  15

Trp Asp Pro

<210> SEQ ID NO 6
<211> LENGTH: 23
<212> TYPE: PRT
<213> ORGANISM: Artificial
<220> FEATURE:
<223> OTHER INFORMATION: Description of Artificial Sequence:  Fibrin-
      binding peptide

<400> SEQUENCE: 6

Gly Gly Arg Gly Trp Gln Pro Cys Pro Trp Glu Ser Trp Thr Phe Cys
1               5                   10                  15

Trp Asp Pro Gly Gly Gly Lys
            20

<210> SEQ ID NO 7
<211> LENGTH: 16
<212> TYPE: PRT
<213> ORGANISM: Artificial
<220> FEATURE:
<223> OTHER INFORMATION: Description of Artificial Sequnce:  Fibrin-
      binding peptide

<400> SEQUENCE: 7

Gly Trp Gln Pro Cys Pro Trp Glu Ser Trp Thr Phe Cys Trp Asp Pro
1               5                   10                  15

<210> SEQ ID NO 8
<211> LENGTH: 20
<212> TYPE: PRT
<213> ORGANISM: Artificial
<220> FEATURE:
<223> OTHER INFORMATION: Description of Artificial Sequence:  Fibrin-
      binding peptide

<400> SEQUENCE: 8

Gly Trp Gln Pro Cys Pro Trp Glu Ser Trp Thr Phe Cys Trp Asp Pro
1               5                   10                  15

Gly Gly Gly Lys
            20

<210> SEQ ID NO 9
<211> LENGTH: 20
<212> TYPE: PRT
<213> ORGANISM: Artificial
<220> FEATURE:
<223> OTHER INFORMATION: Description of Artificial Sequnce:  Fibrin-
      binding peptide
<220> FEATURE:
<221> NAME/KEY: misc_feature
<223> OTHER INFORMATION: Xaa=8-amino-3,6-dioxaoctanoic acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 9

Ser Gly Ser Gly Xaa Trp Gln Pro Cys Pro Trp Glu Ser Trp Thr Phe
1               5                   10                  15
```

Cys Trp Asp Pro
        20

<210> SEQ ID NO 10
<211> LENGTH: 24
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: misc_feature
<223> OTHER INFORMATION: Xaa=8-amino-3,6-dioxaoctanoic acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 10

Ser Gly Ser Gly Xaa Trp Gln Pro Cys Pro Trp Glu Ser Trp Thr Phe
1               5                   10                  15

Cys Trp Asp Pro Gly Gly Gly Lys
        20

<210> SEQ ID NO 11
<211> LENGTH: 15
<212> TYPE: PRT
<213> ORGANISM: Artificial
<220> FEATURE:
<223> OTHER INFORMATION: Description of Artificial Sequnce:  Fibrin-
      binding peptide
<220> FEATURE:
<221> NAME/KEY: misc_feature
<223> OTHER INFORMATION: Xaa=2-Cyclohexyl-L-alanine
<220> FEATURE:
<221> NAME/KEY: misc_feature
<222> LOCATION: (11)..(11)
<223> OTHER INFORMATION: Xaa can be any naturally occurring amino acid

<400> SEQUENCE: 11

Trp Gln Pro Cys Pro Trp Glu Ser Trp Thr Xaa Cys Trp Asp Pro
1               5                   10                  15

<210> SEQ ID NO 12
<211> LENGTH: 19
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: misc_feature
<223> OTHER INFORMATION: Xaa=2-Cyclohexyl-L-alanine
<220> FEATURE:
<221> NAME/KEY: misc_feature
<222> LOCATION: (11)..(11)
<223> OTHER INFORMATION: Xaa can be any naturally occurring amino acid

<400> SEQUENCE: 12

Trp Gln Pro Cys Pro Trp Glu Ser Trp Thr Xaa Cys Trp Asp Pro Gly
1               5                   10                  15

Gly Gly Lys

<210> SEQ ID NO 13
<211> LENGTH: 15
<212> TYPE: PRT
<213> ORGANISM: Artificial
<220> FEATURE:
<223> OTHER INFORMATION: Description of Artificial Sequnce:  Fibrin-
      binding peptide
<220> FEATURE:

```
<221> NAME/KEY: misc_feature
<223> OTHER INFORMATION: Xaa=L-4-Fluorophenylalanine
<220> FEATURE:
<221> NAME/KEY: misc_feature
<222> LOCATION: (11)..(11)
<223> OTHER INFORMATION: Xaa can be any naturally occurring amino acid

<400> SEQUENCE: 13

Trp Gln Pro Cys Pro Trp Glu Ser Trp Thr Xaa Cys Trp Asp Pro
1               5                   10                  15

<210> SEQ ID NO 14
<211> LENGTH: 19
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: misc_feature
<223> OTHER INFORMATION: Xaa=L-4-Fluorophenylalanine
<220> FEATURE:
<221> NAME/KEY: misc_feature
<222> LOCATION: (11)..(11)
<223> OTHER INFORMATION: Xaa can be any naturally occurring amino acid

<400> SEQUENCE: 14

Trp Gln Pro Cys Pro Trp Glu Ser Trp Thr Xaa Cys Trp Asp Pro Gly
1               5                   10                  15

Gly Gly Lys

<210> SEQ ID NO 15
<211> LENGTH: 15
<212> TYPE: PRT
<213> ORGANISM: Artificial
<220> FEATURE:
<223> OTHER INFORMATION: Description of Artificial Sequnce: Fibrin-
      binding peptide
<220> FEATURE:
<221> NAME/KEY: misc_feature
<223> OTHER INFORMATION: Xaa=L-3,4-difluorophenylalanine
<220> FEATURE:
<221> NAME/KEY: misc_feature
<222> LOCATION: (11)..(11)
<223> OTHER INFORMATION: Xaa can be any naturally occurring amino acid

<400> SEQUENCE: 15

Trp Gln Pro Cys Pro Trp Glu Ser Trp Thr Xaa Cys Trp Asp Pro
1               5                   10                  15

<210> SEQ ID NO 16
<211> LENGTH: 19
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: misc_feature
<223> OTHER INFORMATION: Xaa=L-3,4-difluorophenylalanine
<220> FEATURE:
<221> NAME/KEY: misc_feature
<222> LOCATION: (11)..(11)
<223> OTHER INFORMATION: Xaa can be any naturally occurring amino acid

<400> SEQUENCE: 16

Trp Gln Pro Cys Pro Trp Glu Ser Trp Thr Xaa Cys Trp Asp Pro Gly
1               5                   10                  15

Gly Gly Lys
```

<210> SEQ ID NO 17
<211> LENGTH: 16
<212> TYPE: PRT
<213> ORGANISM: Artificial
<220> FEATURE:
<223> OTHER INFORMATION: Description of Artificial Sequnce: Fibrin-
      binding peptide

<400> SEQUENCE: 17

Gly Trp Gln Pro Cys Pro Trp Glu Ser Trp Thr Phe Cys Trp Asp Pro
1               5                   10                  15

<210> SEQ ID NO 18
<211> LENGTH: 20
<212> TYPE: PRT
<213> ORGANISM: Artificial
<220> FEATURE:
<223> OTHER INFORMATION: Description of Artificial Sequnce: Fibrin-
      binding peptide

<400> SEQUENCE: 18

Gly Trp Gln Pro Cys Pro Trp Glu Ser Trp Thr Phe Cys Trp Asp Pro
1               5                   10                  15

Gly Gly Gly Lys
            20

<210> SEQ ID NO 19
<211> LENGTH: 17
<212> TYPE: PRT
<213> ORGANISM: Artificial
<220> FEATURE:
<223> OTHER INFORMATION: Description of Artificial Sequnce: Fibrin-
      binding peptide

<400> SEQUENCE: 19

Arg Gly Trp Gln Pro Cys Pro Trp Glu Ser Trp Thr Phe Cys Trp Asp
1               5                   10                  15

Pro

<210> SEQ ID NO 20
<211> LENGTH: 21
<212> TYPE: PRT
<213> ORGANISM: Artificial
<220> FEATURE:
<223> OTHER INFORMATION: Description of Artificial Sequnce: Fibrin-
      binding peptide

<400> SEQUENCE: 20

Arg Gly Trp Gln Pro Cys Pro Trp Glu Ser Trp Thr Phe Cys Trp Asp
1               5                   10                  15

Pro Gly Gly Gly Lys
            20

<210> SEQ ID NO 21
<211> LENGTH: 16
<212> TYPE: PRT
<213> ORGANISM: Artificial
<220> FEATURE:
<223> OTHER INFORMATION: Description of Artificial Sequnce: Fibrin-
      binding peptide

<400> SEQUENCE: 21

Arg Trp Gln Pro Cys Pro Trp Glu Ser Trp Thr Phe Cys Trp Asp Pro
1               5                   10                  15

<210> SEQ ID NO 22
<211> LENGTH: 20

```
<212> TYPE: PRT
<213> ORGANISM: Artificial
<220> FEATURE:
<223> OTHER INFORMATION: Description of Artificial Sequence:  Fibrin-
      binding peptide

<400> SEQUENCE: 22

Arg Trp Gln Pro Cys Pro Trp Glu Ser Trp Thr Phe Cys Trp Asp Pro
1               5                   10                  15

Gly Gly Gly Lys
            20

<210> SEQ ID NO 23
<211> LENGTH: 23
<212> TYPE: PRT
<213> ORGANISM: Artificial
<220> FEATURE:
<223> OTHER INFORMATION: Description of Artificial Sequnce:  Fibrin-
      binding peptide

<400> SEQUENCE: 23

Ser Gly Ser Gly Ser Gly Ser Gly Trp Gln Pro Cys Pro Trp Glu Ser
1               5                   10                  15

Trp Thr Phe Cys Trp Asp Pro
            20

<210> SEQ ID NO 24
<211> LENGTH: 27
<212> TYPE: PRT
<213> ORGANISM: Artificial
<220> FEATURE:
<223> OTHER INFORMATION: Description of Artificial Sequence:  Fibrin-
      binding peptide

<400> SEQUENCE: 24

Ser Gly Ser Gly Ser Gly Ser Gly Trp Gln Pro Cys Pro Trp Glu Ser
1               5                   10                  15

Trp Thr Phe Cys Trp Asp Pro Gly Gly Gly Lys
            20                  25

<210> SEQ ID NO 25
<211> LENGTH: 18
<212> TYPE: PRT
<213> ORGANISM: Artificial
<220> FEATURE:
<223> OTHER INFORMATION: Description of Artificial Sequnce:  Fibrin-
      binding peptide

<400> SEQUENCE: 25

Lys Lys Gly Trp Gln Pro Cys Pro Trp Glu Ser Trp Thr Phe Cys Trp
1               5                   10                  15

Asp Pro

<210> SEQ ID NO 26
<211> LENGTH: 22
<212> TYPE: PRT
<213> ORGANISM: Artificial
<220> FEATURE:
<223> OTHER INFORMATION: Description of Artificial Sequence:  Fibrin-
      binding peptide

<400> SEQUENCE: 26

Lys Lys Gly Trp Gln Pro Cys Pro Trp Glu Ser Trp Thr Phe Cys Trp
1               5                   10                  15

Asp Pro Gly Gly Gly Lys
            20
```

```
<210> SEQ ID NO 27
<211> LENGTH: 21
<212> TYPE: PRT
<213> ORGANISM: Artificial
<220> FEATURE:
<223> OTHER INFORMATION: Description of Artificial Sequnce: Fibrin-
      binding peptide

<400> SEQUENCE: 27

Lys Gly Lys Gly Lys Gly Trp Gln Pro Cys Pro Trp Glu Ser Trp Thr
1               5                   10                  15

Phe Cys Trp Asp Pro
            20

<210> SEQ ID NO 28
<211> LENGTH: 25
<212> TYPE: PRT
<213> ORGANISM: Artificial
<220> FEATURE:
<223> OTHER INFORMATION: Description of Artificial Sequence: Fibrin-
      binding peptide

<400> SEQUENCE: 28

Lys Gly Lys Gly Lys Gly Trp Gln Pro Cys Pro Trp Glu Ser Trp Thr
1               5                   10                  15

Phe Cys Trp Asp Pro Gly Gly Gly Lys
            20                  25

<210> SEQ ID NO 29
<211> LENGTH: 16
<212> TYPE: PRT
<213> ORGANISM: Artificial
<220> FEATURE:
<223> OTHER INFORMATION: Description of Artificial Sequnce: Fibrin-
      binding peptide
<220> FEATURE:
<221> NAME/KEY: misc_feature
<223> OTHER INFORMATION: Xaa=O-(2-Acetamido-2-deoxy- -D-
      galactopyranosyl)-L-serine
<220> FEATURE:
<221> NAME/KEY: misc_feature
<222> LOCATION: (1)..(1)
<223> OTHER INFORMATION: Xaa can be any naturally occurring amino acid

<400> SEQUENCE: 29

Xaa Trp Gln Pro Cys Pro Trp Glu Ser Trp Thr Phe Cys Trp Asp Pro
1               5                   10                  15

<210> SEQ ID NO 30
<211> LENGTH: 20
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: misc_feature
<223> OTHER INFORMATION: Xaa=O-(2-Acetamido-2-deoxy- -D-
      galactopyranosyl)-L-serine
<220> FEATURE:
<221> NAME/KEY: misc_feature
<222> LOCATION: (1)..(1)
<223> OTHER INFORMATION: Xaa can be any naturally occurring amino acid

<400> SEQUENCE: 30

Xaa Trp Gln Pro Cys Pro Trp Glu Ser Trp Thr Phe Cys Trp Asp Pro
1               5                   10                  15

Gly Gly Gly Lys
```

20

<210> SEQ ID NO 31
<211> LENGTH: 16
<212> TYPE: PRT
<213> ORGANISM: Artificial
<220> FEATURE:
<223> OTHER INFORMATION: Description of Artificial Sequnce: Fibrin-
      binding peptide
<220> FEATURE:
<221> NAME/KEY: misc_feature
<223> OTHER INFORMATION: Xaa=Tetrahydrofuran-2-carboxylic acid
<220> FEATURE:
<221> NAME/KEY: misc_feature
<222> LOCATION: (1)..(1)
<223> OTHER INFORMATION: Xaa can be any naturally occurring amino acid

<400> SEQUENCE: 31

Xaa Trp Gln Pro Cys Pro Trp Glu Ser Trp Thr Phe Cys Trp Asp Pro
1               5                   10                  15

<210> SEQ ID NO 32
<211> LENGTH: 20
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: misc_feature
<223> OTHER INFORMATION: Xaa=Tetrahydrofuran-2-carboxylic acid
<220> FEATURE:
<221> NAME/KEY: misc_feature
<222> LOCATION: (1)..(1)
<223> OTHER INFORMATION: Xaa can be any naturally occurring amino acid

<400> SEQUENCE: 32

Xaa Trp Gln Pro Cys Pro Trp Glu Ser Trp Thr Phe Cys Trp Asp Pro
1               5                   10                  15

Gly Gly Gly Lys
            20

<210> SEQ ID NO 33
<211> LENGTH: 19
<212> TYPE: PRT
<213> ORGANISM: Artificial
<220> FEATURE:
<223> OTHER INFORMATION: Description of Artificial Sequnce: Fibrin-
      binding peptide

<400> SEQUENCE: 33

Arg Arg Gly Gly Trp Gln Pro Cys Pro Trp Glu Ser Trp Thr Phe Cys
1               5                   10                  15

Trp Asp Pro

<210> SEQ ID NO 34
<211> LENGTH: 23
<212> TYPE: PRT
<213> ORGANISM: Artificial
<220> FEATURE:
<223> OTHER INFORMATION: Description of Artificial Sequence: Fibrin-
      binding peptide

<400> SEQUENCE: 34

Arg Arg Gly Gly Trp Gln Pro Cys Pro Trp Glu Ser Trp Thr Phe Cys
1               5                   10                  15

Trp Asp Pro Gly Gly Gly Lys
            20

-continued

<210> SEQ ID NO 35
<211> LENGTH: 17
<212> TYPE: PRT
<213> ORGANISM: Artificial
<220> FEATURE:
<223> OTHER INFORMATION: Description of Artificial Sequnce: Fibrin-
      binding peptide
<220> FEATURE:
<221> NAME/KEY: misc_feature
<223> OTHER INFORMATION: Xaa=8-amino-3,6-dioxaoctanoic acid
<220> FEATURE:
<221> NAME/KEY: misc_feature
<222> LOCATION: (2)..(2)
<223> OTHER INFORMATION: Xaa can be any naturally occurring amino acid

<400> SEQUENCE: 35

Ser Xaa Trp Gln Pro Cys Pro Trp Glu Ser Trp Thr Phe Cys Trp Asp
1               5                   10                  15

Pro

<210> SEQ ID NO 36
<211> LENGTH: 21
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: misc_feature
<223> OTHER INFORMATION: Xaa=8-amino-3,6-dioxaoctanoic acid
<220> FEATURE:
<221> NAME/KEY: misc_feature
<222> LOCATION: (2)..(2)
<223> OTHER INFORMATION: Xaa can be any naturally occurring amino acid

<400> SEQUENCE: 36

Ser Xaa Trp Gln Pro Cys Pro Trp Glu Ser Trp Thr Phe Cys Trp Asp
1               5                   10                  15

Pro Gly Gly Gly Lys
            20

<210> SEQ ID NO 37
<211> LENGTH: 15
<212> TYPE: PRT
<213> ORGANISM: Artificial
<220> FEATURE:
<223> OTHER INFORMATION: Description of Artificial Sequnce: Fibrin-
      binding peptide
<220> FEATURE:
<221> NAME/KEY: misc_feature
<223> OTHER INFORMATION: Xaa=trans-4-hydroxy-L-proline
<220> FEATURE:
<221> NAME/KEY: misc_feature
<222> LOCATION: (5)..(5)
<223> OTHER INFORMATION: Xaa can be any naturally occurring amino acid

<400> SEQUENCE: 37

Trp Gln Pro Cys Xaa Trp Glu Ser Trp Thr Phe Cys Trp Asp Pro
1               5                   10                  15

<210> SEQ ID NO 38
<211> LENGTH: 19
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: misc_feature
<223> OTHER INFORMATION: Xaa=trans-4-hydroxy-L-proline
<220> FEATURE:

```
<221> NAME/KEY: misc_feature
<222> LOCATION: (5)..(5)
<223> OTHER INFORMATION: Xaa can be any naturally occurring amino acid

<400> SEQUENCE: 38

Trp Gln Pro Cys Xaa Trp Glu Ser Trp Thr Phe Cys Trp Asp Pro Gly
1               5                   10                  15

Gly Gly Lys

<210> SEQ ID NO 39
<211> LENGTH: 19
<212> TYPE: PRT
<213> ORGANISM: Artificial
<220> FEATURE:
<223> OTHER INFORMATION: Description of Artificial Sequnce:  Fibrin-
      binding peptide

<400> SEQUENCE: 39

Gly Pro Pro Gly Trp Gln Pro Cys Pro Ala Glu Ser Trp Thr Phe Cys
1               5                   10                  15

Trp Asp Pro

<210> SEQ ID NO 40
<211> LENGTH: 23
<212> TYPE: PRT
<213> ORGANISM: Artificial
<220> FEATURE:
<223> OTHER INFORMATION: Description of Artificial Sequence:  Fibrin-
      binding peptide

<400> SEQUENCE: 40

Gly Pro Pro Gly Trp Gln Pro Cys Pro Ala Glu Ser Trp Thr Phe Cys
1               5                   10                  15

Trp Asp Pro Gly Gly Gly Lys
            20

<210> SEQ ID NO 41
<211> LENGTH: 19
<212> TYPE: PRT
<213> ORGANISM: Artificial
<220> FEATURE:
<223> OTHER INFORMATION: Description of Artificial Sequnce:  Fibrin-
      binding peptide

<400> SEQUENCE: 41

Gly Gly Arg Gly Trp Gln Pro Cys Pro Ala Glu Ser Trp Thr Phe Cys
1               5                   10                  15

Trp Asp Pro

<210> SEQ ID NO 42
<211> LENGTH: 23
<212> TYPE: PRT
<213> ORGANISM: Artificial
<220> FEATURE:
<223> OTHER INFORMATION: Description of Artificial Sequence:  Fibrin-
      binding peptide

<400> SEQUENCE: 42

Gly Gly Arg Gly Trp Gln Pro Cys Pro Ala Glu Ser Trp Thr Phe Cys
1               5                   10                  15

Trp Asp Pro Gly Gly Gly Lys
            20

<210> SEQ ID NO 43
<211> LENGTH: 18
```

```
<212> TYPE: PRT
<213> ORGANISM: Artificial
<220> FEATURE:
<223> OTHER INFORMATION: Description of Artificial Sequnce:  Fibrin-
      binding peptide

<400> SEQUENCE: 43

Lys Lys Gly Trp Gln Pro Cys Pro Ala Glu Ser Trp Thr Phe Cys Trp
1               5                   10                  15

Asp Pro

<210> SEQ ID NO 44
<211> LENGTH: 22
<212> TYPE: PRT
<213> ORGANISM: Artificial
<220> FEATURE:
<223> OTHER INFORMATION: Description of Artificial Sequence:  Fibrin-
      binding peptide

<400> SEQUENCE: 44

Lys Lys Gly Trp Gln Pro Cys Pro Ala Glu Ser Trp Thr Phe Cys Trp
1               5                   10                  15

Asp Pro Gly Gly Gly Lys
            20

<210> SEQ ID NO 45
<211> LENGTH: 21
<212> TYPE: PRT
<213> ORGANISM: Artificial
<220> FEATURE:
<223> OTHER INFORMATION: Description of Artificial Sequnce:  Fibrin-
      binding peptide

<400> SEQUENCE: 45

Lys Gly Lys Gly Lys Gly Trp Gln Pro Cys Pro Ala Glu Ser Trp Thr
1               5                   10                  15

Phe Cys Trp Asp Pro
            20

<210> SEQ ID NO 46
<211> LENGTH: 25
<212> TYPE: PRT
<213> ORGANISM: Artificial
<220> FEATURE:
<223> OTHER INFORMATION: Description of Artificial Sequnce:  Fibrin-
      binding peptide

<400> SEQUENCE: 46

Lys Gly Lys Gly Lys Gly Trp Gln Pro Cys Pro Ala Glu Ser Trp Thr
1               5                   10                  15

Phe Cys Trp Asp Pro Gly Gly Gly Lys
            20                  25

<210> SEQ ID NO 47
<211> LENGTH: 16
<212> TYPE: PRT
<213> ORGANISM: Artificial
<220> FEATURE:
<223> OTHER INFORMATION: Description of Artificial Sequnce:  Fibrin-
      binding peptide

<400> SEQUENCE: 47

Gly Trp Gln Pro Cys Pro Ala Glu Ser Trp Thr Phe Cys Trp Asp Pro
1               5                   10                  15

<210> SEQ ID NO 48
```

```
<211> LENGTH: 20
<212> TYPE: PRT
<213> ORGANISM: Artificial
<220> FEATURE:
<223> OTHER INFORMATION: Description of Artificial Sequence:  Fibrin-
      binding peptide

<400> SEQUENCE: 48

Gly Trp Gln Pro Cys Pro Ala Glu Ser Trp Thr Phe Cys Trp Asp Pro
1               5                   10                  15

Gly Gly Gly Lys
            20

<210> SEQ ID NO 49
<211> LENGTH: 16
<212> TYPE: PRT
<213> ORGANISM: Artificial
<220> FEATURE:
<223> OTHER INFORMATION: Description of Artificial Sequnce:  Fibrin-
      binding peptide

<400> SEQUENCE: 49

Gly Trp Gln Pro Cys Pro Ala Glu Ser Trp Thr Phe Cys Trp Asp Pro
1               5                   10                  15

<210> SEQ ID NO 50
<211> LENGTH: 20
<212> TYPE: PRT
<213> ORGANISM: Artificial
<220> FEATURE:
<223> OTHER INFORMATION: Description of Artificial Sequence:  Fibrin-
      binding peptide

<400> SEQUENCE: 50

Gly Trp Gln Pro Cys Pro Ala Glu Ser Trp Thr Phe Cys Trp Asp Pro
1               5                   10                  15

Gly Gly Gly Lys
            20

<210> SEQ ID NO 51
<211> LENGTH: 23
<212> TYPE: PRT
<213> ORGANISM: Artificial
<220> FEATURE:
<223> OTHER INFORMATION: Description of Artificial Sequnce:  Fibrin-
      binding peptide

<400> SEQUENCE: 51

Ser Gly Ser Gly Ser Gly Ser Gly Trp Gln Pro Cys Pro Ala Glu Ser
1               5                   10                  15

Trp Thr Phe Cys Trp Asp Pro
            20

<210> SEQ ID NO 52
<211> LENGTH: 27
<212> TYPE: PRT
<213> ORGANISM: Artificial
<220> FEATURE:
<223> OTHER INFORMATION: Description of Artificial Sequence:  Fibrin-
      binding peptide

<400> SEQUENCE: 52

Ser Gly Ser Gly Ser Gly Ser Gly Trp Gln Pro Cys Pro Ala Glu Ser
1               5                   10                  15

Trp Thr Phe Cys Trp Asp Pro Gly Gly Gly Lys
            20                  25
```

```
<210> SEQ ID NO 53
<211> LENGTH: 15
<212> TYPE: PRT
<213> ORGANISM: Artificial
<220> FEATURE:
<223> OTHER INFORMATION: Description of Artificial Sequnce:  Fibrin-
      binding peptide
<220> FEATURE:
<221> NAME/KEY: misc_feature
<223> OTHER INFORMATION: Xaa=L-4-Fluorophenylalanine
<220> FEATURE:
<221> NAME/KEY: misc_feature
<222> LOCATION: (11)..(11)
<223> OTHER INFORMATION: Xaa can be any naturally occurring amino acid

<400> SEQUENCE: 53

Trp Gln Pro Cys Pro Ala Glu Ser Trp Thr Xaa Cys Trp Asp Pro
1               5                   10                  15

<210> SEQ ID NO 54
<211> LENGTH: 19
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: misc_feature
<223> OTHER INFORMATION: Xaa=L-4-Fluorophenylalanine
<220> FEATURE:
<221> NAME/KEY: misc_feature
<222> LOCATION: (11)..(11)
<223> OTHER INFORMATION: Xaa can be any naturally occurring amino acid

<400> SEQUENCE: 54

Trp Gln Pro Cys Pro Ala Glu Ser Trp Thr Xaa Cys Trp Asp Pro Gly
1               5                   10                  15

Gly Gly Lys

<210> SEQ ID NO 55
<211> LENGTH: 15
<212> TYPE: PRT
<213> ORGANISM: Artificial
<220> FEATURE:
<223> OTHER INFORMATION: Description of Artificial Sequnce:  Fibrin-
      binding peptide
<220> FEATURE:
<221> NAME/KEY: misc_feature
<223> OTHER INFORMATION: Xaa=2-Cyclohexyl-L-alanine
<220> FEATURE:
<221> NAME/KEY: misc_feature
<222> LOCATION: (11)..(11)
<223> OTHER INFORMATION: Xaa can be any naturally occurring amino acid

<400> SEQUENCE: 55

Trp Gln Pro Cys Pro Ala Glu Ser Trp Thr Xaa Cys Trp Asp Pro
1               5                   10                  15

<210> SEQ ID NO 56
<211> LENGTH: 19
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: misc_feature
<223> OTHER INFORMATION: Xaa=2-Cyclohexyl-L-alanine
<220> FEATURE:
<221> NAME/KEY: misc_feature
<222> LOCATION: (11)..(11)
<223> OTHER INFORMATION: Xaa can be any naturally occurring amino acid
```

<400> SEQUENCE: 56

Trp Gln Pro Cys Pro Ala Glu Ser Trp Thr Xaa Cys Trp Asp Pro Gly
1               5                   10                  15

Gly Gly Lys

<210> SEQ ID NO 57
<211> LENGTH: 15
<212> TYPE: PRT
<213> ORGANISM: Artificial
<220> FEATURE:
<223> OTHER INFORMATION: Description of Artificial Sequnce: Fibrin-
      binding peptide
<220> FEATURE:
<221> NAME/KEY: misc_feature
<223> OTHER INFORMATION: Xaa=L-3,4-difluorophenylalanine
<220> FEATURE:
<221> NAME/KEY: misc_feature
<222> LOCATION: (11)..(11)
<223> OTHER INFORMATION: Xaa can be any naturally occurring amino acid

<400> SEQUENCE: 57

Trp Gln Pro Cys Pro Ala Glu Ser Trp Thr Xaa Cys Trp Asp Pro
1               5                   10                  15

<210> SEQ ID NO 58
<211> LENGTH: 19
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: misc_feature
<223> OTHER INFORMATION: Xaa=L-3,4-difluorophenylalanine
<220> FEATURE:
<221> NAME/KEY: misc_feature
<222> LOCATION: (11)..(11)
<223> OTHER INFORMATION: Xaa can be any naturally occurring amino acid

<400> SEQUENCE: 58

Trp Gln Pro Cys Pro Ala Glu Ser Trp Thr Xaa Cys Trp Asp Pro Gly
1               5                   10                  15

Gly Gly Lys

<210> SEQ ID NO 59
<211> LENGTH: 15
<212> TYPE: PRT
<213> ORGANISM: Artificial
<220> FEATURE:
<223> OTHER INFORMATION: Description of Artificial Sequnce: Fibrin-
      binding peptide
<220> FEATURE:
<221> NAME/KEY: misc_feature
<223> OTHER INFORMATION: Xaa=Tetrahydrofuran-2-carboxylic acid
<220> FEATURE:
<221> NAME/KEY: misc_feature
<222> LOCATION: (1)..(1)
<223> OTHER INFORMATION: Xaa can be any naturally occurring amino acid

<400> SEQUENCE: 59

Xaa Trp Gln Pro Cys Pro Ala Glu Ser Trp Thr Phe Cys Trp Asp
1               5                   10                  15

<210> SEQ ID NO 60
<211> LENGTH: 20
<212> TYPE: PRT
<213> ORGANISM: Artificial
<220> FEATURE:
<223> OTHER INFORMATION: Description of Artificial Sequence: Fibrin-

```
                                binding peptide
<220> FEATURE:
<221> NAME/KEY: misc_feature
<223> OTHER INFORMATION: Xaa=Tetrahydrofuran-2-carboxylic acid
<220> FEATURE:
<221> NAME/KEY: misc_feature
<222> LOCATION: (1)..(1)
<223> OTHER INFORMATION: Xaa can be any naturally occurring amino acid

<400> SEQUENCE: 60

Xaa Trp Gln Pro Cys Pro Ala Glu Ser Trp Thr Phe Cys Trp Asp Pro
1               5                   10                  15

Gly Gly Gly Lys
            20

<210> SEQ ID NO 61
<211> LENGTH: 20
<212> TYPE: PRT
<213> ORGANISM: Artificial
<220> FEATURE:
<223> OTHER INFORMATION: Description of Artificial Sequnce:  Fibrin-
      binding peptide
<220> FEATURE:
<221> NAME/KEY: misc_feature
<223> OTHER INFORMATION: Xaa=8-amino-3,6-dioxaoctanoic acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 61

Ser Gly Ser Gly Xaa Trp Gln Pro Cys Pro Ala Glu Ser Trp Thr Phe
1               5                   10                  15

Cys Trp Asp Pro
            20

<210> SEQ ID NO 62
<211> LENGTH: 24
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: misc_feature
<223> OTHER INFORMATION: Xaa=8-amino-3,6-dioxaoctanoic acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 62

Ser Gly Ser Gly Xaa Trp Gln Pro Cys Pro Ala Glu Ser Trp Thr Phe
1               5                   10                  15

Cys Trp Asp Pro Gly Gly Gly Lys
            20

<210> SEQ ID NO 63
<211> LENGTH: 19
<212> TYPE: PRT
<213> ORGANISM: Artificial
<220> FEATURE:
<223> OTHER INFORMATION: Description of Artificial Sequnce:  Fibrin-
      binding peptide

<400> SEQUENCE: 63

Arg Arg Gly Gly Trp Gln Pro Cys Pro Ala Glu Ser Trp Thr Phe Cys
1               5                   10                  15

Trp Asp Pro
```

```
<210> SEQ ID NO 64
<211> LENGTH: 23
<212> TYPE: PRT
<213> ORGANISM: Artificial
<220> FEATURE:
<223> OTHER INFORMATION: Description of Artificial Sequence: Fibrin-
      binding peptide

<400> SEQUENCE: 64

Arg Arg Gly Gly Trp Gln Pro Cys Pro Ala Glu Ser Trp Thr Phe Cys
1               5                   10                  15

Trp Asp Pro Gly Gly Gly Lys
            20

<210> SEQ ID NO 65
<211> LENGTH: 19
<212> TYPE: PRT
<213> ORGANISM: Artificial
<220> FEATURE:
<223> OTHER INFORMATION: Description of Artificial Sequnce: Fibrin-
      binding peptide
<220> FEATURE:
<221> NAME/KEY: misc_feature
<223> OTHER INFORMATION: Xaa= trans-4-hydroxy-L-proline
<220> FEATURE:
<221> NAME/KEY: misc_feature
<222> LOCATION: (9)..(9)
<223> OTHER INFORMATION: Xaa can be any naturally occurring amino acid

<400> SEQUENCE: 65

Arg Arg Gly Gly Trp Gln Pro Cys Xaa Trp Glu Ser Trp Thr Phe Cys
1               5                   10                  15

Trp Asp Pro

<210> SEQ ID NO 66
<211> LENGTH: 23
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: misc_feature
<223> OTHER INFORMATION: Xaa= trans-4-hydroxy-L-proline
<220> FEATURE:
<221> NAME/KEY: misc_feature
<222> LOCATION: (9)..(9)
<223> OTHER INFORMATION: Xaa can be any naturally occurring amino acid

<400> SEQUENCE: 66

Arg Arg Gly Gly Trp Gln Pro Cys Xaa Trp Glu Ser Trp Thr Phe Cys
1               5                   10                  15

Trp Asp Pro Gly Gly Gly Lys
            20

<210> SEQ ID NO 67
<211> LENGTH: 16
<212> TYPE: PRT
<213> ORGANISM: Artificial
<220> FEATURE:
<223> OTHER INFORMATION: Description of Artificial Sequnce: Fibrin-
      binding peptide

<400> SEQUENCE: 67

Arg Trp Gln Pro Cys Pro Trp Glu Ser Trp Thr Phe Cys Trp Asp Pro
1               5                   10                  15
```

```
<210> SEQ ID NO 68
<211> LENGTH: 20
<212> TYPE: PRT
<213> ORGANISM: Artificial
<220> FEATURE:
<223> OTHER INFORMATION: Description of Artificial Sequence:  Fibrin-
      binding peptide

<400> SEQUENCE: 68

Arg Trp Gln Pro Cys Pro Trp Glu Ser Trp Thr Phe Cys Trp Asp Pro
1               5                   10                  15

Gly Gly Gly Lys
            20

<210> SEQ ID NO 69
<211> LENGTH: 16
<212> TYPE: PRT
<213> ORGANISM: Artificial
<220> FEATURE:
<223> OTHER INFORMATION: Description of Artificial Sequnce:  Fibrin-
      binding peptide
<220> FEATURE:
<221> NAME/KEY: misc_feature
<223> OTHER INFORMATION: Xaa=2-Cyclohexyl-L-alanine
<220> FEATURE:
<221> NAME/KEY: misc_feature
<222> LOCATION: (12)..(12)
<223> OTHER INFORMATION: Xaa can be any naturally occurring amino acid

<400> SEQUENCE: 69

Arg Trp Gln Pro Cys Pro Ala Glu Ser Trp Thr Xaa Cys Trp Asp Pro
1               5                   10                  15

<210> SEQ ID NO 70
<211> LENGTH: 20
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: misc_feature
<223> OTHER INFORMATION: Xaa=2-Cyclohexyl-L-alanine
<220> FEATURE:
<221> NAME/KEY: misc_feature
<222> LOCATION: (12)..(12)
<223> OTHER INFORMATION: Xaa can be any naturally occurring amino acid

<400> SEQUENCE: 70

Arg Trp Gln Pro Cys Pro Ala Glu Ser Trp Thr Xaa Cys Trp Asp Pro
1               5                   10                  15

Gly Gly Gly Lys
            20

<210> SEQ ID NO 71
<211> LENGTH: 16
<212> TYPE: PRT
<213> ORGANISM: Artificial
<220> FEATURE:
<223> OTHER INFORMATION: Description of Artificial Sequnce:  Fibrin-
      binding peptide
<220> FEATURE:
<221> NAME/KEY: misc_feature
<223> OTHER INFORMATION: Xaa=2-Cyclohexyl-L-alanine
<220> FEATURE:
<221> NAME/KEY: misc_feature
<222> LOCATION: (12)..(12)
<223> OTHER INFORMATION: Xaa can be any naturally occurring amino acid

<400> SEQUENCE: 71

Gly Trp Gln Pro Cys Pro Ala Glu Ser Trp Thr Xaa Cys Trp Asp Pro
```

-continued

```
<210> SEQ ID NO 72
<211> LENGTH: 20
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: misc_feature
<223> OTHER INFORMATION: Xaa=2-Cyclohexyl-L-alanine
<220> FEATURE:
<221> NAME/KEY: misc_feature
<222> LOCATION: (12)..(12)
<223> OTHER INFORMATION: Xaa can be any naturally occurring amino acid

<400> SEQUENCE: 72

Gly Trp Gln Pro Cys Pro Ala Glu Ser Trp Thr Xaa Cys Trp Asp Pro
1               5                   10                  15

Gly Gly Gly Lys
            20

<210> SEQ ID NO 73
<211> LENGTH: 17
<212> TYPE: PRT
<213> ORGANISM: Artificial
<220> FEATURE:
<223> OTHER INFORMATION: Description of Artificial Sequnce:  Fibrin-
      binding peptide

<400> SEQUENCE: 73

Arg Gly Trp Gln Pro Cys Pro Trp Glu Ser Trp Thr Phe Cys Trp Asp
1               5                   10                  15

Pro

<210> SEQ ID NO 74
<211> LENGTH: 21
<212> TYPE: PRT
<213> ORGANISM: Artificial
<220> FEATURE:
<223> OTHER INFORMATION: Description of Artificial Sequence:  Fibrin-
      binding peptide

<400> SEQUENCE: 74

Arg Gly Trp Gln Pro Cys Pro Trp Glu Ser Trp Thr Phe Cys Trp Asp
1               5                   10                  15

Pro Gly Gly Gly Lys
            20

<210> SEQ ID NO 75
<211> LENGTH: 17
<212> TYPE: PRT
<213> ORGANISM: Artificial
<220> FEATURE:
<223> OTHER INFORMATION: Description of Artificial Sequnce:  Fibrin-
      binding peptide

<400> SEQUENCE: 75

Arg Gly Trp Gln Pro Cys Pro Ala Glu Ser Trp Thr Phe Cys Trp Asp
1               5                   10                  15

Pro

<210> SEQ ID NO 76
<211> LENGTH: 21
<212> TYPE: PRT
<213> ORGANISM: Artificial
```

```
<220> FEATURE:
<223> OTHER INFORMATION: Description of Artificial Sequence:  Fibrin-
      binding peptide

<400> SEQUENCE: 76

Arg Gly Trp Gln Pro Cys Pro Ala Glu Ser Trp Thr Phe Cys Trp Asp
1               5                   10                  15

Pro Gly Gly Gly Lys
            20

<210> SEQ ID NO 77
<211> LENGTH: 17
<212> TYPE: PRT
<213> ORGANISM: Artificial
<220> FEATURE:
<223> OTHER INFORMATION: Description of Artificial Sequnce:  Fibrin-
      binding peptide
<220> FEATURE:
<221> NAME/KEY: misc_feature
<223> OTHER INFORMATION: Xaa=2-Cyclohexyl-L-alanine
<220> FEATURE:
<221> NAME/KEY: misc_feature
<222> LOCATION: (13)..(13)
<223> OTHER INFORMATION: Xaa can be any naturally occurring amino acid

<400> SEQUENCE: 77

Arg Gly Trp Gln Pro Cys Pro Ala Glu Ser Trp Thr Xaa Cys Trp Asp
1               5                   10                  15

Pro

<210> SEQ ID NO 78
<211> LENGTH: 21
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: misc_feature
<223> OTHER INFORMATION: Xaa=2-Cyclohexyl-L-alanine
<220> FEATURE:
<221> NAME/KEY: misc_feature
<222> LOCATION: (13)..(13)
<223> OTHER INFORMATION: Xaa can be any naturally occurring amino acid

<400> SEQUENCE: 78

Arg Gly Trp Gln Pro Cys Pro Ala Glu Ser Trp Thr Xaa Cys Trp Asp
1               5                   10                  15

Pro Gly Gly Gly Lys
            20

<210> SEQ ID NO 79
<211> LENGTH: 17
<212> TYPE: PRT
<213> ORGANISM: Artificial
<220> FEATURE:
<223> OTHER INFORMATION: Description of Artificial Sequnce:  Fibrin-
      binding peptide
<220> FEATURE:
<221> NAME/KEY: misc_feature
<223> OTHER INFORMATION: Xaa=2-Cyclohexyl-L-alanine
<220> FEATURE:
<221> NAME/KEY: misc_feature
<222> LOCATION: (13)..(13)
<223> OTHER INFORMATION: Xaa can be any naturally occurring amino acid

<400> SEQUENCE: 79

Arg Gly Trp Gln Pro Cys Pro Ala Glu Ser Trp Thr Xaa Cys Trp Asp
1               5                   10                  15
```

Pro

```
<210> SEQ ID NO 80
<211> LENGTH: 21
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: misc_feature
<223> OTHER INFORMATION: Xaa=2-Cyclohexyl-L-alanine
<220> FEATURE:
<221> NAME/KEY: misc_feature
<222> LOCATION: (13)..(13)
<223> OTHER INFORMATION: Xaa can be any naturally occurring amino acid

<400> SEQUENCE: 80

Arg Gly Trp Gln Pro Cys Pro Ala Glu Ser Trp Thr Xaa Cys Trp Asp
1               5                   10                  15

Pro Gly Gly Gly Lys
            20

<210> SEQ ID NO 81
<211> LENGTH: 16
<212> TYPE: PRT
<213> ORGANISM: Artificial
<220> FEATURE:
<223> OTHER INFORMATION: Description of Artificial Sequnce: Fibrin-
      binding peptide
<220> FEATURE:
<221> NAME/KEY: misc_feature
<223> OTHER INFORMATION: Xaa=2-Cyclohexyl-L-alanine
<220> FEATURE:
<221> NAME/KEY: misc_feature
<222> LOCATION: (12)..(12)
<223> OTHER INFORMATION: Xaa can be any naturally occurring amino acid

<400> SEQUENCE: 81

Gly Trp Gln Pro Cys Pro Ala Glu Ser Trp Thr Xaa Cys Trp Asp Pro
1               5                   10                  15

<210> SEQ ID NO 82
<211> LENGTH: 20
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: misc_feature
<223> OTHER INFORMATION: Xaa=2-Cyclohexyl-L-alanine
<220> FEATURE:
<221> NAME/KEY: misc_feature
<222> LOCATION: (12)..(12)
<223> OTHER INFORMATION: Xaa can be any naturally occurring amino acid

<400> SEQUENCE: 82

Gly Trp Gln Pro Cys Pro Ala Glu Ser Trp Thr Xaa Cys Trp Asp Pro
1               5                   10                  15

Gly Gly Gly Lys
            20

<210> SEQ ID NO 83
<211> LENGTH: 16
<212> TYPE: PRT
<213> ORGANISM: Artificial
<220> FEATURE:
<223> OTHER INFORMATION: Description of Artificial Sequnce: Fibrin-
      binding peptide
```

```
<400> SEQUENCE: 83

Arg Trp Gln Pro Cys Pro Ala Glu Ser Trp Thr Phe Cys Trp Asp Pro
1               5                   10                  15

<210> SEQ ID NO 84
<211> LENGTH: 20
<212> TYPE: PRT
<213> ORGANISM: Artificial
<220> FEATURE:
<223> OTHER INFORMATION: Description of Artificial Sequence:  Fibrin-
      binding peptide

<400> SEQUENCE: 84

Arg Trp Gln Pro Cys Pro Ala Glu Ser Trp Thr Phe Cys Trp Asp Pro
1               5                   10                  15

Gly Gly Gly Lys
            20

<210> SEQ ID NO 85
<211> LENGTH: 16
<212> TYPE: PRT
<213> ORGANISM: Artificial
<220> FEATURE:
<223> OTHER INFORMATION: Description of Artificial Sequnce:  Fibrin-
      binding peptide
<220> FEATURE:
<221> NAME/KEY: misc_feature
<223> OTHER INFORMATION: xaa=2-Cyclohexyl-L-alanine
<220> FEATURE:
<221> NAME/KEY: misc_feature
<222> LOCATION: (12)..(12)
<223> OTHER INFORMATION: Xaa can be any naturally occurring amino acid

<400> SEQUENCE: 85

Arg Trp Gln Pro Cys Pro Ala Glu Ser Trp Thr Xaa Cys Trp Asp Pro
1               5                   10                  15

<210> SEQ ID NO 86
<211> LENGTH: 20
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: misc_feature
<223> OTHER INFORMATION: Xaa=2-Cyclohexyl-L-alanine
<220> FEATURE:
<221> NAME/KEY: misc_feature
<222> LOCATION: (12)..(12)
<223> OTHER INFORMATION: Xaa can be any naturally occurring amino acid

<400> SEQUENCE: 86

Arg Trp Gln Pro Cys Pro Ala Glu Ser Trp Thr Xaa Cys Trp Asp Pro
1               5                   10                  15

Gly Gly Gly Lys
            20

<210> SEQ ID NO 87
<211> LENGTH: 19
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: MOD_RES
<222> LOCATION: (19)..(19)
<223> OTHER INFORMATION: 5-Carboxyfluorescein-NH2
```

```
<400> SEQUENCE: 87

Trp Gln Pro Cys Pro Trp Glu Ser Trp Thr Phe Cys Trp Asp Pro Gly
1               5                   10                  15

Gly Gly Lys

<210> SEQ ID NO 88
<211> LENGTH: 23
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: MOD_RES
<222> LOCATION: (23)..(23)
<223> OTHER INFORMATION: 5-Carboxyfluorescein-NH2

<400> SEQUENCE: 88

Gly Pro Pro Gly Trp Gln Pro Cys Pro Trp Glu Ser Trp Thr Phe Cys
1               5                   10                  15

Trp Asp Pro Gly Gly Gly Lys
            20

<210> SEQ ID NO 89
<211> LENGTH: 23
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: MOD_RES
<222> LOCATION: (23)..(23)
<223> OTHER INFORMATION: 5-Carboxyfluorescein-NH2

<400> SEQUENCE: 89

Gly Gly Arg Gly Trp Gln Pro Cys Pro Trp Glu Ser Trp Thr Phe Cys
1               5                   10                  15

Trp Asp Pro Gly Gly Gly Lys
            20

<210> SEQ ID NO 90
<211> LENGTH: 20
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: MOD_RES
<222> LOCATION: (20)..(20)
<223> OTHER INFORMATION: 5-Carboxyfluorescein-NH2

<400> SEQUENCE: 90

Gly Trp Gln Pro Cys Pro Trp Glu Ser Trp Thr Phe Cys Trp Asp Pro
1               5                   10                  15

Gly Gly Gly Lys
            20

<210> SEQ ID NO 91
<211> LENGTH: 24
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: misc_feature
```

```
<223> OTHER INFORMATION: Xaa=8-amino-3,6-dioxaoctanoic acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MOD_RES
<222> LOCATION: (24)..(24)
<223> OTHER INFORMATION: 5-Carboxyfluorescein-NH2

<400> SEQUENCE: 91

Ser Gly Ser Gly Xaa Trp Gln Pro Cys Pro Trp Glu Ser Trp Thr Phe
1               5                   10                  15

Cys Trp Asp Pro Gly Gly Gly Lys
            20

<210> SEQ ID NO 92
<211> LENGTH: 19
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: misc_feature
<223> OTHER INFORMATION: Xaa=2-Cyclohexyl-L-alanine
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: MOD_RES
<222> LOCATION: (18)..(18)
<223> OTHER INFORMATION: 5-Carboxyfluorescein-NH2

<400> SEQUENCE: 92

Trp Gln Pro Cys Pro Trp Glu Ser Trp Thr Xaa Cys Trp Asp Pro Gly
1               5                   10                  15

Gly Gly Lys

<210> SEQ ID NO 93
<211> LENGTH: 19
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: misc_feature
<223> OTHER INFORMATION: Xaa=L-4-Fluorophenylalanine
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: MOD_RES
<222> LOCATION: (19)..(19)
<223> OTHER INFORMATION: 5-Carboxyfluorescein-NH2

<400> SEQUENCE: 93

Trp Gln Pro Cys Pro Trp Glu Ser Trp Thr Xaa Cys Trp Asp Pro Gly
1               5                   10                  15

Gly Gly Lys

<210> SEQ ID NO 94
<211> LENGTH: 19
<212> TYPE: PRT
<213> ORGANISM: Artificial
<220> FEATURE:
<223> OTHER INFORMATION: Description of Artificial Sequence:  Fibrin-
      binding peptide
```

```
<220> FEATURE:
<221> NAME/KEY: misc_feature
<223> OTHER INFORMATION: Xaa=L-3,4-difluorophenylalanine
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: MOD_RES
<222> LOCATION: (19)..(19)
<223> OTHER INFORMATION: 5-Carboxyfluorescein-NH2

<400> SEQUENCE: 94

Trp Gln Pro Cys Pro Trp Glu Ser Trp Thr Xaa Cys Trp Asp Pro Gly
1               5                   10                  15

Gly Gly Lys

<210> SEQ ID NO 95
<211> LENGTH: 20
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: MOD_RES
<222> LOCATION: (20)..(20)
<223> OTHER INFORMATION: 5-Carboxyfluorescein-NH2

<400> SEQUENCE: 95

Gly Trp Gln Pro Cys Pro Trp Glu Ser Trp Thr Phe Cys Trp Asp Pro
1               5                   10                  15

Gly Gly Gly Lys
            20

<210> SEQ ID NO 96
<211> LENGTH: 21
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: MOD_RES
<222> LOCATION: (21)..(21)
<223> OTHER INFORMATION: 5-Carboxyfluorescein-NH2

<400> SEQUENCE: 96

Arg Gly Trp Gln Pro Cys Pro Trp Glu Ser Trp Thr Phe Cys Trp Asp
1               5                   10                  15

Pro Gly Gly Gly Lys
                20

<210> SEQ ID NO 97
<211> LENGTH: 20
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: MOD_RES
<222> LOCATION: (20)..(20)
<223> OTHER INFORMATION: 5-Carboxyfluorescein-NH2

<400> SEQUENCE: 97

Arg Trp Gln Pro Cys Pro Trp Glu Ser Trp Thr Phe Cys Trp Asp Pro
1               5                   10                  15

Gly Gly Gly Lys
```

```
<210> SEQ ID NO 98
<211> LENGTH: 27
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: MOD_RES
<222> LOCATION: (27)..(27)
<223> OTHER INFORMATION: 5-Carboxyfluorescein-NH2

<400> SEQUENCE: 98

Ser Gly Ser Gly Ser Gly Ser Gly Trp Gln Pro Cys Pro Trp Glu Ser
1               5                   10                  15

Trp Thr Phe Cys Trp Asp Pro Gly Gly Gly Lys
            20                  25

<210> SEQ ID NO 99
<211> LENGTH: 22
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: MOD_RES
<222> LOCATION: (22)..(22)
<223> OTHER INFORMATION: 5-Carboxyfluorescein-NH2

<400> SEQUENCE: 99

Lys Lys Gly Trp Gln Pro Cys Pro Trp Glu Ser Trp Thr Phe Cys Trp
1               5                   10                  15

Asp Pro Gly Gly Gly Lys
            20

<210> SEQ ID NO 100
<211> LENGTH: 25
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: MOD_RES
<222> LOCATION: (25)..(25)
<223> OTHER INFORMATION: 5-Carboxyfluorescein-NH2

<400> SEQUENCE: 100

Lys Gly Lys Gly Lys Gly Trp Gln Pro Cys Pro Trp Glu Ser Trp Thr
1               5                   10                  15

Phe Cys Trp Asp Pro Gly Gly Gly Lys
            20                  25

<210> SEQ ID NO 101
<211> LENGTH: 20
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: misc_feature
<223> OTHER INFORMATION: Xaa=O-(2-Acetamido-2-deoxy- -D-
      galactopyranosyl)-L-serine
<220> FEATURE:
<221> NAME/KEY: misc_feature
<222> LOCATION: (1)..(1)
```

-continued

```
<223> OTHER INFORMATION: Xaa can be any naturally occurring amino acid
<220> FEATURE:
<221> NAME/KEY: MOD_RES
<222> LOCATION: (20)..(20)
<223> OTHER INFORMATION: 5-Carboxyfluorescein-NH2

<400> SEQUENCE: 101

Xaa Trp Gln Pro Cys Pro Trp Glu Ser Trp Thr Phe Cys Trp Asp Pro
1               5                   10                  15

Gly Gly Gly Lys
            20

<210> SEQ ID NO 102
<211> LENGTH: 20
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: misc_feature
<223> OTHER INFORMATION: Xaa=Tetrahydrofuran-2-carboxylic acid
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MOD_RES
<222> LOCATION: (20)..(20)
<223> OTHER INFORMATION: 5-Carboxyfluorescein-NH2

<400> SEQUENCE: 102

Xaa Trp Gln Pro Cys Pro Trp Glu Ser Trp Thr Phe Cys Trp Asp Pro
1               5                   10                  15

Gly Gly Gly Lys
            20

<210> SEQ ID NO 103
<211> LENGTH: 23
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: MOD_RES
<222> LOCATION: (23)..(23)
<223> OTHER INFORMATION: 5-Carboxyfluorescein-NH2

<400> SEQUENCE: 103

Arg Arg Gly Gly Trp Gln Pro Cys Pro Trp Glu Ser Trp Thr Phe Cys
1               5                   10                  15

Trp Asp Pro Gly Gly Gly Lys
            20

<210> SEQ ID NO 104
<211> LENGTH: 23
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: MOD_RES
<222> LOCATION: (23)..(23)
<223> OTHER INFORMATION: 5-Carboxyfluorescein-NH2

<400> SEQUENCE: 104

Gly Pro Pro Gly Trp Gln Pro Cys Pro Ala Glu Ser Trp Thr Phe Cys
1               5                   10                  15
```

Trp Asp Pro Gly Gly Gly Lys
            20

<210> SEQ ID NO 105
<211> LENGTH: 23
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: MOD_RES
<222> LOCATION: (23)..(23)
<223> OTHER INFORMATION: 5-Carboxyfluorescein-NH2

<400> SEQUENCE: 105

Gly Gly Arg Gly Trp Gln Pro Cys Pro Ala Glu Ser Trp Thr Phe Cys
1               5                   10                  15

Trp Asp Pro Gly Gly Gly Lys
            20

<210> SEQ ID NO 106
<211> LENGTH: 20
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: MOD_RES
<222> LOCATION: (20)..(20)
<223> OTHER INFORMATION: 5-Carboxyfluorescein-NH2

<400> SEQUENCE: 106

Gly Trp Gln Pro Cys Pro Ala Glu Ser Trp Thr Phe Cys Trp Asp Pro
1               5                   10                  15

Gly Gly Gly Lys
            20

<210> SEQ ID NO 107
<211> LENGTH: 20
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: MOD_RES
<222> LOCATION: (20)..(20)
<223> OTHER INFORMATION: 5-Carboxyfluorescein-NH2

<400> SEQUENCE: 107

Gly Trp Gln Pro Cys Pro Ala Glu Ser Trp Thr Phe Cys Trp Asp Pro
1               5                   10                  15

Gly Gly Gly Lys
            20

<210> SEQ ID NO 108
<211> LENGTH: 27
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: MOD_RES
<222> LOCATION: (27)..(27)
<223> OTHER INFORMATION: 5-Carboxyfluorescein-NH2

```
<400> SEQUENCE: 108

Ser Gly Ser Gly Ser Gly Ser Gly Trp Gln Pro Cys Pro Ala Glu Ser
1               5                   10                  15

Trp Thr Phe Cys Trp Asp Pro Gly Gly Gly Lys
            20                  25

<210> SEQ ID NO 109
<211> LENGTH: 19
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: misc_feature
<223> OTHER INFORMATION: Xaa=2-Cyclohexyl-L-alanine
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: MOD_RES
<222> LOCATION: (19)..(19)
<223> OTHER INFORMATION: 5-Carboxyfluorescein-NH2

<400> SEQUENCE: 109

Trp Gln Pro Cys Pro Ala Glu Ser Trp Thr Xaa Cys Trp Asp Pro Gly
1               5                   10                  15

Gly Gly Lys

<210> SEQ ID NO 110
<211> LENGTH: 24
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: misc_feature
<223> OTHER INFORMATION: Xaa=8-amino-3,6-dioxaoctanoic acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MOD_RES
<222> LOCATION: (24)..(24)
<223> OTHER INFORMATION: 5-Carboxyfluorescein-NH2

<400> SEQUENCE: 110

Ser Gly Ser Gly Xaa Trp Gln Pro Cys Pro Ala Glu Ser Trp Thr Phe
1               5                   10                  15

Cys Trp Asp Pro Gly Gly Gly Lys
            20

<210> SEQ ID NO 111
<211> LENGTH: 23
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: MOD_RES
<222> LOCATION: (23)..(23)
<223> OTHER INFORMATION: 5-Carboxyfluorescein-NH2

<400> SEQUENCE: 111

Arg Arg Gly Gly Trp Gln Pro Cys Pro Ala Glu Ser Trp Thr Phe Cys
1               5                   10                  15
```

```
Trp Asp Pro Gly Gly Gly Lys
            20

<210> SEQ ID NO 112
<211> LENGTH: 20
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: MOD_RES
<222> LOCATION: (20)..(20)
<223> OTHER INFORMATION: 5-Carboxyfluorescein-NH2

<400> SEQUENCE: 112

Arg Trp Gln Pro Cys Pro Trp Glu Ser Trp Thr Phe Cys Trp Asp Pro
1               5                   10                  15

Gly Gly Gly Lys
            20

<210> SEQ ID NO 113
<211> LENGTH: 20
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: MOD_RES
<222> LOCATION: (20)..(20)
<223> OTHER INFORMATION: 5-Carboxyfluorescein-NH2

<400> SEQUENCE: 113

Arg Trp Gln Pro Cys Pro Ala Glu Ser Trp Thr Phe Cys Trp Asp Pro
1               5                   10                  15

Gly Gly Gly Lys
            20

<210> SEQ ID NO 114
<211> LENGTH: 20
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: misc_feature
<223> OTHER INFORMATION: Xaa=2-Cyclohexyl-L-alanine
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: MOD_RES
<222> LOCATION: (20)..(20)
<223> OTHER INFORMATION: 5-Carboxyfluorescein-NH2

<400> SEQUENCE: 114

Arg Trp Gln Pro Cys Pro Ala Glu Ser Trp Thr Xaa Cys Trp Asp Pro
1               5                   10                  15

Gly Gly Gly Lys
            20

<210> SEQ ID NO 115
<211> LENGTH: 20
<212> TYPE: PRT
<213> ORGANISM: Artificial
<220> FEATURE:
```

-continued

<223> OTHER INFORMATION: Description of Artificial Sequence: Fibrin-
      binding peptide
<220> FEATURE:
<221> NAME/KEY: misc_feature
<223> OTHER INFORMATION: Xaa=2-Cyclohexyl-L-alanine
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: MOD_RES
<222> LOCATION: (20)..(20)
<223> OTHER INFORMATION: 5-Carboxyfluorescein-NH2

<400> SEQUENCE: 115

Gly Trp Gln Pro Cys Pro Ala Glu Ser Trp Thr Xaa Cys Trp Asp Pro
1               5                   10                  15

Gly Gly Gly Lys
            20

<210> SEQ ID NO 116
<211> LENGTH: 21
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: MOD_RES
<222> LOCATION: (21)..(21)
<223> OTHER INFORMATION: 5-Carboxyfluorescein-NH2

<400> SEQUENCE: 116

Arg Gly Trp Gln Pro Cys Pro Trp Glu Ser Trp Thr Phe Cys Trp Asp
1               5                   10                  15

Pro Gly Gly Gly Lys
            20

<210> SEQ ID NO 117
<211> LENGTH: 21
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: misc_feature
<223> OTHER INFORMATION: Xaa=2-Cyclohexyl-L-alanine
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: MOD_RES
<222> LOCATION: (21)..(21)
<223> OTHER INFORMATION: 5-Carboxyfluorescein-NH2

<400> SEQUENCE: 117

Arg Gly Trp Gln Pro Cys Pro Ala Glu Ser Trp Thr Xaa Cys Trp Asp
1               5                   10                  15

Pro Gly Gly Gly Lys
            20

<210> SEQ ID NO 118
<211> LENGTH: 21
<212> TYPE: PRT
<213> ORGANISM: Artificial
<220> FEATURE:
<223> OTHER INFORMATION: Description of Artificial Sequence: Fibrin-
      binding peptide
<220> FEATURE:

```
<221> NAME/KEY: misc_feature
<223> OTHER INFORMATION: Xaa=2-Cyclohexyl-L-alanine
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: MOD_RES
<222> LOCATION: (21)..(21)
<223> OTHER INFORMATION: 5-Carboxyfluorescein-NH2

<400> SEQUENCE: 118

Arg Gly Trp Gln Pro Cys Pro Ala Glu Ser Trp Thr Xaa Cys Trp Asp
1               5                   10                  15

Pro Gly Gly Gly Lys
            20

<210> SEQ ID NO 119
<211> LENGTH: 20
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: misc_feature
<223> OTHER INFORMATION: Xaa=2-Cyclohexyl-L-alanine
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: MOD_RES
<222> LOCATION: (20)..(20)
<223> OTHER INFORMATION: 5-Carboxyfluorescein-NH2

<400> SEQUENCE: 119

Gly Trp Gln Pro Cys Pro Ala Glu Ser Trp Thr Xaa Cys Trp Asp Pro
1               5                   10                  15

Gly Gly Gly Lys
            20

<210> SEQ ID NO 120
<211> LENGTH: 20
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: MOD_RES
<222> LOCATION: (20)..(20)
<223> OTHER INFORMATION: 5-Carboxyfluorescein-NH2

<400> SEQUENCE: 120

Arg Trp Gln Pro Cys Pro Ala Glu Ser Trp Thr Phe Cys Trp Asp Pro
1               5                   10                  15

Gly Gly Gly Lys
            20

<210> SEQ ID NO 121
<211> LENGTH: 20
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: misc_feature
<223> OTHER INFORMATION: Xaa=2-Cyclohexyl-L-alanine
<220> FEATURE:
```

```
<221> NAME/KEY: misc_feature
<222> LOCATION: (12)..(12)
<223> OTHER INFORMATION: Xaa can be any naturally occurring amino acid
<220> FEATURE:
<221> NAME/KEY: MOD_RES
<222> LOCATION: (20)..(20)
<223> OTHER INFORMATION: 5-Carboxyfluorescein-NH2

<400> SEQUENCE: 121

Arg Trp Gln Pro Cys Pro Ala Glu Ser Trp Thr Xaa Cys Trp Asp Pro
1               5                   10                  15

Gly Gly Gly Lys
            20

<210> SEQ ID NO 122
<211> LENGTH: 19
<212> TYPE: PRT
<213> ORGANISM: Artificial
<220> FEATURE:
<223> OTHER INFORMATION: Description of Artificial Sequence:  Fibrin-
      binding peptide

<400> SEQUENCE: 122

Trp Gln Pro Cys Pro Trp Glu Ser Trp Thr Phe Cys Trp Asp Pro Gly
1               5                   10                  15

Gly Gly Lys

<210> SEQ ID NO 123
<211> LENGTH: 19
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: MOD_RES
<222> LOCATION: (19)..(19)
<223> OTHER INFORMATION: (DSPE-PG4-Glut)-NH2

<400> SEQUENCE: 123

Trp Gln Pro Cys Pro Ala Glu Ser Trp Thr Phe Cys Trp Asp Pro Gly
1               5                   10                  15

Gly Gly Lys

<210> SEQ ID NO 124
<211> LENGTH: 19
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: MOD_RES
<222> LOCATION: (19)..(19)
<223> OTHER INFORMATION: (DPPE-PG4-Glut-)-NH2

<400> SEQUENCE: 124

Trp Gln Pro Cys Pro Ala Glu Ser Trp Thr Phe Cys Trp Asp Pro Gly
1               5                   10                  15

Gly Gly Lys

<210> SEQ ID NO 125
<211> LENGTH: 27
<212> TYPE: PRT
<213> ORGANISM: Artificial
<220> FEATURE:
<223> OTHER INFORMATION: Description of Artificial Sequence:  Fibrin-
      binding peptide
```

```
<220> FEATURE:
<221> NAME/KEY: MOD_RES
<222> LOCATION: (27)..(27)
<223> OTHER INFORMATION: (DSPE-PG4-Glut)-NH2

<400> SEQUENCE: 125

Ser Gly Ser Gly Ser Gly Ser Gly Trp Gln Pro Cys Pro Trp Glu Ser
1               5                   10                  15

Trp Thr Phe Cys Trp Asp Pro Gly Gly Gly Lys
            20                  25

<210> SEQ ID NO 126
<211> LENGTH: 20
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: MOD_RES
<222> LOCATION: (20)..(20)
<223> OTHER INFORMATION: (DSPE-PG4-Glut)-NH2

<400> SEQUENCE: 126

Gly Trp Gln Pro Cys Pro Trp Glu Ser Trp Thr Phe Cys Trp Asp Pro
1               5                   10                  15

Gly Gly Gly Lys
            20

<210> SEQ ID NO 127
<211> LENGTH: 24
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: misc_feature
<223> OTHER INFORMATION: Xaa=8-amino-3,6-dioxaoctanoic acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MOD_RES
<222> LOCATION: (24)..(24)
<223> OTHER INFORMATION: (DSPE-PG4-Glut)-NH2

<400> SEQUENCE: 127

Ser Gly Ser Gly Xaa Trp Gln Pro Cys Pro Trp Glu Ser Trp Thr Phe
1               5                   10                  15

Cys Trp Asp Pro Gly Gly Gly Lys
            20

<210> SEQ ID NO 128
<211> LENGTH: 20
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: MOD_RES
<222> LOCATION: (20)..(20)
<223> OTHER INFORMATION: (DSPE-PG4-Glut)-NH2

<400> SEQUENCE: 128

Arg Trp Gln Pro Cys Pro Trp Glu Ser Trp Thr Phe Cys Trp Asp Pro
1               5                   10                  15
```

-continued

Gly Gly Gly Lys
        20

<210> SEQ ID NO 129
<211> LENGTH: 20
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: misc_feature
<223> OTHER INFORMATION: Xaa=2-Cyclohexyl-L-alanine
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: MOD_RES
<222> LOCATION: (20)..(20)
<223> OTHER INFORMATION: (DSPE-PG4-Glut)-NH2

<400> SEQUENCE: 129

Arg Trp Gln Pro Cys Pro Ala Glu Ser Trp Thr Xaa Cys Trp Asp Pro
1               5                   10                  15

Gly Gly Gly Lys
        20

<210> SEQ ID NO 130
<211> LENGTH: 20
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: misc_feature
<223> OTHER INFORMATION: Xaa=2-Cyclohexyl-L-alanine
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: MOD_RES
<222> LOCATION: (20)..(20)
<223> OTHER INFORMATION: (DSPE-PG4-Glut)-NH2

<400> SEQUENCE: 130

Arg Trp Gln Pro Cys Pro Ala Glu Ser Trp Thr Xaa Cys Trp Asp Pro
1               5                   10                  15

Gly Gly Gly Lys
        20

<210> SEQ ID NO 131
<211> LENGTH: 19
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: MOD_RES
<222> LOCATION: (19)..(19)
<223> OTHER INFORMATION: (DPPE-Glut-PG2-JJ)-NH2

<400> SEQUENCE: 131

Trp Gln Pro Cys Pro Ala Glu Ser Trp Thr Phe Cys Trp Asp Pro Gly
1               5                   10                  15

Gly Gly Lys

```
<210> SEQ ID NO 132
<211> LENGTH: 21
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: MOD_RES
<222> LOCATION: (21)..(21)
<223> OTHER INFORMATION: (DPPE-Pro9-Glut-Ttda-Dga)-NH2

<400> SEQUENCE: 132

Trp Gln Pro Cys Pro Ala Glu Ser Trp Thr Phe Cys Trp Asp Pro Gly
1               5                   10                  15

Ser Ala Gly Ser Lys
            20

<210> SEQ ID NO 133
<211> LENGTH: 21
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: MOD_RES
<222> LOCATION: (21)..(21)
<223> OTHER INFORMATION: (DPPE-Pro9-Glut-Ttda-Dga)-NH2

<400> SEQUENCE: 133

Trp Gln Pro Cys Pro Ala Glu Ser Trp Thr Phe Cys Trp Asp Pro Gly
1               5                   10                  15

Ala Gly Ser Gly Lys
            20

<210> SEQ ID NO 134
<211> LENGTH: 21
<212> TYPE: PRT
<213> ORGANISM: Artificial
<220> FEATURE:
<223> OTHER INFORMATION: Description of Artificial Sequence:  Fibrin-
      binding peptide

<400> SEQUENCE: 134

Trp Gln Pro Cys Pro Ala Glu Ser Trp Thr Phe Cys Trp Asp Pro Gly
1               5                   10                  15

Ser Ala Gly Ser Lys
            20

<210> SEQ ID NO 135
<211> LENGTH: 21
<212> TYPE: PRT
<213> ORGANISM: Artificial
<220> FEATURE:
<223> OTHER INFORMATION: Description of Artificial Sequence:  Fibrin-
      binding peptide

<400> SEQUENCE: 135

Trp Gln Pro Cys Pro Ala Glu Ser Trp Thr Phe Cys Trp Asp Pro Gly
1               5                   10                  15

Ala Gly Ser Gly Lys
            20

<210> SEQ ID NO 136
<211> LENGTH: 20
<212> TYPE: PRT
<213> ORGANISM: Artificial
```

```
<220> FEATURE:
<223> OTHER INFORMATION: Description of Artificial Sequence:  Fibrin-
      binding peptide
<220> FEATURE:
<221> NAME/KEY: misc_feature
<223> OTHER INFORMATION: Xaa=8-amino-3,6-dioxaoctanoic acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 136

Trp Gln Pro Cys Pro Ala Glu Ser Trp Thr Phe Cys Trp Asp Pro Gly
1               5                   10                  15

Gly Gly Lys Xaa
            20

<210> SEQ ID NO 137
<211> LENGTH: 6
<212> TYPE: PRT
<213> ORGANISM: Artificial
<220> FEATURE:
<223> OTHER INFORMATION: Description of Artificial Sequence:  Fibrin-
      binding peptide

<400> SEQUENCE: 137

Gly Ser Ala Gly Ser Lys
1               5

<210> SEQ ID NO 138
<211> LENGTH: 6
<212> TYPE: PRT
<213> ORGANISM: Artificial
<220> FEATURE:
<223> OTHER INFORMATION: Description of Artificial Sequence:  Fibrin-
      binding peptide

<400> SEQUENCE: 138

Gly Ala Gly Ser Gly Lys
1               5

<210> SEQ ID NO 139
<211> LENGTH: 6
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: misc_feature
<223> OTHER INFORMATION: Xaa=8-amino-3,6-dioxaoctanoic acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 139

Gly Gly Gly Lys Xaa Xaa
1               5

<210> SEQ ID NO 140
<211> LENGTH: 20
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: MOD_RES
<222> LOCATION: (1)..(1)
<223> OTHER INFORMATION: Allyloxycarbonyl
```

<400> SEQUENCE: 140

Arg Trp Gln Pro Cys Pro Ala Glu Ser Trp Thr Phe Cys Trp Asp Pro
1               5                   10                  15

Gly Gly Gly Lys
            20

<210> SEQ ID NO 141
<211> LENGTH: 20
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: MOD_RES
<222> LOCATION: (1)..(1)
<223> OTHER INFORMATION: Allyloxycarbonyl
<220> FEATURE:
<221> NAME/KEY: MOD_RES
<222> LOCATION: (20)..(20)
<223> OTHER INFORMATION: 5-Carboxyfluorescein-NH2

<400> SEQUENCE: 141

Arg Trp Gln Pro Cys Pro Ala Glu Ser Trp Thr Phe Cys Trp Asp Pro
1               5                   10                  15

Gly Gly Gly Lys
            20

<210> SEQ ID NO 142
<211> LENGTH: 20
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: MOD_RES
<222> LOCATION: (1)..(1)
<223> OTHER INFORMATION: Allyloxycarbonyl

<400> SEQUENCE: 142

Arg Trp Gln Pro Cys Pro Trp Glu Ser Trp Thr Phe Cys Trp Asp Pro
1               5                   10                  15

Gly Gly Gly Lys
            20

<210> SEQ ID NO 143
<211> LENGTH: 20
<212> TYPE: PRT
<213> ORGANISM: Artificial
<220> FEATURE:
<223> OTHER INFORMATION: Description of Artificial Sequence:  Fibrin-
      binding peptide
<220> FEATURE:
<221> NAME/KEY: misc_feature
<223> OTHER INFORMATION: Xaa=2-Cyclohexyl-L-alanine
<220> FEATURE:
<221> NAME/KEY: MOD_RES
<222> LOCATION: (1)..(1)
<223> OTHER INFORMATION: Allyloxycarbonyl
<220> FEATURE:
<221> NAME/KEY: misc_feature
<222> LOCATION: (12)..(12)
<223> OTHER INFORMATION: Xaa can be any naturally occurring amino acid

<400> SEQUENCE: 143

Arg Trp Gln Pro Cys Pro Ala Glu Ser Trp Thr Xaa Cys Trp Asp Pro
1               5                   10                  15

```
Gly Gly Gly Lys
            20

<210> SEQ ID NO 144
<211> LENGTH: 19
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: MOD_RES
<222> LOCATION: (19)..(19)
<223> OTHER INFORMATION: (NH2-PG2-JJ)

<400> SEQUENCE: 144

Trp Gln Pro Cys Pro Ala Glu Ser Trp Thr Phe Cys Trp Asp Pro Gly
1               5                   10                  15

Gly Gly Lys

<210> SEQ ID NO 145
<211> LENGTH: 21
<212> TYPE: PRT
<213> ORGANISM: Artificial
<220> FEATURE:
<223> OTHER INFORMATION: Description of Artificial Sequence: Fibrin-
      binding peptide
<220> FEATURE:
<221> NAME/KEY: MOD_RES
<222> LOCATION: (21)..(21)
<223> OTHER INFORMATION: (Dga-Ttda)-NH2

<400> SEQUENCE: 145

Trp Gln Pro Cys Pro Ala Glu Ser Trp Thr Phe Cys Trp Asp Pro Gly
1               5                   10                  15

Ser Ala Gly Ser Lys
            20
```

FIBRIN-BINDING PEPTIDES AND CONJUGATES THEREOF

RELATED APPLICATIONS

This application is a continuation of U.S. application Ser. No. 12/517,239, filed Jun. 2, 2009, now published, which is the United States national stage filing of corresponding international application number PCT/US2007/025403 filed on Dec. 11, 2007, now expired, which claims priority to and benefit of U.S. Provisional Application No. 60/869,472, filed Dec. 11, 2006, now expired, the contents of which are hereby incorporated by reference in its entirety.

The instant application contains a Sequence Listing which is being submitted in compliance with the code set forth in the tables in WIPO Standard ST.25 (1998), Appendix 2 via EFS-WEB and is hereby incorporated by reference in its entirety.

FIELD OF THE INVENTION

The present invention relates to fibrin-binding peptides, polypeptides and compositions for the detection and treatment of pathological conditions associated with fibrin deposition or accumulation, such as intravascular thrombosis and conditions associated with angiogenic processes. The invention includes compounds for diagnostic and/or therapeutic applications comprising fibrin-binding peptides. It also includes methods of making and using such peptides, compounds and compositions.

BACKGROUND OF THE INVENTION

Thrombus associated diseases are vascular conditions that develop due to the presence of a clot. Such diseases are a major cause of mortality, and therefore developing thrombus-specific diagnosis, treatment, and detection methodologies and reagents is of great clinical importance. Pulmonary embolism (PE), deep-vein thrombosis (DVT), stroke, and atherosclerosis are examples of thrombus-associated diseases.

DVT is a condition in which blood clots form in the deep blood vessels of the legs and groin. These clots can block the flow of blood from the legs back to the heart. Sometimes, a piece of a clot is detached and carried by the bloodstream through the heart to a blood vessel, where it lodges and reduces, or blocks, the flow of blood to a vascular tissue. This is called an embolism. If such a clot lodges in pulmonary blood vessel it can be fatal.

In the United States alone an estimated 600,000 patients suffer from PE's each year. In approximately 378,000 of these patients, PE goes undetected, and approximately 114,000 of these patients later die due to complications associated with the disease. This high mortality is partly due to the absence of clinical symptoms in many cases and to the significant limitations associated with currently available methods of investigation and detection.

Fibrin is also associated with various cancers. The existence of heterogeneous pattern of fibrin/fibrinogen deposition in various tumor types is a concept supported by a substantial body of correlative and indirect evidence suggesting that fibrin/fibrinogen is important in tumor stoma formation (see, for instance: Costantini V, Zacharski L R. Fibrin and cancer. *Thromb Haemost.* 1993; 69:406; Dvorak H F. Thrombosis and cancer. *Hum Pathol.* 1987; 18:275; Dvorak H F, Nagy J A, Berse B, et al. Vascular permeability factor, fibrin, and the pathogenesis of tumor stroma formation, *Ann N Y Acad. Sci.* 1992; 667:101; Cavanagh P G, Sloane B F, Honn K V. Role of the coagulation system in tumor-cell-induced platelet aggregation and metastasis. *Hemostasis.* 1988; 18:37 and Bardos H, Molnar P, Csecsei G, Adany R. Fibrin deposition in primary and metastatic human brain tumours. *Blood Coagul Fibrinolysis.* 1996; 7:536). Indeed, many significant hemostatic abnormalities have been described in patients with cancer, including disseminated intravascular coagulation, hemorrhagic events, and migratory thrombophlebitis. Hemostatic complications are a common cause of death in patients with cancer. Many tumor cells possess strong procoagulant activities that promote the local activation of the coagulation system. Tumor-mediated activation of the coagulation cascade has been implicated in both the formation of tumor stroma and the promotion of hematogenous metastasis. Fibrin matrix, moreover, is known to promote the migration of a substantial number of distinct cell types, including both transformed cells, macrophages, and fibroblasts. In particular, much like in a healing wound, the deposition of fibrin/fibrinogen, along with other adhesive glycoproteins, into the extracellular matrix (ECM) have been shown to serve as a scaffold to support binding of growth factors and to promote the cellular responses of adhesion, proliferation, and migration during angiogenesis and tumor cell growth (see, for instance: Dvorak H F, Nagy J A, Berse B, et al. Vascular permeability factor, fibrin, and the pathogenesis of tumor stroma formation, *Ann N Y Acad. Sci.* 1992; 667:101; Rickles F R, Patierno S, Fernandez P M. Tissue Factor, Thrombin, and Cancer. *Chest.* 2003; 124:58 S-68S; Brown H F, Van der Water L, Hervey V S, Dvorak H F. Fibrinogen influx and accumulation of cross-linked fibrin in healing wounds and in tumor stroma. *Am J Pathol.* 1988; 130:4559; Dvorak H F, Hervey V S, Estrella P, Brown L F, Mc-Donagh J, Dvorak A M. Fibrin containing gels induce angiogenesis: implication for tumor stroma generation and wound healing. *Lab Invest.* 1987; 57:673 and Rickles F R, Patierno S, Fernandez P M. Tissue Factor, Thrombin and Cancer. *Cest.* 2003; 124:58 S-68S). Most solid tumors in humans contain considerable amounts of cross-linked fibrin, suggesting that it is important in tumor stroma formation. Studies indicate that both fibrinogen and fibrin localize at the tumor-host cell interface (see, for instance: Rickles F R, Patierno S, Fernandez P M. Tissue Factor, Thrombin and Cancer. *Cest.* 2003; 124:58 S-68S; Costantini V, Zacharski L R, Memoli V A et al. Fibrinogen deposition without thrombin generation in primary human breast cancer. *Cancer Res.* 1991; 51: 349-353 and Simpson-Haidaris P J and Rybarczyky B. Tumors and Fibrinogen: The Role of Fibrinogen as an Extracellular Matrix Protein. *Ann. N.Y. Acad. Sci.,* 2001 936(1): 406-425). Fibrin matrices promote neovascularization, supporting the notion that fibrin may facilitate tumor stroma formation by mechanisms that are analogous to wound repair.

Moreover, a correlation seems to exist between plasma fibrinogen levels and tumor size, depth of tumor invasion and metastasis (See, for instance, Lee J H, Ryu K W, Kim S, Bae J M. Preoperative plasma fibrinogen levels in gastric cancer patients correlate with extent of tumor. *Hepatogastroenterology* 2004; 51:1860-3). In addition, it is known that fibrin/platelets are involved in protecting tumor cells from the action of the circulating natural killers units provided by human immune system thus improving the survival of circulating tumor (See, for instance, Palumbo J S, et al. platelets and fibrin(ogen) increase metastatic potential by impeding natural killer cell-mediated elimination of tumor cells. *Blood,* 2005; 105:178). This implies, for example, that a conventional tumor therapy using antibodies that target tumors may not effectively treat tumors containing fibrin because these tumor are protected by fibrin.

Thus, visualization of fibrin deposition and targeted inhibition/destruction of established vasculature and clotted fibrin is considered an important tool against malignant disease progression. Consequently, there remains a need for improved fibrin-binding compounds for use in sensitive diagnosis and specific therapy of pathological conditions associated with fibrin deposition, and, particularly, of solid tumors.

Fibrin also has been implicated in angiogenic processes. In a developing embryo, the primary vascular network is established by in situ differentiation of meso-dermal cells in a process called vasculogenesis. After embryonic vasculogenesis it is believed that all subsequent generation of new blood vessels, in the embryo or in adults, is governed by the sprouting or splitting of new capillaries from the pre-existing vasculature in a process called angiogenesis (Pepper, M. et al., 1996. Enzyme Protein, 49:138-162; Risau, W., 1997. Nature, 386:671-674). Angiogenesis is not only involved in embryonic development and normal tissue growth and repair, it is also involved in the female reproductive cycle, establishment and maintenance of pregnancy, and in repair of wounds and fractures.

In addition to normal angiogenic processes, angiogenic events also are involved in a number of important pathological processes, notably tumor growth and metastasis, and other conditions in which blood vessel proliferation is increased, such as diabetic retinopathy, psoriasis, arthropathies and rheumatoid arthritis. Indeed, angiogenesis is so important in the transition of a tumor from hyperplastic to neoplastic growth, that inhibition of angiogenesis has shown promise as a cancer therapy (Kim, K. et al., 1993. Nature, 362:841-844). In these pathological processes, fibrin provides the structural mesh required for the generation of new blood vessels.

There is a need, therefore, for sensitive and effective assays to detect the presence of fibrin and fibrin-associated diseases. More specifically there is a need for non-invasive reagents that can specifically bind fibrin and can be used to detect pathological thrombic conditions as well as conditions associated with pathological angiogenic processes.

SUMMARY OF THE INVENTION

In answer to the need for improved materials and methods for detecting, localizing, measuring and treating fibrin clots, and pathological processes associated with fibrin, we have now surprisingly discovered several non-naturally occurring polypeptides that exhibit an unexpectedly high degree of fibrin-specific binding. These polypeptides are capable of superior fibrin specific binding compared to previously known peptides and have improved physical properties such as solubility.

Another aspect of the present invention relates to modifications of the foregoing peptides to provide fibrin specific imaging agents by conjugation to a detectable label. For example, compounds in which a fibrin-binding peptide is conjugated to a radiolabel, an enzymatic label, a label detectable by magnetic resonance imaging (MRI) such as MR paramagnetic chelates or microparticles, conjugation to or incorporation into an ultrasound contrast agent such as gas-filled microvesicles (e.g. microbubbles, microparticles, microspheres, emulsions, or liposomes), or conjugation to an optical imaging agent, including optical dyes. Binding moieties according to the present invention are useful in any application where binding, detecting or isolating fibrin or its fragments is advantageous.

The present invention also relates to modifications of the foregoing peptides to provide fibrin specific therapeutics by conjugation to a therapeutic agent. Such agents may include, for example, a chemotherapeutic, a cytotoxic agent, a radiotherapeutic agent, a tumoricidal agent, or a thrombolytic agent. In a preferred embodiment, a peptide is modified by conjugation to a radiotherapeutic agent comprising a therapeutic radionuclide.

A particularly advantageous use of the binding moieties disclosed herein is in a method of imaging thrombi, and pathological processes associated with fibrin in vivo. Such processes include, for example, pulmonary embolism (PE), deep-vein thrombosis (DVT), stroke, atherosclerosis, and cancer, particularly solid tumors. The method entails the use of fibrin specific binding moieties according to the invention for detecting thrombi or fibrin-associated pathological processes, where the binding moieties have been detectably labeled for use as imaging agents, including magnetic resonance imaging (MRI) contrast agents, x-ray imaging agents, radiopharmaceutical imaging agents, ultrasound imaging agents, and optical imaging agents.

In addition, the newly discovered fibrin binders can also be used advantageously to detect numerous other pathophysiologies in which fibrin plays a role. In these cases, fibrin imaging can be a useful direct or surrogate marker for diagnosis or therapeutic monitoring. For example, peritoneal adhesions often occur after surgery or inflammatory processes, and are comprised of a fibrin network, fibroblasts, macrophages, and new blood vessels. Patients suffering from rheumatoid arthritis, lupus, or septic arthritis often have bits of fibrin-containing tissues called rice bodies in the synovial fluid of their joints. In thrombotic thrombocytopenic purpura, a type of anemia, fibrin deposits in arterioles cause turbulent blood flow, resulting in stress and destruction of the red blood cells. The fibrin binding moieties of the instant invention can be used in the detection and diagnosis of such fibrin-related disorders.

The fibrin specific agents can also be used to detect other conditions including but not limited to hypoxia or ischemia of the heart, kidney, liver, lung, brain, or other organs, as well as the detection of tumors, diabetic retinopathy, early or high-risk atherosclerosis, and other autoimmune and inflammatory disorders. Fibrin specific agents also can provide both direct or surrogate markers of disease models in which hypoxia and angiogenesis are expected to play a role. In hypoxic conditions, for example, fibrin(ogen) is expressed under the control of hypoxia-inducible factor 1 (HIF-1).

The fibrin-binding peptides of the invention may also be used therapeutically to treat pathophysiologies in which fibrin plays a role, including, but not limited to, fibrin clots, tumors, hypoxia or ischemia of various organs, pathological processes associated with angiogenesis, peritoneal adhesions, rheumatoid arthritis, lupus, septic arthritis, and thrombotic thrombocytopenic purpura. For example, the fibrin-binding peptides may be conjugated to an appropriate therapeutic radionuclide and used for radiotherapy, particularly to treat tumors. Additionally, the fibrin-binding peptides may be conjugated to an appropriate therapeutic agent.

These and other aspects of the present invention will become apparent with reference to the following detailed description.

DEFINITIONS

Figure 1:
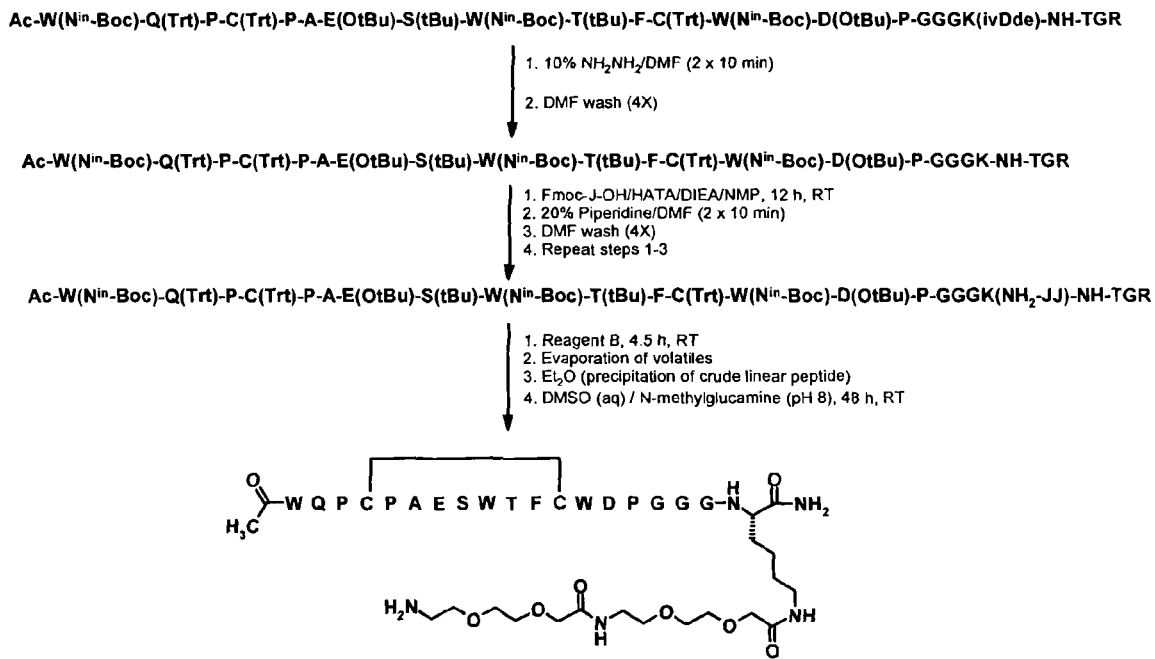
FIG. 1 illustrates a method for the preparation of a representative linker-functionalized peptide according to the present invention.

As used herein, unless otherwise specified, the term "polypeptide" is used to refer to a compound of two or more amino acids joined through the main chain (as opposed to side chain) by a peptide amide bond (—C(O)NH—). The term "peptide" is used interchangeably herein with "polypeptide" but is generally used to refer to polypeptides having fewer than 25 amino acids.

The term "fibrin-derived polypeptide" refers to any subcomponent of fibrin or fragment of fibrin that is immunologically cross-reactive with fibrin, including immunologically reactive fragments of the protein.

The term "binding" refers to the determination by standard assays, including those described herein, that a binding polypeptide recognizes and binds reversibly to a given target. Such standard assays include, but are not limited to equilibrium dialysis, gel filtration, and the monitoring of spectroscopic changes that result from binding.

The term "specificity" refers to a binding polypeptide having a higher binding affinity for one target over another. The term "fibrin specificity" refers to a fibrin binding moiety having a higher affinity for fibrin than for an irrelevant target. Binding specificity can be characterized by a dissociation equilibrium constant ($K_D$) or an association equilibrium constant ($K_a$) for the two tested target materials, or can be any measure of relative binding strength.

The term "binding moiety" as used herein refers to any molecule capable of forming a binding complex with another molecule. "Fibrin binding moiety" is a binding moiety that forms a complex with a clot, soluble or insoluble fibrin, or a soluble or insoluble fragment of fibrin having a structure or characteristic exhibited by fibrin but not fibrinogen. Included among such soluble or insoluble fragments of fibrin are fragments defined as "fibrin-derived" polypeptides. Fibrin-derived polypeptides, for the purposes of this invention will be used as a collective term for the DD, DD-dimer, and DD(E) polypeptides described herein. Such fibrin-derived polypeptides are typically generated by proteolytic treatment of crosslinked fibrin but retain structural features unique to fibrin.

Specific fibrin-binding peptides are described herein (including, for example, those included in Tables 1 and 2) and hybrid and chimeric peptides incorporating such peptides.

In addition to the detectable labels described further herein, the binding polypeptides may be linked or conjugated to a therapeutic agent including a radiotherapeutic agent, a cytotoxic agent, a tumoricidal agent or enzyme, a thrombolytic agent or enzyme (e.g., tPA, plasmin, streptokinase, urokinase, hirudin), a liposome (e.g., loaded with a therapeutic agent such as a thrombolytic, an ultrasound appropriate gas, or both). In addition, binding polypeptides of the invention may be bound or linked to a solid support, well, plate, bead, tube, slide, filter, or dish. All such modified fibrin-binding moieties are also considered fibrin-binding moieties so long as they retain the ability to bind fibrin or fibrin-derived polypeptides.

A "labelling group" or "detectable label," as used herein, is a group or moiety capable of generating a signal that is detectable. In particular a labeling group or diagnostic label may generate a signal for diagnostic imaging, such as magnetic resonance imaging, radioimaging, ultrasound imaging, x-ray imaging, light imaging, or carry a moiety such as a radioactive metal or other entity that may be used in radiotherapy or other forms of therapy.

The terms "therapeutic agent" or "therapeutic" refer to a compound or an agent having a beneficial, therapeutic or cytotoxic effect in vivo. Therapeutic agents include those compositions referred to as, for example, bioactive agents, cytotoxic agents, drugs, chemotherapy agents, radiotherapeutic agents, genetic material, etc.

The term "patient" as used herein refers to any mammal, especially humans.

The term "pharmaceutically acceptable" carrier or excipient refers to a non-toxic carrier or excipient that can be administered to a patient, together with a compound of this invention, such that it does not destroy the biological or pharmacological activity thereof.

The following common abbreviations are used throughout this specification: Ac₂O—acetic anhydride, CAN—acetonitrile, Ac—acetyl, API-ES—Atmospheric pressure ionization electrospray, BOP—benzotriazol-1-yloxy-tris(dimethylamino)-phosphonium hexafluorophosphate, Bn—benzyl, Cbz—benzyloxycarboxyl, CF5-NHS—5 carboxyfluorescein, succinimidyl ester (single isomer), Cha—2-Cyclohexyl-L-alanine, DCC—dicyclohexylcarbodiimide, DCM—Dichloromethane, Ddhh—12,26-diamino-1,1'-dioxo-3,6,9,16,19,22-hexaoxahexacosanoyl, Dga—diglycolyl, 3-oxapentan-1,5-di-oyl, DIC—N,N'-diisopropylcarbodiimide, DIEA—N,N-Diisopropylethylamine, DMA—dimethylacetamide, DMF—Dimethylformamide, DMSO—Dimethyl sulfoxide, DPPE—1,2-Dipalmitoyl-sn-glycero-3-phosphoethanolamine, commonly also identified as dipalmitoylphosphatidylethanolamine, DPPG—1,2-Dipalmitoyl-sn-glycero-3-[phosphor-rac-(1-glycerol)]sodium salt, commonly also identified as dipalmitoylphosphatidylglycerol, DPPS—1,2-Dipalmitoyl-sn-glycero-phospho-L-serine, commonly also identified as dipalmitoylphosphatidylserine, DSPA—1,2-Distearoyl-sn-glycero-phosphate sodium salt, commonly also identified as distearoylphosphatdic acid, DSPE—1,2-Distearoyl-sn-glycerol-3-phosphoethanolamine, commonly also identified as distearoylphosphatidylethanolamine, DSPE-PG4-NH₂—{1,2-Distearoyl-sn-glycero-3-phosphoethanolamine-N-[amino(polyethylene glycol)2000]}, DPPE-PG4-NH₂—{1,2-Dipalmitoyl-sn-glycero-3-phosphoethanolamine-N-[amino(polyethylene glycol)2000]}, DSPE-PEG1000—distearoyl-glycero-phosphoethanolamine-N-methoxy(polyethylene glycol)1000, DSPS—1,2-Distearoyl-sn-glycero-3-(phosphor-L-serine), commonly also identified as distearoylphosphatidylserine, DSG—disuccinimidylglutarate, EDAC, 1-ethyl 3-(3-dimethylaminopropyl)carbodiimide HCl, EtOH—ethanol, Et₂O—diethyl ether, EtOAc—Ethyl acetate, Fmoc—9-Fluoroenylmethoxyloxycarbonyl, Ffe4—L-4-Fluorophenylalanine, F34fe—L-3,4-difluorophenylalanine, Glut—Glutaryl, pentan-1,5-di-oyl, HOAc—acetic acid, HOAt—1-hydroxy-7-azabenzotriazole, HPLC—High performance liquid chromatography, Hypt4—trans-4-hydroxy-L-proline, Fmoc-J or Fmoc-Adoa—Fmoc-8-amino-3,6-dioxaoctanoic acid, HATU—N-{(Dimethylamino)-1H-1,2,3-triazolo(4,5-b)pyridine-1-ylmethylene]-N-methylenemethanaminium hexafluorophosphate-N-oxide, HBTU—2-(1H-Benzotriazole-1-yl)-1,1,3,3-tetramethyluronium hexafluorophosphate, HOBt—N-Hydroxybenzotriazole, ivDde—(4,4-dimethyl-2,6-dioxocyclohex-1-ylidene)-3-methylbutyl, MALDI—Matrix Assisted Laser Desorption Ionization, Neg. ion—Negative ion, MeOH—methanol, MS—mass spectrum, NHS—N-hydroxysuccinimide, NMM—N-Methylmorpholine, NMP—N-Methylpyrrolidone, PEG—polyethylene glycol (if followed by a number, e.g. PEG4000, this identifies the approximate mean molecular weight of the polydispersed PEG polymer, i.e. about 4000 daltons in the example), PFE—perfluoroethanol, Pip—Piperidine, Pd/C—palladium on carbon catalyst, Pd(PPh$_3$)$_4$—Tetrakis(triphenyl-phosphine)palladium(0), Pos. Ion—Positive ion, PyBOP—benzotriazol-1-yl-oxytripyrrolidinophosphonium hexafluorophosphate, Pyr—pyridine, $t_R$—Retention time (minutes), Reagent B (TFA:H$_2$O:phenol:triisopropylsilane, 88:5:5:2), SATA—S-Acetylthiolacetyl, S(Galnac)-O-(2-Acetamido-2-deoxy-α-D-galactopyranosyl)-L-serine, SPPS—solid phase peptide synthesis, stearate—sodium stearate, Su—Succinimidyl, SuO—Succinimidyloxy, t-Bu—tert-Butyl, TEA—Triethylamine, Thf2ca—Tetrahydrofuran-2-carboxylic acid, TFA—Trifluoroacetic Acid, TIPS—Triisopropylsilane, 9-fluorenylmethyloxycarbonyl (fmoc or Fmoc), Ttda—4,7,10-trioxamidecane-1,13-diamino, Tuda—3,6,9-Trioxaundecane-1,1'-di-oyl, Aloc—Allyloxycarbonyl, Boc—tert-Butoxycarbonyl, DSG—Di-N-hydroxysuccinimidyl-glutarate, PEG3400-NHS—Polyethyleneglycol 3400 N-hydroxysuccinimidyl ester, Pmc—2,2,5,7,8-pentamethylchroman—6—sulfonyl, Trt—Trityl, DMAC—dimethylacetamide.

ABBREVIATIONS FOR AMINO ACIDS

| Amino Acid | 3-letter | 1-letter |
| --- | --- | --- |
| alanine | ala | A |
| arginine | arg | R |
| asparagine | asn | N |
| aspartic acid | asp | D |
| cysteine | cys | C |
| glutamic acid | glu | E |
| glutamine | gln | Q |
| glycine | gly | G |
| histidine | his | H |
| isoleucine | ile | I |
| leucine | leu | L |
| lysine | lys | K |
| methionine | met | M |
| phenylalanine | phe | F |
| proline | pro | P |
| serine | ser | S |
| threonine | thr | T |
| tryptophan | trp | W |
| tyrosine | tyr | Y |
| valine | val | V |

DETAILED DESCRIPTION OF THE INVENTION

The present invention provides novel binding moieties for fibrin. Such binding moieties make possible the efficient detection, imaging and localization of fibrin or fibrin-derived peptides in a solution or system that contains fibrin or fibrin-derived polypeptides. In particular, the binding moieties of this invention, when appropriately labeled, are useful for detecting, imaging and localizing fibrin-containing thrombi or other fibrin specific pathophysiologies, and can thus be used to form a variety of diagnostic and therapeutic agents for diagnosing and treating pathological conditions associated with, for example, angiogenesis, thrombosis and cancer, particularly solid tumors. The preferred binding moieties of the present invention bind fibrin and/or fibrin-derived polypeptides with high affinity, i.e., acting at low, physiologically relevant concentrations, comparable to known anti-fibrin antibodies and other fibrin-binding proteins and represent an improvement over previously known fibrin binding moieties.

Utilizing the techniques described below (including techniques described in the Examples section), the polypeptides shown in Table 1 and in Table 2 were unexpectedly found to have superior fibrin-specific binding along with excellent physical properties as compared to previously known peptides. In particular, substitution of Ala for Trp at position 6 of a previously known peptide, Ac-WQPC*PWESWTFC*WDPGGGK-NH$_2$ (SEQ ID NO. 122), resulted in improved potency as well as a more hydrophilic peptide as demonstrated by HPLC. The improved properties of this substitution were unexpected as replacing either of the other Trp residues in the peptide lead to no or reduced fibrin binding.

Another method that was used to modify the peptide Ac-WQPC*PWESWTF*CWDPGGGK-NH$_2$ (SEQ ID NO. 122), was attaching amino acids at the N- or C-terminus. In general attachment of amino acids at the C-terminus did not dramatically change the potency of the peptides. However when polar amino acids (such as Arg) were added to the N-terminus, improvement in binding was observed. Considering the importance of the Trp at position 1, the introduction of polarity with beneficial effects was unexpected.

Another modification that led to improvements in potency was the introduction of the unusual amino acid cyclohexylalanine (Cha) for Phe at position 11. Considering that substituted phenyl alanine derivatives led to weaker binding, it was not anticipated that changing to the more bulky, less aromatic residue would improve potency. The combination of these three modifications led to further improved potency.

Table 1 below provides for each of the fibrin-binding peptides of the invention, its sequence, the sequence of the fibrin-binding moiety prepared and tested, analytical data for these peptides (including HPLC data and mass spectral data) and, for most of the peptides, binding affinity measurements compared to a previously known fibrin-binding peptide having the sequence Ac-WQPC*PWESWTFC*WDPGGGK-NH$_2$, (SEQ ID NO. 122) (relative IC$_{50}$=1). A relative IC$_{50}$ lower than 1 indicates better binding than the comparative peptide.

Note that the fibrin-binding moieties prepared and tested included the linker GGGK at the C terminus and in some cases an Ac-group at the N terminus. The invention encompasses fibrin-binding moieties with or without the GGGK linker and/or the Ac-group, as well as such moieties with a different or additional linker, such as those described herein. Note that for Seq005 peptides were prepared with additional linkers: Ac-WQPCPAESWTFCWDPGSAGSK-NH$_2$, (Seq005-P2) (SEQ ID NO. 134) [HPLC Data: System D, $t_R$ 3.53; Mass Spectral Data: Neg. ion:[M-H]:2377.8, [M-2H]/2:1188.4] including linker GSAGSK (SEQ ID NO. 137) and Ac-WQPC*PAESWTFC*WDPGAGSGK-NH$_2$, (Seq005-P3) (SEQ ID NO. 135) [HPLC Data: System D, $t_R$ 3.54; Mass Spectral Data: Neg. ion:[M-H]:2348.1, [M-2H]/2:1173.4], including linker GAGSGK (SEQ ID NO. 138). As shown in Example 21, the alternative linkers did not compromise the ability of targeted microvesicles with Seq005 to bind to fibrin.

TABLE 1

Fibrin-binding peptides

| Seq. ID | Sequence | Prepared Sequence | Prepared Sequence ID | HPLC Data (System, $t_R$) | Mass Spectral Data (Mode: Ions) | Rel IC$_{50}$(n = 2, Competition FP assay) |
|---|---|---|---|---|---|---|
| Seq005 | WQPC*PAESWTFC*WDP (SEQ ID NO. 1) | Ac-WQPC*PAESWTFC*WDPGGGK-NH$_2$ (SEQ ID NO. 2) | Seq005-P | B, 4.93 | Neg. ion: [M − H]: 2189.6; [M − 2H]/2: 1094.4 | 0.875 |
| Seq014 | GPPGWQPC*PWESWTFC*WDP (SEQ ID NO. 3) | Ac-GPPGWQPC*PWESWTFC*WDPGGGK-NH$_2$ (SEQ ID NO. 4) | Seq014-P | A, 4.70 | Neg. ion: [M + Na − 2H]: 2636.8; [M − 2H]/2: 1306.2 | 0.235 |
| Seq015 | GGRGWQPC*PWESWTFC*WDP (SEQ ID NO. 5) | Ac-GGRGWQPC*PWESWTFC*WDPGGGK-NH$_2$ (SEQ ID NO. 6) | Seq015-P | A, 4.44 | Pos. ion: [2M + 3H]/3: 1756.9; [M + 2H]/2: 1317.3; [M + 3H]/3: 876.1 | 0.370 |
| Seq016 | GWQPC*PWESWTFC*WDP (SEQ ID NO. 7) | Ac-GWQPC*PWESWTFC*WDPGGGK-NH$_2$ (SEQ ID NO. 8) | Seq016-P | B, 4.08 | Neg. ion: [M − H]: 2160.2; [M − 2H]/2: 1180.5; [M − 3H]/3: 786.8 | 1.04 |
| Seq017 | SGSGJWQPC*PWESWTFC*WDP (SEQ ID NO. 9) | Ac-SGSGJWQPC*PWESWTFC*WDPGGGK-NH$_2$ (SEQ ID NO. 10) | Seq017-P | B, 3.96 | Neg. ion: [M − H]: 2738.7; [M − 2H]/2: 1369.1 | 0.714 |
| Seq018 | WQPC*PWESWT-Cha-C*WDP (SEQ ID NO. 11) | Ac-WQPC*PWESWT-Cha-C*WDPGGGK-NH$_2$ (SEQ ID NO. 12) | Seq018-P | B, 4.27 | Neg. ion: [M − H]: 2311.8; [M − 2H]/2: 1154.8 | 0.494 |
| Seq019 | WQPC*PWESWT-Ffe4-C*WDP (SEQ ID NO. 13) | Ac-WQPC*PWESWT-Ffe4-C*WDPGGGK-NH$_2$ (SEQ ID NO. 14) | Seq019-P | B, 4.26 | Neg. ion: [M − H]: 2322.6; [M − 2H]/2: 1160.4 | 0.601 |
| Seq020 | WQPC*PWESWT-F34fe-C*WDP (SEQ ID NO. 15) | Ac-WQPC*PWESWT-F34fe-C*WDPGGGK-NH$_2$ (SEQ ID NO. 16) | Seq020-P | B, 4.33 | Neg. ion: [M − H]: 2341.2; [M − 2H]/2: 1169.8 | 0.428 |
| Seq021 | GWQPC*PWESWTFC*WDP (SEQ ID NO. 17) | GWQPC*PWESWTFC*WDPGGGK-NH$_2$ (SEQ ID NO. 18) | Seq021-P | B, 3.94 | Neg. ion: [M − H]: 2319.6; [M − 2H]/2 1159.3 | 0.622 |
| Seq022 | RGWQPC*PWESWTFC*WDP (SEQ ID NO. 19) | RGWQPC*PWESWTFC*WDPGGGK-NH$_2$ (SEQ ID NO. 20) | Seq022-P | B, 3.79 | Pos. ion [M + 2H]/2: 1239.3; [M + 3H]/3: 826.8 | 0.511 |
| Seq023 | RWQPC*PWESWTFC*WDP (SEQ ID NO. 21) | RWQPC*PWESWTFC*WDPGGGK-NH$_2$ (SEQ ID NO. 22) | Seq023-P | B, 3.77 | Pos. ion [M + 2H]/2: 1211.6; [M + 3H]/3: 807.6 | 0.47 |
| Seq024 | SGSGSGSGWQPC*PWESWTFC*WDP (SEQ ID NO. 23) | Ac-SGSGSGSGWQPC*PWESWTFC*WDPGGGK-NH$_2$ (SEQ ID NO. 24) | Seq024-P | B, 3.89 | Neg. ion: [M − 2H]/2: 1439.8 | 0.527 |

TABLE 1-continued

Fibrin-binding peptides

| Seq. ID | Sequence | Prepared Sequence | Prepared Sequence ID | HPLC Data (System, $t_R$) | Mass Spectral Data (Mode: Ions) | Rel IC$_{50}$(n = 2, Competition FP assay) |
| --- | --- | --- | --- | --- | --- | --- |
| Seq025 | KKGWQPC*PWESWTFC*WDP (SEQ ID NO. 25) | Ac-KKGWQPC*PWESWTFC*WDPGGGK-NH$_2$ (SEQ ID NO. 26) | Seq025-P | A, 4.26 | Neg. ion: [M − H]: 2618.8; [M − 2H]/2: 1308.1 | 0.357 |
| Seq026 | KGKGKGWQPC*PWESWTFC*WDP (SEQ ID NO. 27) | Ac-KGKGKGWQPC*PWESWTFC*WDPGGGK-NH$_2$ (SEQ ID NO. 28) | Seq026-P | A, 4.11 | Neg. ion: [M − H]: 2860.5; [M − 2H]/2: 1429.6 | 0.595 |
| Seq027 | S(Galnac)-WQPC*PWESWTFC*WDP (SEQ ID NO. 29) | Ac-S(Galnac)-WQPC*PWESWTFC*WDPGGGK-NH$_2$ (SEQ ID NO. 30) | Seq027-P | B, 3.95 | Neg. ion: [M − H]: 2595.5; [M − 2H]/2: 1297.0 | 0.5595 |
| Seq028 | Thf2ca-WQPC*PWESWTFC*WDP (SEQ ID NO. 31) | Thf2ca-WQPC*PWESWTFC*WDPGGGK-NH$_2$ (SEQ ID NO. 32) | Seq028-P | B, 4.23 | Neg. ion: [M − H]: 2416.8; [M − 2H]/2: 1208.6 | 0.616 |
| Seq029 | RRGGWQPC*PWESWTFC*WDP (SEQ ID NO. 33) | Ac-RRGGWQPC*PWESWTFC*WDPGGGK-NH$_2$ (SEQ ID NO. 34) | Seq029-P | A, 4.32 | Pos. ion: [M + 2H]/2: 1366.4; [M + 3H]/3: 911.8; [M + 3H + Na]/4: 689.8 | 0.125 |
| Seq031 | S(Galnac)-JWQPC*PWESWTFC*WDP (SEQ ID NO. 35) | Ac-S(Galnac)-JWQPC*PWESWTFC*WDPGGGK-NH$_2$ (SEQ ID NO. 36) | Seq031-P | B, 3.95 | Neg. ion: [M − H]: 2740.4; [M − 2H]/2: 1369.3 | 1.15 |
| Seq032 | WQPC*-Hypt4-WESWTFC*WDP (SEQ ID NO. 37) | Ac-WQPC*-Hypt4-WESWTFC*WDPGGGK-NH$_2$ (SEQ ID NO. 38) | Seq032-P | B, 4.12 | Mode: Neg. -ion: [M − H]: 2320.7; [M − 2H]/2: 1159.4 | 0.55 |
| Seq034 | GPPGWQPC*PAESWTFC*WDP (SEQ ID NO. 39) | Ac-GPPGWQPC*PAESWTFC*WDPGGGK-NH$_2$ (SEQ ID NO. 40) | Seq034-P | D, 3.49 | Neg. Ion-[M − H]: 2498.9, [M − 2H]/2: 1248.4 | § |
| Seq035 | GGRGWQPC*PAESWTFC*WDP (SEQ ID NO. 41) | Ac-GGRGWQPC*PAESWTFC*WDPGGGK-NH$_2$ (SEQ ID NO. 42) | Seq035-P | D, 3.29 | Neg. Ion-[M − H]: 2516.7, [M + TFA-2H]/2: 1314.7, [M − 2H]/2: 1257.9 | § |
| Seq036 | KKGWQPC*PAESWTFC*WDP (SEQ ID NO. 43) | Ac-KKGWQPC*PAESWTFC*WDPGGGK-NH$_2$† (SEQ ID NO. 44) | Seq036-P | D, 4.91 | Neg. Ion-[M − H]: 2916.6, [2M − 3H]/3: 1943.6, [M − 2H]/2: 1457.6 | § |
| Seq037 | KGKGKGWQPC*PAESWTFC*WDP (SEQ ID NO. 45) | Ac-KGKGKGWQPC*PAESWTFC*WDPGGGK-NH$_2$ † (SEQ ID NO. 46) | Seq037-P | D, 5.26 | Neg. Ion-[2M − 3H]/3: 2242.8, 2225.4, [M − 2H]/2: 1681.2 | § |
| Seq038 | GWQPC*PAESWTFC*WDP (SEQ ID NO. 47) | GWQPC*PAESWTFC*WDPGGGK-NH$_2$ ‡ (SEQ ID NO. 48) | Seq038-P | D, 3.76 | Neg. Ion-[M − H]: 2288.6, [M − 2H]/2: 1143.9 | § |

TABLE 1-continued

Fibrin-binding peptides

| Seq. ID | Sequence | Prepared Sequence | Prepared Sequence ID | HPLC Data (System, $t_R$) | Mass Spectral Data (Mode: Ions) | Rel IC$_{50}$(n = 2, Competition FP assay) |
|---|---|---|---|---|---|---|
| Seq039 | GWQPC*PAE SWTFC*WDP (SEQ ID NO. 49) | Ac-GWQPC*PAES WTFC*WDPGG GK-NH$_2$ (SEQ ID NO. 50) | Seq039-P | D, 3.44 | Neg. Ion-[M − H]: 2247.9, [M − 2H]/2: 1122.9 | § |
| Seq040 | SGSGSGSGW QPC*PAESWT FC*WDP (SEQ ID NO. 51) | Ac-SGSGSGSGWQ PC*PAESWTFC *WDPGGGK-NH$_2$ (SEQ ID NO. 52) | Seq040-P | D, 3.25 | Neg. Ion-[2M − 3H]/3: 1844.3, [M − 2H]/2: 1382.8 | § |
| Seq041 | WQPC*PAES WT-Ffe4-C*WDP (SEQ ID NO. 53) | Ac-WQPC*PAESW T-Ffe4-C*WDPGGGK-NH$_2$ (SEQ ID NO. 54) | Seq041-P | D, 3.65 | Neg. Ion-[M − H]: 2207.7, [M − 2H]/2: 1103.4 | § |
| Seq042 | WQPC*PAES WT-Cha-C*WDP (SEQ ID NO. 55) | Ac-WQPC*PAESW T-Cha-C*WDPGGGK-NH$_2$ (SEQ ID NO. 56) | Seq042-P | D, 3.69 | Neg. Ion-[M − H]: 2195.7, [M − 2H]/2: 1097.4 | § |
| Seq043 | WQPC*PAES WT-F34fe-C*WDP (SEQ ID NO. 57) | Ac-WQPC*PAESW T-F34fe-C*WDPGGGK-NH$_2$ (SEQ ID NO. 58) | Seq043-P | D, 3.73 | Neg. Ion-[M − H]: 2225.4, [M − 2H]/2: 1111.9 | § |
| Seq044 | Thf2ca-WQPC*PAES WTFC*WDP (SEQ ID NO. 59) | Thf2ca-WQPC*PAESW TFC*WDPGGG K-NH$_2$ (SEQ ID NO. 60) | Seq044-P | D, 3.71 | Neg. Ion-[M − H]: 2245.6, [M − 2H]/2: 1122.3. | § |
| Seq045 | SGSGJWQPC* PAESWTFC* WDP (SEQ ID NO. 61) | Ac-SGSGJWQPC*P AESWTFC*WD PGGGK-NH$_2$ (SEQ ID NO. 62) | Seq045-P | D, 3.34 | Neg. ion-[M − 2H]/2: 1311.3 | § |
| Seq046 | RRGGWQPC* PAESWTFC* WDP (SEQ ID NO. 63) | Ac-RRGGWQPC*P AESWTFC*WD PGGGK-NH$_2$ (SEQ ID NO. 64) | Seq046-P | D, 3.12 | Pos. ion-[2M + 3H]/3: 1745.4, [M + 2H]/2: 1309.5, [M + 3H]/3: 873.3 | § |
| Seq047 | RRGGWQPC*-Hypt4-WESWTFC*W DP (SEQ ID NO. 65) | Ac-RRGGWQPC*-Hypt4-WESWTFC*WD PGGGK-NH$_2$ (SEQ ID NO. 66) | Seq047-P | G, 4.5 | Mode: Pos. ion; [M + 2H]/2: 1375.0, [M + 3H]/3: 917.3. [M + Na + 3H]/4: 693.8, [M + 2Na + 3H]/5: 558.9 | 0.75 |
| Seq048 | RWQPC*PWE SWTFC*WDP (SEQ ID NO. 67) | Ac-RWQPC*PWES WTFC*WDPGG GK-NH$_2$ (SEQ ID NO. 68) | Seq048-P | B, 3.72 | Neg. Ion: [M − H]: 2461.8, [M − 2H]/2: 1230.0, [M + TFA-2H]/2: 1286.8 | § |

TABLE 1-continued

Fibrin-binding peptides

| Seq. ID | Sequence | Prepared Sequence | Prepared Sequence ID | HPLC Data (System, $t_R$) | Mass Spectral Data (Mode: Ions) | Rel IC$_{50}$(n = 2, Competition FP assay) |
|---|---|---|---|---|---|---|
| Seq049 | RWQPC*PAESWT-Cha-C*WDP (SEQ ID NO. 69) | Ac-RWQPC*PAESWT-Cha-C*WDPGGGK-NH$_2$ (SEQ ID NO. 70) | Seq049-P | D, 3.43 | Neg. ion: [M − H]: 2352.9, [M − 2H]/2: 1175.4, [M + TFA-2H]/2: 1232.2 | § |
| Seq050 | GWQPC*PAESWT-Cha-C*WDP (SEQ ID NO. 71) | GWQPC*PAESWT-Cha-C*WDPGGGK-NH$_2$† (SEQ ID NO. 72) | Seq050-P | D, 3.92 | Neg. ion: [M − H]: 2294.7, [M − 2H]/2: 1146.9 (as Aloc peptide) | § |
| Seq051 | RGWQPC*PWESWTFC*WDP (SEQ ID NO. 73) | Ac-RGWQPC*PWESWTFC*WDPGGK-NH$_2$ (SEQ ID NO. 74) | Seq051-P | D, 3.64 | Neg. ion: [M − H]: 2517.9, [M − 2H]/2: 1258.8, [M + TFA-2H]/2: 1315.5 | § |
| Seq052 | RGWQPC*PAESWTFC*WDP (SEQ ID NO. 75) | Ac-RGWQPC*PAESWTFC*WDPGGK-NH$_2$ (SEQ ID NO. 76) | Seq052-P | D, 3.46 | Neg. Ion: [M − H]: 2403.3, [M − 2H]/2: 1200.9 | § |
| Seq053 | RGWQPC*PAESWT-Cha-C*WDP (SEQ ID NO. 77) | Ac-RGWQPC*PAESWT-Cha-C*WDPGGGK-NH$_2$ (SEQ ID NO. 78) | Seq053-P | D, 3.48 | Neg. ion: [M − H]: 2409.0, [M − 2H]/2: 1204.1, [M + TFA-2H]/2: 1261.1 | § |
| Seq054 | RGWQPC*PAESWT-Cha-C*WDP (SEQ ID NO. 79) | RGWQPC*PAESWT-Cha-C*WDPGGGK-NH$_2$‡ (SEQ ID NO. 80) | Seq054-P | D, 3.91 | Neg. ion: [M − H]: 2451.0, [M − 2H]/2: 1224.7, [M + TFA-2H]/2: 1282.2 (as Aloc peptide) | § |
| Seq055 | GWQPC*PAESWT-Cha-C*WDP (SEQ ID NO. 81) | Ac-GWQPC*PAESWT-Cha-C*WDPGGGK-NH$_2$ (SEQ ID NO. 82) | Seq055-P | D, 3.59 | Neg. ion: [[M − H]: 2253.1, [M − 2H]/2: 1125.9 | § |
| Seq056 | RWQPC*PAESWTFC*WDP (SEQ ID NO. 83) | RWQPC*PAESWTFC*WDPGGGK-NH$_2$‡ (SEQ ID NO. 84) | Seq056-P | D, 3.71 | Neg. ion: [M − H]: 2388.0, [M − 2H]/2: 1193.4, [M + TFA-2H]/2: 1250.8 (as Aloc peptide) | § |
| Seq057 | RWQPC*PAESWT-Cha-C*WDP (SEQ ID NO. 85) | RWQPC*PAESWT-Cha-C*WDPGGGK-NH$_2$‡ (SEQ ID NO. 86) | Seq057-P | D, 3.71 | Neg. ion: [M − H]: 2394.0, [M − 2H]/2: 1196.4, [M + TFA-2H]/2: 1252.9 (as Aloc peptide) | § |

† = Analytical data reported for peptide bearing the ivDde group on N$^\epsilon$ of all lysine groups of the peptide except for the C-terminal lysine.
‡ = Analytical data reported for N-terminal Aloc-protected peptide.
§ = Direct binding assay conducted using CF5 labeled peptide, see table 2.

The details of the HPLC systems used are set forth in the Examples section. Details of fibrin-binding assays are also set forth in the Examples section.

Changes from the known peptide, Ac-WQPC*PWESWTFC*WDPGGGK-NH$_2$ (SEQ ID NO. 122), also referred to herein as Seq000, are underlined, but omissions from this sequence (e.g. initial Ac, etc.) are not highlighted. Thus, for example, within the peptide of the invention coded as Seq005, the amino acid therein defined as "A" replaces, in that same position, the corresponding amino acid "W" in the prior art peptide, Seq000.

As used in Table 1 and elsewhere herein, the designation "C*" refers to a cysteine residue that contributes to a disulfide bond.

As shown in Table 1, all of the peptides described therein have equivalent or far superior binding than the comparative peptide.

Table 2 below provides for each of the 5-carboxyfluorescein labeled fibrin-binding peptides included therein, its sequence, HPLC data, mass spectral data and, for most of the peptides, binding affinity measurements compared to the previously known fibrin-binding peptide having the sequence Ac-WQPC*PWESWTFC*WDPGGGK-NH$_2$(Seq000) (SEQ ID NO. 122).

TABLE 2

Fibrin Binding Peptides-5-Carboxyfluorescein Labeled Peptides

| Seq. ID | Sequence | HPLC Data (System, $t_R$) | Mass Spectral Data (Mode; Ions) | KD (μM) Direct Binding (n = 2) |
|---|---|---|---|---|
| Seq000-CF5 | Ac-WQPC*PWESWTFC*WDPGGGK(CF5)-NH$_2$ (SEQ ID NO. 87) | F, 14.78 | Neg. ion; [M − 2H]/2: 1330.9; [M − 3H]/3: 886.9; [M − 4H]/4: 665.0 | 0.39 |
| Seq014-CF5 | Ac-GPPGWQPC*PWESWTFC*WDPGGK(CF5)-NH$_2$ (SEQ ID NO. 88) | D, 4.31 | Neg. ion; [M − 2H]/2: 1485.2, [2M − 3]/3: 1981.8 | 0.25 |
| Seq015-CF5 | Ac-GGRGWQPC*PWESWTFC*WDPGGGK(CF5)-NH$_2$ (SEQ ID NO. 89) | D, 4.10 | Neg. ion: [M − 2H]/2: 1494.9, [2M − 3H]/3: 1993.5, [3M + Na − 5H]/4: 2249.1 | 0.29 |
| Seq016-CF5 | Ac-GWQPC*PWESWTFC*WDPGGGK(CF5)-NH$_2$ (SEQ ID NO. 90) | D, 4.35 | Neg. ion; [M − 2H]/2: 1359.4, [2M − 3H]/3: 1812.9 | 0.23 |
| Seq017-CF5 | Ac-SGSGJWQPC*PWESWTFC*WDPGGGK(CF5)-NH$_2$ (SEQ ID NO. 91) | D, 4.15 | Neg. ion; [M − 2H]/2: 1547.8 | 0.45 |
| Seq018-CF5 | Ac-WQPC*PWESWT-Cha-C*WDPGGGK(CF5)-NH$_2$ (SEQ ID NO. 92) | D, 4.49 | Neg. ion; [M − H]: 2670.3, [M − 2H]/2: 1333.9, [M − 3H]/3: 888.7 | 0.20 |
| Seq019-CF5 | Ac-WQPC*PWESWT-Ffe4-C*WDPGGGK(CF5)-NH$_2$ (SEQ ID NO. 93) | D, 4.50 | Neg. ion; [M − 2H]/2: 1339.8 | 1.02 |
| Seq020-CF5 | Ac-WQPC*PWESWT-F34fe-C*WDPGGGK(CF5)-NH$_2$ (SEQ ID NO. 94) | D, 4.56 | Neg. ion; [2M − 3]/3: 1798.5; [M − 2H]/2: 1348.7 | 0.70 |
| Seq021-CF5 | GWQPC*PWESWTFC*WDPGGGK(CF5)-NH$_2$ (SEQ ID NO. 95) | D, 4.31 | Neg. ion; [M − 2H]/2: 1338.9, [M − 3H]/3: 892.0 | N/D |
| Seq022-CF5 | RGWQPC*PWESWTFC*WDPGGGK(CF5)-NH$_2$ (SEQ ID NO. 96) | D, 3.99 | Neg. ion; [2M − 3H]/3: 1889.3, [M − 2H]/2: 1416.4, [M − 3H]/3: 944.0 | 0.28 |
| Seq023-CF5 | RWQPC*PWESWTFC*WDPGGGK(CF5)-NH$_2$ (SEQ ID NO. 97) | D, 4.00 | Neg. ion; [M − 2H]/2: 1387.9, [M − 3H]/3: 925.0 | 0.11 |

TABLE 2-continued

Fibrin Binding Peptides-5-Carboxyfluorescein Labeled Peptides

| Seq. ID | Sequence | HPLC Data (System, $t_R$) | Mass Spectral Data (Mode; Ions) | KD (μM) Direct Binding (n = 2) |
|---|---|---|---|---|
| Seq024-CF5 | Ac-SGSGSGSGWQPC*PWESWTFC*WDPGGGK(CF5)-NH$_2$ (SEQ ID NO. 98) | D, 4.11 | Neg. ion; [M − 2H]/2: 1619.1, [2M − 3H]/3: 2158.5 | 0.47 |
| Seq025-CF5 | Ac-KKGWQPC*PWESWTFC*WDPGGK(CF5)-NH$_2$ (SEQ ID NO. 99) | D, 3.94 | Neg. ion; [M − 2H]/2: 1487.7, [2M − 3H]/3: 1984.5 | 0.71 |
| Seq026-CF5 | Ac-KGKGKGWQPC*PWESWTFC*WDPGGGK(CF5)-NH$_2$ (SEQ ID NO. 100) | D, 3.79 | Neg. ion; [M − 2H]/2: 1608.6, [2M − 3H]/3: 2145.1 | 0.76 |
| Seq027-CF5 | Ac-S(Galnac)-WQPC*PWESWTFC*WDPGGGK(CF5)-NH$_2$ (SEQ ID NO. 101) | D, 4.16 | Neg. ion; [M − 2H]/2: 1476.4, [2M − 3H]/3: 1968.6, [2M − 6H]/6: 984.5 | 0.50 |
| Seq028-CF5 | Thf2ca-WQPC*PWESWTFC*WDPGGGK(CF5)-NH$_2$ (SEQ ID NO. 102) | D, 4.13 | Neg. ion; [M + Na-2H]: 2740.2; [M + Na-3H]/2: 1370.1 [M − 2H]/2: 1359.0, [M − 3H]/3: 905.4 | 1.21 |
| Seq029-CF5 | Ac-RRGGWQPC*PWESWTFC*WDPGGGK(CF5)-NH$_2$ (SEQ ID NO. 103) | D, 4.15 | Neg. ion; [M − 2H]/2: 1543.7, [2M − 3H]/3: 2059.8, [M − 3H]/3: 1029.0 | N/D |
| Seq034-CF5 | Ac-GPPGWQPC*PAESWTFC*WDPGGK(CF5)-NH$_2$ (SEQ ID NO. 104) | D, 3.45 | Neg. ion; [M − H]: 2857.4; [M − 2H]/2: 1228.0 | 0.31 |
| Seq035-CF5 | Ac-GGRGWQPC*PAESWTFC*WDPGGK(CF5)-NH$_2$ (SEQ ID NO. 105) | D, 3.88 | Neg. Ion; [2M − 3H]/3: 1916.3, [M − 2H]/2: 1437.4 | 0.52 |
| Seq038-CF5 | GWQPC*PAESWTFC*WDPGGGK(CF5)-NH$_2$ (SEQ ID NO. 106) | D, 3.87 | Neg. ion; [M − 2H]/2: 1280.8 | 0.24 |
| Seq039-CF5 | Ac-GWQPC*PAESWTFC*WDPGGGK(CF5)-NH$_2$ (SEQ ID NO. 107) | D, 4.04 | Neg. ion; [M − 2H]/2: 1302.7 | 0.24 |
| Seq040-CF5 | Ac-SGSGSGSGWQPC*PAESWTFC*WDPGGGK(CF5)-NH$_2$ (SEQ ID NO. 108) | D, 3.82 | Neg. ion; [2M − 3H]/3: 2083.1, [M − 2H]/2: 1561.8, [M − 3H]/: 1040.7 | 0.53 |
| Seq042-CF5 | Ac-WQPC*PAESWT-Cha-C*WDPGGGK(C | D, 4.29 | Neg. ion; [M − H]: 2554.6, [M − 2H]/2: 1276.9 | 0.17 |

TABLE 2-continued

Fibrin Binding Peptides-5-Carboxyfluorescein Labeled Peptides

| Seq. ID | Sequence | HPLC Data (System, $t_R$) | Mass Spectral Data (Mode; Ions) | KD (µM) Direct Binding (n = 2) |
|---|---|---|---|---|
| | F5)-NH$_2$ (SEQ ID NO. 109) | | | |
| Seq045-CF5 | Ac-SGSGJWQPC*PAESWTFC*WDPGGGK(CF5)-NH$_2$ (SEQ ID NO. 110) | D, 3.90 | Neg. ion; [M – H]: 2982.0, [M – 2H]/2: 1489.9 | 0.57 |
| Seq046-CF5 | Ac-RRGGWQPC*PAESWTFC*WDPGGGK(CF5)-NH$_2$ (SEQ ID NO. 111) | D, 3.50 | Pos. ion; [M + 2H]/2: 1488.9, [M + 3H]/3: 992.7 | 0.22 |
| Seq048-CF5 | Ac-RWQPC*PWESWTFC*WDPGGGK(CF5)-NH$_2$ (SEQ ID NO. 112) | D, 4.26 | Neg. ion; [M – 2H]/2: 1409.1, [2M – 3H]/3: 1879.1 | 0.11 |
| Seq049-CF5 | Ac-RWQPC*PAESWTFC*WDPGGGK(CF5)-NH$_2$ (SEQ ID NO. 113) | D, 3.94 | Neg. ion; [M – H]: 2704.5, [2M – 3H]/3: 1802.6, [M – 2H]/2: 1351.3 | 0.21 |
| Seq050-CF5 | Ac-RWQPC*PAESWT-Cha-C*WDPGGGK(CF5)-NH$_2$ (SEQ ID NO. 114) | D, 4.04 | Neg. ion; [M – H]: 2710.9, [2M – 3H]/3: 1806.4, [M – 2H]/2: 1354.5 | 0.08 |
| Seq051-CF5 | GWQPC*PAESWT-Cha-C*WDPGGGK(CF5)-NH$_2$ (SEQ ID NO. 115) | D, 4.03 | Neg. ion; [M – H]: 2569.5, [M – 2H]/2: 1283.8, [2M – 3H]/3: 1712.1 | 0.06 |
| Seq052-CF5 | Ac-RGWQPC*PWESWTFC*WDPGGGK(CF5)-NH$_2$ (SEQ ID NO. 116) | D, 4.17 | Neg. ion; [3M – 4H]/4: 2157.7, [2M – 3H]/3: 1917.3, [M – 2H]/2: 1437.9 | 0.53 |
| Seq053-CF5 | Ac-RGWQPC*PAESWT-Cha-C*WDPGGGK(CF5)-NH$_2$ (SEQ ID NO. 117) | D, 4.04 | Neg. ion; [M – H]: 2767.5, [2M – 3H]/3: 1844.1, [M – 2H]/2: 1383.0 | 0.10 |
| Seq054-CF5 | RGWQPC*PAESWT-Cha-C*WDPGGGK(CF5)-NH$_2$ (SEQ ID NO. 118) | D, 3.91 | Neg. ion; [M – H]: 2726.1, [2M – 3H]/3: 1816.9, [M – 2H]/2: 1362.0 | 0.05 |
| Seq055-CF5 | Ac-GWQPC*PAESWT-Cha-C*WDPGGGK(CF5)-NH$_2$ (SEQ ID NO. 119) | D, 4.20 | Neg. ion; [M – H]: 2611.6, [M – 2H]/2: 1304.8, [2M – 3H]/3: 1740.2 | 0.08 |
| Seq056-CF5 | RWQPC*PAESWTFC*WDPGGGK(CF5)-NH$_2$ (SEQ ID NO. 120) | D, 3.81 | Neg. ion; [M – H]: 2663.1, [2M – 3H]/3: 1774.2, [M – 2H]/2: 1330.3 | 0.06 |

TABLE 2-continued

Fibrin Binding Peptides-5-Carboxyfluorescein Labeled Peptides

| Seq. ID | Sequence | HPLC Data (System, $t_R$) | Mass Spectral Data (Mode; Ions) | KD (µM) Direct Binding (n = 2) |
|---|---|---|---|---|
| Seq057-CF5 | RWQPC*PAESW T-Cha-C*WDPGGGK(CF5)-NH$_2$ (SEQ ID NO. 121) | D, 3.91 | Neg. ion; [M − H]: 2668.2, [M − 2H]/2: 1333.3 | 0.03 |

The details of the HPLC systems used are set forth in the Examples section. Details of fibrin-binding assays are also set forth in the Examples section.

As shown in Table 2, all of the 5-carboxyfluorescein labeled fibrin-binding peptides described therein have equivalent or far superior binding than the comparative fibrin-binding peptide.

Table 3 below, provides residue abbreviations and the corresponding structure of some of the commonly used residues referenced in Table 1 and Table 2 above.

thesis, etc. Solid-phase synthesis is preferred. See Stewart et al., Solid-Phase Peptide Synthesis (W.H. Freeman Co., San Francisco, 1989); Merrifield, J. Am. Chem. Soc., 85:2149-2154 (1963); Bodanszky and Bodanszky, The Practice of Peptide Synthesis (Springer-Verlag, New York, 1984), incorporated herein by reference.

A fibrin-binding peptide according to the present invention is preferably purified once it has been isolated or synthesized. For purification purposes, there are many standard methods that may be employed, including reversed-phase high-pres-

TABLE 3

Abbreviations for Residues

| Residue Abbreviation | Structure | Residue Abbreviation | Structure |
|---|---|---|---|
| Cha | 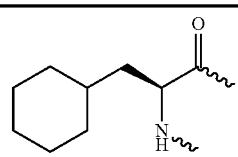 | S(Galnac) | 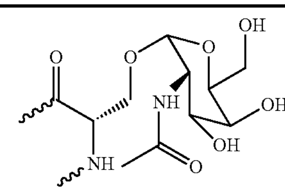 |
| Ffe4 | 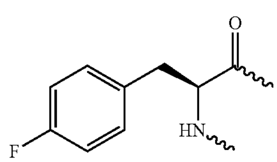 | Thf2ca | 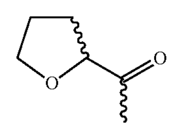 |
| F34fe | 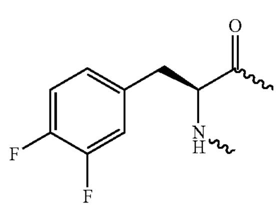 | Hypt4 | 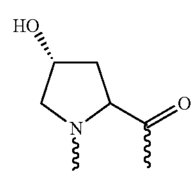 |
| Btn | 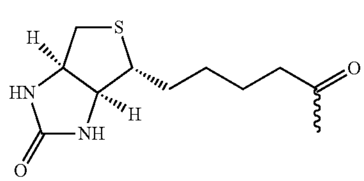 | CF5 | 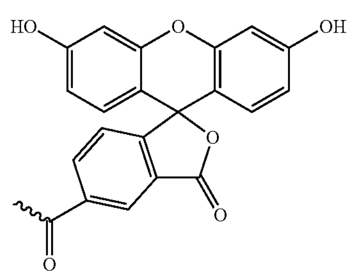 |

Direct synthesis of the fibrin-binding peptides of the invention may be accomplished using conventional techniques, including solid-phase peptide synthesis, solution-phase synthesis, etc.

sure liquid chromatography (RP-HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can also be used to separate peptides based on their charge. The degree of purity of the polypeptide may be determined by various methods, including identification of a major large peak on HPLC. A polypeptide that produces a single peak that is at least 95% of the input material on an HPLC column is preferred. Even more preferable is a polypeptide that produces a single peak that is at least 97%, at least 98%, at least 99% or even 99.5% or more of the input material on an HPLC column.

In order to ensure that the fibrin-binding peptide obtained is the desired peptide for use in compositions of the present invention, analysis of the peptide composition may be carried out. Such composition analysis may be conducted using high resolution mass spectrometry to determine the molecular weight of the peptide. Alternatively, the amino acid content of the peptide can be confirmed by hydrolyzing the peptide in aqueous acid, and separating, identifying and quantifying the components of the mixture using HPLC, or an amino acid analyzer. Protein sequencers, which sequentially degrade the peptide and identify the amino acids in order, may also be used to determine definitely the sequence of the peptide.

The fibrin binding polypeptides of the invention may be conformationally restrained by disulfide linkages between the two cysteine residues in their sequence. This conformational restraint ensures that the peptides have a binding structure that contributes to the peptides' affinity for fibrin and their specificity for fibrin over fibrinogen. Other methods for constraining peptides which would retain a similar conformation and fibrin specificity for the peptide have been described in the art and may be used herein.

Modification or Optimization of Binding Polypeptides

Modification or optimization of the fibrin-binding polypeptides is within the scope of the present invention. Specifically, a polypeptide sequence of the invention can be further modified to optimize its potency, pharmacokinetic behavior, stability and/or other biological, physical and chemical properties.

Substitution of Amino Acid Residues

Substitutions of amino acids within the same class (e.g., substituting one basic amino acid for another) are well known in the art. For example, one can make the following isosteric and/or conservative amino acid changes in the parent polypeptide sequence with the expectation that the resulting polypeptides would have a similar or improved profile of the properties described above:

Substitution of alkyl-substituted hydrophobic amino acids: Including alanine, leucine, isoleucine, valine, norleucine, S-2-aminobutyric acid, S-cyclohexylalanine or other simple alpha-amino acids substituted by an aliphatic side chain from 1-10 carbons including branched, cyclic and straight chain alkyl, alkenyl or alkynyl substitutions.

Substitution of aromatic-substituted hydrophobic amino acids: Including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy (from $C_1$-$C_4$)-substituted forms of the previous listed aromatic amino acids, illustrative examples of which are: 2-, 3-, or 4-aminophenylalanine, 2-, 3-, or 4-chlorophenylalanine, 2-, 3-, or 4-methylphenylalanine, 2-, 3-, or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2'-, 3'-, or 4'-methyl-2-, 3- or 4-biphenylalanine, and 2- or 3-pyridylalanine.

Substitution of amino acids containing basic functions: Including arginine, lysine, histidine, ornithine, 2,3-diaminopropionic acid, homoarginine, alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of acidic amino acids: Including aspartic acid, glutamic acid, homoglutamic acid, tyrosine, alkyl, aryl, aralkyl, and heteroaryl sulfonamides of 2,3-diaminopropionic acid, ornithine or lysine and tetrazole-substituted alkyl amino acids.

Substitution of side chain amide residues: Including asparagine, glutamine, and alkyl or aromatic substituted derivatives of asparagine or glutamine.

Substitution of hydroxyl containing amino acids: Including serine, threonine, homoserine, 2,3-diaminopropionic acid, and alkyl or aromatic substituted derivatives of serine or threonine.

It is also understood that the amino acids within each of the categories listed above may be substituted for another of the same group.

Substitution of Amide Bonds

Another type of modification within the scope of the invention is the substitution of amide bonds within the backbone of a binding polypeptide. For example, to reduce or eliminate undesired proteolysis, or other degradation pathways which diminish serum stability, resulting in reduced or abolished bioactivity, or to restrict or increase conformational flexibility, it is common to substitute amide bonds within the backbone of the peptides with functionality that mimics the existing conformation or alters the conformation in the manner desired. Such modifications may produce increased binding affinity or improved pharmacokinetic behavior. It is understood that those knowledgeable in the art of peptide synthesis can make the following amide bond-changes for any amide bond connecting two amino acids with the expectation that the resulting peptides could have the same or improved activity: insertion of alpha-N-methylamides or peptide amide backbone thioamides, removal of the carbonyl to produce the cognate secondary amines, replacement of one amino acid with an aza-aminoacid to produce semicarbazone derivatives, and use of E-olefins and substituted E-olefins as amide bond surrogates.

Introduction of D-Amino Acids

Another approach within the scope of the invention is the introduction of D-alanine, or another D-amino acid, distal or proximal to a labile peptide bond. In this case it is also understood to those skilled in the art that such D-amino acid substitutions can, and at times, must be made, with D-amino acids whose side chains are not conservative replacements for those of the L-amino acid being replaced. This is because of the difference in chirality and hence side-chain orientation, which may result in the accessing of a previously unexplored region of the binding site of the target which has moieties of different charge, hydrophobicity, steric requirements, etc., than that serviced by the side chain of the replaced L-amino acid.

Modifications to Improve Pharmacokinetic or Pharmacodynamic Properties

It is also understood that use of the binding moieties of the invention in a particular application may necessitate modifications of the peptide or formulations of the peptide to improve pharmacokinetic and pharmacodynamic behavior. It is expected that the properties of the peptide may be changed by attachment of moieties anticipated to bring about the desired physical or chemical properties. Such moieties affecting the pharmacokinetic and pharmacodynamic behavior may be appended to the peptide using acids or amines, via amide bonds or urea bonds, respectively, to the N- or C-terminus of the peptide, or to the pendant amino group of a suitably located lysine or lysine derivative, diaminopropionic acid, ornithine, or other amino acid in the peptide that possesses a pendant amine group or a pendant alkoxyamino or hydrazine group. The moieties introduced may be groups that are hydrophilic, basic, or nonpolar alkyl or aromatic groups depending on the peptide of interest and the extant requirements for modification of its properties.

Glycosylation of Amino Acid Residues

Yet another modification within the scope of the invention is to employ glycosylated amino acid residues (e.g. serine, threonine or asparagine residues), singly or in combination in either the binding moiety or the linker moiety or both. Glycosylation, which may be carried out using standard conditions, may be used to enhance solubility, alter pharmacokinetics and pharmacodynamics or to enhance binding via a specific or non-specific interaction involving the glycosidic moiety. In another approach glycosylated amino acids such as O-(2-acetamido-2-deoxy-3,4,6-tri-O-acetyl-(3-D-glucopyranosyl) serine or the analogous threonine derivative (either the D- or L-amino acids) may be incorporated into the peptide during manual or automated solid phase peptide synthesis, or in manual or automated solution phase peptide synthesis. Similarly D- or L-N$^\gamma$-(2-acetamido-2-deoxy-3,4,6-tri-O-acetyl-β-D-glucopyranosyl)-asparagine can be employed. The use of amino acids glycosylated on a pendant oxygen, nitrogen or sulfur function by the agency of suitably functionalized and activated carbohydrate moieties that can be employed in glycosylation is anticipated. Such carbohydrate functions could be monosaccharides, disaccharides or even larger assemblies of oligosaccharides (Kihlberg, January (2000) Glycopeptide synthesis. In: Fmoc Solid Phase Peptide Synthesis—A Practical Approach (Chan, W. C. and White, P. D. Eds) Oxford University Press, New York, N.Y. Chap. 8, pp 195-213).

Also anticipated is the appendage of carbohydrate functions to amino acids by means other than glycosylation via activation of a leaving group at the anomeric carbon. Linkage of the amino acid to the glycoside is not limited to the formation of a bond to the anomeric carbon of the carbohydrate function. Instead, linkage of the carbohydrate moiety to the amino acid could be through any suitable, sufficiently reactive oxygen atom, nitrogen atom, carbon atom or other pendant atom of the carbohydrate function via methods employed for formation of C-heteroatom, C—C or heteroatom-heteroatom (examples are S—S, O—N, N—N, P—O, P—N) bonds known in the art.

Formation of Salts

It is also within the scope of the invention to form different salts that may increase the water solubility or the ease of formulation of these peptides. These may include, but are not restricted to, N-methylglucamine (meglumine), acetate, oxalates, ascorbates etc.

Structural Modifications which Retain Structural Features

Yet another modification within the scope of the invention is truncation of cyclic polypeptides. The cyclic nature of many polypeptides of the invention limits the conformational space available to the peptide sequence, particularly within the cycle. Therefore truncation of the peptide by one or more residues distal or even proximal to the cycle, at either the N-terminal or C-terminal region may provide truncated peptides with similar or improved biological activity. A unique sequence of amino acids, even as small as three amino acids, which is responsible for the binding activity, may be identified, as noted for RGD peptides. See e.g., E. F. Plow et al., Blood (1987), 70(1), 110-5; A. Oldberg et al., Journal of Biological Chemistry (1988), 263(36), 19433-19436; R. Taub et al., Journal of Biological Chemistry (1989 Jan. 5), 264(1), 259-65; A. Andrieux et al., Journal of Biological Chemistry (1989 Jun. 5), 264(16), 9258-65; and U.S. Pat. Nos. 5,773,412 and 5,759,996, each of which is incorporated herein by reference in its entirety.

It has also been shown in the literature that large peptide cycles can be substantially shortened, eliminating extraneous amino acids, but substantially including the critical binding residues. See U.S. Pat. No. 5,556,939, which is incorporated herein by reference in its entirety. Shortened cyclic peptides can be formed using disulfide bonds or amide bonds of suitably located carboxylic acid groups and amino groups.

Furthermore, D-amino acids can be added to the peptide sequence to stabilize turn features (especially in the case of glycine). In another approach alpha, beta, gamma or delta dipeptide or turn mimics (such as α, β, γ, or δ turn mimics) some of which are shown in structures 1, 2 and 3, below, can be employed to mimic structural motifs and turn features in a peptide and simultaneously provide stability from proteolysis and enhance other properties such as, for example, conformational stability and solubility (structure 1: Hart et al., *J. Org. Chem.*, 64, 2998-2999 (1999); structure 2: Hanessian et al., "Synthesis of a Versatile Peptidomimetic Scaffold" in *Methods in Molecular Medicine*, Vol. 23: Peptidomimetics Protocols, W. M. Kazmierski Ed. (Humana Press Inc. Totowa N.J. 1999), Chapter 10, pp. 161-174; structure 3: WO 01/16135.

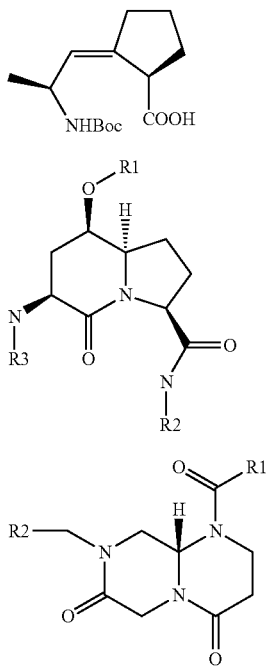

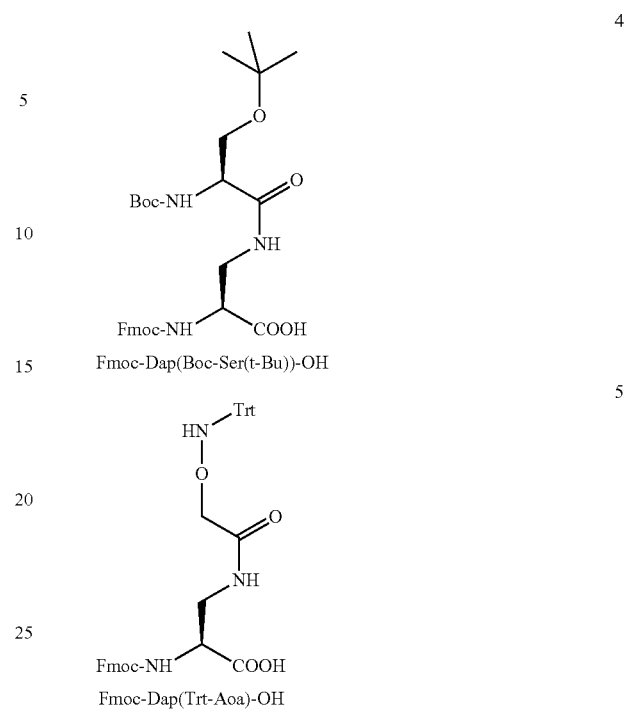

Fmoc-Dap(Boc-Ser(t-Bu))-OH

Fmoc-Dap(Trt-Aoa)-OH

Substitution of Disulfide Mimetics

Also included within the scope of the invention is the substitution of disulfide mimetics for disulfide bonds within the binding polypeptides of the invention. For disulfide-containing peptides of the invention, the disulfide bonds might need to be replaced to avoid certain difficulties that are sometimes posed by the presence of a disulfide bond. For example, when generating $^{99m}$Tc (or other radionuclide)-based radiopharmaceuticals or certain other constructs with binding peptides of the invention, the presence of the disulfide bond can be a significant problem. The integrity of the disulfide bond is difficult to maintain during procedures designed to incorporate $^{99m}$Tc via routes that are reliant upon the reduction of pertechnetate ion and subsequent incorporation of the reduced Tc species into substances bearing Tc-compatible chelating groups. This is because the disulfide bond is rather easily reduced by the reducing agents commonly used in kits devised for one-step preparation of radiopharmaceuticals. Therefore, the ease with which the disulfide bond can be reduced during Tc chelation may require substitution with mimetics of the disulfide bonds. Accordingly, another modification within the scope of the invention is to substitute the disulfide moiety with mimetics, utilizing the methods disclosed herein or known to those skilled in the art, while retaining the activity and other desired properties of the binding polypeptides used in the invention:

Oxime Linker

The oxime moiety has been employed as a linker by investigators in a number of contexts. Of the most interest is the work by Wahl, F and Mutter, M, *Tetrahedron Lett.* (1996) 37, 6861-6864). The amino acids containing an aminoalcohol function (4), and containing an alkoxyamino function (5), are incorporated into the peptide chain, not necessarily at the end of the peptide chain. After formation of the peptide, the sidechain protecting groups are removed. The aldehyde group is unmasked and an oxime linkage is formed.

Lanthionine Linker

Lanthionines are cyclic sulfides, wherein the disulfide linkage (S—S) is replaced by a (C—S) linkage. Thus the lability to reduction is far lower and this linkage should be stable to stannous chloride. Lanthionines may be prepared by a number of methods.

Preparation of Lanthionines Using Bromoacetylated Peptides

Lanthionines are readily prepared using known methods. See, for example, Robey et al. (Robey, F. A. and Fields, R. L. Anal. Biochem. (1989) 177, 373-377) and Inman, et al. (Inman, J. K.; Highet, P. F.; Kolodny, N.; and Robey, F. A. Bioconjugate Chem. (1991) 2, 458-463; Ploinsky, A. Cooney, M. C. Toy-Palmer, A. Osapay, G. and Goodman, M. J. Med. Chem. (1992) 35, 4185-4194; Mayer, J. P.; Zhang, J.; and Liu, C. F. in: Tam, J. P. and Kaumaya, P. T. P. (eds), "Peptides, Frontiers of Peptide Science," Proceedings of the 15$^{th}$ American Peptide Symposium, June 14-19 Nashville, Term. Klumer Academic Pub. Boston. pp 291-292; Wakao, Norihiro; Hino, Yoichi; Ishikawa, Ryuichi. Jpn. Kokai Tokkyo Koho (1995), 7 pp. JP 07300452 A2 19951114 Heisei; JP 95-49692 19950309; JP 94-41458 19940311 have published in this area. Preparation of peptides using Boc automated peptide synthesis followed by coupling the peptide terminus with bromoacetic acid gives bromoacetylated peptides in good yield. Cleavage and deprotection of the peptides is accomplished using HF/anisole. If the peptide contains a cysteine group its reactivity can be controlled with low pH. If the pH of the medium is raised to 6-7, then either polymerization or cyclization of the peptide takes place. Polymerization is favored at high (100 mg/mL) concentration, whereas cyclization is favored at lower concentrations (1 mg/mL), e.g., in Scheme 1 below, 6 cyclizes to 7.

Scheme 1-Example of Cyclization of Cysteine with a Pendant Bromoacetamide Function

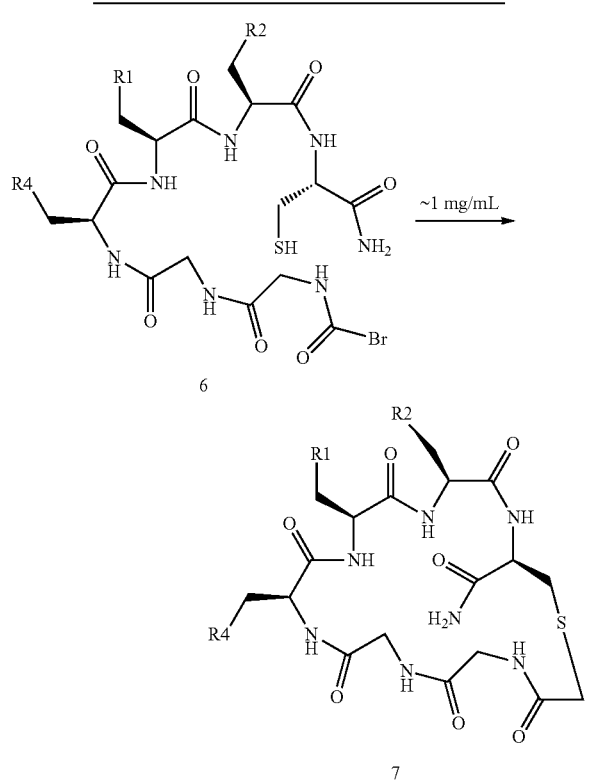

Inman et al. demonstrated the use of $N^\alpha$-(Boc)-$N^\epsilon$-[N-(bromoacetyl)-β-alanyl]-L-lysine as a carrier of the bromoacetyl group that could be employed in Boc peptide synthesis thus allowing placement of a bromoacetyl bearing moiety anywhere in a sequence. In preliminary experiments they found that peptides with 4-6 amino acids separating the bromoacetyl-lysine derivative from a cysteine tend to cyclize, indicating the potential utility of this strategy.

Preparation of Lanthionines via Cysteine Thiol Addition to Acrylamides

Several variants of this strategy may be implemented. Resin-bound serine can be employed to prepare the lanthionine ring on resin either using a bromination-dehydrobromination-thiol addition sequence or by dehydration with disuccinimidyl carbonate followed by thiol addition. Ploinsky et al., M. *J. Med. Chem.*, 35:4185-4194 (1992); Mayer et al., "Peptides, Frontiers of Peptide Science", in *Proceedings of the 15th American Peptide Symposium*, Tam & Kaumaya (eds), Jun. 14-19, 1995, Nashville, Tenn. (Klumer Academic Pub. Boston) pp. 291-292. Conjugate addition of thiols to acrylamides has also been amply demonstrated and a reference to the addition of 2-mercaptoethanol to acrylamide is provided. Wakao et al., Jpn. Kokai Tokkyo Koho, J P 07300452 A2 (1995).

Diaryl Ether or Diarylamine Linkage

Diaryl Ether Linkage From Intramolecular Cyclization of Aryl Boronic Acids and Tyrosine The reaction of arylboronic acids with phenols, amines and heterocyclic amines in the presence of cupric acetate, in air, at ambient temperature, in dichloromethane using either pyridine or triethylamine as a base to provide unsymmetrical diaryl ethers and the related amines in good yields (as high as 98%) has been reported. See, Evans et al., *Tetrahedron Lett.*, 39:2937-2940 (1998); Chan et al., *Tetrahedron Lett.*, 39:2933-2936 (1998); Lam et al., *Tetrahedron Lett.*, 39:2941-2944 (1998). In the case of N-protected tyrosine derivatives as the phenol component the yields were also as high as 98%. This demonstrates that amino acid amides (peptides) are expected to be stable to the transformation and that yields are high. Precedent for an intramolecular reaction exists in view of the facile intramolecular cyclizations of peptides to lactams, intramolecular biaryl ether formation based on the $S_NAr$ reaction and the generality of intramolecular cyclization reactions under high dilution conditions or on resin, wherein the pseudo-dilution effect mimics high dilution conditions.

Formation of Cyclic Peptides with a Lactam Linkage via Intramolecular Native Chemical Ligation

Scheme 2-Formation of Cyclic Peptides with a Thiazolidine Linkage via Intramolecular Reaction of Peptide Aldehydes with Cysteine Moieties

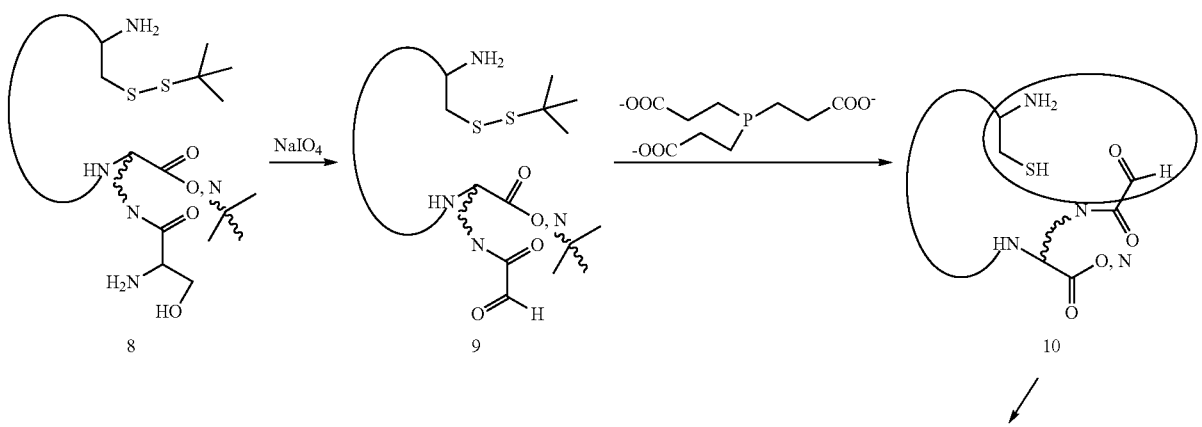

-continued

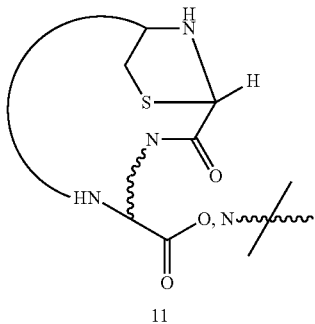
11

15

Another approach that may be employed involves intramolecular cyclization of suitably located vicinal amino mercaptan functions (usually derived from placement of a cysteine at a terminus of the linear sequence or tethered to the sequence via a side-chain nitrogen of a lysine, for example) and aldehyde functions to provide thiazolidines which result in the formation of a bicyclic peptide, one ring of which is that formed by the residues in the main chain, and the second ring being the thiazolidine ring. Scheme 2, above, provides an example. The required aldehyde function can be generated by sodium metaperiodate cleavage of a suitably located vicinal aminoalcohol function, which can be present as an unprotected serine tethered to the chain by appendage to a side chain amino group of a lysine moiety. In some cases, the required aldehyde function is generated by unmasking of a protected aldehyde derivative at the C-terminus or the N-terminus of the chain. An example of this strategy is found in: Botti, P.; Pallin, T. D. and Tam, J. P. J. Am. Chem. Soc. 1996, 118, 10018-10034.

Lactams Based on Intramolecular Cyclization of Pendant Amino Groups with Carboxyl Groups on Resin Macrocyclic peptides can be prepared by lactam formation by either head to tail or by pendant group cyclization. The basic strategy is to prepare a fully protected peptide wherein it is possible to remove selectively an amine protecting group and a carboxy protecting group. Orthogonal protecting schemes have been developed. Of those that have been developed, the allyl, trityl and Dde methods have been employed most. See, Mellor et al., "Synthesis of Modified Peptides," in *Fmoc Solid Phase Synthesis: A Practical Approach*, White and Chan (eds) ([Oxford University Press, New York, 2000]), Chapt. 6, pp. 169-178. The Dde approach is of interest because it utilizes similar protecting groups for both the carboxylic acid function (Dmab ester) and the amino group (Dde group). Both are removed with 2-10% hydrazine in DMF at ambient temperature. Alternatively, the Dde can be used for the amino group and the allyl group can be used for the carboxyl.

A lactam function, available by intramolecular coupling via standard peptide coupling reagents (such as HATU, PyBOP etc), could act as a surrogate for the disulfide bond. The Dde/Dmab approach is shown in Scheme 3a, below.

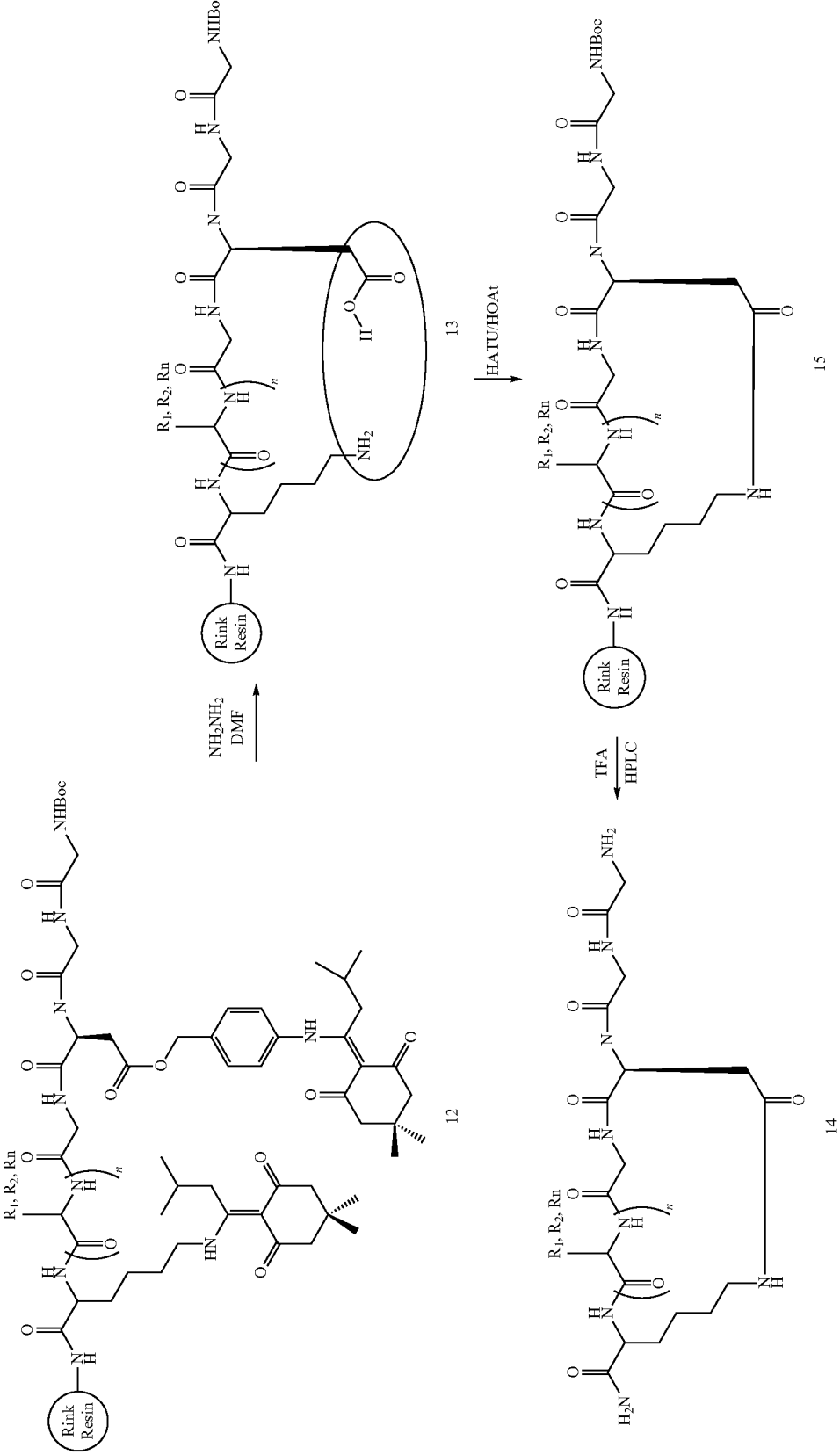

Thus, a linear sequence containing, for example, the Dde-protected lysine and Dmab ester may be prepared on a Tentagel-based Rink amide resin at low load (~0.1-0.2 mmol/g). Deprotection of both functions with hydrazine is then followed by on-resin cyclization to give the desired products.

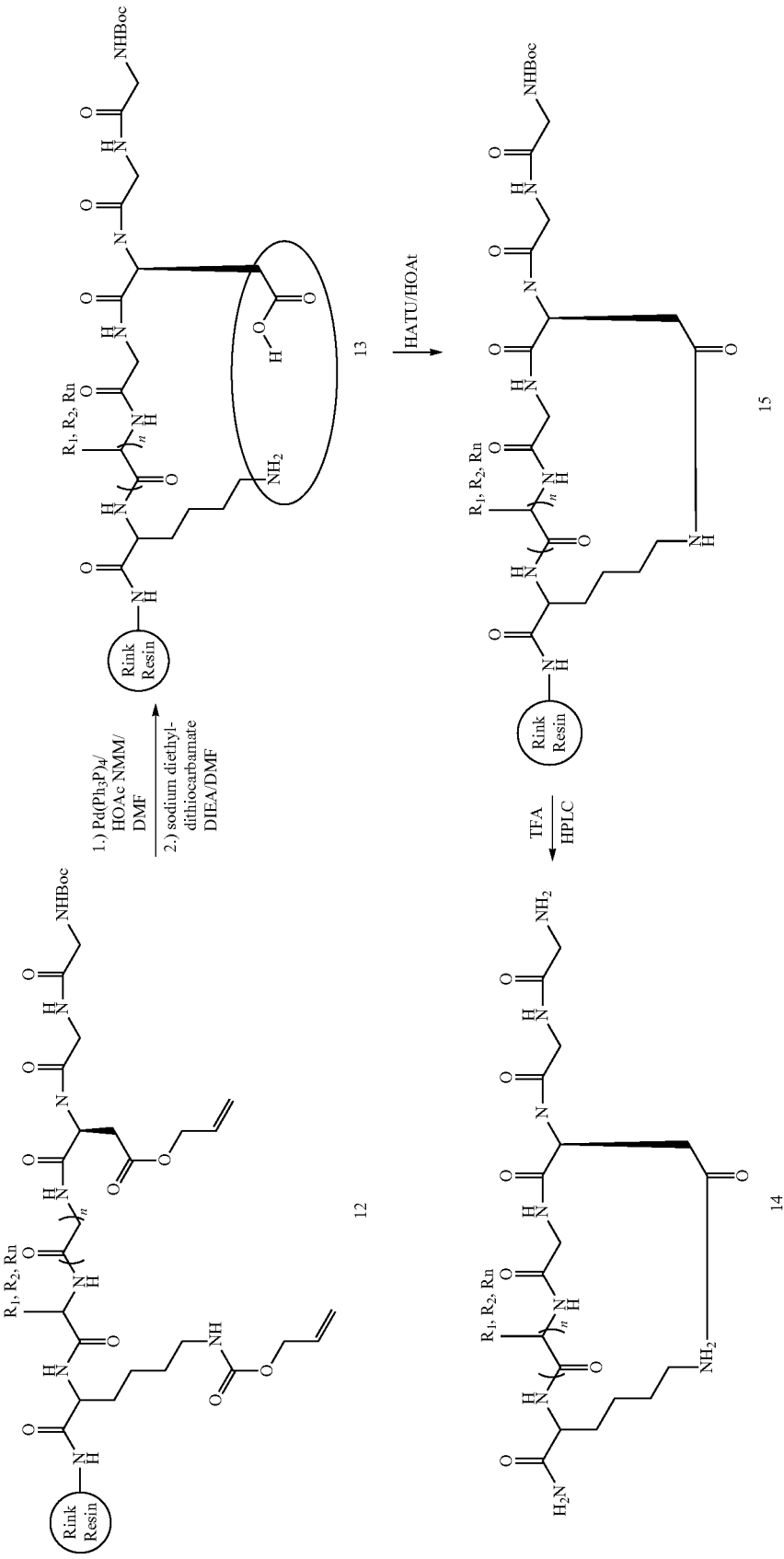

In the allyl approach, shown in Scheme 3b, the pendant carboxyl which is to undergo cyclization is protected as an allyl ester and the pendant amino group is protected as an alloc group. On resin, both are selectively unmasked by treatment with palladium tris-triphenylphosphine in the presence of N-methylmorpholine and acetic acid in DMF. Residual palladium salts are removed using sodium diethyldithiocarbamate in the presence of DIEA in DMF, followed by subsequent washings with DMF. The lactam ring is then formed employing HATU/HOAt in the presence of N-methylmorpholine. Other coupling agents can be employed as described above. The processing of the peptide is then carried out as described above to provide the desired peptide lactam.

Subsequently cleavage from resin and purification may also be carried out. For functionalization of the N-terminus of the peptide, it is understood that amino acids, such as trans-4-(iV-Dde)methylaminocyclohexane carboxylic acid, trans-4-(iV-Dde)methylaminobenzoic acid, or their alloc congeners could be employed. Yet another approach is to employ the safety catch method to intramolecular lactam formation during cleavage from the resin.

Cyclic Peptides Based on Olefin Metathesis

The Grubbs reaction (Scheme 4, below) involves the metathesis/cyclization of olefin bonds and is illustrated as shown below. See, Schuster et al., *Angewandte. Chem. Int. Edn Engl.*, 36:2036-2056 (1997); Miller et al., *J. Am. Chem. Soc.*, 118:9606-9614 (1996).

Scheme 4-Grubbs Olefin Metathesis Cyclization

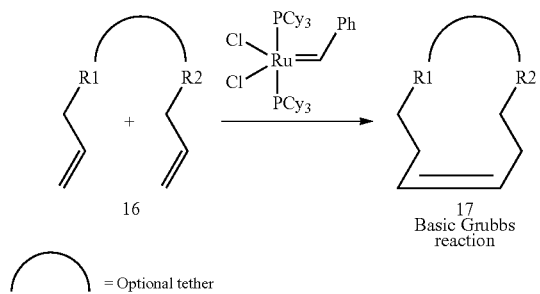

16

17
Basic Grubbs reaction

= Optional tether

It is readily seen that, if the starting material is a diolefin (16), the resulting product will be cyclic compound 17. The reaction has in fact been applied to creation of cycles from olefin-functionalized peptides. See, e.g., Pernerstorfer et al., *Chem. Commun.*, 20:1949-50 (1997); Covalent capture and stabilization of cylindrical β-sheet peptide assemblies, Clark et al., *Chem. Eur. J.*, 5(2):782-792 (1999); Highly efficient synthesis of covalently cross-linked peptide helices by ring-closing metathesis, Blackwell et al., *Angew. Chem., Int. Ed.*, 37(23):3281-3284 (1998); Synthesis of novel cyclic protease inhibitors using Grubbs olefin metathesis, Ripka et al., *Med. Chem. Lett.*, 8(4):357-360 (1998); Application of Ring-Closing Metathesis to the Synthesis of Rigidified Amino Acids and Peptides, Miller et al., *J. Am. Chem. Soc.*, 118(40):9606-9614 (1996); Supramolecular Design by Covalent Capture, Design of a Peptide Cylinder via Hydrogen-Bond-Promoted Intermolecular Olefin Metathesis, Clark et al., *J. Am. Chem. Soc.*, 117(49):12364-12365 (1995); Synthesis of Conformationally Restricted Amino Acids and Peptides Employing Olefin Metathesis, Miller et al., *J. Am. Chem. Soc.*, 117(21): 5855-5856 (1995). One can prepare either C-allyated amino acids or possibly N-allyated amino acids and employ them in this reaction in order to prepare carba-bridged cyclic peptides as surrogates for disulfide bond containing peptides.

One may also prepare novel compounds with olefinic groups. Functionalization of the tyrosine hydroxyl with an olefin-containing tether is one option. The lysine ε-amino group may be another option with appendage of the olefin-containing unit as part of an acylating moiety, for example. If instead the lysine side chain amino group is alkylated with an olefin containing tether, it can still function as a point of attachment for a reporter as well. The use of 5-pentenoic acid as an acylating agent for the lysine, ornithine, or diaminopropionic side chain amino groups is another possibility. The length of the olefin-containing tether can also be varied in order to explore structure activity relationships.

Manipulation of Peptide Sequences

Other modifications within the scope of the invention include manipulations of peptide sequences which can be expected to yield peptides with similar or improved biological properties. These include amino acid translocations (swapping amino acids in the sequence), use of retro-inverso peptides in place of the original sequence or a modified original sequence, peptoids, retro-inverso peptoid sequences, and synthetic peptides. Structures wherein specific residues are peptoid instead of peptidic, which result in hybrid molecules, neither completely peptidic nor completely peptoid, are contemplated as well.

The peptides or conjugates of the invention may include one or more protecting groups on any appropriate amino or carboxylic groups or other appropriate functional groups. Unless otherwise noted, the term "protecting group" refers to a protective group adapted to preserve the characteristic chemical function of the functional group to which it is bound. For example, protecting groups may be used to preserve amino or carboxyl functions and may include, for example, Fmoc, benzyl, benzyloxycarbonyl or alkyl esters or other groups commonly intended for protection of such functions. Additional protecting groups are disclosed in, for example, T. W. Green, Protective Groups in Organic Synthesis (Wiley, NY 1981).

In appropriate circumstances the peptides or conjugates of the invention may also include a "deactivating group", which refers to a chemical group that is able to chemically react with, for example, the N terminal (—NH2) or C-terminal (—COOH) group of the peptide unit, transforming it through a chemical reaction, into a suitable derivative thereof that maintains the specificity of the corresponding peptide moiety toward fibrin, but is unable to chemically react with, respectively, a carboxyl or an amino functionality on a different moiety, and thus may not be involved in carboxamido reactions. Such groups may include acetyl (also referred to as CH3(CO)— or Ac), amino groups and derivatives thereof such as, for example, —NH2, —NH(CH3), H2NOC—CH2—NH—.

Multimeric constructs including fibrin-binding peptides of the invention may be prepared using known linkers and techniques, such as, for example, those set forth in co-pending U.S.S.N. (US 2005/0147555), incorporated herein by reference in its entirety. In a preferred embodiment homodimers including fibrin-binding peptides may be prepared. Such dimeric compounds have increased avidity and thus exhibit better binding to fibrin.

In the practice of the present invention, a determination of the affinity of the fibrin-binding moiety for fibrin relative to fibrinogen is a useful measure, and is referred to as specificity for fibrin. Standard assays for quantitating binding and determining affinity include equilibrium dialysis, equilibrium binding, gel filtration, or the monitoring of numerous spectroscopic changes (such as a change in fluorescence polarization) that may result from the interaction of the binding moiety and its target. These techniques measure the concentration of bound and free ligand as a function of ligand (or protein) concentration. The concentration of bound polypeptide ([Bound]) is related to the concentration of free polypeptide ([Free]) and the concentration of binding sites for the polypeptide, i.e., on fibrin, (N), as described in the following equation:

$$[Bound]=N\times[Free]/((1/K_a)+[Free]).$$

A solution of the data to this equation yields the association constant, $K_a$, a quantitative measure of the binding affinity. The association constant, $K_a$ is the reciprocal of the dissociation constant, $K_D$. The $K_D$ is more frequently reported in measurements of affinity. A peptide having a $K_D$ 1.5 times higher for fibrinogen than for fibrin would be considered low-specificity fibrin binder. A peptide having a $K_D$ 10 times greater for fibrinogen than fibrin would be a moderate-specificity fibrin binder, and a peptide having a $K_D$ 100 times or more greater for fibrinogen than for fibrin would be termed highly specific for fibrin. Preferably the peptides and agents of the present invention have a $K_D$ at least 1.5 times higher for fibrinogen than for fibrin, more preferably at least 10 times higher, even more preferably at least 100 times, and most preferably at least 1000 times higher. Preferred fibrin binding polypeptides have a $K_D$ for fibrin in the range of 1 nanomolar (nM) to 100 micromolar (µM) and includes $K_D$ values of at least 10 nM, at least 20 nM, at least 40 nM, at least 60 nM, at least 80 nM, at least 1 µM, at least 5 µM, at least 10 µM, at least 20 µM, at least 40 µM, at least 60 µM, and at least 80 µM.

Where fibrin binding moieties are employed as imaging agents, other aspects of binding specificity may become more important: Imaging agents operate in a dynamic system in that binding of the imaging agent to the target is not in a stable equilibrium state throughout the imaging procedure. For example, when the imaging agent is initially injected, the concentration of imaging agent and of agent-target complex rapidly increases. Shortly after injection, however, the circulating (free) imaging agent starts to clear through the kidneys or liver, and the plasma concentration of imaging agent begins to drop. This drop in the concentration of free imaging agent in the plasma eventually causes the agent-target complex to dissociate. The usefulness of an imaging agent depends on the difference in rate of agent-target dissociation relative to the clearing rate of the agent. Ideally, the dissociation rate will be slow compared to the clearing rate, resulting in a long imaging time during which there is a high concentration of agent-target complex and a low concentration of free imaging agent (background signal) in the plasma. The dissociation rate of the complex is controlled by the dissociation rate constant, $k_o$ff. Because higher values of $k_o$ff correspond to faster dissociation rates, it is preferable to obtain binding peptides which have a low $k_o$ff for use as imaging agents.

The fibrin-binding moieties according to this invention will be extremely useful for detection and/or imaging of fibrin in vitro or in vivo, and particularly for detection and/or imaging of fibrin clots and pathological angiogenic processes. Any suitable method of assaying or imaging fibrin may be employed.

For detection of fibrin or fibrin-derived polypeptides in solution, a binding moiety according to the invention can be detectably labeled, e.g., fluorescently labeled, radiolabeled or enzymatically labeled, then contacted with the solution, and thereafter formation of a complex between the binding moiety and the fibrin target can be detected. As an example, a fluorescently labeled fibrin binding peptide may be used for in vitro fibrin detection assays, wherein the peptide is added to a solution to be tested for fibrin under conditions allowing binding to occur. The complex between the fluorescently labeled fibrin-binding peptide and fibrin can be detected and quantified by measuring the increased fluorescence polarization arising from the fibrin-bound peptide relative to that of the free peptide.

Alternatively, a sandwich-type ELISA assay may be used, wherein a fibrin binding moiety is immobilized on a solid support such as a plastic tube or well, then the solution suspected of containing fibrin or a fibrin-derived polypeptide is contacted with the immobilized binding moiety, non-binding materials are washed away, and complexed polypeptide is detected using a suitable detection reagent, such as a monoclonal antibody recognizing fibrin. The monoclonal antibody is detectable by conventional means known in the art, including being detectably labeled, e.g., radiolabeled, conjugated with an enzyme such as horseradish peroxidase and the like, or fluorescently labeled.

For detection or purification of soluble fibrin or fibrin-derived polypeptides in or from a solution, a binding moiety of the invention can be immobilized on a solid substrate such as a chromatographic support or other porous material, then the immobilized binder can be loaded or contacted with the solution under conditions suitable for formation of a binding moiety/fibrin complex. The non-binding portion of the solution can be removed and the complex may be detected, e.g., using an anti-fibrin or anti-binding moiety antibody, or the fibrin target may be released from the binding moiety at appropriate elution conditions.

A particularly preferred use for the polypeptides according to the present invention is for creating visually readable images of thrombi and pathologic angiogenic processes, to aid in the diagnosis, monitoring and treatment of such disorders. The fibrin binding polypeptides disclosed herein may be converted to imaging reagents for detecting thrombi by conjugating the polypeptides with a label appropriate for diagnostic detection. Such labels, referred to, for example, as a detectable label or a diagnostically effective any moiety, include any moiety detectable by imaging procedures, that is to say any moiety able to provide, to improve or, in any way, to advantageously modify the signal detected by a diagnostic imaging technique including, for instance, magnetic resonance imaging (MRI), radioimaging, X-ray imaging, light imaging, ultrasound imaging, thus enabling the registration of diagnostically useful, preferably contrasted, images when used in association with the said techniques. Examples of detectable labels or diagnostically effective moieties according to the invention include, for instance, chelated gamma ray or positron emitting radionuclides; paramagnetic metal ions in the form of chelated or polychelated complexes, X-ray absorbing agents including atoms having atomic number higher than 20; an ultrasound contrast agent, including for example gas-filled microvesicle, a dye molecule; a fluorescent molecule; a phosphorescent molecule; a molecule absorbing in the UV spectrum; a quantum dot; a molecule capable of absorption within near or far infrared radiations and, in general, all the moieties which generate a detectable substance.

Preferably, a peptide of the invention exhibiting a strong ability to bind fibrin is conjugated or linked (directly or via a linker) to a label appropriate for the detection methodology to be employed. For example, the fibrin binder may be conjugated with a paramagnetic chelate suitable for magnetic resonance imaging (MRI), with a radiolabel suitable for x-ray imaging, with an ultrasound microsphere or liposome suitable for ultrasound detection, or with an optical imaging dye.

Alternatively, a peptide of the invention exhibiting a strong ability to bind fibrin is conjugated or linked (directly or via a linker) to a therapeutic agent. Such compounds are useful for treatment or alleviation of diseases associated with fibrin.

Additional modifications within the scope of the invention include introduction of linkers or spacers between the targeting sequence of the fibrin binding peptide and the detectable label or therapeutic agent. Use of such linkers/spacers may improve the relevant properties of the binding peptide (e.g., improve the binding ability, increase serum stability, adjust hydrophobicity or hydrophilicity, providing improved pharmacokinetic and pharmacodynamic properties, etc.). Indeed, use of an appropriate linker and/or spacer may provide an optimal distance between the fibrin-binding peptide and the detectable label or therapeutic agent, which may in turn improve the targeting capability of the compounds of the invention. These linkers may include, but are not restricted to, substituted or unsubstituted, saturated or unsaturated, straight or branched alkyl chains, derivatized or underivatized polyethylene glycol, polyoxyethylene or polyvinylpyridine chains, one or more amino acids (and preferably 3 or more amino acids and most preferably at least 4 or 6 amino acids, peptides from straight, branched or cyclic amino acids, sugars, or aliphatic or aromatic spacers common in the art, substituted or unsubstituted polyamide chains; derivatized or underivatized polyamine, polyester, polyethylenimine, polyacrylate, poly(vinylalcohol), polyglycerol, or oligosaccharide (e.g., dextran) chains; glycosylated amino acid residues, alternating block copolymers; malonic, succinic, glutaric, adipic and pimelic acids; caproic acid; simple diamines and dialcohols; any of the other linkers disclosed herein as well as any other simple polymeric linker known in the art, for instance as described in WO 98/18497 and WO 98/18496.

Furthermore, linkers that are combinations of the moieties described above, can also be employed to confer special advantage to the properties of the peptide. The linker may be a linear or branched and is preferably at least a divalent linking moiety. A "divalent linking moiety is a chain including two functional groups allowing for its conjugation with a peptide on one side and a detectable label or therapeutic agent on another. Preferably the divalent linking moiety permits conjugation with the terminal amino or carboxyl groups of the peptide and an appropriate functional group on the detectable label or therapeutic agent. A "functional group" refers to specific groups of atoms within molecules or moieties that are responsible for the characteristic chemical reaction of those molecules or moieties and may include, for example, the —$NH_2$ or —COOH groups of peptides, as well as other active groups of detactable labels or therapeutic agents, such, as for example, amino, thiol or carboxyl groups.

The linker may also be a polyfunctional linking moiety or polyfunctional linker, which refers to a linear or branched chain including at least 3 functional groups, one of them connecting the linking moiety with the peptide, and the remainder connecting the linking moiety with at least two detectable labels and/or therapeutic agents. Such polyfunctional linking moieties may include, for example, N-branched Lysine systems (see, f. i., Veprek, P et al., J. Pept. Sci. 5, 5 (1999); 5, 203 (1999), polycarboxylic compounds and suitable derivative thereof in which the carboxylic group(s) are in a suitably activated or protected form, polyaminated compounds and suitable derivative thereof in which the amino group(s) are in a suitably activated or protected form, and amino acids and poly-amino acids such as polyornithine, polyarginine, polyglutamic acid, polyaspartic acid.

Lipid molecules with linkers may be attached to allow formulation of ultrasound bubbles, liposomes or other aggregation based constructs. Such constructs could be employed as agents for targeting and delivery of a diagnostic reporter, a therapeutic agent (e.g., a chemical "warhead" for therapy) or a combination of these.

In the present invention an especially preferred linker is GGGK. Additionally, the linkers GSAGSK (SEQ ID NO. 137) and GAGSGK (SEQ ID NO. 138) are also preferred.

In general, the technique of using a detectably labeled fibrin binding moiety is based on the premise that the label generates a signal that is detectable outside the patient's body. When the detectably labeled fibrin binding moiety is administered to the patient suspected of having a fibrin related disorder (such as a thrombus or pathological angiogenic process), the high affinity of the fibrin binding moiety for fibrin causes the binding moiety to bind to fibrin and accumulate label at the site of interest. The signal generated by the labeled peptide is detected by a scanning device which will vary according to the type of label used, and the signal is then converted to an image of the area.

Magnetic Resonance Imaging

The fibrin binding moieties of the present invention may advantageously be conjugated with a MRI detectable moiety, such as, for example, a paramagnetic metal chelator or iron particles (such as superparamagnetic FeO particles) in order to form a contrast agent for use in MRI. Preferred paramagnetic metal ions have atomic numbers 21-31, 39, 42, 43, 44, 49 or 57-83. This includes ions of the transition metal or lanthanide series which have one, and more preferably five or more, unpaired electrons and a magnetic moment of at least 1.7 Bohr magneton. The preferred paramagnetic metal is selected from the group consisting of Fe(2+), Fe(3+), Cu(2+), Ni(2+), Rh(2+), Co(2+), Cr(3+), Gd(3+), Eu(3+), Dy(3+), Tb(3+), Pm(3+), Nd(3+), Tm(3+), Ce(3+), Y(3+), Ho(3+), Er(3+), La(3+), Yb(3+), Mn(3+), Mn(2+). Gd(3+) (also referred to as Gd(III)) is particularly preferred for MRI due to its high relaxivity and low toxicity, and the availability of only one biologically accessible oxidation state. Gd(III) chelates have been used for clinical and radiologic MR applications since 1988, and approximately 30% of MR exams currently employ a gadolinium-based contrast agent. Additionally, fibrin-binding moieties of the present invention also can be conjugated with other MRI detectable moieties, such as, for example, one or more superparamagnetic particles.

The practitioner will select a metal according to dose required to detect a thrombus and considering other factors such as toxicity of the metal to the subject. See, Tweedle et al., Magnetic Resonance Imaging (2nd ed.), vol. 1, Partain et al., eds. (W.B. Saunders Co. 1988), pp. 796-7. Generally, the desired dose for an individual metal will be proportional to its relaxivity, modified by the biodistribution, pharmacokinetics and metabolism of the metal. The trivalent cation, $Gd^{3+}$ is particularly preferred for MRI contrast agents, due to its high relaxivity and low toxicity, with the further advantage that it exists in only one biologically accessible oxidation state, which minimizes undesired metabolization of the metal by a patient. Another useful metal is $Cr^{3+}$, which is relatively inexpensive.

A chelator (also called a chelating ligand or chelating agent) is a chemical moiety, agent, compound or molecule having one or more polar groups that act as a ligand for, and complex with, a paramagnetic metal. Suitable chelators are known in the art and include acids with methylene phosphonic acid groups, methylene carbohydroxamine acid groups, carboxyethylidene groups, or carboxymethylene groups. In a preferred embodiment the chelators includes cyclic or linear polyamino polycarboxylic or polyphosphonic acids and contains at least one amino, thiol or carboxyl group. Examples of chelators include, but are not limited to, a polyaminopolycarboxylic acid and the derivatives thereof, comprising, for example, diethylenetriamine pentaacetic acid (DTPA) and derivatives thereof such as benzo-DTPA, dibenzo-DTPA, phenyl-DTPA, diphenyl-DTPA, benzyl-DTPA, dibenzyl DTPA; N,N-bis[2-[(carboxymethyl)[(methylcarbamoyl)methyl]amino]ethyl]-glycine (DTPA-BMA); N-[2-[bis(carboxymethyl)amino]-3-(4-ethoxyphenyl)propyl)]-N-[2-[bis(carboxymethyl)amino]ethylglycine (EOB-DTPA); 4-carboxy-5,8,11-tris(carboxymethyl)-1-phenyl-2-oxa-5,8,11-triazamidecan-13-oic acid (BOPTA); N,N-Bis[2-[bis[2-(1,1-dimethylethoxy)-2-oxoethyl]amino]ethyl]-L-glutamic acid 1-(1,1-dimethylethyl) ester N,N-bis[2-[bis(carboxymethyl)amino]ethyl]L-glutamic acid (DTPA-GLU); DTPA conjugated with Lys (DTPA-Lys); ethylenediaminetetraacetic acid (EDTA); 1,4,7,10-teraazacyclododecane 1,4,7,-triacetic acid (DO3A) and derivatives thereof including, for example, [10-(2-hydroxypropyl)-1,4,7,10-teraazacyclododecane 1,4,7,-triacetic acid (HPDO3A); 1,4,7-triazacyclononane N,N',N''-triacetic acid (NOTA); 2-methyl-1,4,7,10-tetraazacyclotetradecane-1,4,7,10-tetraacetic acid (MCTA); 6-[bis(carboxymethyl)amino]tetrahydro-6-methyl-1H-1,4-diazepine-1,4(5H)-diacetic acid (AAZTA) provided by WO03008390 application, incorporated herein by reference, and derivatives thereof; 1,4,7,10-tetraazacyclotetradecane-1,4,7,10-tetraacetic acid (DOTA) and derivatives thereof, including for instance, benzo-DOTA, dibenzo-DOTA, (α,α',α'',α''')-tetramethyl-1,4,7,10-tetraazacyclotetradecane-1,4,7,10-tetraacetic acid (DOTMA); or 1,4,8,11-tetraazacyclotetradecane-N,N',N'',N'''-tetraacetic acid (TETA); or corresponding compounds wherein one or more of the carboxylic groups is replaced by a phosphonic and/or phosphinic group, including, for instance, N,N'-bis-(pyridoxal-5-phosphate) ethylenediamine-N,N'-diacetic acid (DPDP); ethylenedinitrilotetrakis(methylphosphonic) acid (EDTP), 1,4,7,10-tetraazacyclotetradecane-1,4,7,10-tetra (methylenephosphonic) acid (DOTP), the phosphonoalkylpolyaza macrocyclic compounds for instance disclosed in U.S. Pat. No. 5,362,476 and U.S. Pat. No. 5,409,689 and the linear phosphonoalkyl derivatives disclosed in U.S. Pat. No. 6,509,324; or of macrocyclic chelants such as texaphirines, porphyrins, phthalocyanines.

Additional chelating ligands are ethylenebis-(2-hydroxyphenylglycine) (EHPG), and derivatives thereof, including 5-Cl-EHPG, 5Br-EHPG, 5-Me-EHPG, 5t-Bu-EHPG, and 5sec-Bu-EHPG; bis-2 (hydroxybenzyl)-ethylene-diaminediacetic acid (HBED) and derivatives thereof, derivatives of 1,3-propylenediaminetetraacetic acid (PDTA) and triethylenetetraaminehexaacetic acid (TTHA); derivatives of 1,5,10-N,N',N''-tris(2,3-dihydroxybenzoyl)-tricatecholate (LICAM) and 1,3,5-N,N',N''-tris(2,3-dihydroxybenzoyl) aminomethylbenzene (MECAM). Examples of representative chelators and chelating groups contemplated by the present invention are described in, for example, WO 98/18496, WO 86/06605, WO 91/03200, WO 95/28179, WO 96/23526, WO 97/36619, PCT/US98/01473, PCT/US98/20182, and U.S. Pat. No. 4,899,755, all of which are hereby incorporated by reference.

Figure 6A:
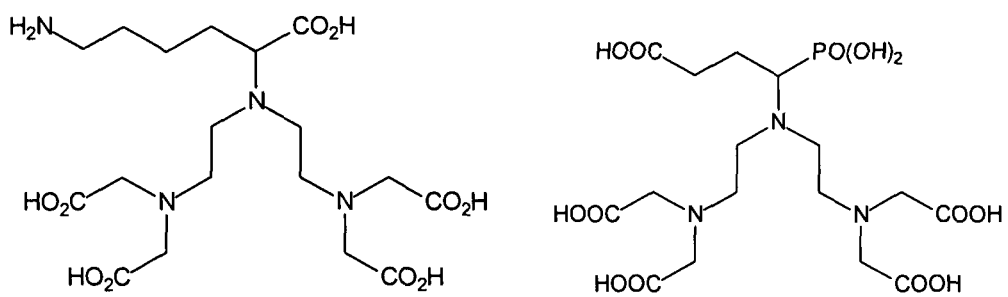
FIGS. 6a, 6b, 6c, illustrate examples of preferred chelators for either $^{111}$In and lanthanides such as paramagnetic $Gd^{3+}$ or radioactive lanthanides such as, for example, $^{177}$Lu, $^{90}$Y, $^{153}$Sm, and $^{166}$Ho.
Figure 6A:
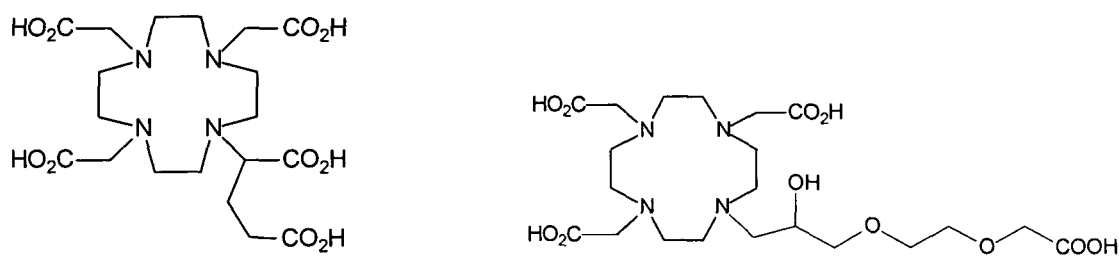
Figure 6B:
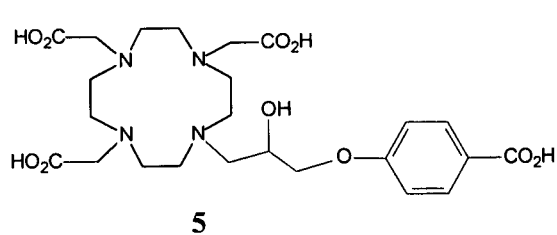
Figure 6B:
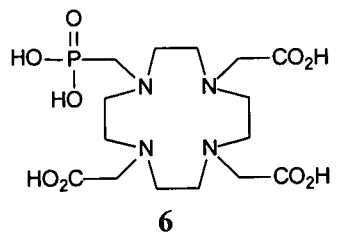
Figure 6B:
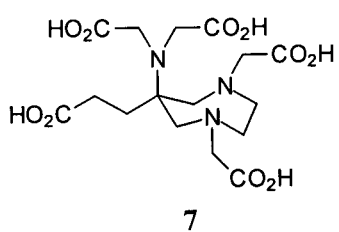
Figure 6B:
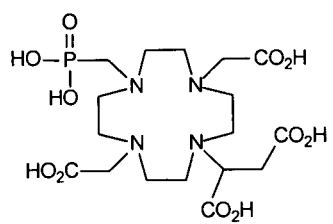
Figure 6B:
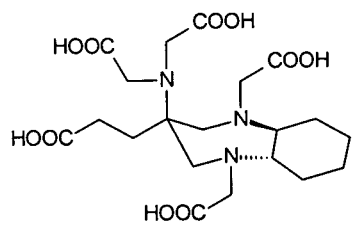
Figure 6B:
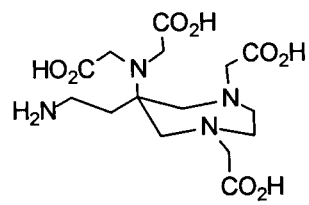
Figure 6B:
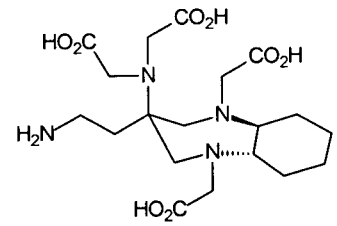
Figure 6B:
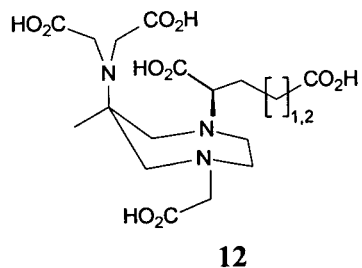
Figure 6B:
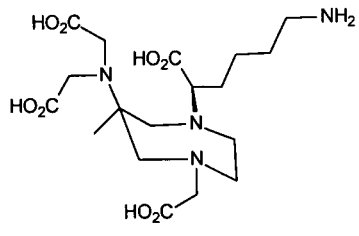
Figure 6C:
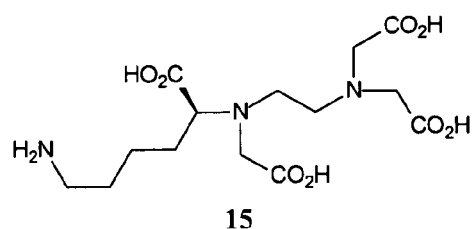
Figure 6C:
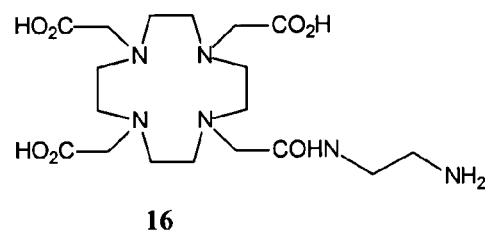
Figure 6C:
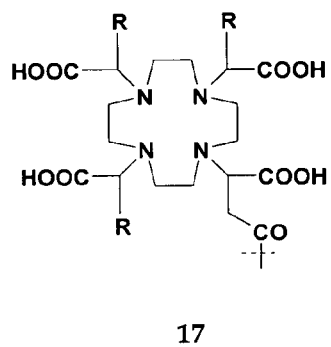
Figure 6C:
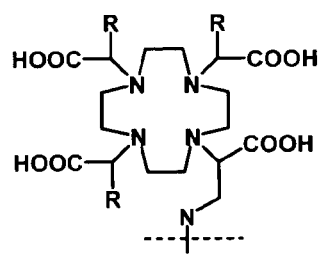
Figure 6C:
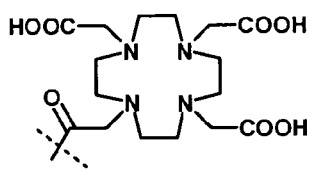
Figure 6C:
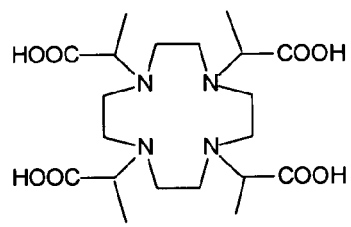
Figure 6C:
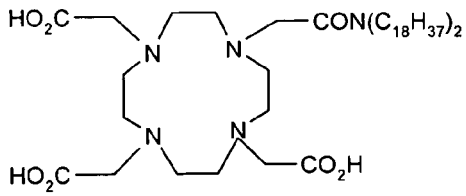
Figure 6C:
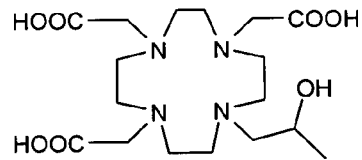

Preferred ligands according to the present invention are set forth in FIGS. 6a to 6c, together with suitable bibliographic references concerning their preparation.

Particularly preferred are: DTPA, DTPA-GLU, DTPA-Lys, DOTA, AAZTA, and the following AAZTA derivatives:

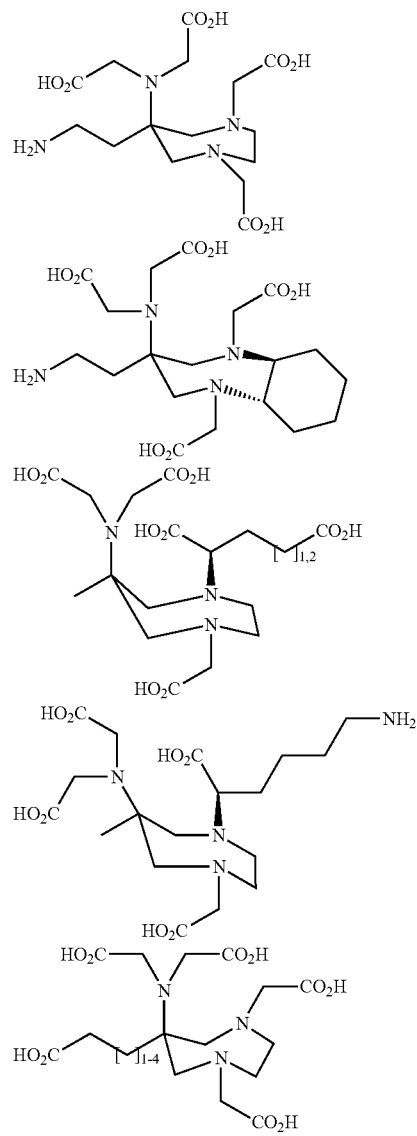

In accordance with the present invention, the chelator of the MRI contrast agent is coupled to the fibrin binding moiety directly or via a linker. The positioning of the chelator should be selected so as not to interfere with the binding affinity or specificity of the fibrin binding moiety. Preferably, the chelate will be appended either to the N terminus or the C terminus, however the chelate may also be attached anywhere within the sequence. In a preferred embodiment, a chelator having a free central carboxylic acid group (e.g., DTPA-Asp(β.-COOH)—OtBu) makes it easy to attach at the N-terminus of the peptide by formation of an amide bond. The chelate could also be attached at the C-terminus with the aid of a linker. Alternatively, isothiocyanate conjugation chemistry could be employed as a way of linking the appropriate isothiocyanto group bearing DTPA to a free amino group anywhere within the peptide sequence.

In general, the fibrin binding moiety can be bound directly or covalently to the metal chelator (or other detectable label), or it may be coupled or conjugated to the metal chelator using a linker, which may be, without limitation, amide, urea, acetal, ketal, double ester, carbonyl, carbamate, thiourea, sulfone, thioester, ester, ether, disulfide, lactone, imine, phosphoryl, or phosphodiester linkages; substituted or unsubstituted saturated or unsaturated alkyl chains; linear, branched, or cyclic amino acid chains of a single amino acid or different amino acids (e.g., extensions of the N- or C-terminus of the fibrin binding moiety); derivatized or underivatized polyethylene glycol, polyoxyethylene, or polyvinylpyridine chains; substituted or unsubstituted polyamide chains; derivatized or underivatized polyamine, polyester, polyethylenimine, polyacrylate, poly(vinyl alcohol), polyglycerol, or oligosaccharide (e.g., dextran) chains; alternating block copolymers; malonic, succinic, glutaric, adipic and pimelic acids; caproic acid; simple diamines and dialcohols; and other simple polymeric linkers known in the art (see, e.g., WO 98/18497, WO 98/18496) or other linkers discussed herein. Preferably the molecular weight of the linker can be tightly controlled. The molecular weights can range in size from less than 100 to greater than 1000. Preferably the molecular weight of the linker is less than 100. In addition, it may be desirable to utilize a linker that is biodegradable in vivo to provide efficient routes of excretion for the imaging reagents of the present invention. Depending on their location within the linker, such biodegradable functionalities can include ester, double ester, amide, phosphoester, ether, acetal, and ketal functionalities.

In general, known methods can be used to couple the metal chelate and the fibrin binding moiety using such linkers. See, e.g., WO 95/28967, WO 98/18496, WO 98/18497 and discussion therein. The fibrin binding moiety can be linked through its N- or C-terminus via an amide bond, for example, to a metal coordinating backbone nitrogen of a metal chelate or to an acetate arm of the metal chelate itself. The present invention contemplates linking of the chelate on any position, provided the metal chelate retains the ability to bind the metal tightly in order to minimize toxicity. Similarly, the fibrin binding moiety may be modified or elongated in order to generate a locus for attachment to a metal chelate, provided such modification or elongation does not eliminate its ability to bind fibrin.

MRI contrast reagents prepared according to the disclosures herein may be used in the same manner as conventional MRI contrast reagents. When imaging a thrombus, certain MR techniques and pulse sequences may be preferred to enhance the contrast of the thrombus to the background blood and tissues. These techniques include (but are not limited to), for example, black blood angiography sequences that seek to make blood dark, such as fast spin echo sequences (see, e.g., Alexander et al., Magnetic Resonance in Medicine, 40(2): 298-310 (1998)) and flow-spoiled gradient echo sequences (see, e.g., Edelman et al., Radiology, 177(1): 45-50 (1990)). These methods also include flow independent techniques that enhance the difference in contrast due to the $T_1$ difference of contrast-enhanced thrombus and blood and tissue, such as inversion-recovery prepared or saturation-recovery prepared sequences that will increase the contrast between thrombus and background tissues. In addition, since the present invention does not significantly alter $T_2$, methods of $T_2$ preparation may also prove useful (see, e.g., Gronas et al., Journal of Magnetic Resonance Imaging, 7(4): 637-643 (1997)). Finally, magnetization transfer preparations may also improve contrast with these agents (see, e.g., Goodrich et al., Investigative Radiology, 31(6): 323-32 (1996)).

The labeled reagent is administered to the patient in the form of an injectable composition. The method of administering the MRI contrast agent is preferably parenterally, meaning intravenously, intraarterially, intrathecally, interstitially, or intracavitarilly. For imaging thrombi, intravenous or intraarterial administration is preferred. For MRI, it is contemplated that the subject will receive a dosage of contrast agent sufficient to enhance the MR signal at the site of a thrombus at least 10%. After injection with the fibrin binding moiety-containing MRI reagent, the patient is scanned in the MRI machine to determine the location of any thrombi. In therapeutic settings, upon thrombus localization, a thrombolytic can be immediately administered, if necessary, and the patient can be subsequently scanned to visualize thrombus degradation.

Ultrasound Imaging

When ultrasound is transmitted through a substance, the acoustic properties of the substance will depend upon the velocity of the transmissions and the density of the substance. Changes in the acoustic properties will be most prominent at the interface of different substances (solids, liquids, gases). Ultrasound contrast agents are intense sound wave reflectors because of the acoustic differences between liquid (e.g., blood) and gas-containing microvesicles, such as microbubbles or microballoons, liposomes, or microspheres dissolved therein. Because of their size, ultrasound microvesicles, liposomes, microspheres, and the like may remain for a longer time in the blood stream after injection than other detectable moieties; a targeted fibrin-specific ultrasound agent therefore may demonstrate superior imaging of thrombi and sites of angiogenesis.

In this aspect of the invention, the fibrin binding moiety may be linked to a material which is useful for ultrasound imaging. The materials are employed to form microvesicles (e.g., liposomes, microbubbles, microspheres, or emulsions) containing a liquid or gas which functions as the detectable label (e.g., an echogenic gas or material capable of generating an echogenic gas). Materials for the preparation of such microvesicles include amphiphilic compounds such as surfactants, lipids, sphingolipids, oligolipids, or phospholipids, proteins, polypeptides, carbohydrates, and synthetic or natural polymeric materials. See, for further description of suitable materials and methods, WO 98/53857, WO 98/18498, WO 98/18495, WO 98/18497, WO 98/18496, and WO 98/18501, incorporated herein by reference in their entirety.

For contrast agents comprising suspensions of stabilized microbubbles (a preferred embodiment), amphiphilic components are preferred. Suitable amphiphilic components include phospholipids; lysophospholipids; fatty acids, such as palmitic acid, stearic acid, arachidonic acid or oleic acid; lipids bearing polymers, such as chitin, hyaluronic acid, polyvinylpyrrolidone or polyethylene glycol (PEG), also referred as "pegylated lipids"; lipids bearing sulfonated mono-di-, oligo- or polysaccharides; cholesterol, cholesterol sulfate or cholesterol hemisuccinate; tocopherol hemisuccinate; lipids with ether or ester-linked fatty acids; polymerized lipids; diacetyl phosphate; dicetyl phosphate; ceramides; polyoxyethylene fatty acid esters (such as polyoxyethylene fatty acid stearates), polyoxyethylene fatty alcohols, polyoxyethylene fatty alcohol ethers, polyoxyethylated sorbitan fatty acid esters, glycerol polyethylene glycol ricinoleate, ethoxylated soybean sterols, ethoxylated castor oil or ethylene oxide (EO) and propylene oxide (PO) block copolymers; sterol aliphatic acid esters including, cholesterol butyrate, cholesterol isobutyrate, cholesterol palmitate, cholesterol stearate, lanosterol acetate, ergosterol palmitate, or phytosterol n-butyrate; sterol esters of sugar acids including cholesterol glucuronides, lanosterol glucuronides, 7-dehydrocholesterol glucoronide, ergosterol glucuronide, cholesterol gluconate, lanosterol gluconate, or ergosterol gluconate; esters of sugar acids and alcohols including lauryl glucoronide, stearoyl glucoronide, myristoyl glucoronide, lauryl gluconate, myristoyl gluconate, or stearoyl gluconate; esters of sugars with aliphatic acids including sucrose laurate, fructose laurate, sucrose palmitate, sucrose stearate, glucuronic acid, gluconic acid or polyuronic acid; saponins including sarsasapogenin, smilagenin, hederagenin, oleanolic acid, or digitoxigenin; glycerol or glycerol esters including glycerol tripalmitate, glycerol distearate, glycerol tristearate, glycerol dimyristate, glycerol trimyristate, glycerol dilaurate, glycerol trilaurate, glycerol dipalmitate, long chain alcohols including n-decyl alcohol, lauryl alcohol, myristyl alcohol, cetyl alcohol, or n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-β-D-mannopyranoside; 12-(((7'-diethylaminocoumarin-3-yl)carbonyl)methyl-amino) octadecanoic acid; N-[12-(((7'-diethylaminocoumarin-3-yl)carbonyl)methylamino)-octadecanoyl]-2-aminopalmitic acid; N-succinyldioleylphosphatidylethanolamine; 1,2-dioleyl-sn-glycerol; 1,2-dipalmitoyl-sn-3-succinylglycerol; 1,3-dipalmitoyl-2-succinyl-glycerol; 1-hexadecyl-2-palmitoylglycerophosphoethanolamine or palmitoylhomocysteine; alkylamines or alkylammonium salts, comprising at least one ($C_{10}$-$C_{20}$), preferably ($C_{14}$-$C_{18}$), alkyl chain, such as, for instance, N-stearylamine, N,N'-distearylamine, N-hexadecylamine, N,N'-dihexadecylamine, N-stearylammonium chloride, N,N'-distearylammonium chloride, N-hexadecylammonium chloride, N,N'-dihexadecylammonium chloride, dimethyldioctadecylammonium bromide (DDAB), hexadecyltrimethylammonium bromide (CTAB); tertiary or quaternary ammonium salts comprising one or preferably two ($C_{10}$-$C_{20}$), preferably ($C_{14}$-$C_{18}$), acyl chain linked to the N-atom through a ($C_3$-$C_6$) alkylene bridge, such as, for instance, 1,2-distearoyl-3-trimethylammonium-propane (DSTAP), 1,2-dipalmitoyl-3-trimethylammonium-propane (DPTAP), 1,2-oleoyl-3-trimethylammonium-propane (DOTAP), 1,2-distearoyl-3-dimethylammonium-propane (DSDAP); and mixtures or combinations thereof According to a preferred embodiment, at least one of the compounds forming the microbubbles' envelope is a phospholipid, optionally in admixture with any of the other above-cited materials. According to the present description, the term "phospholipids" is intended to encompass any amphiphilic phospholipid compound, the molecules of which are capable of forming a stabilizing film of material (typically in the form of a mono-molecular layer) at the gas-water boundary interface in the final microbubbles' suspension. Accordingly, these materials are also referred to in the art as "film-forming phospholipids".

Amphiphilic phospholipid compounds typically contain at least one phosphate group and at least one, preferably two, lipophilic long-chain hydrocarbon groups.

Examples of suitable phospholipids include esters of glycerol with one or preferably two residues of fatty acids (the same or different) and phosphoric acid, wherein the phosphoric acid residue is in turn bonded to a hydrophilic group, such as, for example, choline (phosphatidylcholines—PC), serine (phosphatidylserines—PS), inositol (phosphatidylinositol), glycerol (phosphatidylglycerols—PG), ethanolamine (phosphatidylethanolamines—PE), and the like groups. Esters of phospholipids with only one residue of fatty acid are generally referred to in the art as the "lyso" forms of the phospholipids or lysophospholipids. Fatty acids present in the phospholipids are in general long chain aliphatic acids, typically containing from 12 to 24 carbon atoms, preferably from 14 to 22, the aliphatic chain mat contain one or more unsaturations or is preferably completely saturated. Examples of suitable fatty acids included in the phospholipids include, for example, lauric acid, myristic acid, palmitic acid, stearic acid, arachidic acid, behenic acid, oleic acid, linoleic acid, and linolenic acid. Preferably, saturated fatty acids such as myristic acid, pamitic acid, stearic acid and arachidic acid are employed.

Further examples of phospholipids are phosphatidic acids, i.e., the diesters of glycerol-phosphoric acid with fatty acids; sphingolipids such as sphingomyelins, i.e., those phosphatidylcholine analogs where the residue of glycerol diester with fatty acids is replaced by a ceramide chain, cardiolipins, i.e. the esters of 1,3-diphosphatidylglycerol with a fatty acid, glycolipids such as gangliosides, cerebrosides, etc, glucolipids, sulfatides and glycosphingolipids. As used herein, the term "phospholipids" includes either naturally occurring, semisynthetic or synthetically prepared products that can be employed either singularly or as mixtures. Examples of naturally occurring phospholipids are natural lecithins (phosphatidylcholine (PC) derivatives) such as, typically, soya bean or egg yolk lecithins.

Examples of semisynthetic phospholipids are the partially or fully hydrogenated derivatives of the naturally occurring lecithins.

Examples of synthetic phospholipids, which are a preferred embodiment are e.g., dilauryloyl-phosphatidylcholine ("DLPC"), dimyristoylphosphatidylcholine ("DMPC"), dipalmitoyl-phosphatidylcholine ("DPPC"), diarachidoylphosphatidylcholine ("DAPC"), distearoyl-phosphatidylcholine ("DSPC"), 1-myristoyl-2-palmitoylphosphatidyl-choline ("MPPC"), 1-palmitoyl-2-myristoylphosphatidylcholine ("PMPC"), 1-palmitoyl-2-stearoylphosphatidylcholine ("PSPC"), 1-stearoyl-2-palmitoyl-phosphatidylcholine ("SPPC"), dioleoylphosphatidylycholine ("DOPC"), 1,2Distearoyl-sn-glycero-3-Ethylphosphocholine (Ethyl-DSPC), dilauryloyl-phosphatidylglycerol ("DLPG") and its alkali metal salts, diarachidoylphosphatidylglycerol ("DAPG") and its alkali metal salts, dimyristoylphosphatidylglycerol ("DMPG") and its alkali metal salts, dipalmitoyl-phosphatidylglycerol ("DPPG") and its alkali metal salts, distearolyphosphatidylglycerol ("DSPG") and its alkali metal salts, dioleoylphosphatidylglycerol ("DOPG") and its alkali metal salts, dimyristoyl phosphatidic acid ("DMPA") and its alkali metal salts, dipalmitoyl phosphatidic acid ("DPPA") and its alkali metal salts, distearoyl phosphatidic acid ("DSPA"), diarachidoyl phosphatidic acid ("DAPA") and its alkali metal salts, dimyristoyl phosphatidyl-ethanolamin-e ("DMPE"), dipalmitoyl phosphatidylethanolamine ("DPPE"), distearoyl phosphatidyl-ethanolamine ("DSPE"), dimyristoyl phosphatidylserine ("DMPS"), diarachidoyl phosphatidylserine ("DAPS"), dipalmitoyl phosphatidylserine ("DPPS"), distearoylphosphatidylserine ("DSPS"), dioleoylphosphatidylserine ("DOPS"), dipalmitoyl sphingomyelin ("DPSP"), and distearoyl sphingomyelin ("DSSP").

Preferred phospholipids are fatty acid di-esters of phosphatidylcholine, ethylphosphatidylcholine, phosphatidylglycerol, phosphatidic acid, phosphatidylethanolamine, phosphatidylserine, phophatidylinositol or of sphingomyelin. Particularly preferred phospholipids are DAPC, DSPC, DPPA, DSPA, DMPS, DPPS, DSPS and ethyl-DSPC. Most preferred are DPPS or DSPC. Mixtures of phospholipids can also be used, such as, for instance, mixtures of DSPE, DPPE, DPPC, DSPC and/or DAPC with DSPS, DPPS, DSPA, DPPA, DSPG, DPPG, Ethyl-DSPC and/or Ethyl-DPPC.

Suitable phospholipids further include phospholipids modified by linking a hydrophilic polymer, such as PEG or polypropyleneglycol (PPG) thereto. Phospholipids modified by linking PEG thereto may be referred to herein as pegylated phospholipids. Examples of modified phospholipids are phosphatidylethanolamines (PE) modified with polyethylenglycol (PEG), "PE-PEGs", i.e. phosphatidylethanolamines where the hydrophilic ethanolamine moiety is linked to a PEG molecule of variable molecular weight (e.g. from 300 to 5000 daltons), such as DPPE-PEG, DSPE-PEG, DMPE-PEG or DAPE-PEG (where DAPE is 1,2-diarachidoyl-sn-glycero-3-phosphoethanolamine.) The compositions also may contain other amphiphilic compounds including, for instance, fatty acids, such as palmitic acid, stearic acid, arachidonic acid or oleic acid; sterols, such as cholesterol, or esters of sterols with fatty acids or with sugar acids; glycerol or glycerol esters including glycerol tripalmitate, glycerol distearate, glycerol tristearate, glycerol dimyristate, glycerol trimyristate, glycerol dilaurate, glycerol trilaurate, glycerol dipalmitate; tertiary or quaternary alkyl-ammonium salts, such as 1,2-distearoyl-3-trimethylammonium-propane (DSTAP), 1,2-dipalmitoyl-3-trimethylammonium-propane (DPTAP), and mixtures or combinations thereof.

Preferably, the formulation (and particularly the microbubble envelope) includes at least on component bearing an overall net charge, such as, for instance, a charged amphiphilic material, preferably a lipid or a phospholipid. Examples of phospholipids bearing an overall negative charge are derivatives, in particular fatty acid di-ester derivatives, of phosphatidylserine, such as DMPS, DPPS, DSPS; of phosphatidic acid, such as DMPA, DPPA, DSPA; of phosphatidylglycerol such as DMPG, DPPG and DSPG or of phosphatidylinositol, such as DMPI, DPPI or DPPI. Also modified phospholipids, in particular PEG-modified phosphatidylethanolamines, such as DPPE-PEG or DSPE-PEG, can be used as negatively charged molecules. Also the lyso-form of the above cited phospholipids, such as lysophosphatidylserine derivatives (e.g. lyso-DMPS, -DPPS or -DSPS), lysophosphatidic acid derivatives (e.g. lyso-DMPA, -DPPA or -DSPA) and lysophosphatidylglycerol derivatives (e.g. lyso-DMPG, -DPPG or -DSPG), can advantageously be used as negatively charged compounds. Other examples of negatively charged compounds are bile acid salts such as cholic acid salts, deoxycholic acid salts or glycocholic acid salts; and ($C_{12}$-$C_{24}$), preferably ($C_{14}$-$C_{22}$) fatty acid salts such as, for instance, palmitic acid salts, stearic acid salts, 1,2-dipalmitoyl-sn-3-succinylglycerol salts or 1,3-dipalmitoyl-2-succinylglycerol salts.

Preferably, the negatively charged compound is selected among DPPA, DPPS, DSPG, DSPE-PEG2000, DSPE-PEG5000 or mixtures thereof.

The negatively charged component is typically associated with a corresponding positive counter-ion, which can be mono- (e.g. an alkali metal or ammonium), di- (e.g. an alkaline earth metal) or tri-valent (e.g. aluminium). Preferably the counter-ion is selected among alkali metal cations, such as $Li^+$, $Na^+$, or $K^+$, more preferably $Na^+$.

Examples of phospholipids bearing an overall positive charge are derivatives of ethylphosphatidylcholine, in particular di-esters of ethylphosphatidylcholine with fatty acids, such as 1,2-distearoyl-sn-glycero-3-ethylphosphocholine (Ethyl-DSPC or DSEPC), 1,2-dipalmitoyl-sn-glycero-3-ethylphosphocholine (Ethyl-DPPC or DPEPC). The negative counterion is preferably a halide ion, in particular chloride or bromide ion. Examples of positively charged compounds that can be incorporated into the envelope of microbubbles are mono-, di- tri-, or tetra-alkylammonium salts with a halide counter ion (e.g. chloride or bromide) comprising at least one ($C_{10}$-$C_{20}$), preferably ($C_{14}$-$C_{18}$), alkyl chain, such as, for instance mono- or di-stearylammonium chloride, mono or di-hexadecylammonium chloride, dimethyldioctadecylammonium bromide (DDAB) or hexadecyltrimethylammonium bromide (CTAB). Further examples of positively charged compounds that can be incorporated into the envelope of microbubbles are tertiary or quaternary ammonium salts with a halide counter ion (e.g. chloride or bromide) comprising one or preferably two ($C_{10}$-$C_{20}$), preferably ($C_{14}$-$C_{18}$), acyl chains linked to the N-atom through a ($C_3$-$C_6$) alkylene bridge, such as, for instance, 1,2-distearoyl-3-trimethylammonium-propane (DSTAP), 1,2-dipalmitoyl-3-trimethylammonium-propane (DPTAP), 1,2-oleoyl-3-trimethylammonium-propane (DOTAP) or 1,2-distearoyl-3-dimethylammonium-propane (DSDAP).

DSEPC, DPEPC and/or DSTAP are preferably employed as positively charged compounds in the microbubble envelope.

The positively charged component is typically associated with a corresponding negative counter-ion, which can be mono- (e.g. halide), di- (e.g. sulphate) or tri-valent (e.g. phosphate). Preferably the counter-ion is selected from among the halide ions, such as $F^-$ (fluorine), $Cl^-$ (chlorine) or $Br^-$ (bromine).

Mixtures of neutral and charged compounds, in particular of phospholipids and/or lipids, can be satisfactorily employed to form the microbubble envelope. The amount of charged lipid or phospholipid may vary from about 95 mol % to about 1 mol %, with respect to the total amount of lipid and phospholipid, preferably from 80 mol % to 20 mol %.

Preferred mixtures of neutral phospholipids and charged lipids or phospholipids are, for instance, DPPG/DSPC, DSTAP/DAPC, DPPS/DSPC, DPPS/DAPC, DPPE/DPPG, DSPA/DAPC, DSPA/DSPC and DSPG/DSPC.

In preferred embodiments, the phospholipid is the main component of the stabilizing envelope of the microbubbles, amounting to at least 50% (w/w) of the total amount of components forming the envelope of the gas-filled microbubbles. In some preferred embodiments, substantially the totality of the envelope (at least 90% and up to 100% by weight) can be formed of the phospholipid.

Any of the gases disclosed herein or known to the skilled artisan may be employed; however, inert gases, such as $SF_6$ or perfluorocarbons like $CF_4$, $C_3F_8$ and $C_4F_{10}$, are preferred, optionally in admixture with other gases such as air, nitrogen, oxygen or carbon dioxide The preferred microvesicle suspensions of the present invention may be prepared from phospholipids using known processes, such as, for example, freeze-drying or spray-drying solutions of the crude phospholipids in a suitable solvent or using the processes set forth in EP 554213; U.S. Pat. No. 5,413,774; U.S. Pat. No. 5,578,292; EP 744962; EP 682530; U.S. Pat. No. 5,556,610; U.S. Pat. No. 5,846,518; U.S. Pat. No. 6,183,725; EP 474833; U.S. Pat. No. 5,271,928; U.S. Pat. No. 5,380,519; U.S. Pat. No. 5,531,980; U.S. Pat. No. 5,567,414; U.S. Pat. No. 5,658,551; U.S. Pat. No. 5,643,553; U.S. Pat. No. 5,911,972; U.S. Pat. No. 6,110,443; U.S. Pat. No. 6,136,293; EP 619743; U.S. Pat. No. 5,445,813; U.S. Pat. No. 5,597,549; U.S. Pat. No. 5,686,060; U.S. Pat. No. 6,187,288; and U.S. Pat. No. 5,908,610, which are incorporated by reference herein in their entirety. Preferably, the phospholipids are dissolved in an organic solvent and the solution is dried without going through a liposome formation stage. This can be done by dissolving the phospholipids in a suitable organic solvent together with a hydrophilic stabilizer substance or a compound soluble both in the organic solvent and water and freeze-drying or spray-drying the solution. In this embodiment the criteria used for selection of the hydrophilic stabilizer is its solubility in the organic solvent of choice. Examples of hydrophilic stabilizer compounds soluble in water and the organic solvent are, e.g., a polymer, like polyvinyl pyrrolidone (PVP), polyvinyl alcohol (PVA), polyethylene glycol (PEG), etc., malic acid, glycolic acid, maltol, and the like. Such hydrophilic compounds also aid in homogenizing the microbubbles size distribution and enhance stability under storage. Any suitable organic solvent may be used as long as its boiling point is sufficiently low and its melting point is sufficiently high to facilitate subsequent drying. Typical organic solvents include, for example, dioxane, cyclohexanol, tertiary butanol, tetrachlorodifluoro ethylene ($C_2Cl_4F_2$) or 2-methyl-2-butanol. 2-methyl-2-butanol and $C_2Cl_4F_2$ are preferred.

Prior to formation of the suspension of microvesicles by dispersion in an aqueous carrier, the freeze dried or spray dried phospholipid powders are contacted with air or another gas. When contacted with the aqueous carrier the powdered phospholipids whose structure has been disrupted will form lamellarized or laminarized segments that will stabilize the microbubbles of the gas dispersed therein. This method permits production of suspensions of microbubbles that are stable even when stored for prolonged periods and are obtained by simple dissolution of the dried laminarized phospholipids (which have been stored under a desired gas) without shaking or any violent agitation.

Alternatively, microvesicles, and particularly microbubbles, can be prepared by suspending a gas into an aqueous solution at high agitation speed, as disclosed e.g. in WO 97/29783. Preferably, as disclosed in International patent application WO 04/069284, a microemulsion can be prepared which contains the phospholipids (e.g., DSPC and/or DSPA) in admixture with a lyoprotecting agent (such as, for instance, carbohydrates, sugar alcohols, polyglycols and mixtures thereof, as indicated in detail hereinafter) and optionally other amphiphilic materials (such as stearic acid), dispersed in an emulsion of water and of a water immiscible organic solvent. Preferred organic solvents are those having solubility in water of 1.0 g/l or lower, preferably lower about 0.01 g/l, and include, for instance, pentane, hexane, heptane, octane, nonane, decane, 1-pentene, 2-pentene, 1-octene, cyclopentane, cyclohexane, cyclooctane, 1-methyl-cyclohexane, benzene, toluene, ethylbenzene, 1,2-dimethylbenzene, 1,3-dimethylbenzene, di-butyl ether and di-isopropylketone, chloroform, carbon tetrachloride, 2-chloro-1-(difluoromethoxy)-1,1,2-trifluoroethane (enflurane), 2-chloro-2-(difluoromethoxy)-1,1,1-trifluoroethane (isoflurane), tetrachloro-1,1-difluoroethane, perfluoropentane, perfluorohexane, perfluoroheptane, perfluorononane, perfluorobenzene, perfluorodecalin, methylperfluorobutylether, methylperfluoroisobutylether, ethylperfluorobutylether, ethylperfluoroisobutylether and mixtures thereof. The fibrin binding peptide of the invention conjugated to a phospholipid (e.g. the lipopeptides discussed herein) can be admixed together with the phospholipid forming the microvesicle's envelope, in the microemulsion. Preferably, an aqueous suspension of the fibrin binding peptide-phospholipid conjugate and of a PE-PEG (e.g. DSPE-PEG2000) is first prepared, which is then admixed together with an aqueous-organic emulsion comprising the phospholipid and the lyoprotecting agent. Preferably said mixing is effected under heating, e.g. form about 40° C. to 80° C.

Other excipients or additives may be present either in the dry formulation of the microbubbles or may be added together with the aqueous carrier used for the reconstitution thereof, without necessarily being involved (or only partially involved) in the formation of the stabilizing envelope of the microbubble. These include pH regulators, osmolality adjusters, viscosity enhancers, emulsifiers, bulking agents, etc. and may be used in conventional amounts. For instance compounds like polyoxypropylene glycol and polyoxyethylene glycol as well as copolymers thereof can be used. Examples of viscosity enhancers or stabilizers are compounds selected from linear and cross-linked poly- and oligo-saccharides, sugars and hydrophilic polymers such as polyethylene glycol.

As the preparation of gas-filled microbubbles may involve a freeze drying or spray drying step, it may be advantageous to include in the formulation a lyophilization additive, such as an agent with cryoprotective and/or lyoprotective effect and/or a bulking agent, for example an amino-acid such as glycine; a carbohydrate, e.g. a sugar such as sucrose, mannitol, maltose, trehalose, glucose, lactose or a cyclodextrin, or a polysaccharide such as dextran; or a polyoxyalkyleneglycol such as polyethylene glycol.

In ultrasound applications the contrast agents formed by phospholipid stabilized microbubbles can be administered, for example, in doses such that the amount of phospholipid injected is in the range 0.1 to 200 µg/kg body weight, preferably from about 0.1 to 30 µg/kg.

Other gas containing suspensions include those disclosed in, for example, U.S. Pat. No. 5,798,091, WO 97/29783, also EP 881 915, incorporated herein by reference in their entirety. These agents may be prepared as described in U.S. Pat. No. 5,798,091 or WO97/29783.

Another preferred ultrasound contrast agent comprises ultrasound contrast agents in the form of "microballoons" of "microcapsules". The terms "microballoon" or "microcapsules" (here used interchangeably) refer to gas filled bodies with a material boundary or envelope. More on microballoon formulations and methods of preparation may be found in EP 324 938 (U.S. Pat. No. 4,844,882); U.S. Pat. No. 5,711,933; U.S. Pat. No. 5,840,275; U.S. Pat. No. 5,863,520; U.S. Pat. No. 6,123,922; U.S. Pat. No. 6,200,548; U.S. Pat. No. 4,900,540; U.S. Pat. No. 5,123,414; U.S. Pat. No. 5,230,882; U.S. Pat. No. 5,469,854; U.S. Pat. No. 5,585,112; U.S. Pat. No. 4,718,433; U.S. Pat. No. 4,774,958; WO 95/01187; U.S. Pat. No. 5,529,766; U.S. Pat. No. 5,536,490; and U.S. Pat. No. 5,990,263, the contents of which are incorporated herein by reference.

The preferred microballoons have an envelope including a biodegradable physiologically compatible polymer or, a biodegradable solid lipid. The polymers useful for the preparation of the microballoons of the present invention can be selected from the biodegradable physiologically compatible polymers, such as any of those described in any of the following patents: EP 458745, U.S. Pat. No. 5,711,933, U.S. Pat. No. 5,840,275, EP 554213, U.S. Pat. No. 5,413,774 and U.S. Pat. No. 5,578,292, the entire contents of which are incorporated herein by reference. In particular, the polymer can be selected from biodegradable physiologically compatible polymers, such as polysaccharides of low water solubility, polylactides and polyglycolides and their copolymers, copolymers of lactides and lactones such as .epsilon.-caprolactone, .gamma.-valerolactone and polypeptides. Other suitable polymers include poly(ortho)esters (see e.g., U.S. Pat. No. 4,093,709; U.S. Pat. No. 4,131,648; U.S. Pat. No. 4,138,344; U.S. Pat. No. 4,180,646); polylactic and polyglycolic acid and their copolymers, for instance DEXON (see J. Heller, Biomaterials 1 (1980), 51; poly(DL-lactide-co-.epsilon.-caprolact-one), poly(DL-lactide-co-.gamma.-valerolactone), poly(DL-lactide-co-.gamma-.-butyrolactone), polyalkylcyanoacrylates; polyamides, polyhydroxybutyrate; polydioxanone; poly-.beta.-aminoketones (A. S. Angeloni, P. Ferruti, M. Tramontini and M. Casolaro. The Mannich bases in polymer synthesis: 3. Reduction of poly(beta-aminoketone(s)) to poly(gamma-aminoalcohol(s)) and their N-alkylation to poly(gamma-hydroxyquaternary ammonium salt(s)), Polymer 23, pp 1693-1697, 1982.); polyphosphazenes (Allcock, Harry R. Polyphosphazenes: new polymers with inorganic backbone atoms (Science 193:1214-19 (1976)) and polyanhydrides. The microballoons of the present invention can also be prepared according to the methods of WO-A-96/15815, incorporated herein by reference, where the microballoons are made from a biodegradable membrane comprising biodegradable lipids, preferably selected from mono- di-, tri-glycerides, fatty acids, sterols, waxes and mixtures thereof. Preferred lipids are di- or tri-glycerides, e.g., di- or tri-myristin, -palmityn or -stearin, in particular tripalmitin or tristearin. The microballoons may employ any of the gases disclosed herein of known to the skilled artisan; however, inert gases such as fluorinated gases are preferred. The microballoons may be suspended in a pharmaceutically acceptable liquid carrier with optional additives known to those of ordinary skill in the art and stabilizers.

Other gas-containing contrast agent formulations include microparticles (especially aggregates of microparticles) having gas contained therein or otherwise associated therewith (for example being adsorbed on the surface thereof and/or contained within voids, cavities or pores therein). Methods for the preparation of these agents are as described in EP 0122624; EP 0123235; EP 0365467; U.S. Pat. No. 5,558,857; U.S. Pat. No. 5,607,661; U.S. Pat. No. 5,637,289; U.S. Pat. No. 5,558,856; U.S. Pat. No. 5,137,928; WO 95/21631 or WO 93/13809, incorporated herein by reference in their entirety.

Any of these ultrasound compositions should also be, as far as possible, isotonic with blood. Hence, before injection, small amounts of isotonic agents may be added to any of above ultrasound contrast agent suspensions. The isotonic agents are physiological solutions commonly used in medicine and they comprise aqueous saline solution (0.9% NaCl), 2.6% glycerol solution, 5% dextrose solution, etc. Additionally, the ultrasound compositions may include standard pharmaceutically acceptable additives, including, for example, emulsifying agents, viscosity modifiers, cryoprotectants, lyoprotectants, bulking agents etc.

Any biocompatible gas may be used in the ultrasound contrast agents of the invention. The term "gas" as used herein includes any substances (including mixtures) substantially in gaseous form at the normal human body temperature. The gas may thus include, for example, air, nitrogen, oxygen, $CO_2$, hydrogen, nitrous oxide, a noble or inert gas such as helium, argon, xenon or krypton, a radioactive gas such as $Xe^{133}$ or $Kr^{81}$, a hyperpolarized noble gas such as hyperpolarized helium, xenon or neon, fluorinated gases (including for example, perfluorocarbons, $SF_6$, $SeF_6$) a low molecular weight hydrocarbon (e.g., containing from 1 to 7 carbon atoms), for example, an alkane such as methane, ethane, a propane, a butane, isobutene, isopentane or pentane, a cycloalkane such as cyclobutane or cyclopentane, an alkene such as propene, propadiene or a butene, or an alkyne such as acetylene, an ether, a ketone, an ester, halogenated gases, such as halogenated, fluorinated or perfluorinated low molecular weight hydrocarbons (e.g. containing up to 7 carbon atoms) and/or mixtures thereof.

Fluorinated gases are preferred, in particular perfluorinated gases. Fluorinated gases include materials that contain at least one fluorine atom such as $SF_6$, freons (organic compounds containing one or more carbon atoms and fluorine, i.e., $CF_4$, $C_2F_6$, $C_3F_8$, $C_4F_8$, $C_4F_{10}$, $CBrF_3$, $CCl_2F_2$, $C_2ClF_5$, and $CBrClF_2$), fluorinated hydrocarbons, fluorinated ketones such as perfluoroacetone, fluorinated ethers such as perfluorodiethyl ether and perfluorocarbons. The term perfluorocarbon refers to compounds containing only carbon and fluorine atoms and includes, in particular, saturated, unsaturated, and cyclic perfluorocarbons. The saturated perfluorocarbons, which are usually preferred, have the formula $C_nF_n+2$, where n is from 1 to 12, preferably from 2 to 10, most preferably from 3 to 8 and even more preferably from 3 to 6. Examples of biocompatible, physiologically acceptable perfluorocarbons are: perfluoroalkanes, such as perfluoromethane, perfluoroethane, perfluoropropanes, perfluorobutanes (e.g. perfluoro-n-butane, optionally in admixture with other isomers such as perfluoro-isobutane), perfluoropentanes, perfluorohexanes or perfluoroheptanes; perfluoroalkenes, such as perfluoropropene, perfluorobutenes (e.g. perfluorobut-2ene) or perfluorobutadiene; perfluoroalkynes (e.g. perfluorobut-2-yne); and perfluorocycloalkanes (e.g. perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane). Preferred saturated perfluorocarbons include, for example, $CF_4$, $C_2F_6$, $C_3F_8$, $C_4F_8$, $C_4F_{10}$, $C_5F_{12}$ and $C_6F_{12}$. Most preferably the gas or gas mixture comprises $SF_6$ or a perfluorocarbon selected from the group consisting of $C_3F_8$ $C_4F_8$, $C_4F_{10}$, $C_5F_{12}$, $C_6F_{12}$, $C_7F_{14}$, $C_8F_{18}$, with $C_4F_{10}$ being particularly preferred. See also WO 97/29783, WO 98/53857, WO 98/18498, WO 98/18495, WO 98/18496, WO 98/18497, WO 98/18501, WO 98/05364, WO 98/17324.

In certain circumstances it may be desirable to include a precursor to a gaseous substance (e.g., a material that is capable of being converted to a gas in vivo, often referred to as a "gas precursor"). Preferably the gas precursor and the gas it produces are physiologically acceptable. The gas precursor may be pH-activated, photo-activated, temperature activated, etc. For example, certain perfluorocarbons may be used as temperature activated gas precursors. These perfluorocarbons, such as perfluoropentane, have a liquid/gas phase transition temperature above room temperature (or the temperature at which the agents are produced and/or stored) but below body temperature; thus they undergo a phase shift and are converted to a gas within the human body.

As discussed above, the gas can comprise a mixture of gases. The mixture may comprise any of the above gases in any ratio. In one preferred embodiment, the mixture may include a conventional gas such as nitrogen, air or carbon dioxide and a fluorinated as. Examples of suitable gas mixtures can be found in WO 94/09829, which is herein incorporated by reference. The following combinations are particularly preferred gas mixtures: a mixture of gases (A) and (B) in which, at least one of the gases (B), present in an amount of between 0.5-41% by vol., has a molecular weight greater than 80 daltons and is a fluorinated gas and (A) is selected from the group consisting of air, oxygen, nitrogen, carbon dioxide and mixtures thereof, the balance of the mixture being gas A.

For the use in MRI the microvesicles will preferably contain a hyperpolarized noble gas such as hyperpolarized neon, hyperpolarized helium, hyperpolarized xenon, or mixtures thereof, optionally in admixture with air, $CO_2$, oxygen, nitrogen, helium, xenon, or any of the halogenated hydrocarbons as defined above.

For use in scintigraphy, the microvesicle will preferably contain radioactive gases such as $Xe^{133}$ or $Kr^{81}$ or mixtures thereof, optionally in admixture with air, $CO_2$, oxygen, nitrogen, helium, krypton or any of the halogenated hydrocarbons as defined above.

Since ultrasound vesicles may be larger than the other detectable labels described herein, in one preferred embodiment they are be linked or conjugated to a plurality of fibrin-binding polypeptides in order to increase the targeting efficiency of the agent. Attachment to the ultrasound contrast agents described above (or known to those skilled in the art) may be via direct covalent bond between the fibrin-binding polypeptide and the material used to make the vesicle or via a linker, as described previously. For example, see WO 98/53857 generally for a description of the attachment of a peptide to a bifunctional PEG linker, which is then reacted with a liposome composition. See also, Lanza et al., Ultrasound in Med. & Bio., 23(6):863-870 (1997).

A number of methods may be used to prepare suspensions of microvesicles conjugated to fibrin-binding polypeptides. For example, one may prepare maleimide-derivatized microbubbles by incorporating 5% (w/w) of N-MPB-PE (1,2-dipalmitoyl-sn-glycero-3-phospho-ethanolamine-4-(p-maleimido-phenyl butyramide), (Avanti Polar-Lipids, Inc) in the phospholipid formulation. Then, solutions of mercaptoacetylated fibrin-binding peptides (10 mg/mL in DMF), which have been incubated in deacetylation solution (50 mM sodium phosphate, 25 mM EDTA, 0.5 M hydroxylamine-.HCl, pH 7.5) are added to the maleimide-activated microbubble suspension. After incubation in the dark, under gentle agitation, the peptide conjugated microbubbles may be purified by centrifugation.

Compounds that can be used for derivatization of microvesicles and particularly microbubbles typically include the following components: (a) a hydrophobic portion, compatible with the material forming the envelope of the microbubble or of the microballoon, in order to allow an effective incorporation of the compound in the envelope of the vesicle; said portion is represented typically by a lipid moiety (dipalmitin, distearoyl); and (b) a spacer (typically PEGs of different molecular weights, an amino acid chain, etc.), which may be optional in some cases (for example, microbubbles may for instance present difficulties to be freeze dried if the spacer is too long) or preferred in some others (e.g., peptides may be less active when conjugated to a microballoon with short spacers); and (c) a reactive group capable of reacting with a corresponding reacting moiety on the peptide to be conjugated (e.g., maleimido with the —SH group of cysteine).

Alternatively, fibrin-binding polypeptide conjugated microbubbles may be prepared using biotin/avidin. For example, avidin-conjugated microbubbles may be prepared using a maleimide-activated phospholipid microbubble suspension, prepared as described above, which is added to mercaptoacetylated-avidin (which has been incubated with deacetylation solution). Biotinylated fibrin-binding peptides are then added to the suspension of avidin-conjugated microbubbles, yielding a suspension of microbubbles conjugated to fibrin-binding peptides.

Additionally fibrin binding peptides may be conjugated to phospholipids, these lipopeptides may then be used to prepare gas filled microvesicle ultrasound contrast agents. Preferably, the phospholipid may be selected from the group consisting of: phosphatidylethanolamines and modified phosphatidylethanolamines. The peptide and the phospholipid may be conjugated directly or via a linker, including for example a hydrophilic polymer, an amino acid chain, etc. Particularly preferred phospholipids include phosphatidylethanolamines modified by linking a hydrophilic polymer thereto. Examples of modified phosphatidylethanolamines are phosphatidylethanolamines (PE) modified with polyethylenglycol (PEG), in brief "PE-PEGs", i.e. phosphatidylethanolamines where the hydrophilic ethanolamine moiety is linked to a PEG molecule of variable molecular weight (e.g. from 300 to 5000 daltons), such as DPPE-PEG, DSPE-PEG, DMPE-PEG or DAPE-PEG. DSPE-PEG2000, DSPE-PEG3400, DPPE-PEG2000 and DPPE-PEG3400 are preferred, with DSPE-PEG2000 particularly preferred. Note that a salt form of the phospholipid may be used, such as, for example, the trimethyl ammonium salt, the tetramethylammonium salt, the triethylammonium salt, sodium salt, etc. Methods of preparing such lipopeptides are set forth in the examples.

Some preferred methods of preparing targeted microvesicles with fibrin-binding polypeptides conjugated to phospholipids are included in the examples.

Unless it contains a hyperpolarized gas, known to require special storage conditions, the lyophilized residue may be stored and transported without need of temperature control of its environment and in particular it may be supplied to hospitals and physicians for on site formulation into a ready-to-use administrable suspension without requiring such users to have special storage facilities. Preferably in such a case it can be supplied in the form of a two-component kit, which can include two separate containers or a dual-chamber container. In the former case preferably the container is a conventional septum-sealed vial, wherein the vial containing the lyophilized residue of step b) is sealed with a septum through which the carrier liquid may be injected using an optionally prefilled syringe. In such a case the syringe used as the container of the second component is also used then for injecting the contrast agent. In the latter case, preferably the dual-chamber container is a dual-chamber syringe and once the lyophilizate has been reconstituted and then suitably mixed or gently shaken, the container can be used directly for injecting the contrast agent. In both cases means for directing or permitting application of sufficient bubble forming energy into the contents of the container are provided. However, as noted above, in the stabilized contrast agents according to the invention the size of the gas microbubbles is substantially independent of the amount of agitation energy applied to the reconstituted dried product. Accordingly, no more than gentle hand shaking is generally required to give reproducible products with consistent microbubble size.

It can be appreciated by one of ordinary skilled in the art that other two-chamber reconstitution systems capable of combining the dried powder with the aqueous solution in a sterile manner are also within the scope of the present invention. In such systems, it is particularly advantageous if the aqueous phase can be interposed between the water-insoluble gas and the environment, to increase shelf life of the product. Where a material necessary for forming the contrast agent is not already present in the container (e.g. a targeting ligand to be linked to the phospholipid during reconstitution), it can be packaged with the other components of the kit, preferably in a form or container adapted to facilitate ready combination with the other components of the kit.

No specific container, vial or connection system is required; the present invention may use conventional containers, vials and adapters. The only requirement is a good seal between the stopper and the container. The quality of the seal, therefore, becomes a matter of primary concern; any degradation of seal integrity could allow undesirable substances to enter the vial. In addition to assuring sterility, vacuum retention is essential for products stoppered at ambient or reduced pressures to assure safe and proper reconstitution. The stopper may be a compound or multicomponent formulation based on an elastomer, such as poly(isobutylene) or butyl rubber.

Ultrasound imaging techniques that can be used in accordance with the present invention include known techniques, such as color Doppler, power Doppler, Doppler amplitude, stimulated acoustic imaging, and two- or three-dimensional imaging techniques. Imaging may be done in harmonic (resonant frequency) or fundamental modes, with the second harmonic preferred.

In ultrasound applications the contrast agents formed by phospholipid stabilized microbubbles may, for example, be administered in doses such that the amount of phospholipid injected is in the range 0.1 to 200 µg/kg body weight, preferably from about 0.1 to 30 µg/kg. Microballoons-containing contrast agents are typically administered in doses such that the amount of wall-forming polymer or lipid is from about 10 µg/kg to about 20 mg/kg of body weight.

In a preferred embodiment, the ultrasound contrast agents described herein are conjugated to one or more fibrin-binding moieties. As shown in the examples, these targeted ultrasound contrast agents will localize at blood clots containing fibrin, fibrin-containing tissue or sites of angiogenesis and may be used to image clots, cancer or angiogenic tissue.

The ultrasound contrast agents of the present invention may further be used in a variety of therapeutic imaging methods. The term therapeutic imaging includes within its meaning any method for the treatment of a disease in a patient which comprises the use of a contrast imaging agent (e.g. for the delivery of a therapeutic agent to a selected receptor or tissue), and which is capable of exerting or is responsible to exert a biological effect in vitro and/or in vivo. Therapeutic imaging may advantageously be associated with the controlled localized destruction of the gas-filled microvesicles, e.g. by means of an ultrasound burst at high acoustic pressure (typically higher than the one generally employed in non-destructive diagnostic imaging methods). This controlled destruction may be used, for instance, for the treatment of blood clots (a technique also known as sonothrombolysis), optionally in combination with the localized release of a suitable therapeutic agent. Alternatively, said therapeutic imaging may include the delivery of a therapeutic agent into cells, as a result of a transient membrane permeabilization at the cellular level induced by the localized burst of the microvesicles. This technique can be used, for instance, for an effective delivery of genetic material into the cells; optionally, a drug can be locally delivered in combination with genetic material, thus allowing a combined pharmaceutical/genetic therapy of the patient (e.g. in case of tumor treatment).

The term "therapeutic agent" includes within its meaning any substance, composition or particle which may be used in any therapeutic application, such as in methods for the treatment of a disease in a patient, as well as any substance which is capable of exerting or responsible to exert a biological effect in vitro and/or in vivo. Therapeutic agents thus include any compound or material capable of being used in the treatment (including diagnosis, prevention, alleviation, pain relief or cure) of any pathological status in a patient (including malady, affliction, disease lesion or injury). Examples of therapeutic agents include those discussed herein, such as, for example, drugs, pharmaceuticals, bioactive agents, cytotoxic agents, chemotherapy agents, radiotherapeutic agents, proteins, natural or synthetic peptides, including oligopeptides and polypeptides, vitamins, steroids and genetic material, including nucleosides, nucleotides, oligonucleotides, polynucleotides and plasmids. In a preferred embodiment the therapeutic agent is a drug useful in the treatment of cancer, thrombotic disorders or angiogenic disorders.

Optical Imaging, Sonoluminescence or Photoacoustic Imaging

In another embodiment, the fibrin binding moieties of the invention may be conjugated (directly or via a linker) to an optical, sonolumiscent or photoacoustic label. In a preferred embodiment, the fibrin binding moieties of the invention are conjugated (directly or via a linker) to an optically active imaging moiety. Suitable examples of optically active imaging moieties include, for example, optical dyes, including organic chromophores or fluorophores, having extensive delocalized ring systems and having absorption or emission maxima in the range of 400-1500 nm; a fluorescent molecule such as, for example, fluorescein; a phosphorescent molecule; a molecule absorbing in the UV spectrum; a quantum dot; or a molecule capable of absorption of near or far infrared radiations. One preferred optically active moiety is 5-carboxyfluorescein (CF5).

In accordance with the present invention, a number of optical parameters may be employed to determine the location of fibrin with in vivo light imaging after injection of the subject with an optically-labeled fibrin binding moiety. Optical parameters to be detected in the preparation of an image may include transmitted radiation, absorption, fluorescent or phosphorescent emission, light reflection, changes in absorbance amplitude or maxima, and elastically scattered radiation. For example, biological tissue is relatively translucent to light in the near infrared (NIR) wavelength range of 650-1000 nm. NIR radiation can penetrate tissue up to several centimeters, permitting the use of the fibrin binding moieties of the present invention for optical imaging of fibrin in vivo.

Near infrared dye may include, cyanine or indocyanine derivatives such as, for example, Cy5.5, IRDye800, indocyanine green (ICG), indocyanine green derivatives including the tetrasulfonic acid substituted indocyanine green (TS-ICG), and combinations thereof.

The fibrin binding moieties may be conjugated with photolabels, such as optical dyes, including organic chromophores or fluorophores, having extensive delocalized ring systems and having absorption or emission maxima in the range of 400-1500 nm. The fibrin binding moiety may alternatively be derivatized with a bioluminescent molecule. The preferred range of absorption or emission maxima for photolabels is between 600 and 1000 nm to minimize interference with the signal from hemoglobin. Preferably, photoabsorption labels have large molar absorptivities, e.g. $>10^5$ cm$^{-1}$ M$^{-1}$, while fluorescent optical dyes will have high quantum yields. Examples of optical dyes include, but are not limited to those described in WO 98/18497, WO 98/18496, WO 98/18495, WO 98/18498, WO 98/53857, WO 96/17628, WO 97/18841, WO 96/23524, WO 98/47538, and references cited therein. The photolabels may be covalently linked directly to the fibrin binding moiety or linked to the fibrin binding moiety via a linker, as described previously.

After injection of the optically-labeled fibrin binding moiety, the patient is scanned with one or more light sources (e.g., a laser) in the wavelength range appropriate for the photolabel employed in the agent. The light used may be monochromatic or polychromatic and continuous or pulsed. Transmitted, scattered, or reflected light is detected via a photodetector tuned to one or multiple wavelengths to determine the location of fibrin in the subject. Changes in the optical parameter may be monitored over time to detect accumulation of the optically-labeled reagent at the site of the thrombus. Standard image processing and detecting devices may be used in conjunction with the optical imaging reagents of the present invention.

The optical imaging reagents described above may also be used for acousto-optical or sonoluminescent imaging performed with optically-labeled imaging agents (see, U.S. Pat. No. 5,171,298, WO 98/57666, and references therein). In acousto-optical imaging, ultrasound radiation is applied to the subject and affects the optical parameters of the transmitted, emitted, or reflected light. In sonoluminescent imaging, the applied ultrasound actually generates the light detected. Suitable imaging methods using such techniques are described in WO 98/57666.

Additionally, the fibrin-binding moieties of the invention may be attached to an enzyme substrate that is linked to both a light imaging reporter and a light imaging quencher. The fibrin binding moiety serves to localize the construct to the fibrin-bearing tissue of interest (e.g a tumor), where an enzyme cleaves the enzyme substrate, releasing the light imaging quencher and allowing light imaging of the fibrin-bearing tissue of interest.

Nuclear Imaging (Radionuclide Imaging) and Radiotherapy.

Fibrin-binding moieties also may be conjugated with a radionuclide reporter appropriate for scintigraphy, SPECT, or PET imaging and/or with a radionuclide appropriate for radiotherapy. Constructs in which the fibrin binding moieties are conjugated with both a chelator for a radionuclide useful for diagnostic imaging and a chelator useful for radiotherapy are within the scope of the invention.

For use as a PET agent a peptide is complexed with one of the various positron emitting metal ions, such as $^{51}$Mn, $^{52}$Fe, $^{60}$Cu, $^{68}$Ga, $^{72}$As, $^{94m}$Tc, or $^{110}$In. The binding moieties of the invention can also be labeled by halogenation using radionuclides such as $^{18}$F, $^{124}$I, $^{125}$I, $^{131}$I, $^{123}$I, $^{77}$Br, and $^{76}$Br. Preferred metal radionuclides for scintigraphy or radiotherapy include $^{99m}$Tc, $^{51}$Cr, $^{67}$Ga, $^{68}$Ga, $^{47}$Sc, $^{51}$Cr, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{61}$Cu, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{177}$Lu, $^{198}$Au and $^{199}$Au. The choice of metal will be determined based on the desired therapeutic or diagnostic application.

For example, for diagnostic purposes the preferred radionuclides include $^{64}$Cu, $^{67}$Ga, $^{68}$Ga, $^{99m}$Tc, and $^{111}$In. For therapeutic purposes, the preferred radionuclides include $^{64}$Cu, $^{90}$Y, $^{105}$Rh, $^{111}$In, $^{117m}$Sn, $^{149}$Pm, $^{153}$Sm, $^{161}$Tb, $^{166}$Dy, $^{166}$Ho, $^{175}$Yb, $^{177}$Lu, $^{186-188}$Re, and $^{199}$Au. $^{99m}$Tc is particularly preferred for diagnostic applications because of its low cost, availability, imaging properties, and high specific activity. The nuclear and radioactive properties of Tc-99m make this isotope an ideal scintigraphic imaging agent. This isotope has a single photon energy of 140 keV and a radioactive half-life of about 6 hours, and is readily available from a $^{99}$MO-$^{99m}$Tc generator.

The metal radionuclides may be chelated by a chelators. Suitable chelators include those discussed above, as well as, for example, linear, macrocyclic, terpyridine, and $N_3S$, $N_2S_2$, or $N_4$ chelators, including for example, the ligands disclosed in U.S. Pat. No. 5,367,080, U.S. Pat. No. 5,364,613, U.S. Pat. No. 5,021,556, U.S. Pat. No. 5,075,099, and U.S. Pat. No. 5,886,142, and other chelators known in the art including, but not limited to, HYNIC, and bisamino bisthiol (BAT) chelators (see also U.S. Pat. No. 5,720,934). For example, $N_4$ chelators are described in U.S. Pat. No. 6,143,274; U.S. Pat. No. 6,093,382; U.S. Pat. No. 5,608,110; U.S. Pat. No. 5,665,329; U.S. Pat. No. 5,656,254; and U.S. Pat. No. 5,688,487. Certain $N_3S$ chelators are described in PCT/CA94/00395, PCT/CA94/00479, PCT/CA95/00249 and in U.S. Pat. No. 5,662,885; U.S. Pat. No. 5,976,495; and U.S. Pat. No. 5,780,006. The chelator may also include derivatives of the chelating ligand mercapto-acetyl-acetyl-glycyl-glycine (MAG3), which contains an $N_3S$, and $N_2S_2$ systems such as MAMA (monoamidemonoaminedith-iols), DADS ($N_2$5 diaminedithiols), CODADS and the like. These ligand systems and a variety of others are described in Liu and Edwards, Chem. Rev., 99:2235-2268 (1999) and references therein.

The chelator may also include complexes containing ligand atoms that are not donated to the metal in a tetradentate array. These include the boronic acid adducts of technetium and rhenium dioximes, such as are described in U.S. Pat. No. 5,183,653; U.S. Pat. No. 5,387,409; and U.S. Pat. No. 5,118,797, the disclosures of which are incorporated by reference herein, in their entirety.

In another embodiment, disulfide bonds of a fibrin-binding polypeptide of the invention are used as two ligands for chelation of a radionuclide such as $^{99m}$Tc. In this way the peptide loop is expanded by the introduction of Tc (peptide-S—S-peptide changed to peptide-S—Tc—S-peptide). This has also been used in other disulfide containing peptides in the literature (Chen et al., J. Nucl. Med., 42:1847-1855 (2001)) while maintaining biological activity. The other chelating groups for Tc can be supplied by amide nitrogens of the backbone, another cystine amino acid or other modifications of amino acids.

Particularly preferred metal chelators include those of Formula 1, 2, and 3 (for $^{111}$In and lanthanides such as paramagnetic $Gd^{3+}$ and radioactive lanthanides, such as, for example $^{177}$Lu, $^{90}$Y, $^{153}$Sm, and $^{166}$Ho) and those of Formula 4, 5, and 6 (for radioactive $^{99m}$Tc, $^{186}$Re, and $^{188}$Re) set forth below.

These and other metal chelating groups are described in U.S. Pat. Nos. 6,093,382 and 5,608,110, which are incorporated by reference herein in their entirety. Additionally, the chelating group of Formula 3 is described in, for example, U.S. Pat. No. 6,143,274; the chelating group of Formula 5 is described in, for example, U.S. Pat. Nos. 5,627,286 and 6,093,382, and the chelating group of Formula 6 is described in, for example, U.S. Pat. Nos. 5,662,885; 5,780,006; and 5,976,495.

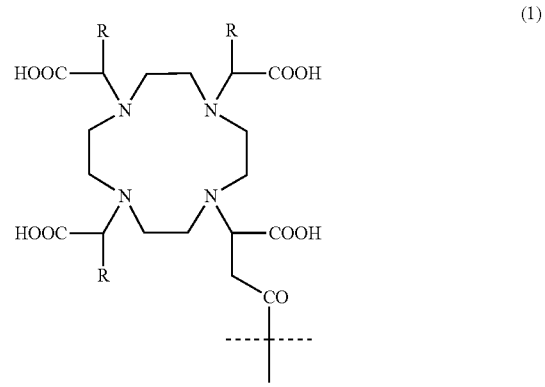

(1)

-continued (2)

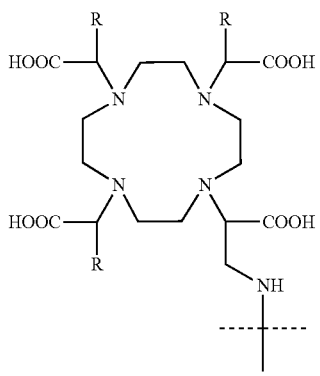

(3)

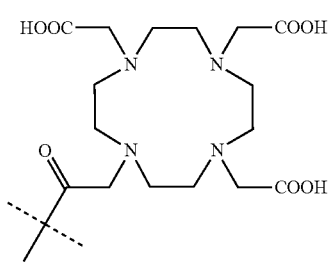

(4a)

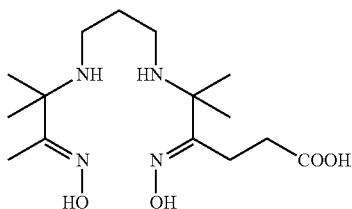

(4b)

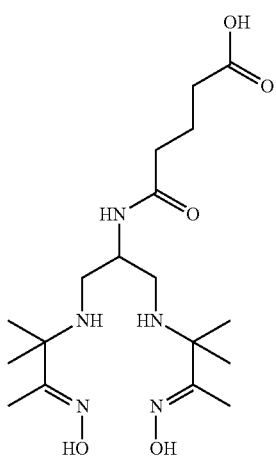

(5a)

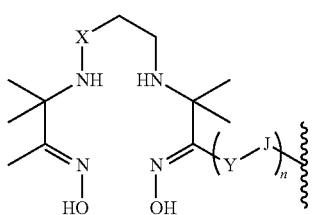

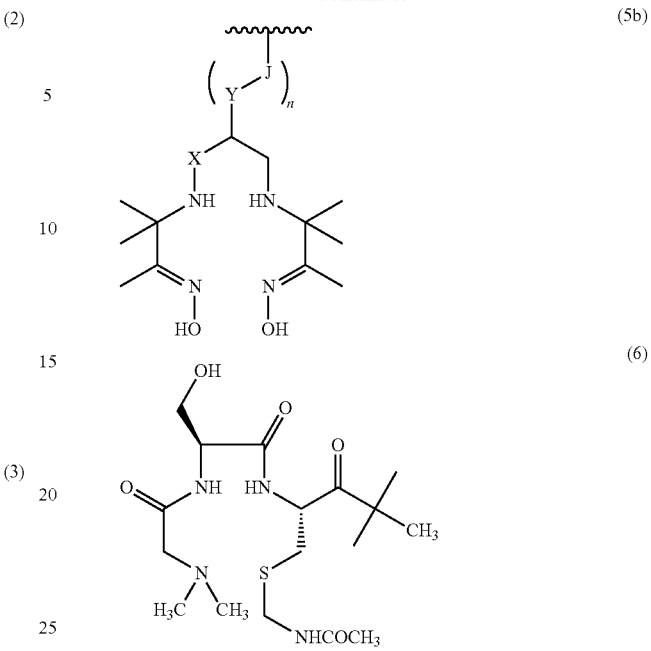

In the above Formulas 1 and 2, R is alkyl, preferably methyl. In the above Formula 5, X is either $CH_2$ or O, Y is either $C_1$-$C_{10}$ branched or unbranched alkyl; Y is aryl, aryloxy, arylamino, arylaminoacyl; Y is arylkyl—where the alkyl group or groups attached to the aryl group are $C_1$-$C_{10}$ branched or unbranched alkyl groups, $C_1$-$C_{10}$ branched or unbranched hydroxy or polyhydroxyalkyl groups or polyalkoxyalkyl or polyhydroxy-polyalkoxyalkyl groups, J is C(=O)—, OC(=O)—, $SO_2$—, NC(=O)—, NC(=S)—, N(Y), NC(=$NCH_3$)—, NC(=NH)—, N=N—, homopolyamides or heteropolyamines derived from synthetic or naturally occurring amino acids; all where n is 1-100. Other variants of these structures are described, for example, in U.S. Pat. No. 6,093,382. The disclosures of each of the foregoing patents, applications and references are incorporated by reference herein, in their entirety.

Chelators may be covalently linked directly to the fibrin-binding moiety or linked to the fibrin-binding polypeptide via a linker, as described previously, and then directly labeled with the radioactive metal of choice (see, WO 98/52618, U.S. Pat. No. 5,879,658, and U.S. Pat. No. 5,849,261).

The selection of a proper radionuclide for use in a particular radiotherapeutic application depends on many factors, including:

a. Physical half-life—This should be long enough to allow synthesis and purification of the radiotherapeutic construct from radiometal and conjugate, and delivery of said construct to the site of injection, without significant radioactive decay prior to injection. Preferably, the radionuclide should have a physical half-life between about 0.5 and 8 days.

b. Energy of the emission(s) from the radionuclide—Radionuclides that are particle emitters (such as alpha emitters, beta emitters and Auger electron emitters) are particularly useful, as they emit highly energetic particles that deposit their energy over short distances, thereby producing highly localized damage. Beta emitting radionuclides are particularly preferred, as the energy from beta particle emissions from these isotopes is deposited within 5 to about 150 cell diameters. Radiotherapeutic agents prepared from these nuclides are capable of killing diseased cells that are relatively close to their site of localization, but cannot travel long distances to damage adjacent normal tissue such as bone marrow.

c. Specific activity (i.e. radioactivity per mass of the radionuclide)—Radionuclides that have high specific activity (e.g., generator produced $^{90}$Y, $^{111}$In, $^{177}$Lu) are particularly preferred. The specific activity of a radionuclide is determined by its method of production, the particular target for which it is produce, and the properties of the isotope in question.

Many of the lanthanides and lanthanoids include radioisotopes that have nuclear properties that make them suitable for use as radiotherapeutic agents, as they emit beta particles. Some of these are listed in the table below.

TABLE 4

| Isotope | Half-Life (days) | Max b-energy (MeV) | Gamma energy (keV) | Approximate range of b-particle (cell diameters) |
|---|---|---|---|---|
| $^{149}$Pm | 2.21 | 1.1 | 286 | 60 |
| $^{153}$Sm | 1.93 | 0.69 | 103 | 30 |
| $^{166}$Dy | 3.40 | 0.40 | 82.5 | 15 |
| $^{166}$Ho | 1.12 | 1.8 | 80.6 | 117 |
| $^{175}$Yb | 4.19 | 0.47 | 396 | 17 |
| $^{177}$Lu | 6.71 | 0.50 | 208 | 20 |
| $^{90}$Y | 2.67 | 2.28 | — | 150 |
| $^{111}$In | 2.810 | Auger electron emitter | 173, 247 | <5*m | wherein: Pm is Promethium, Sm is Samarium, Dy is Dysprosium, Ho is Holmium, Yb is Ytterbium, Lu is Lutetium, Y is Yttrium, In is Indium.

The use of radioactive rhenium isotope as an alternative to above lanthanides and lanthanoids is well known in the art and is encompassed by the invention.

Particularly $^{186/188}$Re isotopes have proved to be of particular interest in nuclear medicine, having a large number of applications in radiopharmaceutical therapy.

Thus, in a preferred embodiment, the invention includes novel radiotherapeutic agents in which fibrin-binding moieties of the inventions are conjugated to a suitably chelated radionuclide that emits ionizing radiations such as beta particles, alpha particles and Auger or Coster-Kroning electrons. More preferably, the fibrin binding moiety of the invention is labelled with a lanthanide or a lanthanoid radionuclide selected from $^{90}$Y, $^{111}$In, $^{149}$Pm, $^{153}$Sm, $^{166}$Dy, $^{166}$Ho, $^{175}$Yb, and $^{177}$Lu. Examples of suitable chelating ligand may be selected from those of FIGS. 6a to 6c.

The compounds of the invention labeled with therapeutic radionuclides can find application either as a radiopharmaceutical that will be used as a first line therapy in the treatment of a disease such as cancer, or in combination therapy, where the radiotherapeutic agents of the invention could be utilized in conjunction with adjuvant chemotherapy (e.g, with one of the other therapeutic agents disclosed herein), or as the therapeutic part of a matched pair therapeutic agent.

In fact, the peptide moiety of the radiotherapeutic of the invention is able to localize the chelated radioactive isotope to the pathologic fibrin deposition, for instance, into thrombi/clots, atherosclerois plaques and inflammation-based damage involved in multiple sclerosis and, especially within solid tumors. The cytotoxic amount of ionizing radiation emitted by the localized radioisotope is thus able to cause the cell death of the pathologic tissue.

Complexes of radioactive technetium are particularly useful for diagnostic imaging and complexes of radioactive rhenium are particularly useful for radiotherapy. In forming a complex of radioactive technetium with the reagents of this invention, the technetium complex, preferably a salt of Tc-99m pertechnetate, is reacted with the reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a reagent of the invention to be labeled and a sufficient amount of reducing agent to label the reagent with Tc-99m.

Alternatively, the complex may be formed by reacting a peptide of this invention conjugated with an appropriate chelator with a pre-formed labile complex of technetium and another compound known as a transfer ligand. This process is known as ligand exchange and is well known to those skilled in the art. The labile complex may be formed using such transfer ligands as tartrate, citrate, gluconate or mannitol, for example. Among the Tc-99m pertechnetate salts useful with the present invention are included the alkali metal salts such as the sodium salt, or ammonium salts or lower alkyl ammonium salts.

Preparation of the complexes of the present invention where the metal is radioactive rhenium may be accomplished using rhenium starting materials in the +5 or +7 oxidation state. Examples of compounds in which rhenium is in the Re(VII) state are $NH_4ReO_4$ or $KReO_4$. Re(V) is available as, for example, [$ReOC_4$](NBu$_4$), [$ReOCl_4$](AsPh4), $ReOCl_3$ (PPh$_3$)$_2$ and as $ReO_2$(pyridine)$^{++}$, where Ph is phenyl and Bu is n-butyl. Other rhenium reagents capable of forming a rhenium complex may also be used.

Radioactively-labeled scintigraphic imaging agents provided by the present invention are provided having a suitable amount of radioactivity. In forming Tc-99m radioactive complexes, it is generally preferred to form radioactive complexes in solutions containing radioactivity at concentrations of from about 0.01 mCi to 100 mCi per mL.

Generally, the unit dose to be administered has a radioactivity of about 0.01 mCi to about 100 mCi, preferably 1 mCi to 20 mCi. The solution to be injected at unit dosage is from about 0.01 mL to about 10 mL.

Typical doses of a radionuclide-labeled fibrin-binding imaging agent according to the invention provide 10-20 mCi for an adult human. After injection of the fibrin-specific radionuclide imaging agent into the patient, a gamma camera calibrated for the gamma ray energy of the nuclide incorporated in the imaging agent is used to image areas of uptake of the agent and quantify the amount of radioactivity present in the site. Imaging of the site in vivo can take place in a matter of a few minutes. However, imaging can take place, if desired, hours or even longer, after the radiolabeled peptide is injected into a patient. In most instances, a sufficient amount of the administered dose will accumulate in the area to be imaged within about 0.1 of an hour to permit the taking of scintiphotos.

Proper dose schedules for the radiotherapeutic compounds of the present invention are known to those skilled in the art. The compounds can be administered using many methods that include, but are not limited to, a single or multiple IV or IP injections, using a quantity of radioactivity that is sufficient to cause damage or ablation of the targeted fibrin-containing tissue, but not so much that substantive damage is caused to non-target (normal tissue). The quantity and dose required is different for different constructs, depending on the energy and half-life of the isotope used, the degree of uptake and clearance of the agent from the body and the mass of the tumor. In general, doses can range from a single dose of about 30-50 mCi to a cumulative dose of up to about 3 Curies for an adult human.

The radiotherapeutic compositions of the invention can include physiologically acceptable buffers, and can require radiation stabilizers to prevent radiolytic damage to the compound prior to injection. Radiation stabilizers are known to those skilled in the art, and may include, for example, para-aminobenzoic acid, ascorbic acid, gentistic acid and the like.

A single, or multi-vial kit that contains all of the components needed to prepare the complexes of this invention, other than the radionuclide, is an integral part of this invention.

A single-vial kit preferably contains a chelating ligand, a source of stannous salt, or other pharmaceutically acceptable reducing agent, if required, and is appropriately buffered with pharmaceutically acceptable acid or base to adjust the pH to a value of about 3 to about 9. The quantity and type of reducing agent used would depend highly on the nature of the exchange complex to be formed. The proper conditions are well known to those that are skilled in the art. It is preferred that the kit contents be in lyophilized form. Such a single vial kit may optionally contain labile or exchange ligands such as glucoheptonate, gluconate, mannitol, malate, citric or tartaric acid and can also contain reaction modifiers such as diethylenetriamine-pentaacetic acid (DPTA), ethylenediamine tetraacetic acid (EDTA), or $\alpha$, $\beta$, or $\gamma$ cyclodextrin that serve to improve the radiochemical purity and stability of the final product. The kit may also contain stabilizers, bulking agents such as mannitol, that are designed to aid in the freeze-drying process, and other additives known to those skilled in the art.

A multi-vial kit preferably contains the same general components but employs more than one vial in reconstituting the radiopharmaceutical. For example, one vial may contain all of the ingredients that are required to form a labile Tc(V) complex on addition of pertechnetate (e.g., the stannous source or other reducing agent). Pertechnetate is added to this vial, and after waiting an appropriate period of time, the contents of this vial are added to a second vial that contains the ligand, as well as buffers appropriate to adjust the pH to its optimal value. After a reaction time of about 5 to 60 minutes, the complexes of the present invention are formed. It is advantageous that the contents of both vials of this multi-vial kit be lyophilized. As above, reaction modifiers, exchange ligands, stabilizers, bulking agents, etc. may be present in either or both vials.

Therapeutic Applications

In another embodiment of the invention, a fibrin-binding moiety of the invention is conjugated to a therapeutic agent (also referred to as a therapeutically active agent or moiety).

Unless otherwise provided, the term "therapeutic" as used herein includes at least partial alleviation of symptoms of a given condition. The therapeutically active agents do not have to produce a complete alleviation of the symptoms to be useful. For example, treatment of an individual can result in a decrease in the size of a tumor or diseased area or a blood clot, or even prevention of an increase in size of the tumor or diseased area, as well as partial alleviation of other symptoms. Alternatively, treatment can also result in the reduction in the number of blood vessels in an area of interest or can prevent an increase in their number. Treatment can also prevent or lessen the number or size of metastatic outgrowths of the main tumor(s).

Suitable examples of therapeutic agents according to the present invention include anticoagulant-thrombolytic or fibrinolytic agents capable of clots lysis, anti-angiogenic agents, cytotoxic agents including chemotherapeutic or tumoricidal agents for selective killing and/or inhibiting the growth of cancer cells and, especially, radiotherapeutic agents.

In one embodiment the therapeutic agent is a thrombolytic or fibrinolytic agent. The fibrin-binding peptides of the present invention can be used to improve the activity of thrombolytic and anti-angiogenic agents by improving their affinity for fibrin and their residence time at a fibrin clot or at a site of pathological angiogenic activity. In this aspect of the invention, hybrid thrombolytic agents are provided by conjugating a fibrin binding polypeptide according to the invention with a thrombolytic agent. Likewise, anti-angiogenic agents are provided by conjugating a fibrin-binding polypeptide according to the invention with an anti-angiogenic agent. The fibrin binding polypeptide portion of the conjugate causes the thrombolytic to "home" to the sites of fibrin clots or sites of angiogenesis, and to improve the affinity of the conjugate for such sites, so that the thrombolytic or anti-angiogenic activity of the conjugate is more localized and concentrated at the sites of interest.

Such conjugates will be especially useful in treating thrombus associated diseases, especially acute myocardial infarction, stroke and pulmonary embolism in mammals, including humans, which method comprises administering to a mammal in need thereof an effective amount of a fibrin binding moiety according to the invention conjugated with a thrombolytic agent. The invention also provides the use of such conjugates in the manufacture of a medicament for the treatment of thrombus associated diseases in mammals, including humans. Suitable thrombolytic agents for use in this aspect of the invention include fibrinolytic enzymes, including plasminogen activators. The term plasminogen activator includes but is not limited to streptokinase, human tissue plasminogen activator (tPA) and urokinase (both single and two-chain forms). Such enzymes are obtained from natural sources or tissues or by recombinant production. Other suitable thrombolytic agents include fibrinolytically active hybrid proteins (see, e.g., EP-A-155 387) which comprise one chain of a 2-chain protease linked to a chain of a different 2-chain protease, at least one of the chains in the hybrid protein being derived from a fibrinolytically active protease; thrombolytic protein conjugates (see, e.g., EP-A-152 736), such as urokinase linked to reversibly blocked plasmin; derivatives of fibrinolytic enzymes in which the catalytic site on the enzyme which is responsible for fibrinolytic activity is blocked by a human protein attached thereto by way of a reversible linking group, for example urokinase reversibly linked to the active center of human plasmin; genetically engineered derivatives including muteins of naturally occurring plasminogen activators; hybrid molecules (see, e.g., EP-A-297 882); reversibly blocked in vivo fibrinolytic enzymes, such as a binary complex between streptokinase and plasminogen, most preferably a p-anisoyl streptokinase/plasminogen complex without internal bond cleavage (anistreplase, described in U.S. Pat. No. 4,808,405); and the like.

The thrombolytic agents and the fibrin binding moieties can be linked or fused in known ways, using the same type of linkers discussed above. Preferred linkers will be substituted or unsubstituted alkyl chains, amino acid chains, polyethylene glycol chains, and other simple polymeric linkers known in the art. More preferably, if the thrombolytic agent is itself a protein, for which the encoding DNA sequence is known, the thrombolytic protein and fibrin binding polypeptide may be coexpressed from the same synthetic gene, created using recombinant DNA techniques. The coding sequence for the fibrin binding polypeptide may be fused in frame with that of the thrombolytic protein, such that the peptide is expressed at the amino- or carboxy-terminus of the thrombolytic protein, or at a place between the termini, if it is determined that such placement would not destroy the required biological function of either the thrombolytic protein or fibrin binding polypeptide. A particular advantage of this general approach is that concatamerization of multiple, tandemly arranged fibrin binding polypeptides is possible, thereby increasing the number and concentration of fibrin binding sites associated with each thrombolytic protein. In this manner fibrin binding avidity is increased which would be expected to improve the efficacy of the recombinant therapeutic protein.

In addition to thrombolytic agents, the fibrin binding peptides according to this invention can be used to deliver other active agents to sites of fibrin in vivo or in vitro. For example, small molecule therapeutics or other therapeutic agents may be linked to one or more fibrin binding peptides and the conjugate administered to a subject or introduced to a fibrin-containing solution, and the fibrin-binding properties of the conjugate will concentrate the small molecule or therapeutic agent at the sites of fibrin accumulation. In a particularly preferred aspect, the fibrin binding peptides of the invention may be used to deliver agents which are active in the presence of fibrin, such as angiogenesis promoters (e.g., fibroblast growth factor). The fibrin binding peptides may also be used to increase the blood clearance half-life of a compound or drug, by causing accumulation of the compound or drug in fibrin clots, from which it will be gradually released.

The fibrin-binding polypeptides of the present invention may also be used to target genetic material to specific cells. For example, the binding peptides of the present invention may be used to localize genetic material to cells or tissue containing fibrin. Thus such constructs may be useful in gene therapy. The genetic material may include nucleic acids, such as RNA or DNA, of either natural or synthetic origin, including recombinant RNA and DNA and antisense RNA and DNA. Types of genetic material that may be used include, for example, genes carried on expression vectors such as plasmids, phagemids, cosmids, yeast artificial chromosomes (YACs) and defective or "helper" viruses, antigene nucleic acids, both single and double stranded RNA and DNA and analogs thereof, such as phosphorothioate and phosphorodithioate oligodeoxynucleotides. Additionally, the genetic material may be combined, for example, with lipids, proteins or other polymers. Delivery vehicles for genetic material may include, for example, a virus particle, a retroviral or other gene therapy vector, a liposome, a complex of lipids (especially cationic lipids) and genetic material, a complex of dextran derivatives and genetic material, etc.

In a preferred embodiment the binding polypeptides of the invention are utilized in gene therapy for treatment of diseases associated with angiogenesis. In this embodiment, genetic material, or one or more delivery vehicles containing genetic material, e.g., useful in treating an angiogenesis-related disease, may be conjugated to one or more fibrin-binding peptides of the invention and administered to a patient.

In the above treatment methods, the compounds may be administered by any convenient route customary for thrombolytic or therapeutic agents, for example parenterally, enterally or intranasaly, and preferably by infusion or bolus injection, or by depot or slow release formulation. In a preferred embodiment, the composition may be formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anaesthetic such as lignocaine to ease pain at the site of the injection. Generally, the ingredients will be supplied either separately or mixed together in unit dosage form, for example, as a dry lyophilized powder or water free concentrate in a hermetically sealed container such as an ampoule or sachette indicating the quantity of active agent in activity units. Where the composition is to be administered by infusion, it can be dispensed with an infusion bottle containing sterile pharmaceutical grade "water for injection" or saline. Where the composition is to be administered by injection, an ampoule of sterile water for injection or saline may be provided so that the ingredients may be mixed prior to administration.

The quantity of material administered will depend on the seriousness of the thromboembolic condition and position and size of the clot. The precise dose to be employed and mode of administration must per force in view of the nature of the complaint be decided according to the circumstances by the physician supervising treatment. In general, dosages of the fibrin binder/thrombolytic agent conjugate will follow the dosages that are routine for the thrombolytic agent alone, although the improved affinity for fibrin added by the fibrin binder component may allow a decrease in the standard thrombolytic dosage. Particular thrombolytics contemplated for use in this therapy (with examples of dose and method of administration) are as follows:

1 streptokinase 1.0-3.0 megaunits over 30 minutes to 3 hours anistreplase 30 units; 2-minute injection tPA (wild-type) 50-150 mg; infusion over up to 6 hours two-chain urokinase 40-100 mg; infusion over up to 6 hours single-chain urokinase (3-12 megaunits) 30-100 mg; infusion over up to 5 hours hybrid plasminogen 20-100 mg; injection or infusion activators and derivatives muteins of plasminogen 10-100 mg; injection or infusion activators In preferred features, the fibrin binding moiety is linked to the thrombolytic agent with a linker encompassing an enzymatic cleavage site, e.g., an enzymatic cleavage site normally cleaved by enzymes in the coagulation cascade, such as Factor Xa, thrombin, or plasmin cleavage sites, etc. The thrombolytic agent preferably would not be activated until it is cleaved from the fibrin binding moiety at the site of the clot. Since cleavage of the thrombolytic agent would occur at the site of the clot, the risk of unwanted bleeding events at sites distant from the clot would be minimized.

Alternatively, a therapeutic thrombolytic can be loaded into an ultrasound vesicle that has been derivatized on its surface with the fibrin binding moieties of the present invention. The vesicle may also be filled with an ultrasound efficient gas, such as, but not limited to, perfluoropropane or perfluorobutane. Once the fibrin-specific vesicle has homed to the site of a thrombus, as monitored by ultrasound, the frequency and energy of the ultrasound waves administered can be altered to result in a controlled release of the thrombolytic at the site of the thrombus (see, e.g., WO 93/25241).

As discussed above fibrin-binding peptides of the present invention also can be used to improve the activity of therapeutic agents such as anti-angiogenic or tumoricidal agents against undesired angiogenesis such as occurs in neoplastic tumors, by homing in on areas undergoing angiogenesis so that the therapeutic activity can be more localized and concentrated at the sites of angiogenesis.

In this aspect of the invention, hybrid agents are provided by conjugating a fibrin-binding polypeptide according to the invention with a therapeutic agent. The therapeutic agent may be a radiotherapeutic, discussed above, a drug, chemotherapeutic or tumoricidal agent, genetic material or a gene delivery vehicle, etc. Such conjugates will be useful in treating angiogenesis-associated diseases, especially neoplastic tumor growth and metastasis, in mammals, including humans, which method comprises administering to a mammal in need thereof an effective amount of a fibrin-binding polypeptide according to the invention conjugated with a therapeutic agent. The invention also provides the use of such conjugates in the manufacture of a medicament for the treatment of angiogenesis associated diseases in mammals, including humans.

Suitable therapeutic agents for use in this aspect of the invention include, but are not limited to: antineoplastic agents, such as platinum compounds (e.g., spiroplatin, cisplatin, and carboplatin), methotrexate, adriamycin, mitomycin, ansamitocin, bleomycin, cytosine, arabinoside, arabinosyl adenine, mercaptopolylysine, vincristine, busulfan, chlorambucil, melphalan (e.g., PAM, L-PAM, or phenylalanine mustard), mercaptopurine, mitotane, procarbazine hydrochloride, dactinomycin (actinomycin D), daunorubcin hydrochloride, doxorubicin hydrochloride, taxol, mitomycin, plicamycin (mithramycin), aminoglutethimide, estramustine phosphate sodium, flutamide, leuprolide acetate, megestrol acetate, tamoxifen citrate, testoiactone, trilostane, amsacrine (m-AMSA), aparaginase (L-aparaginase), Erwina aparaginase, etoposide (VP-16), interferon cx-2a, Interferon cx-2b, teniposide (VM-26, vinblastine sulfate (VLB), vincristine sulfate, bleomycin sulfate, adriamycin, and arabinosyl; antiangiogenic agents such as tyrosine kinase inhibitors with activity toward signaling molecules important in angiogenesis and/or tumor growth such as SU5416 and SU6668 (Sugen/Pharmacia & Upjohn), endostatin (EntreMed), angiostatin (EntreMed), Combrestatin (Oxigene), cyclosporine, 5-fluorouracil, vinblastine, doxorubicin, paclitaxel, daunorubcin, immunotoxins; coagulation factors; antivirals such as acyclovir, amantadine azidothymidine (AZT or Zidovudine), ribavirin and vidarabine monohydrate (adenine arahinoside, ara-A); antibiotics, antimalarials, antiprotozoans such as chloroquine, hydroxychloroquine, metroidazole, quinine and meglumine antimonate; anti-inflammatories such as diflunisal, ibuprofen, indomethacin, meclofenamate, mefenamic acid, naproxen, oxyphenbutazone, phenylbutazone, piroxicam, sulindac, tolmetin, aspirin and salicylates.

As used herein the term "therapeutic" includes at least partial alleviation of symptoms of a given condition. The fibrin-binding peptides and conjugates of the present invention do not have to produce a complete alleviation of symptoms to be useful. For example, treatment of an individual can result in a decrease in the size of a tumor or diseased area, or a blood clot or prevention of an increase in size of the tumor or diseased area or partial alleviation of other symptoms. Treatment can result in reduction in the number of blood vessels in an area of interest or can prevent an increase in the number of blood vessels in an area of interest. Treatment can also prevent or lessen the number or size of metastatic outgrowths of the main tumor(s).

Pharmaceutical Applications

Whether the fibrin binding moieties are to be used in patients for detection and diagnosis or to facilitate the therapy, such uses require that they be treated as pharmaceutical agents. Pharmaceutical compositions of this invention comprise any of the compounds of the present invention, and pharmaceutically acceptable salts thereof, with any pharmaceutically acceptable ingredient, excipient, carrier, adjuvant or vehicle.

Pharmaceutical compositions of this invention can be administered to mammals including humans in a manner similar to other diagnostic or therapeutic agents. The dosage to be administered, and the mode of administration will depend on a variety of factors including age, weight, sex, condition of the patient, and genetic factors, and will ultimately be decided by the attending physician or veterinarian. In general, dosage required for diagnostic sensitivity or therapeutic efficacy will range from about 0.001 to 50,000 µg/kg, more usually 0.01 to 25.0 µg/kg of host body mass.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered by a variety of routes or modes. These include, but not limited, to oral, intratracheal, sublingual, pulmonary, topical, rectal, nasal, buccal, vaginal, parenteral, or via an implanted reservoir. Implanted reservoirs may function by mechanical, osmotic, or other means. The term parenteral as used herein includes intraperitoneal, paravertebral, periarticular, periostal, subcutaneous, intracutaneous, intravenous, intra-arterial, intramuscular, intra-articular, intrasynovial, intrasternal, intrathecal, intralesional and intracranial injection or infusion techniques.

Such compositions are preferably formulated for parenteral administration, and most preferably for intravenous or intra-arterial administration. Generally, and particularly when administration is intravenous or intra-arterial, pharmaceutical compositions may be given as a bolus, as two or more doses separated in time, or as a constant or non-linear flow infusion.

Details concerning dosages, dosage forms, modes of administration, composition and the like are further discussed in a standard pharmaceutical text, such as Remington's Pharmaceutical Sciences, 18th ed., Alfonso R. Gennaro, ed. (Mack Publishing Co., Easton, Pa. 1990), which is hereby incorporated by reference.

As discussed supra, one embodiment of the present invention relates to novel compounds comprising a fibrin-binding moiety conjugated with at least one diagnostically or therapeutically active moiety.

In particular, a preferred embodiment of the present invention includes compounds of general Formula (I)

$$A[-Y(-T)_r]_s \quad (I)$$

wherein

A is a fibrin-binding peptide moiety comprising an amino acid sequence selected from the group consisting of the sequences provided in Table 1 or Table 2;

Y is a suitable linking moiety connecting A with at least one T; when s is 2, the units Y may be the same or different from each other;

T is, independently in each occurrence, a diagnostically or therapeutically active moiety;

s is 1 or 2, r is, independently in each occurrence, an integer from 1 to 8;

or a physiologically acceptable salt thereof

Unless otherwise specified, the phrases "fibrin-binding peptide moiety" or, simply, "peptide moiety," used herein interchangeably, refer to a suitable derivative of the corresponding fibrin-binding peptide of the sequences disclosed herein, in which one or both of the N-terminal (—NH$_2$) and the C-terminal (—COOH) groups of the peptide are functionalized through formation of a carboxamido bond with Y. If the C-terminal or N-terminal group is not functionalized, it may be suitably protected or deactivated. Thus, "fibrin-binding peptide moiety" refers to that moiety resulting from the original amino acid sequence of the fibrin-binding peptide, following the said optional protection/deactivation and the said carboxamido bond(s) formation.

Typically, for instance, in the case of the fibrin-binding peptide having the amino acid sequence of Seq005 as shown in Table 1, H$_2$N-WQPCPAESWTFCWDP-COOH (SEQ ID NO. 1), the corresponding fibrin-binding peptide moieties include, for instance:

-HN-WQPCPAESWTFCWDP-CO—,

Pg-HN-WQPCPAESWTFCWDP-CO—, and

-HN-WQPCPAESWTFCWDP-CO-Pg in which Pg is a suitable protecting/deactivating group.

In the present invention, unless otherwise indicated, the phrase "protecting group", designates a protective group adapted to preserving the function of the functional group to which it is bound. Specifically, protective groups are used to preserve amino function or carboxyl function. Appropriate protective groups may include, for example, benzyl, benzyloxycarbonyl, alkyl or benzyl esters, or other substituents commonly used for the protection of such functions, which are well known to those skilled in the art, for example Fmoc, and protective groups described in conventional manuals such as T. W. Green, Protective Groups in Organic Synthesis (Wiley, N.Y. 1981).

Unless otherwise indicated, the phrase "deactivating group" as used herein, refers to chemical groups that are able to react with the N-terminal (—NH$_2$) or the C-terminal (—COOH) group of the peptide unit transforming it, through a chemical reaction, into a suitable derivative thereof that maintains the specificity of the corresponding peptide moiety toward fibrin, but is unable to chemically react with, respectively, a (—COOH) or an (—NH$_2$) functionality on a different moiety, and thus may not be involved in carboxamido cross-linking reaction.

Suitable examples of deactivating groups comprise Ac, where Ac is CH$_3$(CO)—when used, for instance, to deactivate an (—NH$_2$) terminal group of the peptide chain to the corresponding, unreactive, AcHN— group. On the other side, —NH$_2$ or —NH(CH$_3$), may be, for instance, used to deactivate a terminal —COOH group by providing the corresponding —CONH$_2$ or —CONH(CH$_3$) unreactive amide.

According to a preferred aspect of the invention, within the compounds of Formula (I), A is a fibrin-binding peptide moiety comprising the amino acid sequence of Seq005 as shown in Table 1, H$_2$N-WQPCPAESWTFCWDP-COOH (SEQ ID NO.1), in which each of the W, Q, P, C, A, E, S, T, F and D has the meaning conventionally adopted when defining amino acids according to one letter code and in which the C amino acids in positions 4 and 12 are bonded to each other through a disulfide (—S—S—) bond.

According to another preferred aspect of the invention, within the compounds of Formula (I), s is 1. The compounds of the invention having s=1 include, independently in each occurrence, one or more diagnostically of therapeutically active moiety or moieties T conjugated, through a suitable linking moiety Y, to the N-terminal (—NH$_2$) or, conversely, to the C-terminal (—COOH) group of the peptide moiety, thus resulting in a compound of Formula (I) in which the peptide moiety A is functionalized at only one of its N- or C-terminal groups.

According to another preferred aspect of the invention, within the compounds of Formula (I), s is 2. The compounds of the invention in which s=2 include, independently in each occurrence, one or more diagnostically of therapeutically active moiety or moieties T conjugated, through a suitable linking moiety Y, to each of the N-terminal (—NH$_2$) and the C-terminal (—COOH) groups of the peptide moiety A, thus resulting in compounds of Formula (I) in which the peptide moiety is functionalized at both of the N- and C-terminal groups.

According to another preferred aspect of the invention, within the compounds of Formula (I), r is an integer from 1 to 5.

In one preferred embodiment of the invention Y is a linear or branched divalent linking moiety. The phrase "divalent linking moiety" (or "divalent linker", used herein interchangeably) is intended to include a chain including a functional group which permits the conjugation of the linking moiety with the N- or the C-terminal group of A and, a second functional group which permits conjugation with a diagnostically or a therapeutically effective moiety T.

Unless otherwise indicated, the term "functional group" as used herein refers to specific groups of atoms within molecules or moieties that are responsible for the characteristic chemical reactions of those molecules or moieties. In the context of the invention, the functional groups include the specific, suitably protected or suitably activated —NH$_2$ terminal or —COOH terminal groups of the peptide moiety, of the linking moiety and of the diagnostically or therapeutically active moiety. In addition, these functional groups may include any other amine, thiol, carboxyl group present as a free group or as an optionally activated reactive group on the said linking, diagnostically or therapeutically active moiety, thus allowing other cross-linking or coupling reactions. In a preferred aspect of the present invention, the functional group are suitably protected or suitably activated —NH$_2$ or —COOH groups allowing cross-linking reaction through carboxamido bonds (—NHCO—) and (—CONH—) formation.

Preferably, the divalent linking moiety is a linear $C_1$-$C_{100}$ and, more preferably, a $C_1$-$C_{50}$, and, most preferably, a $C_1$-$C_{35}$ alkyl chain, that is optionally interrupted by one or more groups selected from —O—, —CONH—, —CO—, —NR$_1$— and —NHCO—, and optionally substituted by one or more —R$_2$ group(s), wherein R$_1$ is H or a $C_1$-$C_5$ alkyl group, and R$_2$ is a —CONH$_2$ group or a ($C_1$-$C_5$)alkyl group, that is optionally substituted, in its turn, by a —CONH$_2$ group or by an optionally substituted benzene ring. As discussed supra, the said divalent linker includes two functional groups connecting it, respectively, with A and with T.

Unless otherwise provided, the term "($C_1$-$C_5$) alkyl" as used herein, designates a linear or branched, saturated or unsaturated alkyl substituent comprising from 1 to 5 carbon atoms such as, for example, methyl, ethyl, propyl, isopropyl, butyl, tert-butyl, pentyl and the like, wherein methyl, ethyl and propyl are preferred. More preferably, the divalent linking moiety Y includes one or more sub-units selected, for instance, from homobifunctional and heterobifunctional units and suitable combinations thereof.

Unless otherwise provided, the term "homobifunctional" unit or moiety, refers to a unit or moiety having at least two reactive functional groups which are the same.

Unless otherwise provided, the term "heterobifunctional" unit or moiety, refers to a unit or moiety having at least two different reactive groups.

Suitable examples of homobifunctional units include, for instance, dicarboxylic moieties and diamine moieties having formula, respectively, —OC—Z—CO—, and

—NH—Z—NH—, where Z is a chain preferably selected from the following:

—(CH$_2$)$_n$—,

—CH$_2$—(CH$_2$O)$_m$—,

—(CH$_2$(CH$_2$)$_p$O)$_m$—(CH$_2$)$_m$—,

—(CH$_2$)$_n$—NHCO—(CH$_2$)$_n$—,

—(CH$_2$)$_n$—NHCO—CH$_2$O—(CH$_2$(CH$_2$)$_p$O)$_m$—(CH$_2$)$_m$—,

—(CH$_2$)$_p$—CH(R$_2$)—(CH$_2$)$_m$—,

—(CH$_2$)$_p$—CH(R$_2$)—(CH$_2$)$_m$—NHCO—CH$_2$O—(CH$_2$(CH$_2$)$_p$O)$_m$—(CH$_2$)$_m$—, where n=1-10, m=1-5 and p=0-5, and derivatives thereof in which the carboxylic and the amino group(s) are in a suitably activated or protected form.

Suitable examples of heterobifunctional units, for instance, include:

—HN—(CH$_2$)$_n$—CO—,

HN—(CH$_2$)$_n$—CH(R$_2$)—CO—,

—HN—(CH$_2$)$_2$O—(CH$_2$)$_2$O—CH$_2$—CO—,

—HN—(CH$_2$)$_p$—CH(R$_2$)—(CH$_2$)$_m$CO—,

—OC—CH(NR$_1$)—(CH$_2$)$_m$—NH—,

—OC—(CH$_2$)$_m$—NHOC—(CH$_2$)$_m$O—(CH$_2$)$_m$—NH—,

—HN—(CH$_2$)$_p$—CH(R$_2$)—(CH$_2$)$_m$—NHCO—CH$_2$O—(CH$_2$(CH$_2$)$_p$O)$_m$—(CH$_2$)$_m$—NH—, wherein n, m and p are as above defined, and suitable combinations thereof.

More preferably, the divalent linking moiety Y of the invention comprises one of the following units:

—HN—CH$_2$—CO—,

—OC—(CH$_2$)$_n$—CO—,

—NH—(CH$_2$)$_2$—O—(CH$_2$)$_2$—O—CH$_2$—CO—,

—HN—CH(CONH$_2$)—(CH$_2$)$_m$—NH—,

—NH—CH(CONH$_2$)—(CH$_2$)$_m$—NHCO—(CH$_2$)$_n$—CO—,

—CO—CH$_2$O—(CH$_2$)$_{2-0}$—(CH$_2$)$_2$—NHCO—CH$_2$O—(CH$_2$)$_2$—O—(CH$_2$)$_2$—NH—, or a suitable repetition and/or combination thereof In a particularly preferred aspect of the invention, the divalent linking moiety Y is or comprises the unit -Gly-Gly-Gly-Lys in which Gly is Glycine and Lys is Lysine, also referred to as GGGK.

In a different embodiment of the invention, Y is a linear or branched polyfunctional linking moiety. Unless otherwise provided, "polyfunctional linking moiety", and "polyfunctional linker", used herein interchangeably, refer to a linear or branched chain including at least 3, preferably from 3 to 8 and, more preferably, from 3 to 5 functional groups, one of them connecting the said polyfunctional moiety with the N-terminal (—NH$_2$) or the C-terminal group (—COOH) group of A and the remaining connecting the polyfunctional moiety with at least 2, preferably, from 2 to 7, and, more preferably, from 2 to 5 equal or different diagnostically or therapeutically effective moieties.

Preferably, the said polyfunctional linker Y is a linear or branched $C_1$-$C_{150}$ and, preferably, a $C_1$-$C_{100}$ and, more preferably, a $C_1$-$C_{75}$ alkyl chain, that is optionally interrupted by one or more groups selected from —O—, —CONH—, —CO— —NHCO— and —NR$_3$, and optionally substituted by one or more —R$_4$ group(s), wherein R$_3$ is H or a $C_1$-$C_5$ alkyl group optionally substituted by a —COOH or —NH$_2$ group, and R$_4$ may be a group selected from —NH$_2$, —COOH or a derivative thereof including, for instance, lower alkyl esters or —CONH$_2$ amide, a ($C_1$-$C_5$)alkyl optionally substituted by a group selected from —COOH, —CONH$_2$ and —NHR$_3$ or by an optionally substituted benzene ring, the chain further including at least three functional groups connecting the polyfunctional moiety with A and each of the said remaining functional groups with a diagnostically or therapeutically effective moiety T.

Suitable examples of the said polyfunctional linking moiety may include, for instance:

(a) N-branched lysine systems (see, f. i., Veprek, P et al., J. Pept. Sci. 5, 5 (1999); 5, 203 (1999),
(b) Polycarboxylic compounds and suitable derivative thereof in which the carboxylic group(s) are in a suitably activated or protected form,
(c) polyaminated compounds and suitable derivative thereof in which the amino group(s) are in a suitably activated or protected form,
(d) amino acids and poly-amino acids such as polyornithine, polyarginine, polyglutamic acid, polyaspartic acid.

In a preferred aspect of the invention, the polyfunctional linking moiety Y includes one or more sub-unit(s) selected from the above homobifunctional and heterobifunctional units and one or more sub-unit(s) selected from the following:

—HN—(CH$_2$)$_n$—CH(NR$_3$)—CO—,

—OC—CH(NR$_3$)—(CH$_2$)$_n$—NH—,

—OC—(CH$_2$)$_m$—NR$_3$—(CH$_2$)$_m$—CO—,

—HN—CH(R$_4$)—(CH$_2$)$_m$—CO—,

—HN—CH(R$_4$)—(CH$_2$)$_n$—NH—,

—HN—(CH$_2$)$_p$((CH$_2$)$_p$—CH(R$_4$))—(CH$_2$)$_m$—NH—,

—OC—(CH$_2$)$_p$—((CH$_2$)$_p$—CH(NR$_3$))—(CH$_2$)$_m$—NH—, where n, m, p, R$_3$ and R$_4$ have the above defined meaning In a particularly preferred aspect, the said polyfunctional Y moiety comprises one of the following sub-units:

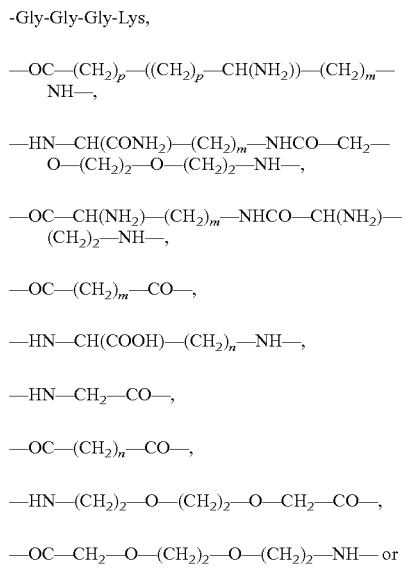

a suitable repetition and/or combination thereof in which each of the H$_2$N— and HOOC— groups of the sub-unit allows carboxamido cross-linking reactions resulting in the possible elongation and/or ramification of the linking moiety.

Any intermediate compounds according to the invention including, for instance, a peptide moiety A conjugated with a suitable, optionally protected Y moiety or with a suitable, optionally protected, sub-unit of a Y moiety constitutes a further object of the present invention. These intermediates and their preparations are, for instance, detailed herein below, in the experimental section.

As a non limiting example, FIG. 1 includes the synthetic procedure for the preparation of a linker functionalized peptide moiety of the invention (Seq005-P) in which the peptide moiety is the one comprising the amino acid sequence of Seq005 as shown in Table 1, and the conjugated linking moiety is -GGGKJJ- (SEQ ID NO. 139) (where J is the Fmoc-8-amino-3,6-dioxaoctanoic acid; see Aldrich Neosystem and Peptides International catalogue).

These novel intermediates including, the peptide moiety conjugated with a suitable linking unit or a suitable sub-unit thereof find application as intermediates for the preparation of the compounds of Formula (I).

According to a preferred aspect of the invention, within the compounds of Formula (I), T is a diagnostically effective moiety or a radiotherapeutic moiety.

The phrase "diagnostically effective moiety" or "imaging effective moiety", used herein interchangeably, refers to any moiety detectable by imaging diagnostic procedures, that is to say any moiety able to provide, to improve or, in any way, to advantageously modify the signal detected by an imaging diagnostic technique including, for instance, magnetic resonance imaging (MRI), radioimaging, x-ray imaging, light imaging, thus enabling the registration of diagnostically useful, preferably contrasted, images when used in association with such techniques.

Examples of diagnostically effective moieties according to the invention include, for instance, chelated gamma ray or positron emitting radionuclides; paramagnetic metal ions in the form of chelated or polychelated complexes, X-ray absorbing agents including atoms of atomic number higher than 20; a dye molecule; a fluorescent molecule; a phosphorescent molecule; a molecule absorbing in the UV spectrum; a quantum dot; a molecule capable of absorption within near or far infrared radiations; moieties detectable by ultrasound and, in general, all moieties which generate a detectable substance. The skilled person in the art well know that the imaging modality to be used have to be selected according to the imaging detectable moiety the diagnostic compounds of the invention include.

MRI Contrast Agents

In a particularly preferred embodiment of the invention, within the compound of Formula (I), T is an MRI detectable moiety.

Compounds of Formula (I) in which T is a MRI detectable moiety are preferred for use as MRI contrast agents.

Accordingly, in one preferred aspect, the present invention relates to novel MRI contrast agents of Formula (I) in which T is a MRI detectable moiety.

Preferably, the said MRI detectable moiety comprises the residue of a chelating ligand labelled with a paramagnetic metal element detectable by Magnetic Resonance Imaging (MRI) techniques.

Preferred paramagnetic metal elements are those having atomic number ranging between 20 and 31, 39, 42, 43, 44, 49 and between 57 and 83. More preferred are paramagnetic metal ions selected from the following: Fe(2+), Fe(3+), Cu(2+), Ni(2+), Rh(2+), Co(2+), Cr(3+), Gd(3+), Eu(3+), Dy(3+), Tb(3+), Pm(3+), Nd(3+), Tm(3+), Ce(3+), Y(3+), Ho(3+), Er(3+), La(3+), Yb(3+), Mn(3+), Mn(2+) wherein Gd(3+) is the most preferred.

The phrase "contrast imaging agent" or "contrast agent" refers to any detectable entity that can be used to in vitro visualize or detect fibrin units or fibrin deposition into or on a biological element including cells, biological fluids and biological tissues originating from a live mammal patient, and preferably, from human patient, as well as the in vivo identification and location of fibrin and fibrin deposition in or on mammalian and, preferably, human body organs, regions or tissues when the said detectable entity is used in association with a suitable diagnostic imaging technique.

The phrase "chelator", "chelating ligand" or "chelating agent", used herein interchangeably, refers to chemical moieties, agents, compounds, or molecules characterized by the presence of polar groups able to a form a complex containing more than one coordinate bond with a transition metal or another metal entity. In a preferred aspect of the invention the chelating ligands include cyclic or linear polyamino polycarboxylic or phosphonic acids and contain at least one amine, thiol, carboxyl group, present as free, optionally activated functionality that is suitable for use in the conjugation reaction with a functional group of the spacer chain Y.

The expression a "residue of a chelating agent", or a "residue of a chelating ligand", used herein interchangeably, refers to that portion of the chelating ligand remaining after the above conjugation. Preferably the conjugation is from an acidic group on the chelating ligand or a suitable derivative thereof with an amino group (—NH2) of the linking moiety Y, or, alternatively, between a suitable reactive amino group of the chelating ligand and a terminal carboxy group (—COOH) of the Y moiety, or a suitable derivative thereof, so as to give rise to a carboxamido linkage. The acidic or the reactive amino group of the chelating ligand involved in the crosslinking reaction is suitably selected in order to not reduce or modify the chelating capability of the ligand residue.

The term "labelled" or "complexed" used in the context of a "chelating ligand labelled with a metal element", refers to the formation of a chelate or coordinate complex between the metal and the chelating ligand.

The term "metal entity" refers to a metal ion that is detectable by an imaging technique. Such metal entities specifically include paramagnetic metal ions that are detectable by imaging techniques such as Magnetic Resonance Imaging (MRI), or to a metal ion (e.g. radionuclide) that is detectable by imaging techniques such as scintigraphic imaging, Single Photon Emission Computed Tomography (SPECT) and Positron Emission Tomography (PET) or even a radionuclide for therapy.

Suitable chelating ligands include those discussed herein, particularly chelating ligands selected from the group consisting of: a polyaminopolycarboxylic acid and the derivative thereof, comprising, for example, diethylenetriamine pentaacetic acid (DTPA) and derivative thereof such as benzo-DTPA, dibenzo-DTPA, phenyl-DTPA, diphenyl-DTPA, benzyl-DTPA, dibenzyl DTPA; N,N-bis[2-[(carboxymethyl)[(methylcarbamoyl)methyl]amino]ethyl]-glycine (DTPA-BMA); N-[2-[bis(carboxymethyl)amino]-3-(4-ethoxyphenyl)propyl)]-N-[2-[bis(carboxymethyl)amino]ethylglycine (EOB-DTPA); 4-carboxy-5,8,11-tris(carboxymethyl)-1-phenyl-2-oxa-5,8,11-triazamidecan-13-oic acid (BOPTA); N,N-Bis[2-[bis[2-(1,1-dimethylethoxy)-2-oxoethyl]amino]ethyl]L-glutamic acid 1-(1,1-dimethylethyl) ester N,N-bis[2-[bis(carboxymethyl)amino]ethyl]L-glutamic acid (DTPA-GLU); DTPA conjugated with Lys (DTPA-Lys); ethylenediaminetetraacetic acid (EDTA); 1,4,7,10-teraazacyclododecane 1,4,7,-triacetic acid (DO3A); 1,4,7,10-tetraazacyclotetradecane-1,4,7,10-tetraacetic acid (DOTA); [10-(2-hydroxypropyl)-1,4,7,10-teraazacyclododecane 1,4,7,-triacetic acid (HPDO3A); 6-[bis(carboxymethyl)amino]tetrahydro-6-methyl-1H-1,4-diazepine-1,4(5H)-diacetic acid (AAZTA) provided by WO03008390 application, incorporated herein by reference, and derivative thereof; 2-methyl-1,4,7,10-tetraazacyclotetradecane-1,4,7,10-tetraacetic acid (MCTA); (α,α',α",α'")-tetramethyl-1,4,7,10-tetraazacyclotetradecane-1,4,7,10-tetraacetic acid (DOTMA); or a polyaminophosphate acid ligand or derivative thereof, in particular, N,N'-bis-(pyridoxal-5-phosphate) ethylenediamine-N,N'-diacetic acid (DPDP), ethylenedinitrilotetrakis(methylphosphonic) acid (EDTP) or a polyaminophosphonic acid ligand and derivative thereof, or polyaminophosphinic acid and derivative thereof, in particular 1,4,7,10-tetraazacyclotetradecane-1,4,7,10-tetrakis[methylphosphonic)] and 1,4,7,10-tetraazacyclotetradecane-1,4,7,10-tetrakis[methylene-(methylphosphinic)]acid; or of macrocyclic chelators such as texaphyrins, porphyrins, phthalocyanines.

Preferred ligand according to the present invention include those of FIGS. 6a to 6c, which also include suitable bibliographic references concerning their preparation.

Particularly preferred are: DTPA, DTPA-GLU, DTPA-Lys, DOTA, AAZTA, and the following derivatives thereof:

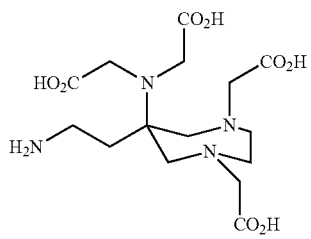

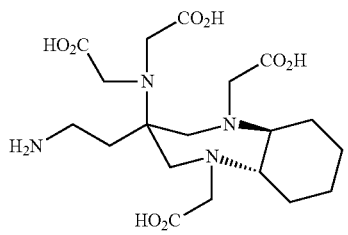

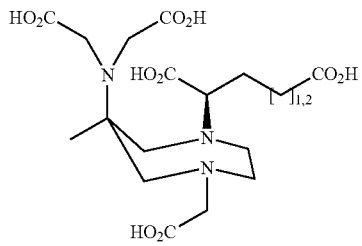

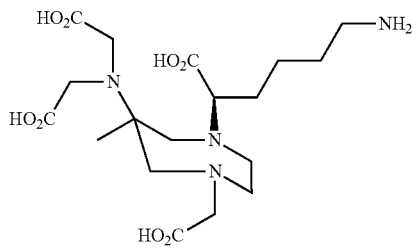

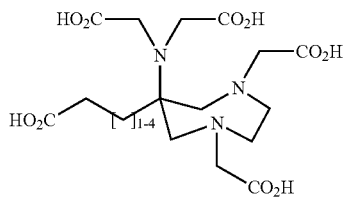

Examples of particularly preferred MRI contrast agents of the invention comprise:

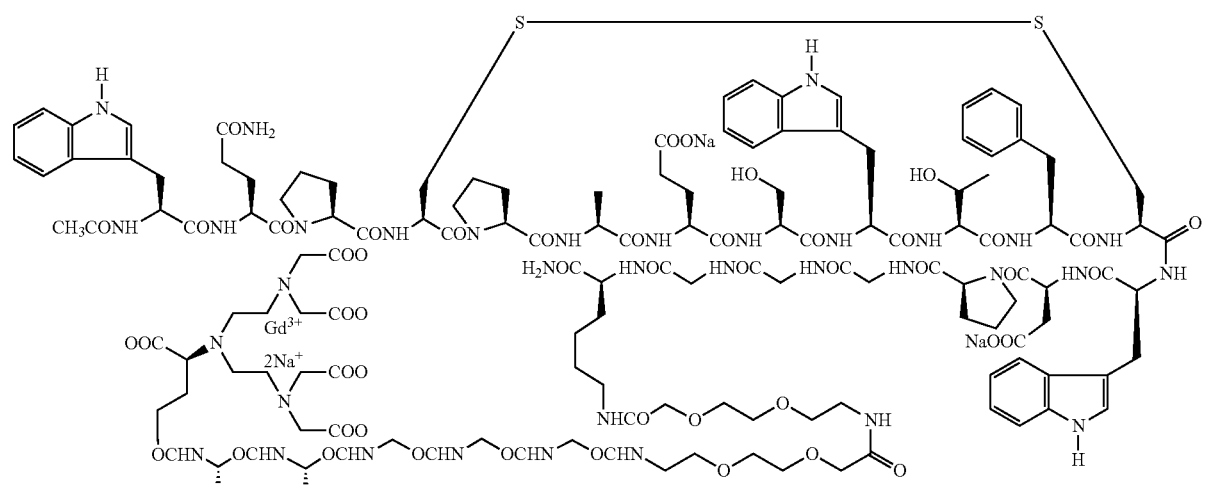
Chelated complex 1
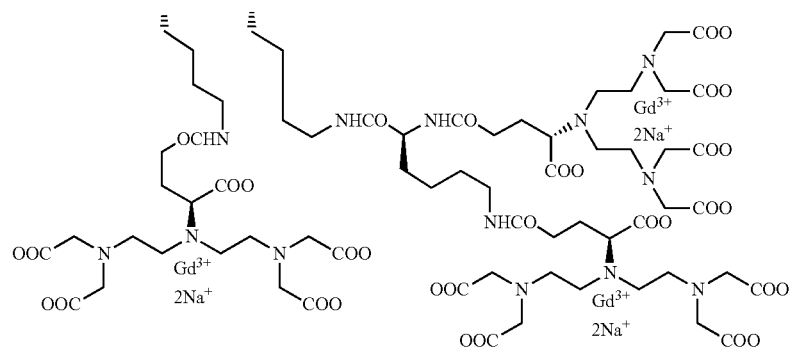
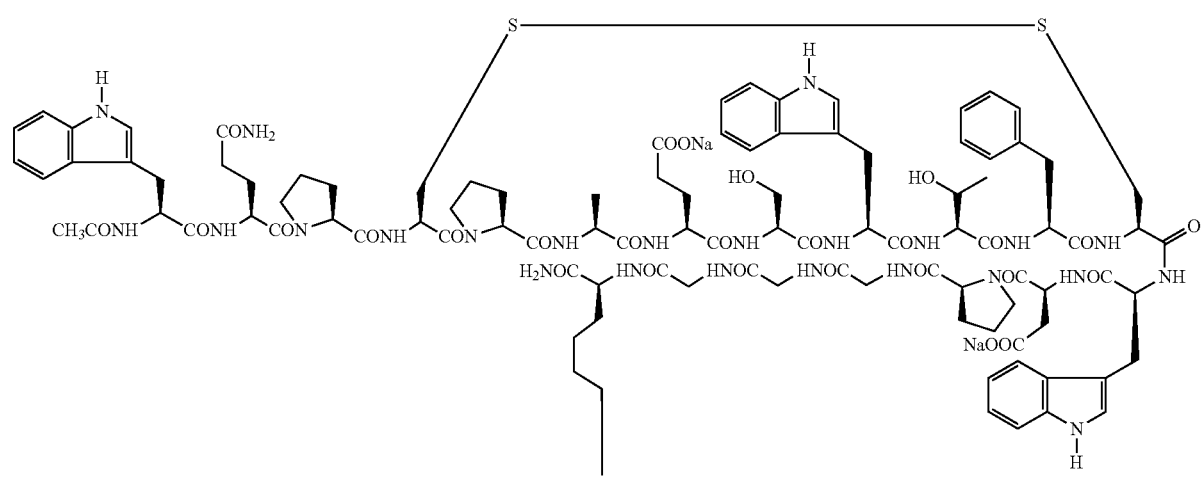
Chelated complex 2

85
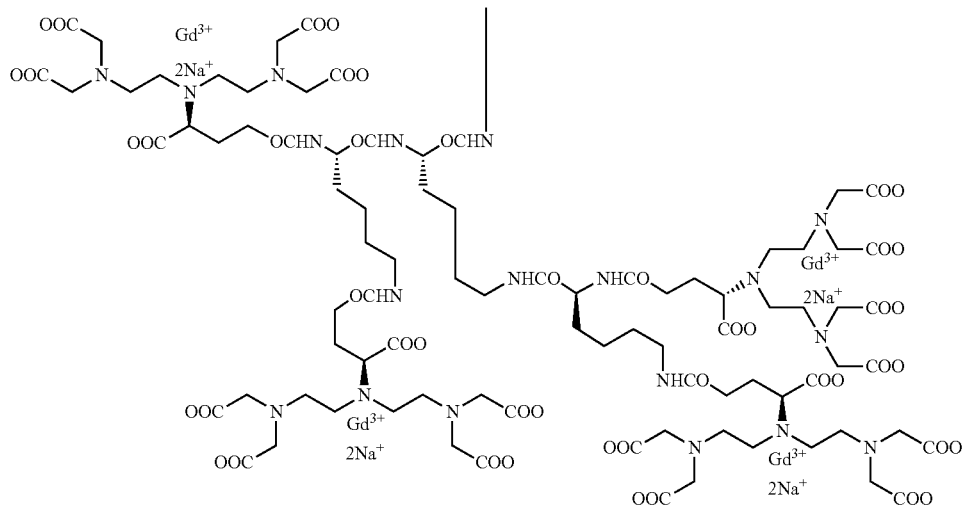
-continued
86
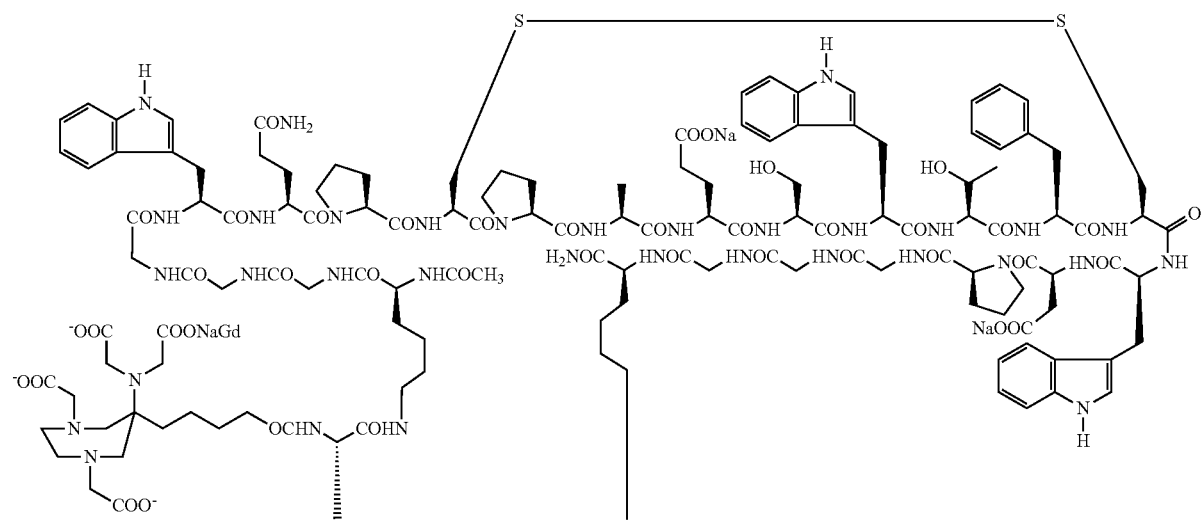
Chelated complex 3
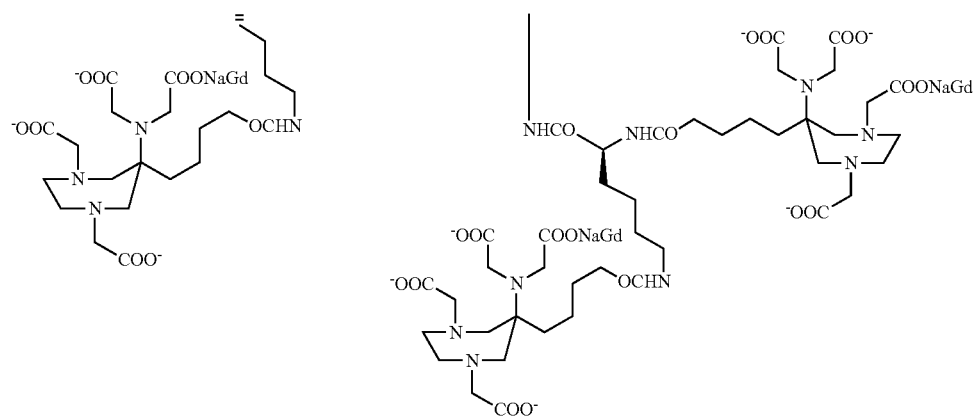

-continued
Chelated complex 4
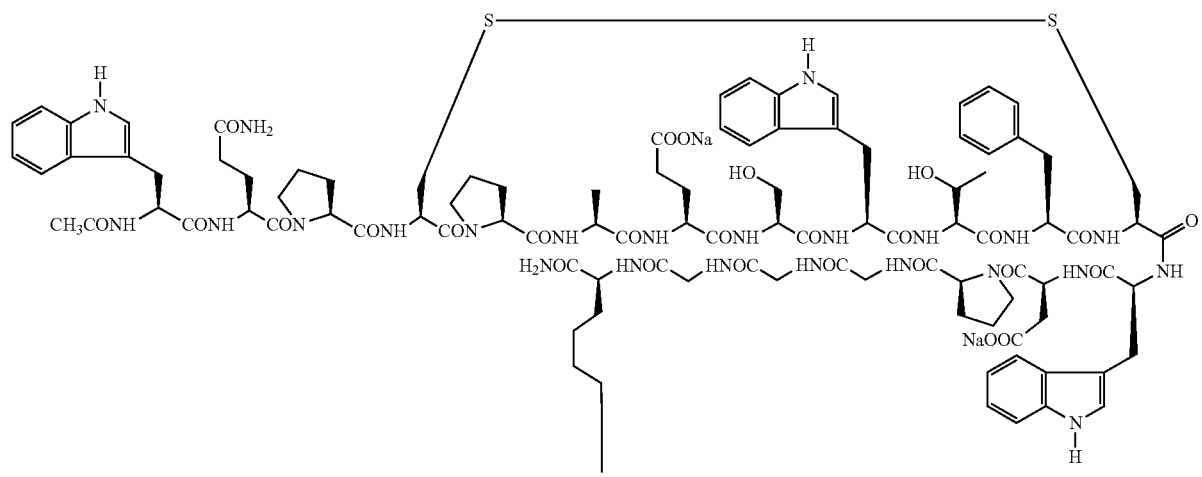
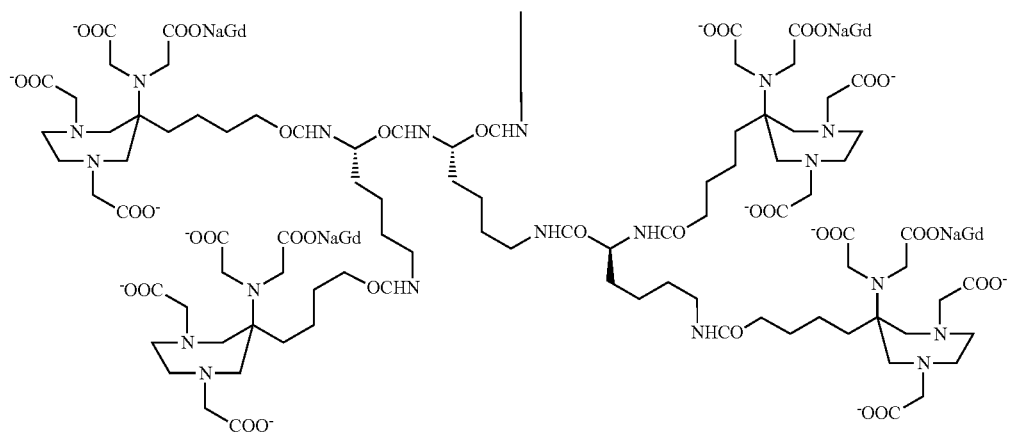
Chelated complex 5
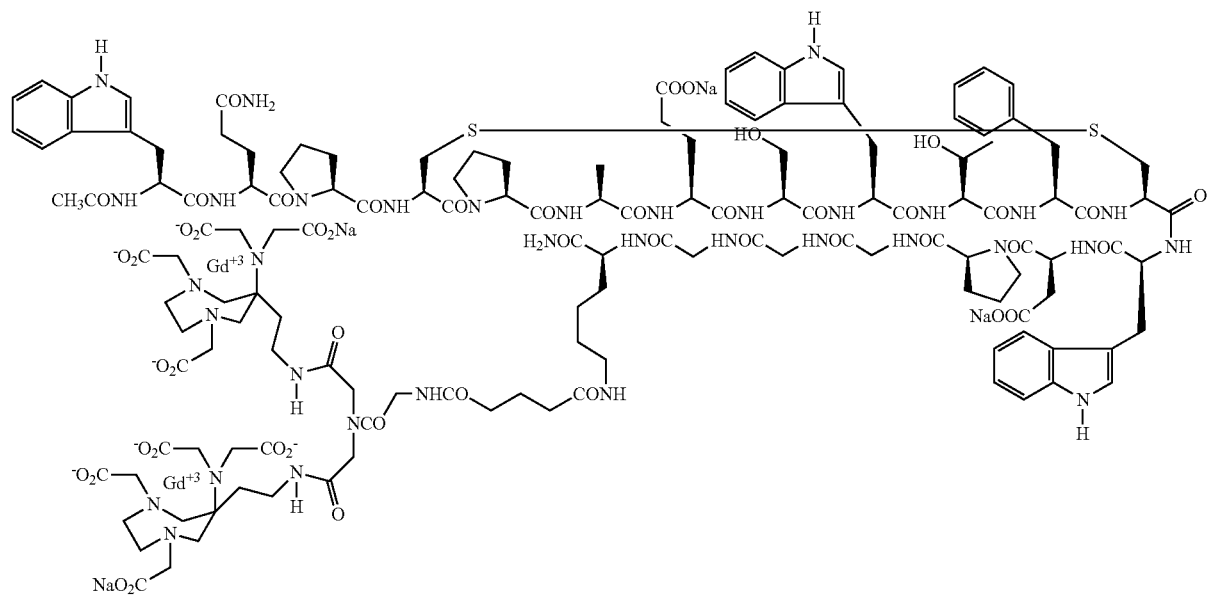

-continued
Chelated complex 6
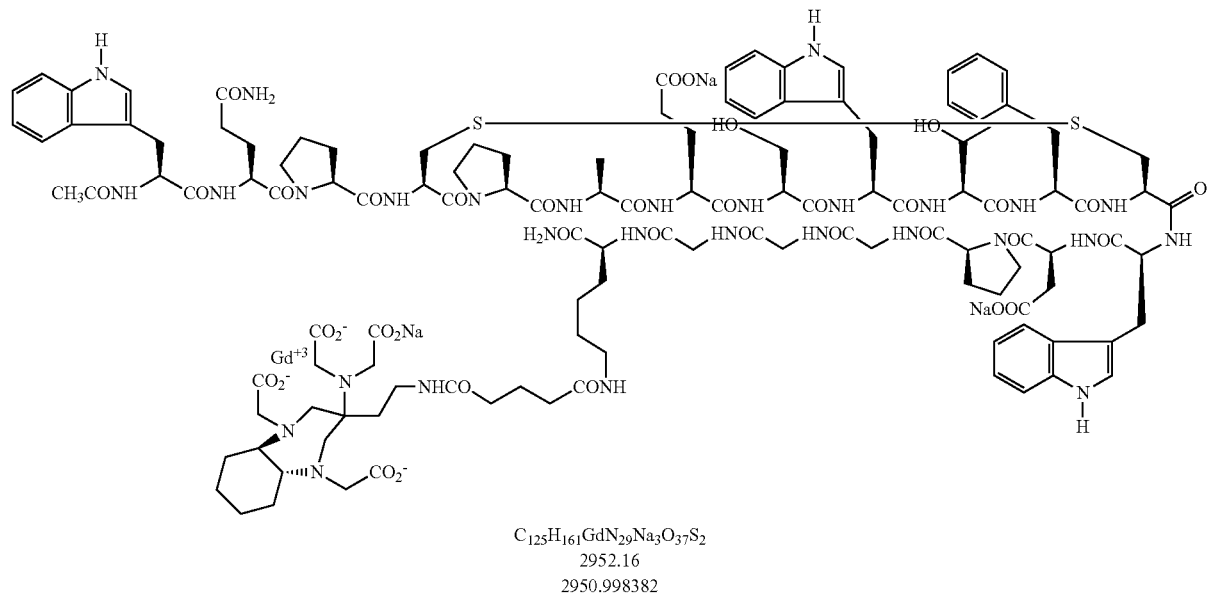
$C_{125}H_{161}GdN_{29}Na_3O_{37}S_2$
2952.16
2950.998382
Chelated complex 7
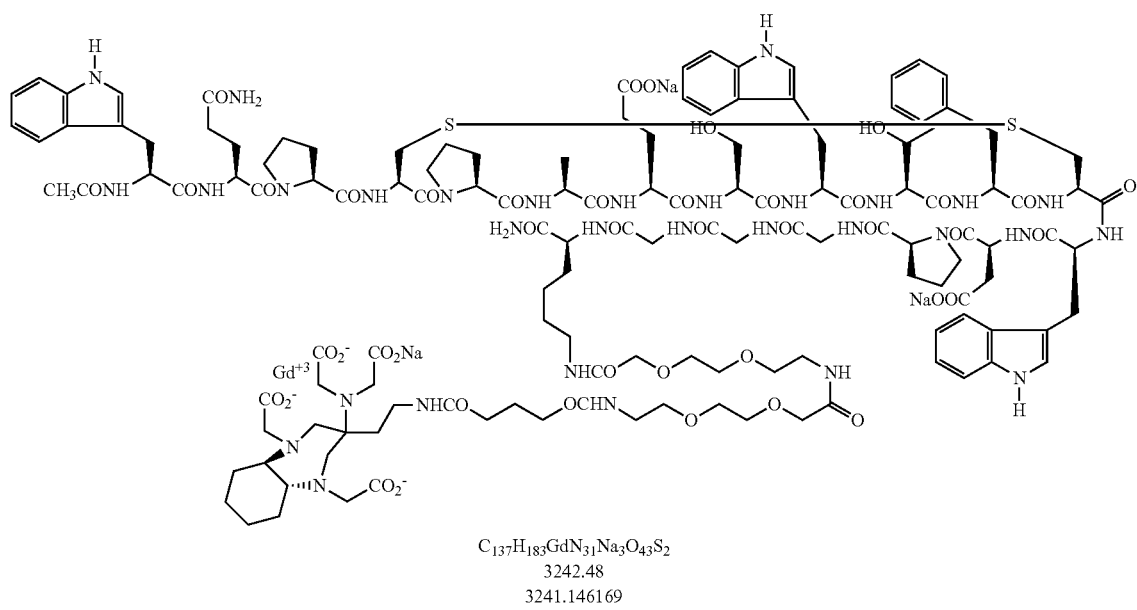
$C_{137}H_{183}GdN_{31}Na_3O_{43}S_2$
3242.48
3241.146169

Chelated complex 8
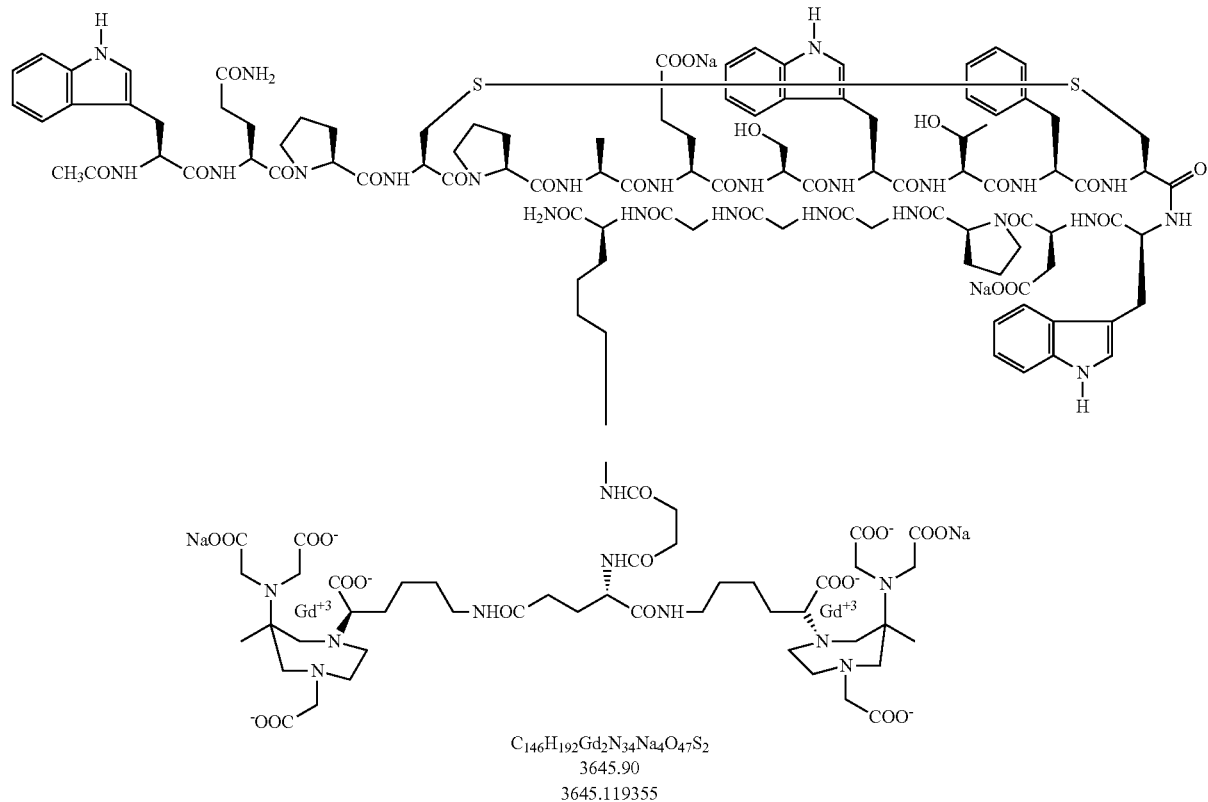
$C_{146}H_{192}Gd_2N_{34}Na_4O_{47}S_2$
3645.90
3645.119355
Chelated complex 9
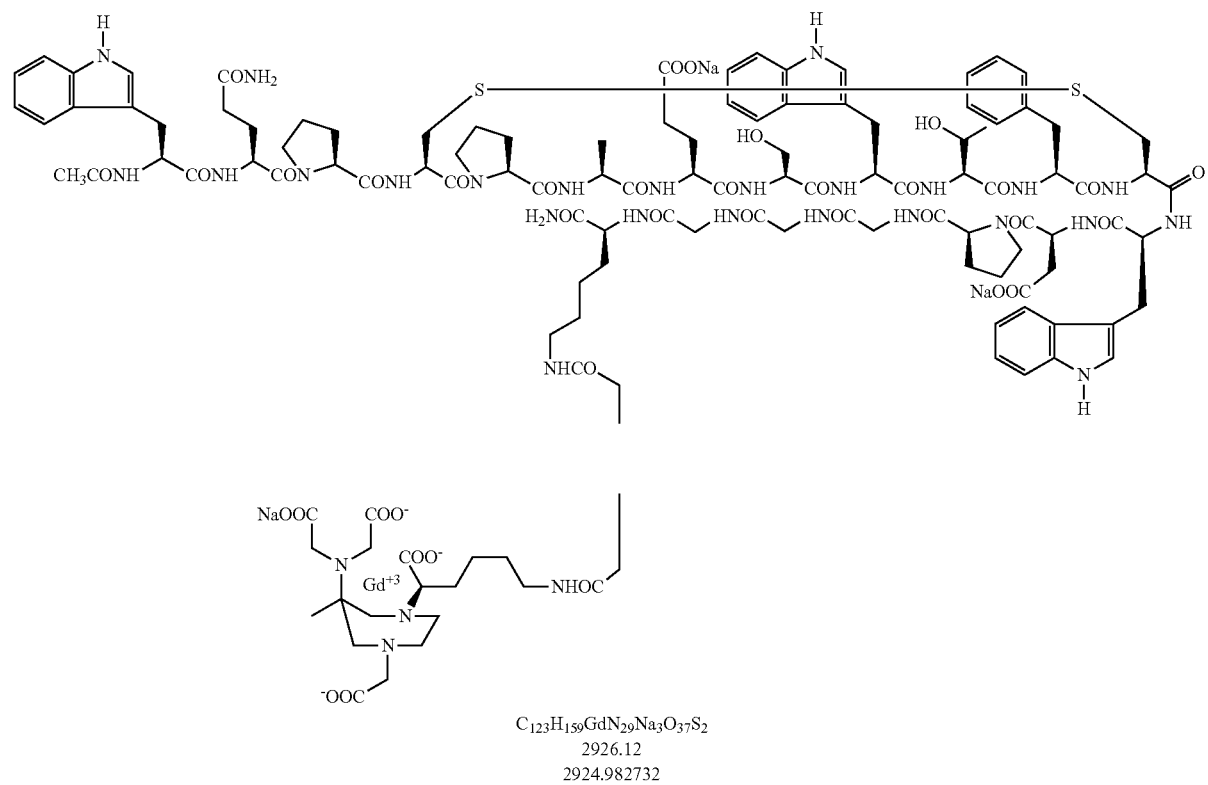
$C_{123}H_{159}GdN_{29}Na_3O_{37}S_2$
2926.12
2924.982732

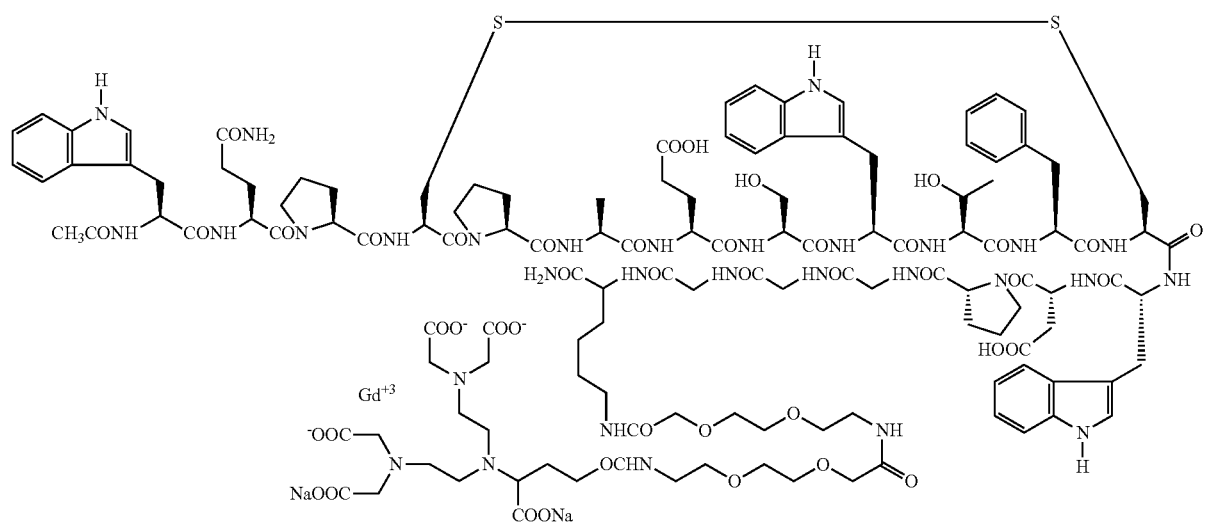

Chelated complex 10

Nuclear Imaging (Radionuclide Imaging) and Radiotherapy

In another preferred embodiment of the invention, within the compounds of Formula (I), T is a radioimaging detectable moiety or a radiotherapeutic moiety.

Compounds of Formula (I) in which T is a radio imaging detectable moiety are preferred for use as radiographic contrast agents.

Accordingly, in another preferred embodiment, the present invention further relates to novel radiographic contrast agents of Formula (I) in which T is a radioimaging detectable moiety.

A "radioimaging detectable moiety" refers to a moiety that is detectable by imaging techniques such as scintigraphic imaging, Single Photon Emission Computed Tomography (SPECT) and Positron Emission Tomography (PET).

Preferably, the radioimaging detectable moiety comprises the residue of a chelating agent labelled with a radionuclide detectable by the said scintigraphic, SPECT or PET imaging techniques.

When T is a radiotherapeutic moiety, it preferably comprises a radionuclide which is therapeutically effective. In a preferred embodiment, the radiotherapeutic moiety comprises the residue of a chelating ligand labelled with a therapeutically active radionuclide.

Together with the chelating ligands discussed above, suitable examples of chelating ligands for radionuclides may be selected from linear, macrocyclic, terpyridine, and $N_3S$, $N_2S_2$, or $N_4$ chelators (see, moreover, ligand disclosed, for instance, in U.S. Pat. No. 5,367,080, U.S. Pat. No. 5,364,613, U.S. Pat. No. 5,021,556, U.S. Pat. No. 5,075,099, U.S. Pat. No. 5,886,142), and other chelating ligands known in the art including, but not limited to, HYNIC, TETA and bisamino bisthiol (BAT) chelators (see also U.S. Pat. No. 5,720,934). For example, $N_4$ chelating ligands are described in U.S. Pat. Nos. 6,143,274; 6,093,382; 5,608,110; 5,665,329; 5,656,254; and 5,688,487. Certain $N_3$5 chelators are described in PCT/CA94/00395, PCT/CA94/00479, PCT/CA95/00249 and in U.S. Pat. Nos. 5,662,885; 5,976,495; and 5,780,006. The chelator may also include derivatives of the chelating ligand mercapto-acetyl-acetyl-glycyl-glycine (MAG3), which contains an $N_3S$, and $N_2S_2$ systems such as MAMA (monoamidemonoaminedithiols), DADS ($N_2S$ diaminedithiols), CODADS and the like. These ligand systems and a variety of others are described in Liu and Edwards, *Chem Rev,* 1999, 99, 2235-2268 and references therein.

The chelator may also include complexes containing ligand atoms that are not donated to the metal in a tetradentate array. These include the boronic acid adducts of technetium and rhenium dioximes, such as are described in U.S. Pat. Nos. 5,183,653; 5,387,409; and 5,118,797, the disclosures of which are incorporated by reference herein, in their entirety.

Preferred radionuclides according to the present invention include $^{99m}Tc$, $^{51}Cr$, $^{67}Ga$, $^{68}Ga$, $^{47}Sc$, $^{167}Tm$, $^{141}Ce$, $^{111}In$, $^{113}In$, $^{168}Yb$, $^{175}Yb$, $^{140}La$, $^{90}Y$, $^{88}Y$, $^{153}Sm$, $^{166}Ho$, $^{165}Dy$, $^{166}Dy$, $^{61}Cu$, $^{62}Cu$, $^{64}Cu$, $^{67}Cu$, $^{97}Ru$, $^{103}Ru$, $^{186}Re$, $^{188}Re$, $^{203}Pb$, $^{211}Bi$, $^{212}Bi$, $^{213}Bi$, $^{214}Bi$, $^{105}Rh$, $^{109}Pd$, $^{117}Sn$, $^{149}Pm$, $^{161}Tb$, $^{177}Lu$, $^{198}Au$, $^{111}Ag$, $^{199}Au$, $^{51}Mn$, $^{52m}Mn$, $^{52}Fe$, $^{60}Cu$, $^{72}As$, $^{94m}Tc$, $^{110}In$, $^{142}Pr$, and $^{159}Gd$.

The choice of a suitable ligand residue depends on the radionuclide used for the ligand labelling. Thus, preferred residues of chelating ligands include those of FIGS. 6a to 6c (for $^{111}In$ lanthanides and radioactive lanthanides, including, for instance $^{177}Lu$, $^{90}Y$, $^{153}Sm$, and $^{166}Ho$ or for $^{67}Ga$, $^{68}Ga$, $^{61}Cu$, $^{62}Cu$, $^{64}Cu$, or $^{67}Cu$) and those of FIGS. 7a to 7b (for radioactive $^{99m}Tc$, $^{186}Re$, and $^{188}Re$). In particular, for metal entities including $^{111}In$, lanthanides and radioactive lanthanides, particularly preferred are the following ligand residues (7)

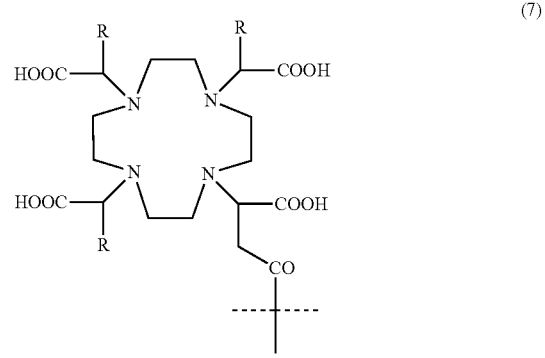

(8)
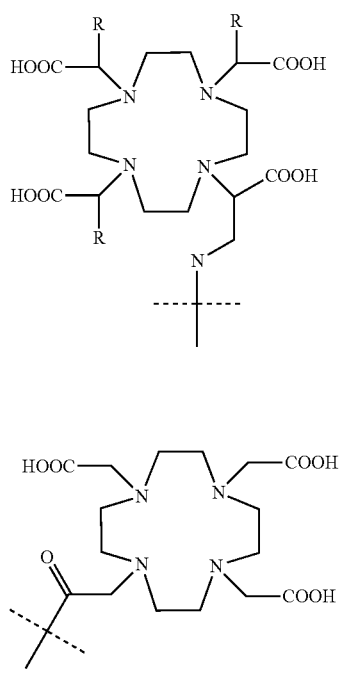

(9)

In the above Formulas 7 and 8, R is an alkyl, preferably methyl.

For $^{99m}$Tc, $^{186}$Re, and $^{188}$Re radionuclides, particularly preferred are the following ligands:

(10)
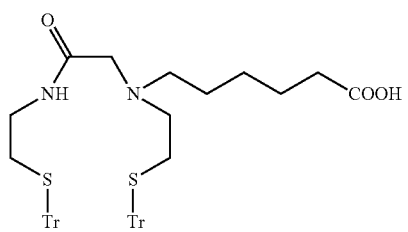

(11)
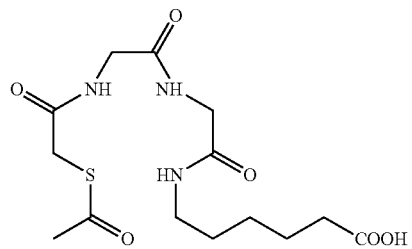

(12)
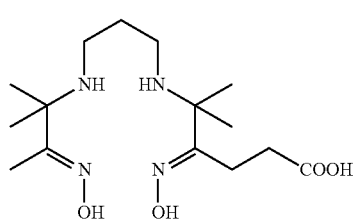

(13)
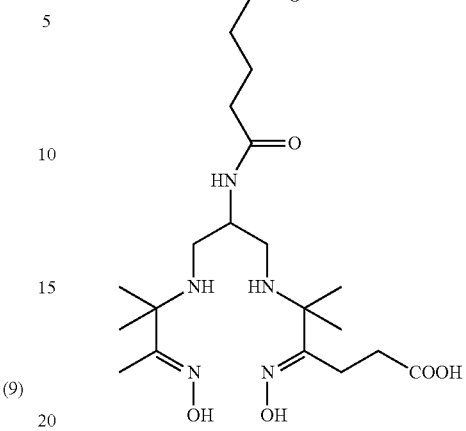

as well as the following ligand residues:

(14)

(15)
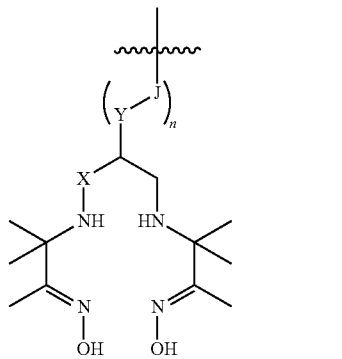

(16)
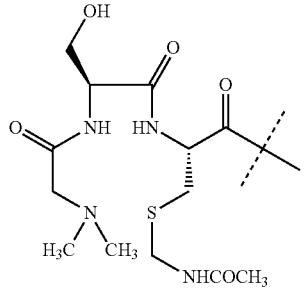

These and other metal chelating groups are described in U.S. Pat. Nos. 6,093,382 and 5,608,110, U.S. Pat. No. 6,143,274; U.S. Pat. Nos. 5,627,286 and 6,093,382, U.S. Pat. Nos. 5,662,885; 5,780,006; and 5,976,495 which are incorporated by reference herein in their entirety. Additionally, the above chelating group of Formula 9 is described in, for example, U.S. Pat. No. 6,143,274; the chelating groups of the above Formula 14 and 15 are described in U.S. Pat. Nos. 5,627,286 and 6,093,382, and the chelating group of Formula 16 is described in, for example, U.S. Pat. Nos. 5,662,885; 5,780, 006; and 5,976,495.

In the Formula 14 and 15, X is either $CH_2$ or O, Y is either $C_1$-$C_{10}$ branched or unbranched alkyl; Y is aryl, aryloxy, arylamino, arylaminoacyl; Y is arylkyl where the alkyl group or groups attached to the aryl group are $C_1$-$C_{10}$ branched or unbranched alkyl groups, $C_1$-$C_{10}$ branched or unbranched hydroxy or polyhydroxyalkyl groups or polyalkoxyalkyl or polyhydroxy-polyalkoxyalkyl groups, J is C(=O)—, OC(=O)—, $SO_2$, NC(=O)—, NC(=S)—, N(Y), NC(=NCH$_3$)—, NC(=NH)—, N=N—, homopolyamides or heteropolyamines derived from synthetic or naturally occurring amino acids; all where n is 1-100. Other variants of these structures are described, for example, in U.S. Pat. No. 6,093,382. The disclosures of each of the foregoing patents, applications and references are incorporated by reference herein, in their entirety.

The choice of the radionuclide will be determined based on the desired therapeutic or diagnostic application. For uses in radiotherapy or radiodiagnostics preferred radionuclides are $^{203}$Pb, $^{67}$Ga, $^{68}$Ga, $^{72}$As, $^{111}$In, $^{113}$In, $^{90}$Y, $^{97}$Ru, $^{61}$Cu, $^{62}$Cu, $^{64}$Cu, $^{52}$Fe, $^{52m}$Mn, $^{140}$La, $^{175}$Yb, $^{153}$Sm, $^{166}$Ho, $^{149}$Pm, $^{177}$Lu, $^{142}$Pr, $^{159}$Gd, $^{212}$Bi, $^{47}$Sc, $^{149}$Pm, $^{67}$Cu, $^{111}$Ag, $^{199}$Au, $^{161}$Tb, $^{51}$Cr, $^{167}$Tm, $^{141}$Ce, $^{168}$Yb, $^{88}$Y, $^{165}$Dy, $^{166}$Dy, $^{97}$Ru, $^{103}$Ru, $^{186}$Re, $^{188}$Re, $^{99m}$Tc, $^{211}$Bi $^{212}$Bi, $^{213}$Bi, $^{214}$Bi, $^{105}$Rh, $^{109}$Pd, $^{117m}$Sn, $^{177}$Sn and $^{199}$Au and oxides and nitrides thereof. For example, for therapeutic purposes (e.g., to provide radiotherapy for primary tumors and metastasis), the preferred radionuclides include $^{64}$Cu, $^{90}$Y, $^{105}$Rh, $^{111}$In, $^{117m}$Sn, $^{149}$Pm, $^{153}$Sm, $^{161}$Tb, $^{166}$Dy, $^{166}$Ho, $^{175}$Yb, $^{177}$Lu, $^{186/188}$Re, and $^{199}$Au, with $^{177}$Lu and $^{90}$Y being particularly preferred. For diagnostic purposes (e.g., to diagnose and monitor therapeutic progress in e.g. primary tumors and metastases) the preferred radionuclides include $^{64}$Cu, $^{67}$Ga, $^{68}$Ga, $^{99m}$Tc, and $^{111}$In.

$^{99m}$Tc is particularly preferred for diagnostic applications because of its low cost, availability, imaging properties, and high specific activity. The nuclear and radioactive properties of $^{99m}$Tc make this isotope an ideal scintigraphic imaging agent. This isotope has a single photon energy of 140 keV and a radioactive half-life of about 6 hours, and is readily available from a $^{99}$Mo-$^{99m}$Tc generator.

Preferred metal radionuclides for use in PET imaging are positron emitting metal ions, such as $^{51}$Mn, $^{52}$Fe, $^{60}$Cu, $^{68}$Ga, $^{72}$As, $^{94m}$Tc, or $^{110}$In.

Figure 7A:
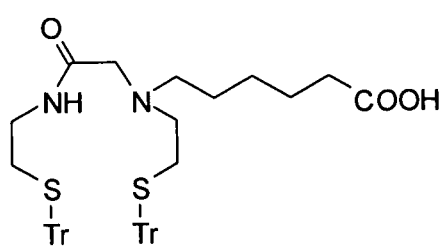
FIGS. 7a, 7b illustrate examples of preferred chelators of radioactive metal ions such as $^{90m}$Tc, $^{186}$Re and $^{188}$Re.
Figure 7A:
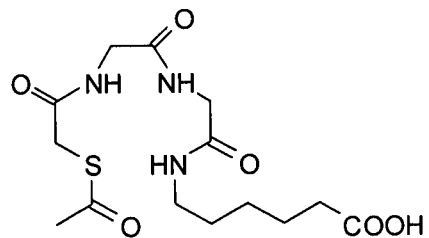
Figure 7A:
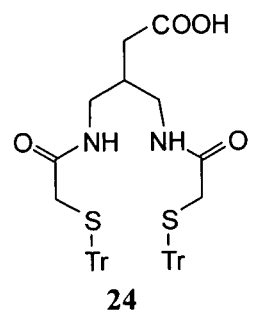
Figure 7A:
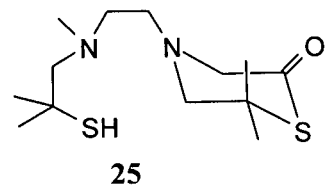
Figure 7A:
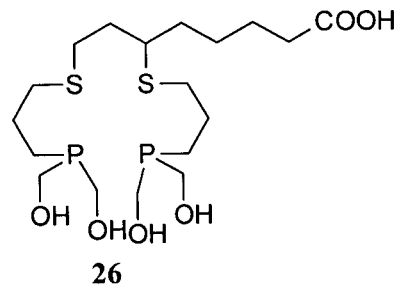
Figure 7A:
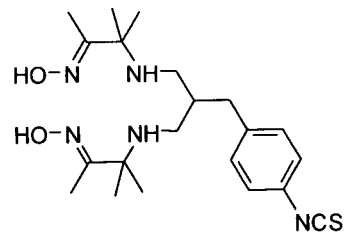
Figure 7A:
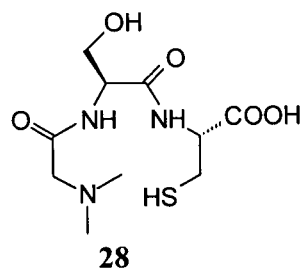
Figure 7B:
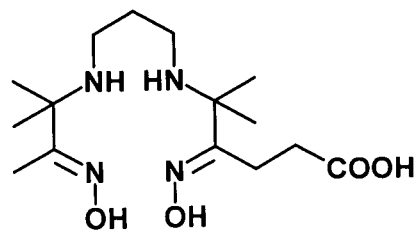
Figure 7B:
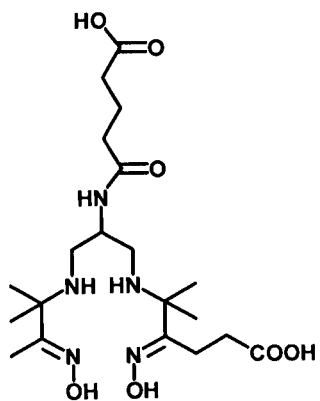
Figure 7B:
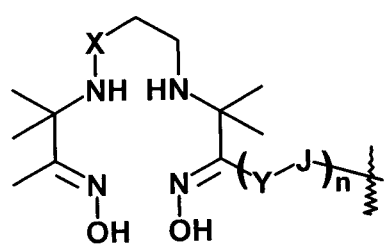
Figure 7B:
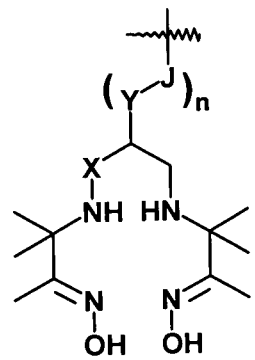
Figure 7B:
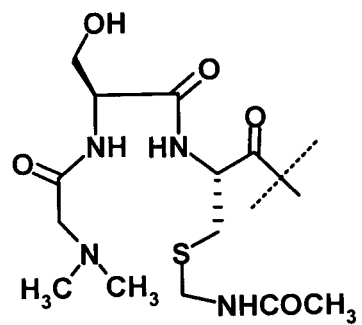

Preferred for scintigraphic applications are radiodiagnostic contrast agents of Formula (I) wherein T is the residue of a chelating ligand of FIGS. 7a to 7b, labelled with radionuclide selected from $^{99m}$Tc and $^{186/188}$Re. More preferred are those in which T is the residue of a chelating ligand of formula from 22 to 33. Particularly preferred for scintigraphic applications are contrast agents of Formula (I) wherein T is a residue of a ligands of formula from 22 to 33 labelled with $^{99m}$Tc.

Preferred radionuclides for use in radiotherapy include $^{64}$Cu, $^{90}$Y, $^{105}$Rh, $^{111}$In, $^{117}$Sn, $^{149}$Pm, $^{153}$Sm, $^{161}$Tb, $^{166}$Dy, $^{166}$Ho, $^{175}$Yb, $^{90}$Y, $^{177}$Lu, $^{186/188}$Re, $^{199}$ and $^{199}$Au, with $^{177}$Lu and $^{90}$Y being particularly preferred.

PET Imaging

In a still further embodiment of the invention, within the compounds of Formula (I), T is an optionally labelled sugar moiety for use, when labelled, in PET Imaging.

Accordingly, in another preferred aspect, the present invention relates to compounds of Formula (I) in which T is a suitably labelled sugar moiety.

In a preferred embodiment of the invention, T includes a sugar moiety labeled by halogenation with radionuclides, such as, $^{124}$I, $^{125}$I, $^{131}$I, $^{123}$I, $^{77}$Br, $^{76}$Br and $^{18}$F, wherein $^{18}$F is particularly preferred.

Therapeutically Effective Agents

In another embodiment of the invention, within the compounds of Formula (I), T is a therapeutic active moiety.

Compounds of Formula (I) in which T is a therapeutic active moiety are new and constitute a further object of the present invention.

Suitable examples of therapeutic active moieties according to the present invention include thrombolytic or fibrinolytic agents capable of lysis of clots, or cytotoxic agents for selective killing and/or inhibiting the growth of, for example, cancer cells, and radiotherapeutic agents.

In one embodiment of the invention T is one of the aforementioned thrombolytic or fibrinolytic agents and, preferably, streptokinase or urokinase. Compounds of Formula (I) in which T includes a thrombolytic or a fibrinolytic agent are useful in treating thrombus associated diseases, especially acute myocardial infarction, in mammals, including humans.

Thus, in a different aspect thereof, the invention relates to the use of a compound of Formula (I) in which T includes a thrombolytic or a fibrinolytic agent for the preparation of a pharmaceutical formulation for treating thrombus associated diseases in mammalian, including humans.

Thus, in a still different aspect thereof, the present invention relates to compounds of Formula (I) in which T is an antineoplastic agent.

Suitable examples of the said agents include, for instance, the previously listed antineoplastic compounds as well as toxins.

In a preferred embodiment of the invention, T is a radiotherapeutic agent comprising a therapeutic radionuclide. Preferably, T is residue of a chelating ligand that is labelled with a therapeutically active radionuclide. These compounds are preferred for use as radiotherapeutic agents according to the invention.

Accordingly, in another embodiment, the invention relates to novel radiotherapeutic agents of Formula (I) in which T is the residue of a chelating ligand suitably labelled with a therapeutically active radionuclide.

Preferred radionuclides for use in radiotherapy include $^{64}$Cu, $^{90}$Y, $^{105}$Rh, $^{111}$In, $^{117m}$Sn, $^{149}$Pm, $^{153}$Sm, $^{161}$Tb, $^{166}$Dy, $^{166}$Ho, $^{175}$Yb, $^{90}$Y, $^{177}$Lu, $^{186/188}$Re, and $^{199}$Au, with $^{177}$Lu and $^{90}$Y being particularly preferred.

The selection of a proper radionuclide for use in a particular radiotherapeutic application depends on many factors, including:

a. Physical half-life—This should be long enough to allow synthesis and purification of the radiotherapeutic construct from radiometal and conjugate, and delivery of said construct to the site of injection, without significant radioactive decay prior to injection. Preferably, the radionuclide should have a physical half-life between about 0.5 and 8 days.

b. Energy of the emission(s) from the radionuclide—Radionuclides that are particle emitters (such as alpha emitters, beta emitters and Auger electron emitters) are particularly useful, as they emit highly energetic particles that deposit their energy over short distances, thereby producing highly localized damage. Beta emitting radionuclides are particularly preferred, as the energy from beta particle emissions from these isotopes is deposited within 5 to about 150 cell diameters. Radiotherapeutic agents prepared from these nuclides are capable of killing diseased cells that are relatively close to their site of localization, but cannot travel long distances to damage adjacent normal tissue such as bone marrow.

c. Specific activity (i.e. radioactivity per mass of the radionuclide)—Radionuclides that have high specific activity (e.g., generator produced $^{90}$Y, $^{111}$In, $^{177}$Lu) are particularly preferred. The specific activity of a radionuclide is determined by its method of production, the particular target for which it is produce, and the properties of the isotope in question.

Many of the lanthanides and lanthanoids include radioisotopes that have nuclear properties that make them suitable for use as radiotherapeutic agents, as they emit beta particles. Some of these are listed in the table below.

TABLE NO. 4

| Isotope | Half-Life (days) | Max b-energy (MeV) | Gamma energy (keV) | Approximate range of b-particle (cell diameters) |
|---|---|---|---|---|
| $^{49}$-Pm | 2.21 | 1.1 | 286 | 60 |
| $^{53}$-Sm | 1.93 | 0.69 | 103 | 30 |
| $^{66}$-Dy | 3.40 | 0.40 | 82.5 | 15 |
| $^{66}$-Ho | 1.12 | 1.8 | 80.6 | 117 |
| $^{75}$-Yb | 4.19 | 0.47 | 396 | 17 |
| $^{77}$-Lu | 6.71 | 0.50 | 208 | 20 |
| $^{0}$-Y | 2.67 | 2.28 | — | 150 |
| $^{11}$-In | 2.810 | Auger electron emitter | 173, 247 | <5*m | wherein: Pm is Promethium, Sm is Samarium, Dy is Dysprosium, Ho is Holmium, Yb is Ytterbium, Lu is Lutetium, Y is Yttrium, In is Indium.

The use of radioactive rhenium isotope as an alternative to above lanthanides and lanthanoids is well known in the art and is encompassed by the invention.

Particularly $^{186/188}$Re isotopes have proved to be of particular interest in nuclear medicine, having a large number of applications in radiopharmaceutical therapy.

Thus, in a preferred embodiment, the invention relates to novel radiotherapeutic agents of Formula (I) wherein T is the residue of a suitably chelated radionuclide that emits ionizing radiations such as beta particles, alpha particles and Auger or Coster-Kroning electrons.

More preferably, T is the residue of a chelating ligand labelled with a lanthanide or a lanthanoid radionuclide selected from $^{90}$Y, $^{111}$In, $^{149}$Pm, $^{153}$Sm, $^{166}$Dy, $^{166}$Ho, $^{175}$Yb, and $^{177}$Lu. Examples of suitable chelating ligand may be selected from those of FIGS. 6a to 6c.

Thus, in a particularly preferred embodiment, the present invention relates to novel radiotherapeutic agent of Formula (I) wherein T is the residue of a chelating ligand of FIGS. 6a to 6c, labelled with a therapeutically active nuclide $^{90}$Y, $^{111}$In or $^{177}$Lu.

In another preferred aspect, the invention relates to novel radiotherapeutic agents of Formula (I) wherein T is the residue of a chelating ligand of Formula 10 to 16 labelled with $^{186}$Re or $^{188}$Re.

The compounds of the invention labeled with therapeutic radionuclides can find application either as radiopharmaceutical that will be used as a first line therapy in the treatment of a disease such as cancer, or in combination therapy, where the radiotherapeutic agents of the invention could be utilized in conjunction with adjuvant chemotherapy (e.g, with one of the other therapeutic agents disclosed herein), or as the therapeutic part of a matched pair therapeutic agent.

In fact, the peptide moiety of the radiotherapeutic of the invention is able to localize the chelated radioactive isotope to the pathologic fibrin deposition, for instance, into thrombi/clots, atherosclerois plaques and inflammation-based damage involved in multiple sclerosis and, especially within solid tumors. The cytotoxic amount of ionizing radiation emitted by the localized radioisotope is thus able to cause the cell death of the pathologic tissue.

Salts

Both the ligands and the paramagnetic or radionuclide chelated compounds of Formula (I) can also be in the form of a physiologically salt.

The term "pharmaceutically acceptable salt", as used herein, refers to derivatives of the compounds of the invention wherein the parent compound is modified by making the acid or basic groups not yet internally neutralized in the form of non-toxic, stable salts which does not destroy the pharmacological activity of the parent compound.

Suitable example of the said salts include: mineral or organic acid salts, of basic residues such as amines; alkali or organic salts of acidic residues such as carboxylic acids; and the like.

Preferred cations of inorganic bases which can be suitably used to prepare salts within the invention comprise ions of alkali or alkaline-earth metals such as potassium, sodium, calcium or magnesium. Preferred cations of organic bases comprise, inter alia, those of primary, secondary and tertiary amines such as ethanolamine, diethanolamine, morpholine, glucamine, N-methylglucamine, N,N-dimethylglucamine.

Preferred anions of inorganic acids which can be suitably used to salify the complexes of the invention comprise the ions of halo acids such as chlorides, bromides, iodides or other ions such as sulfate.

Preferred anions of organic acids comprise those of the acids routinely used in pharmaceutical techniques for the salification of basic substances such as, for instance, acetate, succinate, citrate, fumarate, maleate or oxalate.

Preferred cations and anions of amino acids comprise, for example, those of taurine, glycine, lysine, arginine, ornithine or of aspartic and glutamic acids.

Optical Imaging

In one further preferred embodiment of the invention, T represents an optically active imaging moiety.

Compounds of Formula (I) in which T is an optically active imaging moiety are new and constitute a further object of the present invention. These compounds are preferred for use as for optical imaging contrast agents.

Thus, in a still further embodiment, the invention relates to novel contrast agents for optical imaging having Formula (I), in which T is an optically active imaging moiety.

Suitable examples of optically active imaging moieties include those discussed herein, for instance, a dye molecule; a fluorescent molecule such as, for example, fluorescein; a phosphorescent molecule; a molecule absorbing in the UV spectrum; a quantum dot; or a molecule capable of absorption of near or far infrared radiations.

Optical parameters to be detected in the preparation of an image may include, e.g., transmitted radiation, absorption, fluorescent or phosphorescent emission, light reflection, changes in absorbance amplitude or maxima, and elastically scattered radiation. For example, biological tissue is relatively translucent to light in the near infrared (NIR) wavelength range of 650-1000 nm. NIR radiation can penetrate tissue up to several centimeters, permitting the use of the diagnostic agents of the invention comprising a NIR moiety to image target-containing tissue in vivo.

Near infrared dye may include, cyanine or indocyanine derivatives, such as, for example, Cy5.5, IRDye800, indocyanine green (ICG), indocyanine green derivatives including the tetrasulfonic acid substituted indocyanine green (TS-ICG), and combination thereof.

In another embodiment, the compounds of the invention may include photolabels, such as optical dyes, including organic chromophores or fluorophores, having extensively conjugated and hence delocalized ring systems and having absorption or emission maxima in the range of 400-1500 nm. The compounds of the invention may alternatively be derivatized with a bioluminescent molecule. The preferred range of absorption maxima for photolabels is between 600 and 1000 nm to minimize interference with the signal from hemoglobin. Preferably, photoabsorption labels have large molar absorptivities, e.g. $>10^5$ cm$^{-1}$ M$^{-1}$, while fluorescent optical dyes will have high quantum yields. Examples of optical dyes include, but are not limited, to those described in WO 98/18497, WO 98/18496, WO 98/18495, WO 98/18498, WO 98/53857, WO 96/17628, WO 97/18841, WO 96/23524, WO 98/47538, and references cited therein.

For example, the photolabels may be covalently linked directly to the peptide moiety of the invention, or one or more of them may be linked thereto through a branching chain Y, as described previously.

After injection of the optically-labeled diagnostic derivative according to the invention, the patient is scanned with one or more light sources (e.g., a laser) in the wavelength range appropriate for the photolabel employed in the agent. The light used may be monochromatic or polychromatic and continuous or pulsed. Transmitted, scattered, or reflected light is detected via a photodetector tuned to one or multiple wavelengths to determine the location of target-containing tissue (e.g. angiogenic tissue) in the subject. Changes in the optical parameter may be monitored over time to detect accumulation of the optically-labeled reagent at the target site. Standard image processing and detecting devices may be used in conjunction with the optical imaging reagents of the present invention.

In a preferred embodiment, the invention relates to novel optical imaging agents of Formula (I) wherein T is the residue of a 5-Carboxyfluorescein.

Use of Compounds of Formula I for Imaging and Treating Pathological Conditions Associated with Fibrin, Particularly Tumors As discussed above, the peptide moiety compounds of the invention are able to selectively bind to fibrin and, in particular, to fibrin present in the extracellular matrix (EC) of tumor or connective tissue of stroma thus acting as targeting moiety able to localize an active moiety linked thereto to fibrin depositions and, especially, to fibrin deposition inside solid tumors or metastatic tissues.

The compounds of the present invention may thus find advantageous application for the diagnosis, prevention and treatment of all pathological conditions associated with fibrin deposition, including clots and thromboembolic diseases and, especially, solid tumors and metastatic processes. Moreover, they may advantageously be used to follow up and monitor oncological therapy efficacy and tumor treatment results.

In particular, the compounds of Formula (I) in which T is a diagnostically active moiety according to the invention may find advantageous application for localizing and diagnostically visualizing fibrin deposition associated with atherosclerosis and plaque formation. In a further aspect compounds of the invention allow diagnostic imaging of inflammatory processes, including demyelination processes and axonal damage involved in multiple sclerosis and, in general, of all inflammatory conditions associated with processes in which fibrin plays a role. In an especially preferred aspect, the compounds of Formula (I) in which T is a diagnostically active moiety according to the invention may find advantageous application in localizing and visualizing fibrin content inside solid tumor and metastatic processes.

In a further aspect, the compounds of Formula (I) in which T is a diagnostically active moiety may find application in the non invasive histopathologic grading of solid tumors. A correlation, in fact, exists between the MRI derived measures of the fibrin content inside the tumor mass the compounds of the invention provide and the histopathologic grade of the said solid tumor.

The compounds of Formula (I) in which T is a therapeutically active moiety may find advantageous application for prevention, amelioration and/or treatment of pathological conditions associated with fibrin deposition, including clots and thromboembolic diseases and atherosclerotic plaques and inflammatory damages associated with fibrin deposition. In an especially preferred aspect, the compounds of Formula (I) in which T is a therapeutically active moiety may find advantageous application for preventing, ameliorating and/or treating solid tumors and metastatic processes associated therewith. In an even more preferred embodiment, the compounds of Formula (I) in which T is a radiotherapeutic moiety may be advantageously used to provide radiotherapy to a patient (particularly a human) in need thereof due to the presence of one or more solid tumors and metastatic processes associated therewith.

In another embodiment, the invention concerns pharmaceutical compositions containing, as an active ingredient, at least one compound of Formula (I), including pharmaceutically acceptable salts thereof, in combination with one or more possible pharmaceutically acceptable carriers or excipients.

In an even further aspect thereof, the invention relates to the use of the compounds of Formula (I) in which T is a diagnostically active moiety for the diagnosis in vitro (of ex vivo samples) of pathological systems, including cells, biological fluids and biological tissues originating from a live mammal patient, and preferably, human patient. Additionally, the invention relates to the use of the compounds of Formula (I) in which T is a diagnostically active moiety for the preparation of pharmaceutical compositions for use in the diagnostic imaging, in vivo, of human body organ, regions or tissues, including tumorous or cancerous tissues and inflammations, wherein fibrin depositions occur.

In yet another aspect the invention provides a method for imaging solid tumors or tumorous cells both in vitro (of ex vivo samples) and in vivo, the method comprising the use of a diagnostic imaging agent of the invention and an imaging technique.

Furthermore, the invention provides a method for treating and/or ameliorating solid tumors or tumorous cells in vivo, the method comprising administering a therapeutic agent of the invention.

Preparations

The preparation of the compounds of Formula (I), in which T is the residue of a chelating agent labelled with a paramagnetic metal ion or a radionuclide, either as such or in the form of physiologically acceptable salts, represents a further object of the invention.

Isolation, conjugation and use of fibrin binding moieties (and conjugates thereof with diagnostically or therapeutically active moieties) in accordance with this invention will be further illustrated in the following examples. The specific parameters included in the following examples are intended to illustrate the practice of the invention, and they are not presented to in any way limit the scope of the invention.

EXAMPLES

The following materials were used in performing the Examples below:

Materials:

Fmoc-protected amino acids used were obtained from Nova-Biochem (San Diego, Calif., USA), Advanced ChemTech (Louisville, Ky., USA), Chem-Impex International (Wood Dale Ill., USA), and Multiple Peptide Systems (San Diego, Calif., USA). DPPE, DSPE-PG4-$NH_2$, and DPPE-PG4-$NH_2$ were obtained from Avanti Polar Lipids (Alabaster, Ala.). Fmoc-PEG3400-NHS was obtained from Shearwater Polymers (Huntsville, Ala.). Other reagents were obtained from Aldrich Chemical Co. (Milwaukee, Wis.) and VWR Scientific Products (Bridgeport, N.J.). Solvents for peptide synthesis were obtained from Pharmco Co. (Brookfield, Conn.).

Examples 1-7 and 23 utilize and make reference to procedures A-L described below.

Procedures for Peptide Synthesis

Procedure A

Automated Peptide Solid Phase Peptide Synthesis

Individual peptides were prepared using an ABI 433A instrument (Applied Biosystems, Foster City, Calif.). PAL-Peg-PS-Resin (1.2 g, 0.18 mmol/g) or NovaSyn TGR resin (1.25 g, 0.20 mmol/g) (NovaBiochem, Novato, Calif.) was used for all syntheses. The peptides were assembled on resin using the FastMoc™ protocol. After the synthesis, the resin was washed with DCM (2×) and dried.

Procedure B

Manual Coupling of Amino Acids

DMF was used as the coupling solvent unless otherwise stated. The appropriate Fmoc-amino acid in DMF (0.25M solution, 3 equiv) was treated with HATU (0.5M in NMP, 3.0 equiv) and DIEA (6.0 equiv). The mixture was shaken for ~2 min and then was transferred to the synthesis vessel containing the resin. The vessel was then shaken overnight at ambient temperature. The resin was filtered to remove excess reagents and then washed (4×) with DMF.

Procedure C

Manual Removal of the Fmoc Protecting Group

The resin containing the Fmoc-protected amino acid was treated with 20% piperidine in DMF (v/v, 15.0 mL/g resin) for 10 min. The solution was drained from the resin. This procedure was repeated once and then followed by washing the resin with DMF (4×).

Procedure D

Removal of the ivDde Group (Solid Phase)

The resin containing the ivDde-protected amino acid was treated with 10% (v/v) hydrazine in DMF (10 mL/g resin) for 10 min. The solution was drained from the resin. This procedure was repeated once and then followed by washing the resin with DMF (4×).

Procedure E

Removal of the ivDde Group from Peptides in Solution

The peptide (50 mg) was dissolved in DMF (2.0 mL) and treated with neat hydrazine (40-200 µL) for 10 min. The mixture was diluted with water to a volume of 10 mL and this was directly applied to a C18 reverse phase column and purified by preparative HPLC as described in the general procedures.

Procedure F

Coupling of Fmoc-Adoa (Fmoc-J)

Fmoc-Adoa (2 equiv) and HATU (2 equiv) were dissolved in DMF and DIEA (4 equiv) was added to the mixture. The mixture was stirred for 1 min before transferring the activated acid to the resin. The concentration of reagents was as discussed above for standard peptide couplings. The coupling was continued for 12 h at ambient temperature. The resin was drained of the reactants and washed with DMF (4×). In cases where two Adoa units were appended to the resin, the Fmoc group of the first appended Fmoc-Adoa unit was removed (procedure C), the resin washed with DMF (4×) and followed by coupling of the second Adoa moiety.

Procedure G

Cleavage and Side-Chain Deprotection of Resin Bound Peptides

Reagent B (88:5:5:2-TFA:water:phenol:TIPS-v/v/wt/v), 15 mL/g resin, was added to ~1.0 g of the resin and the vessel was shaken for 4.5 h at ambient temperature. The resin was filtered and washed twice with TFA (5 mL/g resin). The filtrates were combined, concentrated to give a syrup which upon Trituration with 20 mL of $Et_2O$/g of resin gave a solid residue which was stirred for 5-15 min and then centrifuged. The supernatant was decanted and the process was repeated three times. The resulting solid was dried under high vacuum or with a stream of dry nitrogen gas.

Procedure H

Disulfide Cyclization

The precipitate obtained from trituration of the crude cleavage mixture with $Et_2O$ was transferred to a beaker and DMSO (5-10 µL/mg crude peptide) was added. The pH of the solution was adjusted to 8 by adding N-methyl-D-glucamine (10-100 mM in H$_2$O). The mixture was stirred for 48 h and was then purified by preparative HPLC.

Procedure I

Preparation of 5-Carboxyfluorescein (CF5) Derivatives of Peptides

To a solution of a peptide in DMF (15 μL/mg) and DIEA (20 equiv/equiv peptide) was added 5-carboxyfluorescein NHS ester (1.3-1.5 equiv.) in DMF (20 μL/mg). The mixture was stirred for 1-3 h. The reaction was monitored by mass spectroscopy and analytical HPLC. Upon completion of the reaction, the crude was filtered and purified by preparative HPLC.

Procedure J

Preparation of Aloc-Gly-OH

Gly-O-t-Bu.AcOH (1 g, 5.24 mmol) was dissolved in DCM (15 mL), and diallyl pyrocarbonate (1.1 g, 5.91 mmol, 1.13 equiv) was added dropwise. The mixture was stirred at ambient temperature for 0.5 h. Then DIEA (3.7 g, 5 mL, 28.68 mmol, 5.47 equiv) was added. The mixture was stirred at ambient temperature overnight. The volatiles were removed and the crude residue was dissolved in EtOAc (100 mL/g of crude) and the organic layer was washed with 1N HCl (2×). The volatiles were removed and the crude was dried at high vacuum. NMR (500 MHz, CDCl$_3$) indicated a pure product and was consistent with the structure. The crude was then dissolved in a solution of TFA/DCM (1/1, v/v, 25 mL) and the solution was stirred overnight. The volatiles were removed, EtOAc was added to wash any residue from the wall of the flask and then the volatiles were removed on the rotary evaporator. This was repeated. The resulting product was dried overnight at high vacuum. NMR spectroscopy of the material (CDCl$_3$, 500 MHz) was consistent with the expected structure and the purity was found to be sufficient for use in manual coupling protocols.

Procedure K

Preparation of Aloc-Arg(Pmc)-OH

H-Arg(Pmc)-OH (5 g, 11.35 mmol) was dissolved in a mixture of H$_2$O and Dioxane (1/1, v/v, 125 mL), and diallyl pyrocarbonate (6.34 g, 34.05 mmol, 3.0 equiv) was added. The pH of the mixture was adjusted to >10.0 by adding Na$_2$CO$_3$. The mixture was stirred and kept at reflux overnight. The volatiles were removed by rotary evaporation, the crude was dissolved in EtOAc (100 mL/g of crude) and the solution was washed with 1N HCl (2×). The volatiles were removed by rotary evaporation, the crude was dissolved in CHCl$_3$ and the solution was loaded onto a silica gel column. The column was eluted with two column volumes of CHCl$_3$ and then similarly eluted with a 5% solution of MeOH in CHCl$_3$. Fractions containing the desired compound were combined and the volatiles were removed by rotary evaporation and pumping at high vacuum to provide 4.2 g (70% yield) of Aloc-Arg(Pmc)-OH. The proton NMR spectrum (CDCl$_3$, 500 MHz) was consistent with the expected structure and required purity.

Procedure L

Removal of the Aloc Protecting Group from Peptides

The Aloc-protected peptide was dissolved in 5-20 mL/100 mg peptide of a solution of NMM:acetic acid:DMF (1:2:10).

Pd(PPh$_3$)$_4$ (1-10 equiv/equiv peptide) was added. The mixture was stirred for 0.5-4 h. MS and analytical HPLC were used to check the reaction. After the reaction was complete, the crude reaction mixture was diluted to twice its volume with 10%-25% CH$_3$CN in H$_2$O, filtered and purified by preparative HPLC.

Methods for Analysis and Purification

Analytical HPLC

Column: Waters Corp. X-Terra, MS-C$_{18}$; 4.6 mm i.d.×50 mm; 5 μm particle; Eluent A: Water (HPLC Grade with 0.1% TFA by weight); Eluent B: Acetonitrile (0.1% TFA by weight). Initial conditions and gradient elution profiles employed are described in the respective experimental procedures for analysis of the title compounds. Elution rate: 3 mL/min; Detection: UV at 220 nm.

Preparative HPLC Purification

Column: Waters Corp. X-Terra MS-C$_{18}$; 50 mm i.d.×250 mm; 10 μm particle; Eluents: Eluent A: Water (HPLC Grade with 0.1% TFA by weight); Eluent B: Acetonitrile (0.1% TFA by weight); Initial conditions and gradient elution profiles employed are described in the respective experimental procedures for analysis of the title compounds. Elution rate: 100 mL/min; Detection: UV at 220 nm.

Preparative HPLC Purification for Phospholipid Peptide Conjugates

Purification of Phospholipid Peptide Conjugates Employing the Kromasil Prep C4 HPLC Column The reaction mixture was diluted with distilled deionized water and purified on a reverse phase C4 preparative column (Kromasil® Prep C$_4$, particle size 10 μm, pore size 300 Å, 20×250 mm), using a gradient of 50-100% water (0.1% TFA) into CH$_3$OH:CH$_3$CN (1:1, v/v, 0.1% TFA) at 100 mL/min over a period of 30 min. Fractions (15 mL) were analyzed by HPLC (column: YMC C-4, 5 μm, 300 Å, 4.6×250 mm) and the pure product-containing fractions were pooled. Methanol was removed from the combined product-containing eluates by rotary evaporation; the resulting solution was diluted with 10% aqueous acetonitrile, frozen and lyophilized to provide the desired product.

Purification of Phospholipid Peptide Conjugates Employing the Zorbax Prep C-3 HPLC Column The diluted reaction mixture was loaded onto a Zorbax C-3 column (21.2 mm i.d.×150 mm) which was pre-equilibrated with 25% B (CH$_3$CN with 0.1% TFA) at a flow rate of 30 mL/min. The column was eluted at 30 mL/min with the same eluent until the plug of DMF was eluted. The proportion of eluent B was then increased from 25% B to 30% B over 3 min and then ramped to 100% B over 50 min. Fractions (15 mL) were collected and product-containing fractions were pooled, frozen and lyophilized.

HPLC Methods Employed for Analysis of Compounds

HPLC Systems Employed for Analysis of Peptides and Phospholipid-Peptide Conjugates System A: Column: Waters XTerra MS-C18 4.6×50 mm; Particle size: 5 microns; Eluents: A: Water (0.1% TFA), B: Acetonitrile (0.1% TFA); Elution: linear gradient 5-55% B in 7 min; Flow rate: 3 mL/min; Detection: UV, λ=220 nm.

System B: Column: Waters XTerra MS-C18 4.6×50 mm; Particle size: 5 microns; Eluents: A: Water (0.1% TFA), B: Acetonitrile (0.1% TFA); Elution: linear gradient 5-65% B in 7 min; Flow rate: 3 mL/min; Detection: UV, λ=220 nm.

System C: Column: Waters XTerra MS-C18 4.6×50 mm; Particle size: 5 microns; Eluents: A: Water (0.1% TFA), B: Acetonitrile (0.1% TFA); Elution: linear gradient 15-65% B in 7 min; Flow rate: 3 mL/min; Detection: UV, λ=220 nm.

System D: Column: Waters XTerra MS-C18 4.6×50 mm; Particle size: 5 microns; Eluents: A: Water (0.1% TFA), B:

Acetonitrile (0.1% TFA); Elution: Isocratic at 15% B for 1 min, then linear gradient 15-70% B in 6 min; Flow rate: 3 mL/min; Detection: UV, λ=220 nm.

System E: Column: Waters XTerra MS-C18, 4.6 mm i.d.× 50 mm; Particle size: 5 microns; Eluents: A: Water (0.1% TFA), B: Acetonitrile (0.1% TFA); Elution: linear gradient 15-60% B in 6 min; Flow rate: 3.0 mL/min; Detection: UV, λ=220 nm.

System F: Column: YMC C18, 4.6×250 mm; Eluents: A: Water (0.1% TFA), B: Acetonitrile (0.1% TFA), Initial condition: 20% B, Elution: linear gradient 20-80% B in 20 min; Flow rate: 1.0 mL/min; Detection: UV, λ=220 nm.

System G: Column: Waters XTerra MS-C18, 4.6 mm i.d.× 50 mm; Particle size: 5 microns; Eluents: A: Water (0.1% TFA), B: acetonitrile (0.1% TFA); Elution: Initial condition: 10% B, linear gradient 10-50% B over 8 min; Flow rate: 3 mL/min; Detection: UV, λ=220 nm.

System H: Column: Waters XTerra MS-C18 4.6×50 mm; Particle size: 5 microns; Eluents: A: Water (0.1% TFA), B: Acetonitrile (0.1% TFA); Elution: Initial condition: 5% B, linear gradient 5-65% B in 8 min; Flow rate: 3 ml/min; Detection: UV @ 220 nm.

System I: Column: Waters XTerra C-4, 4.6×50 mm; Eluents: A: Water (0.1% TFA), B: Acetonitrile:Methanol (1:1) (0.1% TFA); Elution: Initial condition: 80% B, linear gradient 80-100% B in 6 min.; Flow rate: 3.0 mL/min; Detection: UV, λ=220 nm.

System J: Column: YMC C-4, 4.6×250 mm; Eluents: A: Water (0.1% TFA), B: Acetonitrile:Methanol (1:1)(0.1% TFA); Elution: Initial condition: 80% B, linear gradient 80-100% B in 50 min.; Flow rate: 2.0 mL/min; Detection: UV, λ=220 nm and ELSD: Sensitivity 10, Temp. 51 Deg C., Pressure 2.2 Torr.

System K: Column: YMC C4; 250 mm×4.6 mm i.d.; Particle size: 5.0 microns; Eluents: A:Water (0.1% TFA), B: acetonitrile (0.1% TFA); Elution: Initial condition: 80% B, linear gradient 80-90% B over 100 min, then ramp to 100% B over 1 min, then hold at 100% B for 1 min; Flow rate: 2.0 mL/min; Detection: UV, λ=220 nm and ELSD: Sensitivity 10, Temp. 51 Deg C., Pressure 2.2 Torr.

System L: Column: YMC C-4, 4.6×250 mm; Eluents: A: Water (0.1% TFA), B: Acetonitrile/Methanol (1:1, v/v)(0.1% TFA); Elution: Initial condition: 60% B, linear gradient 60-100% B in 20 min.; Flow rate: 2.0 mL/min; Detection: UV, λ=220 nm and ELSD: Sensitivity 10, Temp. 51 Deg C., Pressure 2.2 Torr.

System M: Column: YMC C-4, 4.6×250 mm; Eluents: A: Water (0.1% TFA), B: Acetonitrile/Methanol (1:1, v/v) (0.1% TFA); Elution: Initial condition: 50% B, linear gradient 50-90% B in 10 min.; Flow rate: 3.0 mL/min; Detection: UV, λ=220 nm and ELSD: Sensitivity 10, Temp. 51 Deg C., Pressure 2.2 Torr.

System N: Column: Zorbax 300SB C-3, 3 mm i.d.×150 mm; 3.5 μm particle; Eluent A: Water (0.1% TFA); Eluent B: Acetonitrile (0.1% TFA). Initial condition: 50% B; Elution: linear gradient 50-90% B over 3 min, hold at 90% B for 11 min; Elution rate: 0.5 mL/min; Detection: UV, λ=220 nm and ELSD: Sensitivity 10, Temp. 51 Deg C., Pressure 2.2 Ton.

System O: Column: YMC C-4, 4.6×50 mm; Eluents: A: Water (0.1% TFA), B: Acetonitrile-Methanol (1:1 v/v) (0.1% TFA); Elution: Initial condition: 75% B, linear gradient 70-100% B in 10 min.; Flow rate: 3.0 mL/min; Detection: UV, λ=220 nm and ELSD: Sensitivity 10, Temp. 51 deg C., Pressure 2.2 Torr.

System P: Column: ES industries MacroSep C4, 4.6×50 mm; Particle size: 5μ; Eluents: A: Water (0.1% TFA), B: Acetonitrile/Methanol (1:1 v/v) (0.1% TFA); Elution: Initial condition: 25% B, linear gradient 25-100% over 7 min; Flow rate; 3 mL/min; Detection: U @ 220 nm Assay of Fibrin Binding Peptides by Direct Binding Fluorescence Polarization (FP) Procedure using 5-Carboxyfluorescein Labeled Peptides Protocol 1. Prepare 1 mL of 40 nM solution of 5-carboxyfluorescein-labeled peptide in HEPES dilution buffer (HDB) with 0.01% Tween.
   HDB (10 mM HEPES, 150 mM NaCl$_2$, 2 mM CaCl$_2$)
2. Dilute the 40 nM solution to obtain 1 ml of a 20 nM solution of the test 5-carboxyfluorescein-labeled peptide.
3. Prepare a solution of DDE at a concentration that will be approximately 5-10 fold greater than the expected K$_D$. For the described assay an 8 μM concentration of DDE was prepared.
4. Mix equal volumes of the DDE solution with the 40 nM peptide solution.
5. Prepare serial dilutions of DDE in a solution consisting of the binding buffer with 0.01% Tween20 and 20 nM of the 5-carboxyfluorescein-labeled peptide.
6. Make dilutions as shown in the following table in a Labsystems 384-well microplate and mix by repeated aspiration and dispensing of the solution into the wells.
7. Centrifuge the plate at 2000 RPM for 5 minutes to remove air pockets in the wells.
8. Read in Tecan Polarion Plate Reader at 485 nm to obtain the anisotropy value.

| Row | Target Protein Solution (μL) | 20 nM Peptide Solution (μL) | HDB Solution (μL) |
|---|---|---|---|
| A | 0 | 8 | 8 |
| B | 0 | 8 | 0 |
| C | 16 uL Row D | 8 | 0 |
| D | 16 uL Row E | 8 | 0 |
| E | 16 uL Row F | 8 | 0 |
| F | 16 uL Row G | 8 | 0 |
| G | 16 uL Row H | 8 | 0 |
| H | 16 uL Row I | 8 | 0 |
| I | 16 uL Row J | 8 | 0 |
| J | 16 uL Row K | 8 | 0 |
| K | 16 uL Row L | 8 | 0 |
| L | 16 uL Row M | 8 | 0 |
| M | 16 uL Row N | 8 | 0 |
| N | 16 uL Row O | 8 | 0 |
| O | 16 uL Row P | 8 | 0 |
| P | 12 μL Target Protein Solution + 12 μL 40 nM Peptide Solution | 0 | 0 |

The anisotropy (in mP—millipolarization units) vs the logarithm of the concentration (micromoles/liter) of the receptor concentration is graphed. The dissociation constant is obtained at the midpoint of the curve whose extrema are $A_{free}$ and $A_{bound}$ where $A_{free}$ is the anisotropy of the free peptide and $A_{bound}$ is the anisotropy of the fully bound peptide. The theory, methods of operation and mathematical analysis is described in, for example, the following reference: Fluorescence Polarization Technical Resource Guide Technical Resource Guide 4$^{th}$ Edn. Invitrogen Corporation•501 Charmany Drive•Madison, Wis. 53719 USA. Particularly, the mathematical analysis of the data and obtaining binding constants is described in Chapter 8: Analysis of FP Binding Data pp 8-2-8-7.

Assay of Fibrin Binding Peptides by Competition Binding Fluorescence Polarization (FP) Procedure Using Competition of Unlabeled Test Peptides vs the Standard 5-Carboxyfluoresein Labeled Peptide Seq000-CF5.

DDE at $10^{-5}$M concentration was aliquoted into a 96-well plate. The standard 5CF-labeled peptide Seq000-CF5 was added to DDE-containing wells to provide an initial tracer concentration of $10^{-6}$M. An aliquot of competitor peptide was added to each well in order to span a concentration range of $10^{-10}$ M to $10^{-3}$M. The peptides were incubated with the DDE/Seq000-CF5 complex for 2 h. Then the anisotropy value was read on the Tecan Polarion Plate Reader at 485 nm. The competition curve was constructed using all of the concentrations of the test peptide. The mathematical analysis of the data and calculation of the $IC_{50}$ for the test peptides was accomplished using the regression routines in Prism Graph Pad™ Software. The theoretical and mathematical basis for the experimental procedure and the data analysis is given in, for example: "Practical Use of Fluorescence Polarization In Competitive Receptor Binding Assays"—Section P of "Receptor Binding Assays" http://www.Ncgc.Nih.Gov/Guidance/Section5.Html#Practical-Fluor-Polar. Copyright© 2005, Eli Lilly and Company and the National Institutes Of Health Chemical Genomics Center. The relative IC50 values for test peptides vs Seq000-CF5 were obtained by division of their IC50 by that obtained by titration of Seq005 into Seq005-CF5/DDE complex. Thus lower relative IC50 indicates a stronger binding peptide. See Tables 1 and 2, supra.

Examples 1-3 below describe the preparation of exemplary peptides Seq016, Seq017, and Seq049.

Example 1

Preparation of
Ac-GWQPC*PWESWTFC*WDPGGGK-NH$_2$
Cyclic (5→13) Peptide (Seq016) (SEQ ID NO. 7)

The peptide sequence was prepared by SPSS from Fmoc-PAL-PEG-PS resin (0.18 mmol/g, 1.38 g, 0.25 mmol) as described in procedure A using an ABI peptide synthesizer employing Fmoc chemistry which was implemented using the FastMoc™ protocol. Cleavage and side-chain deprotection was conducted as described in procedure G and disulfide cyclization was accomplished as described in procedure H. HPLC purification provided 105 mg (17.8% yield) of the purified cyclic peptide.

Example 2

Preparation of
Ac-SGSGJWQPC*PWESWTFC*WDPGGGK-NH$_2$
(Cyclic 9→17) Peptide (Seq017) (SEQ ID NO. 9)

Procedures A, G and H were employed to prepare the peptide on a 0.266 mmol scale and HPLC purification provided 130 mg (18.8% yield) of the pure product.

Example 3

Preparation of
Ac-RWQPC*PAESWT-Cha-C*WDPGGGK-NH$_2$
Cyclic (5→13) Peptide (Seq049) (SEQ ID NO. 69)

The peptide was prepared using the methods of procedures A, G and H. HPLC purification provided a 140 mg (27.5% yield) portion of the product as a fluffy white solid.

Example 4 below and FIG. 1 describe and illustrate the process used for the preparation of Adoa-Adoa linker functionalized Seq005.

Example 4

Preparation of
Ac-WQPC*PAESWTFC*WDPGGGK(JJ)-NH$_2$
Cyclic (4→12) Peptide, (Seq005-JJ) (SEQ ID NO. 136)

The ivDde-protected peptide Ac-W($N^{in}$-Boc)-Q(Trt)-P-C(Trt)-P-A-E(OtBu)-Ser(tBu)-W($N^{in}$-Boc)-T(tBu)-F-C(Trt)-W($N^{in}$-Boc)-D(OtBu)-P-GGGK(ivDde)-NH-TGR was assembled on a 130 μmol scale (0.65 g resin) (procedure A). The ivDde group was removed (procedure D) by treatment of the resin with 10% hydrazine in DMF (6.5 mL) for 10 min (2×). Then the resin was washed with DMF (4×). In a separate flask Fmoc-Adoa (100 mg, 0.26 mmol, 2.0 equiv) in NMP (1 mL) was treated with HATU (99 mg, 0.26 mmol, 2 equiv) in DMF (0.5 mL) and DIEA (67 mg, 91 μL, 0.52 mmol, 4 equiv) for 2 min after which the solution was transferred to the vessel containing the resin followed by agitation of the vessel for 12 h at ambient temperature (procedure F).

The resin was washed with DMF (4×5 mL) and the Fmoc group was removed by treatment with 20% piperidine in DMF (10 mL, 2×10 min) followed by washing (4×10 mL) with DMF (procedure C). Then Fmoc-Adoa was coupled to the resin as described (vide supra) followed by removal of the Fmoc protecting group (vide supra) and washing of the resin. Cleavage and side-chain deprotection (procedure G) was conducted for 4.5 h using Reagent B (10 mL). The resin was drained and washed with TFA (5 mL) and the combined solutions were evaporated and triturated with ether to provide the crude linear peptide as an off-white solid. The solid was dissolved in DMSO (3 mL) after which the pH of the solution was adjusted to 8 by addition of 0.1M aqueous N-methylglucamine. The mixture was stirred for 48 h (procedure H) during which time the reaction was monitored by analytical HPLC and mass spectroscopy. At the end of the reaction period the entire solution was diluted to 15 mL with 10% CH$_3$CN in H$_2$O and the pH was adjusted to 2 by addition of aqueous TFA.

The resulting solution was applied to a preparative reverse-phase C18 column and purified using a linear gradient of 10% CH$_3$CN (0.1% TFA) into H$_2$O (0.1% TFA). Fractions (15 mL) were collected and the pure product-containing fractions were pooled, frozen and lyophilized to provide 42 mg (13% yield) of the peptide as a fluffy white solid which was characterized by HPLC and mass spectroscopy. HPLC: $t_R$ 3.83 min; Column: Waters XTerra MS-C18 4.6×50 mm; Particle size: 5 microns; Eluents: A: Water (0.1% TFA), B: Acetonitrile (0.1% TFA); Elution: linear gradient 5-65% B in 7 min; Flow rate: 3 mL/min; Detection: UV, λ=220 nm. Mass spectrum (API-ES): Neg. ion: [M-H]: 2480.6; [M-2H]/2: 1239.9

Examples 5 and 6 below describe the preparation of peptides bearing N-terminal Aloc-Arginine.

Example 5

Preparation of
Aloc-RWQPC*PWESWTFC*WDPGGGK-NH$_2$
Cyclic (5→13) Peptide (Seq023-Aloc) (SEQ ID NO. 22)

A 0.54 mmol (3 g) portion of W($N^{in}$-Boc)-Q(Trt)-P-C(Trt)-P-W($N^{in}$-Boc)-E(OtBu)-S(tBu)-W($N^{in}$-Boc)-T(tBu)-

F-C(Trt)-W(N$^{in}$-Boc)-D(OtBu)-P-GGG-K(Boc)-PAL-PEG-PS resin was prepared by automated SPSS (procedure A). Aloc-Arg(Pmc) was appended to the N-terminus using a modification of procedure B as follows: The resin was added to a manual solid phase synthesis vessel and suspended in DMF (20 mL) by brief agitation. Aloc-Arg(Pmc)-OH (524 mg, 1.00 mmol, 1.85 equiv), HATU (380 mg, 1.0 mmol, 1.85 equiv) and DIEA (257 mg, 347 µL, 1.98 mmol, 3.67 equiv) were added successively with intervening agitation of the vessel and the vessel was shaken overnight. The coupling reaction was complete as indicated by a negative ninhydrin test. The resin was washed with DCM (3×20 mL) and dried.

Reagent B (88:5:5:2—TFA: water: phenol: TIPS—v/v/wt/v) (25 mL) was added to the vessel and the vessel was shaken at ambient temperature for 5 h. The resin was filtered and washed with TFA (2×5 mL). The combined filtrates were concentrated to a syrup which was triturated with Et$_2$O (20 mL) and the resulting solid was pelleted by centrifugation. The supernatant liquid was decanted and the process was repeated three times (procedure G). The resulting solid was collected and cyclized (48 h) as described (procedure H) and purified by HPLC on a reverse phase C18 column. The product-containing fractions were pooled, frozen and lyophilized to provide 290 mg (21% yield) of the desired product.

Example 6

Preparation of
Aloc-RWQPC*PAESWT-Cha-C*WDPGGGK-NH$_2$
(Seq057-Aloe) (SEQ ID NO. 86)

The peptide was prepared by the methods of procedure A, B, G and H to give 230 mg (26.7% yield) portion of the product as a fluffy white solid.

Figure 2:
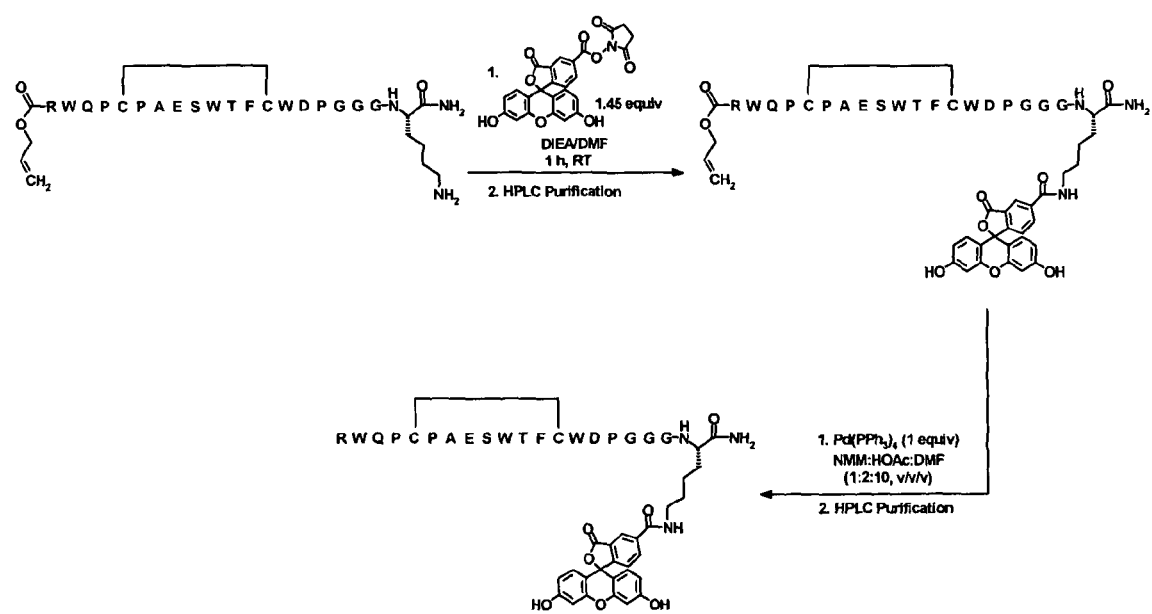
FIG. 2 illustrates a method for the preparation of a representative 5-carboxyfluorescein labeled peptide according to the present invention.

Example 7 below and FIG. 2 describe and illustrate the preparation of 5-carboxyfluorescein derivatives of peptides.

Example 7

Preparation of
RWQPC*PAESWTFC*WDPGGGK(CF5)-NH$_2$
Cyclic (5→13) Peptide (Seq056-CF5) (SEQ ID NO. 120)

The peptide Aloc-RWQPC*PAESWTFC*WDPGGGK-NH$_2$ cyclic (5→13) peptide (Seq056-Aloc) (SEQ ID NO. 140) was prepared by the methods of procedures A, B, G and H and purified by HPLC. The N-terminal Aloc N$^{\epsilon 20}$-CF5 derivative was prepared according to procedure I as follows: The peptide (70 mg, 0.029 mmol) was dissolved in anhydrous DMF (1 mL) with stirring, after which DIEA (0.074 g, 100 µL, 0.572 mmol, 19.7 equiv) was added followed by a solution of CF5-NHS (20 mg, 0.042 mmol, 1.45 equiv) in anhydrous DMF. The mixture was stirred 1 h at ambient temperature. The reaction mixture was diluted to twice its volume with 20% CH$_3$CN in H$_2$O and purified on a C18 reverse phase preparative HPLC column to provide 50 mg (62.8% yield) of Aloe-RWQPC*PAESWTFC*WDPGGGK(CF5)-NH$_2$ (SEQ ID NO. 141) cyclic (5→13) peptide.

The Aloc group of this intermediate was removed according to procedure L as follows: The intermediate was dissolved in a solution of NMM:HOAc:DMF (1:2:10, v/v/v, 5 mL), the mixture was stirred and Pd(PPh$_3$)$_4$ (21 mg, 0.018 mmol, 1.0 equiv) was added. The mixture was stirred 1 h at ambient temperature. Then the reaction mixture was diluted to twice its volume with 10% CH$_3$CN in H$_2$O and purified on a preparative reverse phase C18 column using a linear gradient of CH$_3$CN (0.1% TFA) into H$_2$O (0.1% TFA). The pure product-containing fractions were pooled, frozen and lyophilized to provide 29 mg (60.4% yield) of the product as an orange solid.

Figure 3:
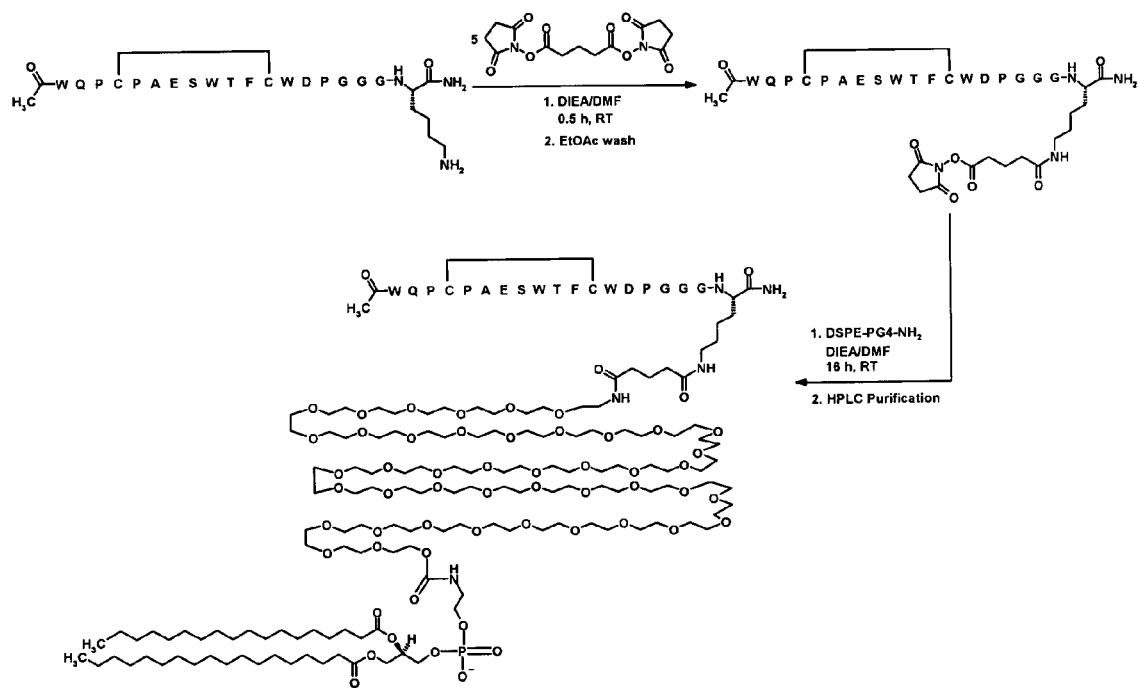
FIG. 3 illustrates a method for the preparation of a representative DSPE-PEG200 peptide conjugate according to the present invention.
Figure 4:
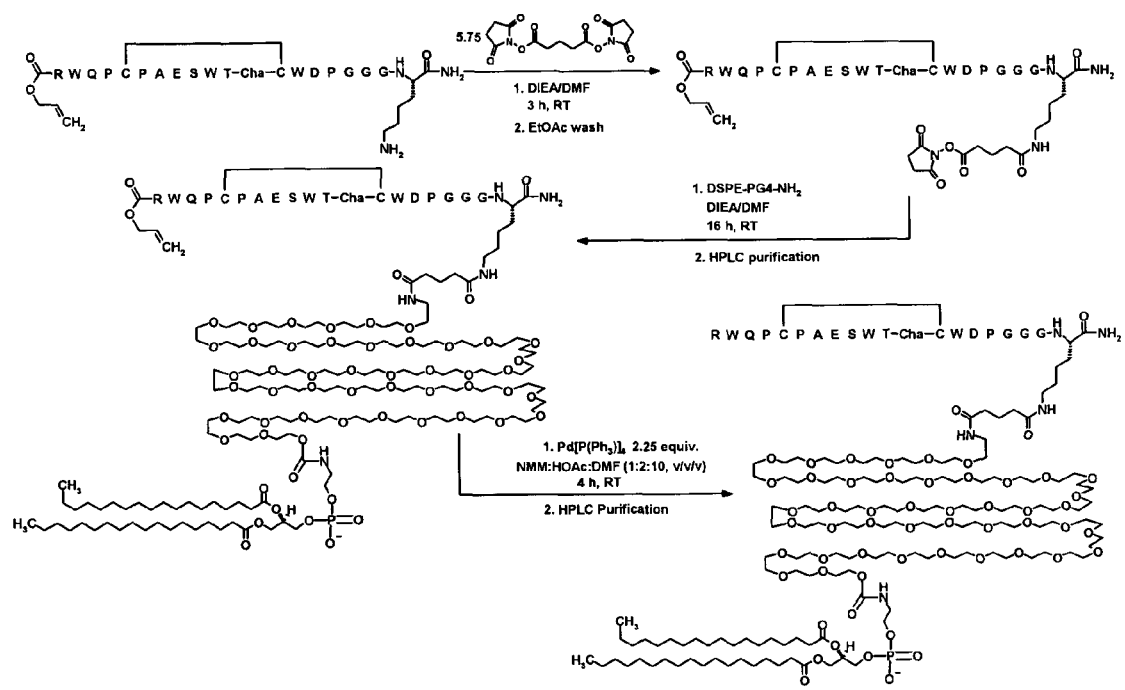
FIG. 4 illustrates a method for the preparation of a representative DSPE-PG4-Glut peptide conjugate according to the present invention.
Figure 5:
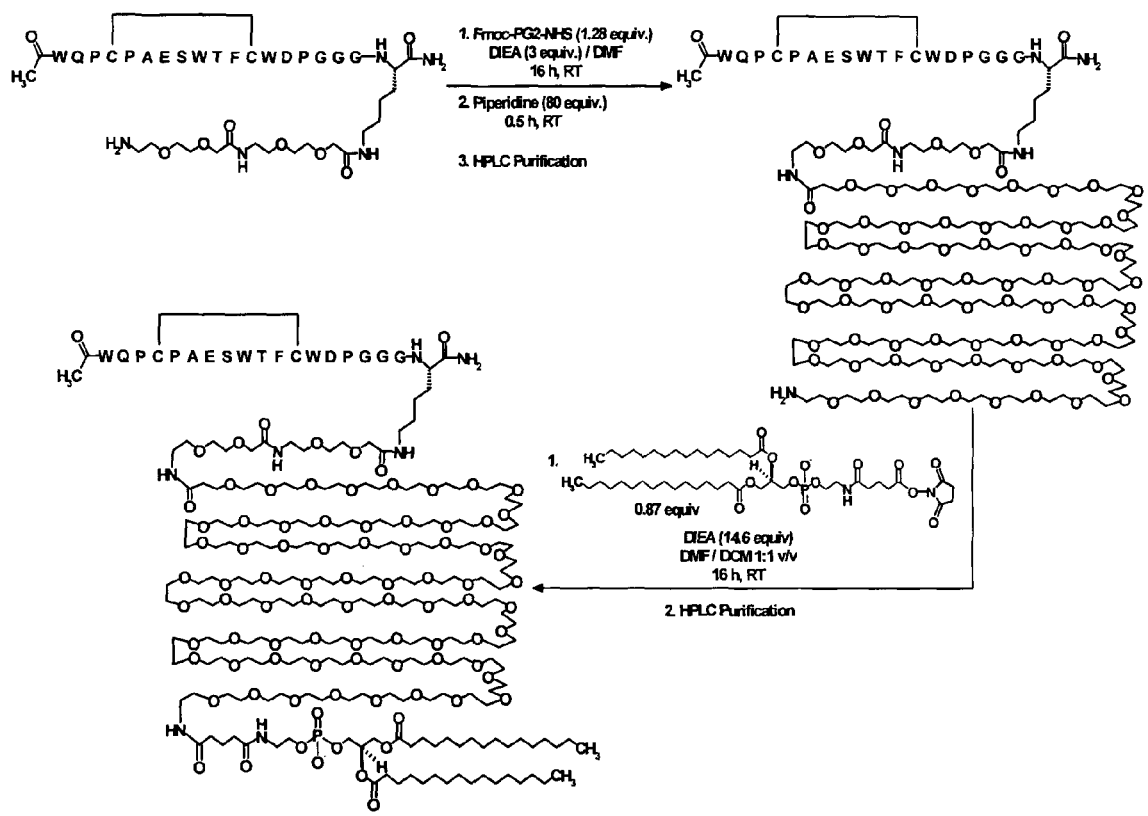
FIG. 5 illustrates a method for the preparation of a representative DPPE-Glut-PG2-JJ peptide conjugate according to the present invention.

Examples 8-16 below and FIGS. 3-5 describe and illustrate the preparation of lipopeptides, particularly DSPE-PG4-peptide conjugates, DPPE-PG4-peptide conjugates, DPPE-PG2-peptide conjugates, and DPPE-Pro9-Glut-Ttda-Dga-peptide conjugates. The following Table 5 sets forth the MS and analytical data for the lipopeptides:

TABLE 5

| | Sequence | HPLC Data (System, $t_R$) | MALDI Mass Spectral Data (Mode: Ions) |
|---|---|---|---|
| Seq005-PL1 | Ac-WQPC*PAESWTFC*WDPGGGK(DSPE-PG4-Glut)-NH$_2$ (SEQ ID NO. 123) | I, 5.612 | Pos. Ion: [M + H]: 5124 |
| Seq005-PL2 | Ac-WQPC*PAESWTFC*WDPGGGK(DPPE-PG4-Glut-)-NH$_2$ (SEQ ID NO. 124) | I, 5.361 | Pos. Ion: [M + H]: 5026 |
| Seq024-PL1 | Ac-SGSGSGSGWQPC*PWESWTFC*WDPGGGK(DSPE-PG4-Glut)-NH$_2$ (SEQ ID NO. 125) | J, 9.25 | Pos. Ion: 5753 [M + H], 1918 [M + 3H]/3, 1439 [M + 4H]/4, 1178 [M + 5H]/5 |
| Seq016-PL1 | Ac-GWQPC*PWESWTFC*WDPGGGK(DSPE-PG4-Glut)-NH$_2$ (SEQ ID NO. 126) | K, 11.40 | Pos. Ion: [M + H]: 5233 |
| Seq017-PL1 | Ac-SGSGJWQPC*PWESWTFC*WDPGGGK(DSPE-PG4-Glut)-NH$_2$ (SEQ ID NO. 127) | K, 10.67 | Pos. Ion: [M + H]: 5565 |
| Seq023-PL1 | RWQPC*PWESWTFC*WDPGGGK(DSPE-PG4-Glut)-NH$_2$ (SEQ ID NO. 128) | L, 15.42 | Pos. Ion: [M + H]: 5290 |
| Seq049-PL1 | Ac-RWQPC*PAESWT-Cha-C*WDPGGGK(DSPE-PG4-Glut)-NH$_2$ (SEQ ID NO. 129) | M, 7.12 | Pos. Ion: [M + H]: 522 |
| Seq057-PL1 | RWQPC*PAESWT-Cha-C*WDPGGGK(DSPE-PG4-Glut)-NH$_2$ (SEQ ID NO. 130) | N, 14.05 | Pos. Ion: [M + H]: 5180 |

TABLE 5-continued

| Sequence | | HPLC Data (System, $t_R$) | MALDI Mass Spectral Data (Mode: Ions) |
|---|---|---|---|
| Seq005-PL3 | Ac-WQPC*PAESWTFC*WDPGGGK(DPPE-Glut-PG2-JJ)-NH$_2$(SEQ ID NO. 131) | O, 5.97 | Pos. Ion: [M + H]: 6656 |
| Seq005-PL4 | Ac-WQPCPAESWTFCWDPGSAGSK(DPPE-Pro9-Glut-Ttda-P-Dga)-NH$_2$(SEQ ID NO. 132) | P, 5.68 | Neg. ion: [2M − 3H]/3: 2905.5, [M + Na − 3H]/2: 2189.6, [M − 2H]/2: 2178.4, [M − 3H]/3: 1452.2 |
| Seq005-PL5 | Ac-WQPCPAESWTFCWDPGAGSGK(DPPE-Pro9-Glut-Ttda-P-Dga)-NH$_2$ (SEQ ID NO. 133) | P, 5.77 | Neg. ion: [2M − 3H]/3: 2884.2, [M − 2H]/2: 2163.3, [M − 3H]/3: 1441.3 |

Example 8

Preparation of Ac-WQPC*PAESWTFC*WDPGGGK(DSPE-PG4-Glut)-NH$_2$ Cyclic (4→12) Peptide (Seq005-PL1) (SEQ ID NO. 123)

A solution of the peptide Ac-WQPC*PAESWTFC*WDPGGGK-NH$_2$ cyclic (4→12) peptide (Seq005) (SEQ ID NO.1) (150 mg, 0.069 mmol) in DMF (1.0 mL) was added to a stirred solution of DSG (0.34 mmol, 112 mg, 5 equiv) and DIEA (15 mg, 20 µL, 0.12 mmol, 1.67 equiv) in DMF (1.0 mL). The mixture was stirred for 0.5 h and the progress of the reaction was monitored by HPLC and MS. Upon completion of the reaction, the volatiles were removed in vacuo and the residue was washed with ethyl acetate (3×10 mL) to remove unreacted DSG. The residue was dried, re-dissolved in anhydrous DMF (1.0 mL) and a solution of DSPE-PG4-NH$_2$ (134 mg, 0.048 mmol) in DMF (1.0 mL) was added followed by DIEA (15 mg, 20 µL, 0.12 mmol, 1.67 equiv). The mixture was stirred for 16 h. The progress of the reaction was monitored by HPLC which indicated that the aminopegylated phospholipid was consumed at 16 h.

The reaction mixture was diluted with distilled, deionized water and purified on a reverse phase preparative column (YMC Prep C$_4$, particle size 10 µm, 30×250 mm), using a gradient of 50-75% water (0.1% TFA) into CH$_3$OH:CH$_3$CN (1:1, v/v, 0.1% TFA) at a flow rate of 30 mL/min over a period of 5 min then ramping to 100% B over 50 min. Fractions (15 mL) were analyzed by HPLC and the pure product-containing fractions were pooled. Methanol was removed from the combined product-containing eluates by rotary evaporation; the resulting solution was diluted with 10% aqueous acetonitrile, frozen and lyophilized to provide 108 mg (44% yield) of the desired product as a fluffy white solid.

Example 9

Preparation of Ac-SGSGSGSGWQPC*PWESWTFC*WDPGGGK (DSPE-PG4-Glut)-NH$_2$ cyclic (12→20) peptide (Seq024-PL1) (SEQ ID NO. 125)

A solution of DSG (50 mg, 0.15 mmol, 4.41 equiv) and DIEA (20 mg, 0.15 mmol, 4.41 equiv) in anhydrous DMF (2.0 mL) was stirred and the peptide Ac-SGSGSGSGWQPC*PWESWTFC*WDPGGGK-NH$_2$ cyclic (12→20) peptide (Seq024) (SEQ ID NO. 23) (100 mg, 0.034 mmol) was added in solid form portionwise to the above solution. The mixture was stirred at room temperature for 30 min. The volume of the reaction mixture was adjusted to 50 mL by addition of EtOAc and the precipitated solid was pelleted by centrifugation followed by decantation of the supernatant. The washing procedure was repeated (3×) to provide the glutaric acid monoamide mono-NHS ester of the peptide, whose identity was confirmed by mass spectral analysis [(M−2H)/2: 1546.1, (M−3H)/3: 1030.5], as a colorless solid.

The glutaric acid monoamide mono-NHS ester of the peptide was dissolved in dry DMF-DCM (2.0 mL, 8:2, v/v). DIEA (40 mg, 54 µL, 0.31 mmol) was added and the mixture was stirred. DSPE-PG4-NH$_2$ (45 mg, 0.038 mmol, 0.9 equiv) was added as a solid and the mixture was stirred for 24 h at ambient temperature. The volume of the mixture was adjusted to 100 mL by addition of CH$_3$OH (50%) and CH$_3$CN—water (1:1) (50%) and the resulting solution was filtered to remove insoluble material.

The filtered solution was loaded onto a C4 reverse phase column (YMC, Prep C$_4$, 10 µM, 100 Å, 30×250 mm) which had been pre-equilibrated with 50% CH$_3$OH and CH$_3$CN (eluent A)–water (eluent B) (1:1) at 30 mL/min. The column was washed with the same eluent until the plug of DMF was eluted from the column. The mobile phase composition was then ramped to 70% B in 1 min and the elution was continued at a linear gradient rate of 1% B/min to 100% B at which time the column was eluted with 100% B until the product was fully eluted from the column. Fractions (15 mL) were collected and those containing the product in >98% purity were collected and concentrated on a rotary evaporator to reduce the content of CH$_3$OH. The concentrated solution was diluted with 10% CH$_3$CN in water, frozen and lyophilized to provide 65 mg (60% yield) of the product as a colorless solid.

Example 10

Preparation of Ac-GWQPC*PWESWTFC*WDPGGGK(DSPE-PG4-Glut)-NH$_2$ Cyclic (5→13) Peptide (Seq016-PL1) (SEQ ID NO. 126)

The peptide Ac-GWQPC*PWESWTFC*WDPGGGK-NH$_2$ cyclic (5→13) peptide (Seq016) (SEQ ID NO. 7) (90 mg, 0.038 mmol) was dissolved in anhydrous DMF (0.5 mL) and this solution was added to a solution of DSG (65 mg, 0.2 mmol, 5.26 equiv) and DIEA (25 mg, 33.8 µL, 0.2 mmol, 5.26 equiv) in anhydrous DMF (0.5 mL) with stirring. The mixture was stirred 2 h and then EtOAc (20 mL) was added resulting in the formation of a solid which was pelleted by centrifugation. The supernatant liquid was decanted and this process was repeated twice to remove remaining DSG. The solid was dried under vacuum (<0.1 mm) for 30 min followed by dissolution by stirring in DMF (0.5 mL). Solid DSPE-PG4-NH$_2$ (53 mg, 0.19 mmol) was added portionwise and the resulting mixture was stirred overnight. The mixture was diluted with water (5 mL) and the crude mixture was purified by preparative HPLC to give 60 mg (30% yield) of the desired product as a white lyophilizate.

Example 11

Preparation of
Ac-SGSGJWQPC*PWESWTFC*WDPGGGK
(DSPE-PG4-Glut)-NH$_2$ Cyclic (9→17) Peptide
(Seq017-PL1) (SEQ ID NO. 127)

The peptide Ac-SGSGJWQPC*PWESWTFC* WDPGGGK-NH$_2$ cyclic (9→17) peptide (Seq017) (SEQ ID NO. 9) (100 mg, 0.039 mmol) was employed using the procedures described for the preparation of SEQ005-PL1. HPLC purification provided 53 mg (25.7% yield) of the target phospholipid-peptide conjugate.

Example 12

Preparation of RWQPC*PWESWTFC*WDPGGGK
(DSPE-PG4-Glut)-NH$_2$ Cyclic (5→13) Peptide
(Seq023-PL1) (SEQ ID NO. 128)

Aloc-RWQPC*PWESWTFC*WDPGGGK-NH$_2$ cyclic (5→13) peptide (Seq023-Aloc) (SEQ ID NO. 142) (100 mg, 0.04 mmol) in DMF (0.5 mL) was added to a solution of DSG (50 mg, 0.153 mmol, 3.825 equiv) in DMF (0.5 mL). DIEA (7.4 mg, 10 μL, 0.057 mmol, 1.43 equiv) was added to the solution and stirring was continued for 1 h at ambient temperature after which mass spectroscopy indicated completion of the reaction. The volatiles were removed under high vacuum to provide a semisolid residue. EtOAc (5 mL) was added to the residue resulting in the formation of a well-defined solid which was pelleted by centrifugation. The supernatant liquid was decanted and the washing process was repeated (5×). This gave a 100 mg (92% yield) portion of a white solid, the intermediate N$^{\epsilon19}$-glutaric acid monoamide mono-NHS ester of the peptide. A second run, conducted in exactly the same manner, provided an additional 100 mg of white solid. Mass spectral analysis was consistent with the presumed structure of the intermediate. The calculated monoisotopic molecular weight of the intermediate NHS ester is 2713. Mass spectral analysis (API-ES negative ion) of the white solid obtained by the above described procedure gave peaks at 1356 [(M−2H)/2] and 1431.6 [(M+TFA-2H)/2].

The glutaric acid monoamide, mono-NHS ester of the peptide (200 mg, 0.074 mmol) was dissolved in DMF (1 mL), and DIEA (11 mg, 15 μL, 0.085 mmol, 1.15 equiv) was added to the stirred solution. DSPE-PG4-NH$_2$ (160 mg, 0.8 equiv) in DMF (1 mL) was added to the mixture and stirring was continued overnight at ambient temperature. The volatiles were removed at high vacuum. The residue was re-dissolved in 13 mL of NMM/HOAc/DMF (1:2:10, v/v/v). Pd(PPh$_3$)$_4$ (300 mg, 3.0 equiv) was added in one portion. The mixture was stirred for 1 h. MS and analytical HPLC indicated completion of the reaction. The crude reaction mixture was diluted with an equal volume of 20% CH$_3$CN in H$_2$O and insoluble material was filtered. The resulting solution was applied directly to a C4 reverse phase HPLC column and purified by preparative HPLC as described for Seq005-PL1. Fractions containing the pure product were pooled, frozen and lyophilized to give 140 mg (29% yield based on the input DSPE-PG4-NH$_2$) of the target compound as a fluffy solid.

Example 13

Preparation of Ac-RWQPC*PAESWT-Cha-
C*WDPGGGK(DSPE-PG4-Glut)-NH$_2$, Cyclic
(5→13) Peptide (Seq049-PL1) (SEQ ID NO. 129)

Ac-RWQPC*PAESWT-Cha-C*WDPGGGK-NH$_2$ (SEQ ID NO. 70) cyclic (5→13) peptide (94 mg, 0.04 mmol, 1.25 equiv) was employed to prepare a 57 mg (34% yield) portion of the target phospholipid peptide conjugate in the same manner as Seq005-PL1.

Example 14

Preparation of RWQPC*PAESWT-Cha-
C*WDPGGGK(DSPE-PG4-Glut)-NH$_2$ Cyclic
(5→13) Peptide (Seq057-PL1) (SEQ ID NO. 130)

A solution of Aloc-RWQPC*PAESWT-Cha-C*WDPGGGK-NH$_2$ cyclic (5→13) peptide (Seq057-Aloc) (SEQ ID NO. 143) (230 mg, 0.096 mmol) in anhydrous DMF (1 mL) was added dropwise to a stirred solution of DSG (180 mg, 0.55 mmol, 5.75 equiv relative to peptide) in anhydrous DMF (0.5 mL) containing DIEA (110 mg, 0.86 mmol, 8.9 equiv relative to peptide). The reaction mixture was stirred for 3 h and the progress of the reaction was monitored by analytical HPLC and mass spectroscopy. The solvents were removed under high vacuum at 30° C. to give a viscous residue. The residue was triturated by addition of EtOAc (15 mL) to the vessel, resulting in the formation of a white solid which was pelleted by centrifugation. The supernatant was decanted and the solid washed (3×) in the same manner and dried using a flow of dry nitrogen gas.

The solid intermediate thus obtained was dissolved in anhydrous DMF (1 mL) with stirring and DIEA (110 mg, 149 μL, 0.86 mmol, 8.9 equiv relative to peptide) was added, followed by the dropwise addition of a solution of DSPE-PG4-NH$_2$ (213 mg, 0.077 mmol, 0.8 equiv) in anhydrous DMF (1 mL). The mixture was stirred at ambient temperature overnight, after which HPLC analysis and mass spectroscopy indicated the consumption of the lipid.

The volatiles were removed under high vacuum and the crude mixture was dissolved in a solution of 13 mL of NMM: HOAc:DMF (1:2:10, v/v/v) with stirring. Pd(PPh$_3$)$_4$ (250 mg, 0.22 mmol, 2.25 equiv relative to peptide) was added to the stirred solution and stirring was continued for 4 h. The solids were filtered and the resulting solution was diluted to twice its volume with a solution of 25% CH$_3$CN in H$_2$O. The resulting solution was loaded onto a Zorbax C-3 column (21.2 mm i.d.×150 mm) which was pre-equilibrated with 25% B (CH$_3$CN with 0.1% TFA) at a flow rate of 30 mL/min. The column was eluted at 30 mL/min with the same eluent until the plug of DMF was eluted. The proportion of eluent B was then increased from 25% B to 30% B over 3 min and then ramped to 100% B over 50 min. Fractions (15 mL) were collected and product-containing fractions were pooled, frozen and lyophilized. HPLC analysis of the isolated product indicated the need for additional purification. The purification was repeated and the product was isolated by freezing the pooled pure product-containing fractions and lyophilization to provide 23 mg (4.5% yield) of the target phospholipid-peptide conjugate.

Example 15 below describes the preparation of lipopeptide DPPE-PG4-peptide conjugates.

Example 15A

Preparation of
Ac-WQPC*PAESWTFC*WDPGGGK(DPPE-PG4-Glut)-NH$_2$ Cyclic (4→12) Peptide (Seq005-PL2)
(SEQ ID NO. 124)

The process is adapted from that used for the preparation of Seq005-PL1 except that DPPE-PG4-NH$_2$ is employed in place of DSPE-PG4-NH$_2$. Thus a solution of the peptide Ac-WQPC*PAESWTFC*WDPGGGK-NH$_2$ cyclic (4→12) peptide (Seq005) (SEQ ID NO. 1) (66 mg, 0.03 mmol) and DIEA (11 mg, 15 µL, 0.085 mmol, 2.84 equiv) in DMF (0.5 mL) was added to a stirred solution of DSG (33 mg, 0.10 mmol, 3.3 equiv) in DMF (0.5 mL). The mixture was stirred for 1 h and the progress of the reaction was monitored by HPLC and MS. Upon completion of the reaction, the volatiles were removed in vacuo and the residue was washed with ethyl acetate (4×5 mL) to remove unreacted DSG from the intermediate peptide glutaric acid monoamide mono-NHS ester.

The resulting solid was dried, re-dissolved in anhydrous DMF (1.00 mL) and stirred with a solution of DPPE-PG4-NH$_2$ (95 mg, 0.035 mmol, 1.16 equiv) in DMF (1.0 mL) for 24 hour. The progress of the reaction was monitored by HPLC, which indicated complete consumption of the intermediate peptide glutaric acid monoamide mono-NHS ester. The solution was diluted with water and purified by reverse phase C4 preparative column (Kromasil® Prep C$_4$, 10 µM, 300 Å, 20×250 mm, flow rate 25 mL/min) using a gradient of 60-100% water (0.1% TFA) and a mixture of CH$_3$OH and CH$_3$CN (1:1, 0.1% TFA) over a period of 30 min. Fractions were collected in 15 mL portions and analyzed by HPLC (Column: YMC C-4, 5 µm, 300 Å, 4.6×250 mm) using an ELSD and a UV detector (λ=220 nm). Pure product-containing fractions were collected and concentrated on a rotary evaporator to remove the methanol from the eluate and the resulting solution was diluted with 10% CH$_3$CN in H$_2$O, frozen and lyophilized to afford 72 mg (48% yield) of the required product as a fluffy white solid.

Example 15B

Preparation of Comparative Peptide Seq000
Conjugated to DSPE-PG4-Glut, Referred to as
Seq000-PL1

Ac-WQPC*PWESWTFC*WDPGGGK(DPPE-PG4-Glut)-NH$_2$ cyclic (4→12) peptide Seq000-PL1 was prepared in a similar manner to the procedure of Example 15A. Thus a solution of the peptide Ac-WQPC*PWESWTFC*WDPGGGK-NH$_2$ cyclic (4→12) peptide (Seq000) (SEQ ID NO. 122) (115 mg, 0.05 mmol) and DIEA (130 mg, 176 µL, 1.0 mmol, 20 equiv) in DMF (2.0 mL) was added to a stirred solution of DSG (100 mg, 0.30 mmol, 6 equiv) in DMF (0.5 mL). The mixture was stirred for 1 h and the progress of the reaction was monitored by HPLC and MS. Upon completion of the reaction, the volatiles were removed in vacuo and the residue was washed with ethyl acetate (4×20 mL) to remove unreacted DSG from the intermediate peptide glutaric acid monoamide mono-NHS ester.

The resulting solid was dried, re-dissolved in anhydrous DMF (1.0 mL) and stirred with a solution of DPPE-PG4-NH$_2$ (160 mg, 0.0573 mmol, 1.11 equiv) in DMF (1.0 mL) for 24 hour. The progress of the reaction was monitored by HPLC, which indicated complete consumption of the intermediate peptide glutaric acid monoamide mono-NHS ester. The solution was diluted with water and purified by reverse phase C4 preparative column (Kromasil® Prep C$_4$, 10 µm, 300 Å, 20×250 mm, flow rate 25 mL/min) using a gradient of 50-100% water (0.1% TFA) and a mixture of CH$_3$OH and CH$_3$CN (1:1, 0.1% TFA) over a period of 30 min. Fractions were collected in 15 mL portions and analyzed by HPLC (Column: YMC C-4, 5 µm, 300 Å, 4.6×250 mm) using an ELSD and a UV detector (λ=220 nm). Pure product-containing fractions were collected and concentrated on a rotary evaporator to remove the methanol from the eluate and the resulting solution was diluted with 10% CH$_3$CN in H$_2$O, frozen and lyophilized to afford 138 mg (52% yield) of the required product as a fluffy white solid.

Mass Spectrum Method: MALDI, Mode: positive ion, [M+Na+2H]: 5199 (average)

HPLC: Ret. time: 5.88 min; Assay: >98% (area %); Column: YMC C-4, 5 µM, 300 Å, 4.6×50 mm; Eluents: A: Water (0.1% TFA), B: Acetonitrile:Methanol (1:1, v/v) (0.1% TFA); Elution: Initial condition: 80% B, linear gradient 80-100% B in 10 min.; Flow rate: 3.0 mL/min; Detection: UV @ 220 nm & ELSD.

Example 16A below and FIG. 5 describe and illustrate the preparation of DPPE-Glut-PG2-peptide conjugates.

Example 16A

Preparation of
Ac-WQPC*PAESWTFC*WDPGGGK(DPPE-Glut-PG2-JJ)-NH$_2$ Cyclic (4→12) Peptide (Seq005-PL3)
(SEQ ID NO. 131)

The peptide, Ac-WQPC*PAESWTFC*WDPGGGK(JJ)-NH$_2$ cyclic (4→12) peptide (Seq005-JJ) (SEQ ID NO. 136) (63 mg, 0.025 mmol) was dissolved in DMF (1.0 mL) and DIEA (9.8 mg, 13.3 µL, 0.076 mmol, 3 equiv) was added. The solution was stirred briefly and a solution of Fmoc-PG2-NHS (111 mg, 0.032 mmol, 1.28 equiv) in DMF (1.0 mL) was added dropwise with stirring. The mixture was stirred for 16 h and HPLC analysis indicated the consumption of the starting peptide. The reaction mixture was treated with piperidine (172 mg, 200 µL, 2.02 mmol, 80 equiv, final concentration ~9% v/v in the reaction mixture) for 30 min after which the reaction mixture was diluted with H$_2$O and purified by preparative HPLC employing a reverse phase C4 column (Kromasil® Prep C$_4$, 10 µm, 300 Å, 20×250 mm) by the following method: elution: the plug of DMF was eluted at the initial condition of 20% CH$_3$CN in H$_2$O (0.1% TFA), then a linear gradient of 20%-80% CH$_3$CN (0.1% TFA) into H$_2$O (0.1% TFA) over a period of 40 min at a flow rate of 25 mL/min was employed to elute the product. Fractions (15 mL) were collected and those containing the pure product (HPLC analysis) were pooled, frozen and lyophilized to provide 70 mg (47% yield) of the PG2-derivatized peptide Ac-WQPC*PAESWTFC*WDPGGGK(NH$_2$-PG2-JJ) (SEQ ID NO. 143)-NH$_2$ cyclic (4→12) peptide.

A solution of Ac-WQPC*PAESWTFC*WDPGGGK(NH$_2$-PG2-JJ)-NH$_2$ (SEQ ID NO. 143) cyclic (4→12) peptide (50 mg, 0.009 mmol, 1.14 equiv) in DMF (1.0 mL) was treated with DIEA (14.8 mg, 20 µL, 0.114 mmol, 14.6 equiv) followed by DPPE-Glut-NHS (7 mg, 0.0078 mmol) in a 1:1 mixture of DMF:CH$_2$Cl$_2$ (1.0 mL) and the mixture was stirred for 16 hr at room temperature. The solution was diluted with H$_2$O to 10 mL and purified by reverse phase C4 preparative column (Kromasil® Prep C$_4$, 10 µM, 300 Å, 10×250 mm, flow rate, 10 mL/min) using a gradient of 50-80% water (0.1% TFA)/acetonitrile:MeOH (1:1, 0.1% TFA) over a period of 40 min. The pure product-containing fractions were pooled, frozen and lyophilized to afford 26 mg (42% yield) of the target compound as a fluffy white solid.

Examples 16B-16C below describe and illustrate the preparation of DPPE-Pro9-Glut-Ttda-Dga-peptide conjugates. Example 16D below describes and illustrates the preparation of a comparative lipopeptide, Seq000-PL2, from Seq000(Adoa-Adoa) and DPPE.

Example 16B

Preparation of Ac-WQPCPAESWTFCWDPG-SAGSK(DPPE-Pro9-Glut-Ttda-Dga)-NH$_2$ Cyclic (4→12) Peptide (Seq005-PL4) (SEQ ID NO. 132)

Preparation of Seq005-P2(0)

Chain elongation of the peptide was conducted on 1.2 g of Fmoc-Pal-Peg-PS resin (0.17 mmol/g) on a 0.2 mmol scale (procedure A) to provide Ac-W(N$^{in}$-Boc)-Q(Trt)-P-C(Trt)-P-A-E(OtBu)-S(tBu)-W(N$^{in}$-Boc)-T(tBu)-F-C(Trt)-W(N$^{in}$-Boc)-D(OtBu)-P-GS(tBu)-A-G-S(tBu)-K (ivDde)-NH-Pal-Peg-PS resin. Resins from two runs were combined. The ivDde group was removed using 20 mL of 10% hydrazine in DMF (2×10 min). Then diglycolic anhydride (0.464 g, 10 eq) and DIEA (0.516 g, 0.7 mL, 4.0 mmol) in DMF (20 mL) were added to the resin and the resin was agitated for 15 h. The resin was washed with DMF (5×20 mL) and then treated with N1-(tert-butoxycarbonyl)-1,3-diamino-4,7,10-trioxamidecane (0.513 g, 1.6 mmol, 4 eq), HATU (0.608 g, 1.6 mmol, 4 eq) and DIEA (0.413 g, 0.558 mL, 3.2 mmol, 8 eq) in DMF (20 mL) for 15 h. The resin was washed with DMF (5×20 mL). The peptide was cleaved from the resin using reagent B (procedure G) and the crude solid peptide was subjected to disulfide cyclization (procedure H). The crude mixture was diluted with water to about five-fold its volume and applied to a Waters XTerra C-18 (250 mm×50 mm i.d.) column and purified using a linear gradient elution of ACN (0.1% TFA) into H$_2$O (0.1% TFA) as described in the procedure titled. The pure product-containing fractions were pooled, frozen and lyophilized to provide 175 mg (16.2% yield) of the peptide as a fluffy white solid.

Preparation of Ac-WQPCPAESWTFCWDPGSAGSK(DPPE-Pro9-Glut-Ttda-Dga)-NH$_2$ Cyclic (4→12) Peptide (Seq005-PL4) from DPPE-Pro9-H and Seq005-P2(Ttda-Dga)

DPPE-(Pro)$_9$-H, 120 mg, 0.077 mmol was added to DSG (100 mg, 0.306 mmol, 4.0 eq) in DMF (2 mL), followed by DIEA (0.059 g, 0.08 mL, 0.46 mmol, 6.0 equiv); the mixture was stirred 4 h. The volatiles were removed under high vacuum. The resulting crude residue was washed twice with EtOAc to remove DSG and remaining traces of DMF and DIEA. The crude was redissolved in DMF (1 mL) and Seq005-P2(Ttda-Dga) [Ac-WQPCPAESWTFCWDPG-SAGSK(Dga-Ttda)-NH$_2$] (SEQ ID NO. 145), (170 mg, 0.063 mmol) in DMF (1 mL) was added, followed by DIEA (0.088 g, 0.12 mL, 0.69 mmol, 11 equiv relative to the added peptide). The mixture was stirred at 40° C. for 15 h. The resulting mixture was diluted with 35% MeOH in water (25 mL) and filtered using a 0.45 micron filter. The solution was purified by preparative HPLC. The pure product containing fractions were combined, frozen and lyophilized to provide the product (90 mg, 32.8% yield) as a fluffy solid.

Example 16C

Preparation of Ac-WQPCPAESWTFCWDP-GAGSGK(DPPE-Pro9-Glut-Ttda-Dga)-NH$_2$Cyclic (4→12) Peptide (Seq005-PL5) (SEQ ID NO. 133)

Preparation of Seq005-P3(Ttda-Dga)

Chain elongation of the peptide was conducted on 1.2 g of Fmoc-Pal-Peg-PS resin (0.17 mmol/g) on a 0.2 mmol scale (procedure A) to provide Ac-W(N$^{in}$-Boc)-Q(Trt)-P-C(Trt)-P-A-E(OtBu)-S(tBu)-W(N$^{in}$-Boc)-T(tBu)-F-C(Trt)-W(N$^{in}$-Boc)-D(OtBu)-P-G-A-G-S(t-Bu)-G-K(ivDde)-NH-Pal-Peg-PS resin. Resins from two runs were combined. The ivDde group was removed using 20 mL of 10% hydrazine in DMF (2×10 min). Then diglycolic anhydride (0.464 g, 10 eq) and DIEA (0.516 g, 0.7 mL, 4.0 mmol) in DMF (20 mL) were added to the resin and the resin was agitated for 15 h. The resin was washed with DMF (5×20 mL) and then treated with N1-(tert-butoxycarbonyl)-1,3-diamino-4,7,10-trioxamidecane (0.385 g, 1.2 mmol, 3 eq), HATU (0.456 g, 1.2 mmol, 3 eq) and DIEA (0.310 g, 0.419 mL, 2.4 mmol, 6 eq) in DMF (15 mL) for 15 h. The resin was washed with DMF (5×20 mL). The peptide was cleaved from the resin using reagent B (procedure G) and the crude solid peptide was subjected to disulfide cyclization (procedure H). The crude mixture was diluted with water to about five-fold its volume and applied to a Waters XTerra C-18 (250 mm×50 mm i.d.) column and purified using a linear gradient elution of ACN (0.1% TFA) into H$_2$O (0.1% TFA) as described in the procedure titled. The pure product-containing fractions were pooled, frozen and lyophilized to provide 227.7 mg (21.3% yield) of the peptide as a fluffy white solid.

Preparation of Ac-WQPCPAESWTFCWDPGAGSGK(DPPE-Pro9-Glut-Ttda-Dga)-NH$_2$cyclic (4→12) peptide (Seq005-PL5) from DPPE-Pro9-H and Seq005-P3(Ttda-Dga)

DSG (75 mg, 0.230 mmol, 3.59 eq) in DMF (0.75 mL) was stirred and to this mixture was added DPPE-(Pro)$_9$-H (100 mg, 0.064 mmol) dissolved in DCM (0.5 mL). Then DIEA (0.03 g, 0.04 mL, 0.23 mmol, 3 equiv) was added and the mixture was stirred 4 h. Mass spectral analysis confirmed the formation of the glutaric acid mono-amide-mono-NHS ester of DPPE-(Pro)$_9$. The volatiles were removed under high vacuum and the crude residue kept for 2 h under high vacuum. The resulting crude residue was triturated and washed with EtOAc to remove DSG and remaining traces of DMF and DIEA. The crude was redissolved in DCM (1 mL) and Seq005-P3(Ttda-Dga) [Ac-WQPCPAESWTFCWDPG-SAGSK(Ttda-Dga)-NH$_2$] (SEQ ID NO. 145), (165 mg, 0.062 mmol) in DMF (1 mL) was added, followed by DIEA (0.088 g, 0.12 mL, 0.69 mmol, 11 equiv relative to the added peptide). The mixture was stirred at 40° C. for 15 h after which HPLC and MS analysis indicated formation of the desired product. The resulting mixture was diluted with 35% MeOH in water (15 mL) and filtered using a 0.45 micron filter. The solution was purified by preparative HPLC on a C2 column. The compound was applied to the column at 25% ACN-MeOH 1:1, v/v (eluent B) in water (eluent A). After the compound was applied and the solvent plug eluted, the eluent composition was ramped to 50% B and then ramped from 50-100% B over 30 min. The pure product containing fractions were combined and most of the MeOH was removed by rotary evaporation. Tert-Butyl alcohol was added to the mixture and the mixture was frozen and lyophilized to give the product (125 mg, 46.5% yield) as a fluffy solid.

Example 16D

Preparation of Comparative Lipopeptide Seq000-PL2

The fully side-chain protected peptide sequence Ac-W(Boc)-Q(Trt)-P-C(Trt)-P-W(Boc)-E(O-t-Bu)-S(t-Bu)-W(Boc)-T($\Psi^{Me,Me}$pro)-F-C(Trt)-W(Boc)-D(O-t-Bu)-P-GGGK(ivDde)-TGR was prepared on a 0.2 mmol scale. The ivDde protecting group was removed from a 400 mg (nominally 0.08 mmol) portion of the resin (procedure D). The resin was washed with DMF (2×20 mL) and DCM (20 mL), re-suspended in DMF (10 mL) and treated with Fmoc-Adoa (154 mg, 0.4 mmol), HOBt (54 mg, 0.4 mmol), DIC (51 mg, 62 µL, 0.4 mmol) and DIEA (139 µL, 0.8 mmol) for 4 h. The reagents were filtered off and the resin was washed with DMF (2×20 mL) and DCM (20 mL). The Fmoc group was removed by treatment with 20% piperidine in DMF (2×20 mL) (modified procedure C) and the resin was washed with DMF (2×20 mL) and DCM (20 mL). Coupling with Fmoc-Adoa and Fmoc removal were repeated. The resin was re-suspended in DMF (7 mL) and treated with 3,6,9-trioxaundecane-1,1'-dioic acid anhydride solution [prepared by the reaction of the corresponding acid (1.0 g, 0.45 mmol)) and DIC (0.56 g, 0.45 mmol) in methylene chloride (5.0 mL) over a period of 12 hr, the solution was filtered and used directly] for 16 hr. The reagents were filtered off and the resin was washed with DCM (2×20 mL) and DMF (2×20 mL), re-suspended in DCM (10 mL) and treated with a solution of dipalmitoyl phosphatidyl ethanolamine (690 mg, 1.0 mmol), HATU (450 mg, 1.0 mmol) DIEA (400 mg) in DCM (5.0 mL) and the mixture was allowed to shake for 26 hr (modified procedure B). The reagents were filtered off and the resin was washed with DMF (2×20 mL) and DCM (2×20 mL) and dried. The resin was then treated with Reagent B (30 mL) for 4 hr (procedure G). The resin was filtered off and the filtrate was concentrated and treated with 200 mL of anhydrous $Et_2O$ and the crude product was collected as a solid by filtration. This provided 400 mg of crude product which was dissolved in DMSO (4.0 mL) after which the pH of the solution was adjusted to 7.5 with an aqueous solution of N-methyl-D-glucamine and stirred 48 h in air to effect formation of the cyclic peptide disulfide. The solution was diluted with water to a volume 40 mL and purified by reverse phase preparative HPLC (Kromasil® Prep $C_4$, 10µ, 300 Å, 20×250 mm, flow rate 10 mL/min) using a gradient of 50-100% water (0.1% TFA)/acetonitrile:MeOH (1:1, 0.1% TFA) over a period of 15 min. The pure product-containing fractions were collected, combined and lyophilized to afford the target compound (28 mg, 10% yield) as a fluffy white solid.

Examples 17-20 below describe processes for preparing targeted microbubbles with fibrin-binding polypeptides conjugated to phospholipids (lipopeptides). Such microbubbles are especially adapted for ultrasound imaging.

Example 17

Preparation of Targeted Microbubbles with DSPC/DPPG Envelope

Example 17

With Comparative Lipopeptide Seq000-PL1

383 mg of a mixture DSPC/DPPG/Seq000-PL1 (molar ratio 47.5/47.5/5, corresponding to 157.5, 148.5 and 77.3 mg of the three components, respectively) and 22.6 g of PEG-4000 were solubilized in 120 g of t-butyl alcohol at 60° C., in a water bath. The solution was filled in vials with 0.8 mL of solution each. The samples were frozen at −45° C. and lyophilized. The air in the headspace was replaced with a mixture of $C_4F_{10}$/Nitrogen (50/50) and vials capped and crimped. The lyophilized samples were reconstituted with 5 mL of $H_2O$ per vial.

Example 17B

With Seq005-PL1

Example 17A was repeated, but replacing Seq000-PL1 with the same relative molar amount of Seq005-PL1.

Example 18

Preparation of Targeted Microbubbles with DPPE/DPPG Envelope

Example 18A

With Comparative Lipopeptide Seq000-PL1

An aqueous suspension of DSPE-PEG1000 (0.5 mg-0.28 µmole) and Seq000-PL1 (3.3 mg-0.63 µmole) was prepared in 500 µL of distilled water at 60° C. to obtain a micellar suspension.

Separately, DPPE (15.8 mg-22.8 µmoles) and DPPG (4.2 mg-5.7 µmoles) were dispersed in a solution of PEG4000 10% in distilled water (20 mL) at 70° C. for 20 minutes. The dispersion was then cooled to room temperature. Perfluoroheptane (1.6 mL) was added to the aqueous phase using a high speed homogenizer (Polytron PT3000, probe diameter of 3 cm) for 1 minute at 10000 rpm, to obtain an emulsion.

The micellar suspension was mixed with the emulsion and the resulting mixture was heated at 80° C. for 1 hour under agitation. After cooling at room temperature (1 hour), the mixture was washed once by centrifugation (200 g/10 min—Sigma centrifuge 3K10) to eliminate the excess of phospholipids. The separated supernatant (containing emulsified microdroplets of solvent) was recovered and re-suspended with the initial volume of a 10% PEG 4000 aqueous solution.

The obtained suspension was sampled into DINER vials (1 mL/vial). Then vials were cooled at −50° C. (Christ Epsilon 2-12DS Freeze Dryer) and freeze-dried at −25° C. and 0.2 mbar for 12 hours, with a final drying step at 30° C. and 0.1 mbar for 7 hours.

The lyophilized product was then exposed to an atmosphere containing $C_4F_{10}$/Nitrogen (50/50 by volume) and the vials were sealed.

The lyophilized product was dispersed in a volume of water twice the initial one by gentle hand shaking.

Example 18B

With Seq017-PL1

Example 18A was repeated by replacing Seq000-PL1 with the same relative molar amount of Seq017-PL1.

Example 18C

With Seq005-PL1

Example 18A was repeated by replacing Seq000-PL1 with the same relative molar amount of Seq005-PL1.

Example 19

Preparation of Targeted Microbubbles with DSPC/DSPG Envelope

Example 19A

DSPC/DSPG Formulation with Comparative Lipopeptide Seq000-PL1

An aqueous suspension of DSPE-PEG1000 (0.5 mg-0.28 μmole) and Seq000-PL1 (3.3 mg-0.63 μmole) was prepared in 5004, of distilled water at 60° C. to obtain a micellar suspension.

Separately, DSPC (18 mg-22.75 μmoles) and DSPG (2 mg-2.53 μmoles) were dissolved in cyclooctane (1.6 mL) at 80° C. This organic phase was added to a PEG4000 10% solution in water (20 mL) using a high speed homogenizer (Polytron T3000, probe diameter of 3 cm) for 1 minute at 9000 rpm, to obtain an emulsion The micellar suspension was mixed with the emulsion and the resulting mixture was heated at 80° C. for 1 hour under agitation. After cooling to room temperature (1 hour), the obtained emulsion was washed once by centrifugation (1500 g/10 min—Sigma centrifuge 3K10) to eliminate the excess of phospholipids. The separated supernatant (containing emulsified microdroplets of solvent) was recovered and re-suspended in the initial volume of a 10% PEG 4000 aqueous solution.

The obtained suspension was sampled into DINER vials (1 mL/vial). Then vials were cooled to −50° C. (Christ Epsilon 2-12DS Freeze Dryer) and freeze-dried at −25° C. and 0.2 mbar for 12 hours, with a final drying step at 30° C. and 0.1 mbar for 7 hours.

The lyophilized product was exposed to an atmosphere containing $C_4F_{10}$/Nitrogen (35/65 by volume) and the vials were sealed.

The lyophilized product was then dispersed in a volume of water twice than the initial one by gentle hand shaking.

Example 19B

DSPC/DSPG Formulation with Comparative Peptide Seq000-PL1

Example 19A was repeated, but using 2.6 mg of DSPE-PEG1000 (1.44 μmoles) and 1.9 mg of Seq000-PL1 (0.36 μmole) to prepare the micellar suspension.

Example 19C

DSPC/DSPG Formulation with Seq024-PL1

Example 19A was repeated, but using 2.6 mg Seq024-PL1 (0.45 μmoles) and 0.8 mg DSPE-PEG1000 (0.45 μmoles) to prepare the micellar suspension.

Example 19D

DSPC/DSPG Formulation with Seq023-PL1

Example 19A was repeated, but using 2.4 mg Seq023-PL1 (0.45 μmoles) and 0.8 mg DSPE-PEG1000 (0.45 μmoles) to prepare the micellar suspension.

Example 19E

DSPC/DSPG Formulation with Seq016-PL1

Example 19A was repeated, but using 2.3 mg Seq016-PL1 (0.45 μmoles) and 0.8 mg DSPE-PEG1000 (0.45 μmoles) to prepare the micellar suspension.

Example 20A-20D

Preparation of Targeted Microbubbles with DSPC/Stearate Envelope

Example 20A

With Comparative Lipopeptide Seq000-PL1

An aqueous suspension of DSPE-PEG1000 (0.5 mg-0.28 μmoles) and Seq000-PL1 12 (3.3 mg-0.63 μmoles) was prepared in 500 μL of distilled water at 60° C. to obtain the micellar suspension.

Separately, DSPC (18.2 mg-23.1 μmoles) and stearate (1.8 mg-5.8 μmoles) were dispersed in a solution of PEG4000 10% in distilled water (20 mL) at 70° C. for 20 minutes. The dispersion was then cooled to room temperature. Perfluoroheptane (1.6 mL) was added to the aqueous phase using a high speed homogenizer (Polytron PT3000, probe diameter of 3 cm) for 1 minute at 11000 rpm, to obtain an emulsion.

The micellar solution was mixed with the emulsion and the resulting mixture was heated at 60° C. for 4 hours under agitation. After cooling to room temperature (1 hour), the obtained emulsion was washed once by centrifugation (200 g/10 min—Sigma centrifuge 3K10) to eliminate the excess of phospholipids. The separated supernatant (containing emulsified microdroplets of solvent) was recovered and re-suspended with the initial volume of a 10% PEG 4000 aqueous solution.

The obtained suspension was sampled into DINER vials (1 ml/vial). Then vials were cooled to −50° C. (Christ Epsilon 2-12DS Freeze Dryer) and freeze-dried at −25° C. and 0.2 mbar for 12 hours, with a final drying step at 30° C. and 0.1 mbar for 7 hours.

The lyophilized product was then exposed to an atmosphere containing $C_4F_{10}$/Nitrogen (35/65 by volume) and the vials were sealed.

The lyophilized product was dispersed in a volume of water twice than the initial one by gentle hand shaking.

Example 20B

With Seq017-PL1

Example 20A was repeated by replacing Seq000-PL1 with the same relative molar amount of Seq017-PL1.

Example 20C

With Seq005-PL1

Example 20A was repeated by replacing Seq000-PL1 with the same relative molar amount of Seq005-PL1.

Example 20D

With Seq016-PL1

Example 20A was repeated by replacing DSPG with 5.8 μmoles of stearate.

Example 20E-20H

Preparation of Targeted Microbubbles with DSPC/DSPA Envelope

Example 20E

With Seq005-PL4

DSPC (16.3 mg-20.58 µmoles), DSPA (3.7 mg-5.15 µmoles) and Seq005-PL4(0.26 µmoles, prepared as described above) were dissolved in cyclooctane (1.6 mL) at 80° C.

The organic suspension was emulsified in a PEG4000 10% aqueous phase (20 mL) using a high speed homogenizer (Polytron PT3000, probe diameter of 3 cm) for 1 minute at 8000 rpm to obtain the emulsion.

The resulting emulsion was heated at 80° C. for 1 hour under stirring. After cooling at room temperature (1 hour), the emulsion was washed once by centrifugation (1500 g/10 min—Sigma centrifuge 3K10) to eliminate the excess of the phospholipid and the separated supernatants (microdroplets) were recovered and re-suspended in twice the initial volume of a 10% PEG 4000 aqueous solution.

The emulsion was sampled in DINER vials (1 mL/vial) and then lyophilized (laboratory freeze-dryer Lyobeta-35 TEL-STAR) according the following sequence.

Freezing: 2 h at −50° C.

Main Drying: 12 h at −25° C. and 0.2 mBar

Final Drying: 6 h at 30° C. and 0.1 mBar

Before redispersion, the lyophilisate was exposed to an atmosphere containing $C_4F_{10}$/air (50/50 by volume). The lyophilized product was then dispersed in a volume of water twice the initial one by gentle hand shaking.

Example 20F

With Seq005-PL4

DSPC (16.3 mg-20.58 µmoles), DSPA (3.7 mg-5.15 µmoles) and Seq005-PL4(0.795 µmoles, prepared as described above) were dissolved in cyclooctane (1.6 mL) at 80° C.

The organic suspension was emulsified in a PEG4000 10% aqueous phase (20 mL) using a high speed homogenizer (Polytron PT3000, probe diameter of 3 cm) for 1 minute at 8000 rpm to obtain the emulsion.

The resulting emulsion was heated at 80° C. for 1 hour under stirring. After cooling at room temperature (1 hour), the emulsion was washed once by centrifugation (1500 g/10 min—Sigma centrifuge 3K10) to eliminate the excess of the phospholipid and the separated supernatants (microdroplets) were recovered and re-suspended in twice the initial volume of a 10% PEG 4000 aqueous solution.

The emulsion was sampled in DIN8R vials (1 mL/vial) and then lyophilized (laboratory freeze-dryer Lyobeta-35 TEL-STAR) according the following sequence.

Freezing: 2 h at −50° C.

Main Drying: 12 h at −25° C. and 0.2 mBar

Final Drying: 6 h at 30° C. and 0.1 mBar

Before redispersion, the lyophilisate was exposed to an atmosphere containing $C_4F_{10}$/air (50/50 by volume). The lyophilized product was then dispersed in a volume of water twice the initial one by gentle hand shaking.

Example 20G

With Seq005-PL5

DSPC (16.3 mg-20.58 µmoles), DSPA (3.7 mg-5.15 µmoles) and Seq005-PL5(0.26 µmoles, prepared as described above) were dissolved in cyclooctane (1.6 mL) at 80° C.

The organic suspension was emulsified in a PEG4000 10% aqueous phase (20 mL) using a high speed homogenizer (Polytron PT3000, probe diameter of 3 cm) for 1 minute at 8000 rpm to obtain the emulsion.

The resulting emulsion was heated at 80° C. for 1 hour under stirring. After cooling at room temperature (1 hour), the emulsion was washed once by centrifugation (1500 g/10 min—Sigma centrifuge 3K10) to eliminate the excess of the phospholipid and the separated supernatants (microdroplets) were recovered and re-suspended in twice the initial volume of a 10% PEG 4000 aqueous solution.

The emulsion was sampled in DINER vials (1 mL/vial) and then lyophilized (laboratory freeze-dryer Lyobeta-35 TEL-STAR) according the following sequence.

Freezing: 2 h at −50° C.

Main Drying: 12 h at −25° C. and 0.2 mBar

Final Drying: 6 h at 30° C. and 0.1 mBar

Before redispersion, the lyophilisate was exposed to an atmosphere containing $C_4F_{10}$/air (50/50 by volume). The lyophilized product was then dispersed in a volume of water twice the initial one by gentle hand shaking.

Example 20H

With Comparative Peptide Seq000-PL2

DSPC (16.3 mg-20.58 µmoles), DSPA (3.7 mg-5.15 µmoles) and Seq000-PL2 (0.26 µmoles, prepared as described above) were dissolved in cyclooctane (1.6 mL) at 80° C.

The organic suspension was emulsified in a PEG4000 10% aqueous phase (20 mL) using a high speed homogenizer (Polytron PT3000, probe diameter of 3 cm) for 1 minute at 8000 rpm to obtain the emulsion.

The resulting emulsion was heated at 80° C. for 1 hour under stirring. After cooling at room temperature (1 hour), the emulsion was washed once by centrifugation (1500 g/10 min—Sigma centrifuge 3K10) to eliminate the excess of the phospholipid and the separated supernatants (microdroplets) were recovered and re-suspended in twice the initial volume of a 10% PEG 4000 aqueous solution.

The emulsion was sampled in DINER vials (1 mL/vial) and then lyophilized (laboratory freeze-dryer Lyobeta-35 TEL-STAR) according the following sequence.

Freezing: 2 h at −50° C.

Main Drying: 12 h at −25° C. and 0.2 mBar

Final Drying: 6 h at 30° C. and 0.1 mBar

Before redispersion, the lyophilisate was exposed to an atmosphere containing $C_4F_{10}$/air (50/50 by volume). The lyophilized product was then dispersed in a volume of water twice the initial one by gentle hand shaking.

Example 21

Dynamic Binding Test of Targeted Microvesicles With Fibrin-Binding Peptides

Preparation of Fibrin-Coated Coverslips

Glass coverslips (40 mm in diameter, Bioptechs Inc., Butler, Pa., USA) were coated with fibrin according the following methodology.

Five mL of a solution of BSA 1% w/v in PBS pH 7.4 were added into a 60 mm Petri Dish containing one coverslip, and incubated at 37° C. for 15 min. Then the coverslip was washed three times with 5 ml of Tween 80/PBS (0.1%, v:v). Twenty five μL of human thrombin solution at 5 U/mL were added per mL of human fibrinogen solution (0.5 mg/mL in 50 mM sodium phosphate, NaCl 280 mM, pH 7.4) and delicately mixed. Five mL of this solution were immediately distributed in each Petri dish. The coverslips were incubated for one hour at 37° C. and then dried overnight at 45° C.

Binding Assay

Binding studies of targeted microvesicles were carried out using a parallel-plate flow chamber (FCS2, Bioptech Inc., Butler, Pa., USA) with a chamber gasket of 0.25 mm in thickness, with a customized adapter for upside-down chamber inversion. The coated coverslip was inserted as a plate of the flow chamber. Gas-filled Microvesicles ($5 \times 10^6$ bubbles/mL in 50% human plasma in PBS) were drawn through the flow chamber using an adjustable infusion pump (Auto Syringe® AS50 Infusion Pump, Baxter, Deerfield, Ill., USA) with a 60 mL syringe (Terumo). The pump flow rate was adjusted to 1 mL/min to obtain the desired shear rate of about $114\ s^{-1}$. After 10 minutes, the flow was stopped and pictures were taken randomly on different positions on the coverslip (on surfaces of about $0.025\ mm^2$) using a 40× objective and a CCD monochrome camera (F-View II, Soft Imaging Systems, Germany) connected to an inverted Olympus IX 50 microscope. The number of microvesicles on each picture was determined, averaged with respect to the total number of pictures and the obtained value was then divided by ten (to obtain the "slope", i.e. the average amount of bound microvesicles per minute).

For each preparation of Examples 17-20, the binding assay was repeated four times thus obtaining an average value of the slope. The slope represents the microvesicle binding rate on the target substrate. For instance, a slope value of 8 indicates that an average of eighty (80) microvesicles was bound on the coated coverslip in ten minutes. A higher slope indicates a better capacity of microvesicles to bind to the target under flow conditions.

In the following Tables 5-10, the binding activity of the microvesicles prepared according to Examples 17-20 above is illustrated. As shown in these Tables, peptides according to the present invention (particularly their respective lipopeptides) show superior activities with respect to the comparative peptide Seq000 (in particular, to corresponding lipopeptides Seq000-PL1 and Seq000-PL2).

TABLE 6

| Fibrin-Binding Lipopeptide | Microvesicle Preparation of Example | Slope |
| --- | --- | --- |
| Seq000-PL1 | 17A | 6.44 |
| Seq005-PL1 | 17B | 8.54 |

TABLE 7

| Fibrin-Binding Lipopeptide | Microvesicle Preparation of Example | Slope |
| --- | --- | --- |
| Seq000-PL1 | 18A | 4.8 |
| Seq017-PL1 | 18B | 8.9 |
| Seq005-PL1 | 18C | 7.2 |

TABLE 8

| Fibrin-Binding Lipopeptide | Microvesicle Preparation of Example | Slope |
| --- | --- | --- |
| Seq000-PL1 | 19A | 4.4 |
| Seq000-PL1 | 19B | 4.9 |
| Seq024-PL1 | 19C | 6.2 |
| Seq023-PL1 | 19D | 8.5 |
| Seq016-PL1 | 19E | 11.5 |

TABLE 9

| Fibrin-Binding Lipopeptide | Microvesicle Preparation of Example | Slope |
| --- | --- | --- |
| Seq000-PL1 | 20A | 1.6 |
| Seq017-PL1 | 20B | 3.1 |
| Seq005-PL1 | 20C | 6.1 |
| Seq016-PL1 | 20D | 8.4 |

TABLE 10

| Fibrin-Binding Lipopeptide | Microvesicle preparation of Example | slope |
| --- | --- | --- |
| Seq005-PL4 | 20E | 6.4 |
| Seq005-PL4 | 20F | 8.0 |
| Seq005-PL5 | 290G | 6.0 |
| Seq000-PL2 | 20H | 4.6 |

Example 22

Preparation of the Chelated Complex 1

The synthetic procedure for the preparation of the Chelated Complex 1 is set forth in Scheme 5.

Scheme 5
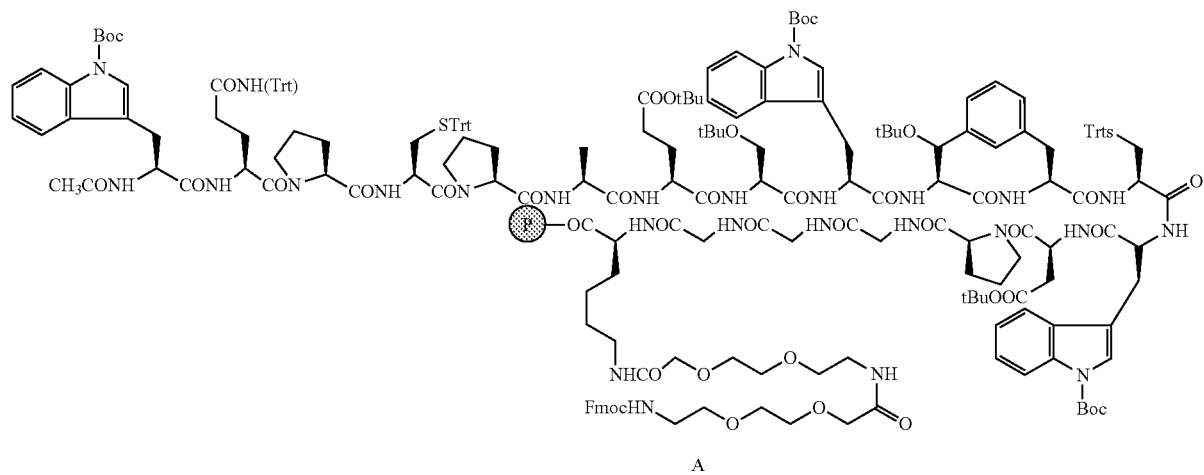
A
1) 50% Morpholine in DMAC
2) Fmoc-GGG-OH, DIC, HOBt, DMAC
3) 50% Morpholine in DMAC
4) Fmoc-Lys(Fmoc)-OH, DIC, HOBt, DMAC
5) 50% Morpholine in DMAC
6) Fmoc-Lys(Fmoc)-OH, DIC, HOBt, DMAC
7) 50% Morpholine in DMAC
8) DTPA-Glu, DIC, HOBt, DMAC
9) Reagent B, Et$_2$O
10) Air oxidation, purification (prep. HPLC)
11) GdCl$_3$, NaOH, pH = 7
12) Desalting
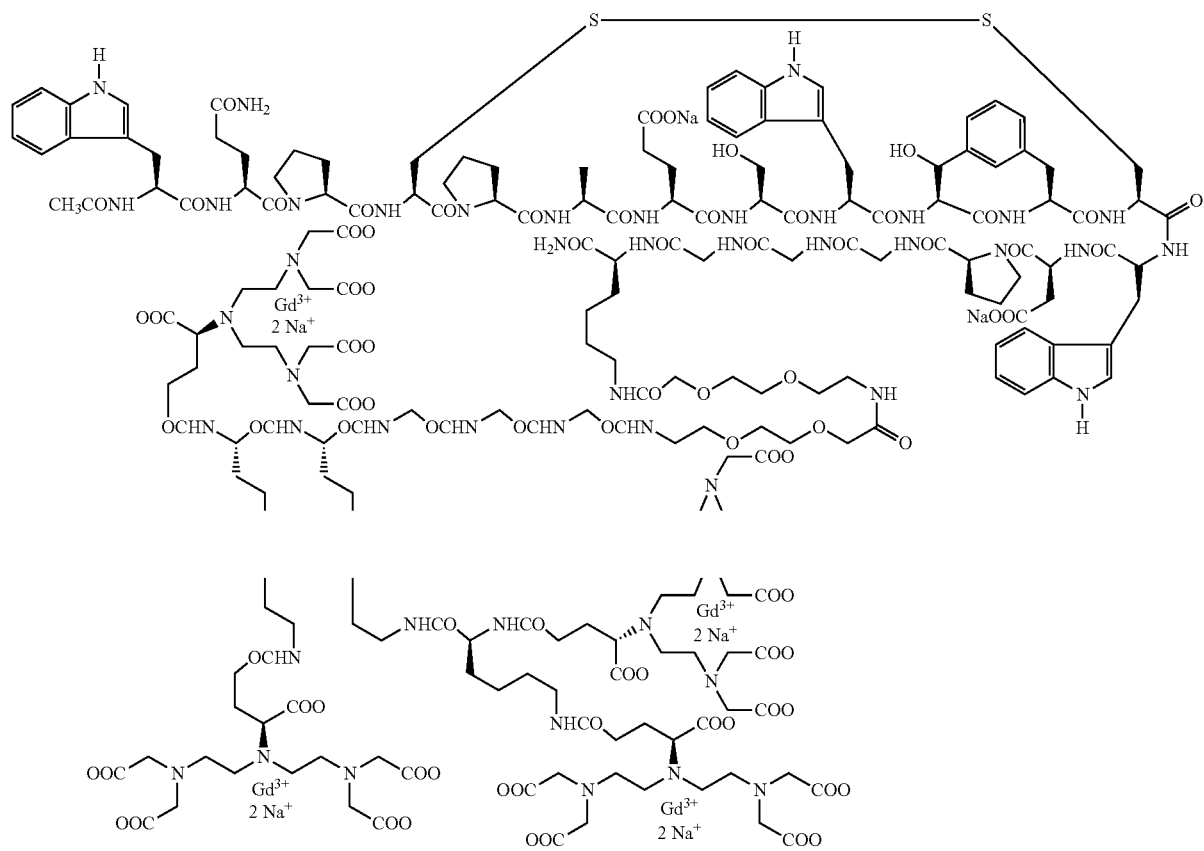

Chelated Complex 1

Fmoc-PAL-PEG-PS resin supported intermediate A prepared as schematized in FIG. 1 (5.00 g; 0.90 mmol) was shaken in a SPPS vessel with DMAC (40 mL) for 1 h to swell the resin. After the solvent was filtered, Fmoc-GGG-OH (1.48 g; 3.60 mmol), HOBt (0.55 g; 3.60 mmol), DIC (0.56 mL; 3.60 mmol) and DMAC (40 mL) were added to the resin, the suspension shaken for 6 h at room temperature, the mixture filtered and the resin washed with DMAC (5×40 mL). The resin was then shaken with 50% morpholine in DMAC (7 mL) for 10 min, the mixture filtered and fresh 50% morpholine in DMAC (7 mL) was added. The suspension was stirred for 20 min then the mixture was filtered and the resin washed with DMAC (5×40 mL). Fmoc-Lys(Fmoc)-OH (2.13 g; 3.60 mmol), HOBt (0.55 g; 3.60 mmol), DIC (0.56 mL; 3.60 mmol) and DMAC (40 mL) were added to the resin, the suspension shaken for 6 h at room temperature, filtered and the resin washed with DMAC (5×40 mL). The resin was then shaken with 50% morpholine in DMAC (7 mL) for 10 min, the mixture filtered and fresh 50% morpholine in DMAC (7 mL) was added. The suspension was stirred for 20 min then the mixture was filtered and the resin washed with DMAC (5×40 mL). Fmoc-Lys(Fmoc)-OH (4.26 g; 7.20 mmol), HOBt (1.10 g; 7.20 mmol), DIC (1.12 mL; 7.20 mmol) and DMAC (40 mL) were added to the resin, the suspension shaken for 6 h at room temperature, filtered and the resin washed with DMAC (5×40 mL). The resin was then shaken with 50% morpholine in DMAC (7 mL) for 10 min, the mixture filtered and fresh 50% morpholine in DMAC (7 mL) was added. The suspension was stirred for 20 min then the mixture was filtered and the resin washed with DMAC (5×40 mL). DTPA-Glu (10.7 g; 14.4 mmol), HOBt (2.20 g; 14.4 mmol), DIC (2.26 mL; 14.4 mmol), DIEA (4.90 mL; 28.8 mmol) and DMAC (40 mL) were added to the resin. The suspension was shaken for 24 h at room temperature, filtered and the resin washed with DMAC (5×40 mL), $CH_2Cl_2$ (5×40 mL) and then vacuum dried. The resin was shaken in a flask with "Reagent B" (150 mL) for 4.5 h. The resin was filtered and the solution was evaporated under reduced pressure to afford an oily crude that, after treatment with $Et_2O$ (40 mL), gave a precipitate. The precipitate was centrifuged, decanted and washed with $Et_2O$ (4×40 mL) to give a white solid (2.10 g). This product (2.10 g) was dissolved in a mixture of DMSO (36 mL) and $H_2O$ (4.0 mL) and the pH adjusted to 8 with D-(−)-N-methyl glucamine (1.23 g). The solution was stirred for 96 hours at room temperature and then purified by preparative HPLC. The fractions containing the product were lyophilized to afford the desired chelating ligand (0.280 g; 0.058 mmol) as a white solid. The ligand (0.240 g; 0.050 mmol) was suspended in $H_2O$ (80 mL) and dissolved by addiction of 0.1 N NaOH (8.50 mL; 0.85 mmol) up to pH 6.5. 5.187 mM aq. $GdCl_3$ (38.3 mL; 0.202 mmol) was added maintaining pH 6.5 by means of 0.1 N NaOH (6.0 mL; 0.60 mmol). The solution was adjusted to pH 7.0 with 0.1 N NaOH and then loaded onto a XAD 1600 column and eluted with a gradient $H_2O$/ACN (the desired product elutes with a percentage of ACN=30) to give, after evaporation, compound the Chelated complex 1, as sodium salt, (0.167 g; 0.029 mmol) as a white solid. Overall yield 3.8%.

Analytical Data for Chelated Complex 1

Mr (Molecular Weight): 5663.73 ($C_{205}H_{276}Gd_4N_{48}Na_{10}O_{83}S_2$)

CE (Capillary Electrophoresis): 88.5% (Area %)

MS (Mass Spectroscopy): Obtained data consistent with Chelated Complex 1 structure Example 23

Preparation of the Chelated Complex 2

The synthetic procedure for the preparation of the Chelated Complex 2 is set forth in Scheme 6.

Scheme 6

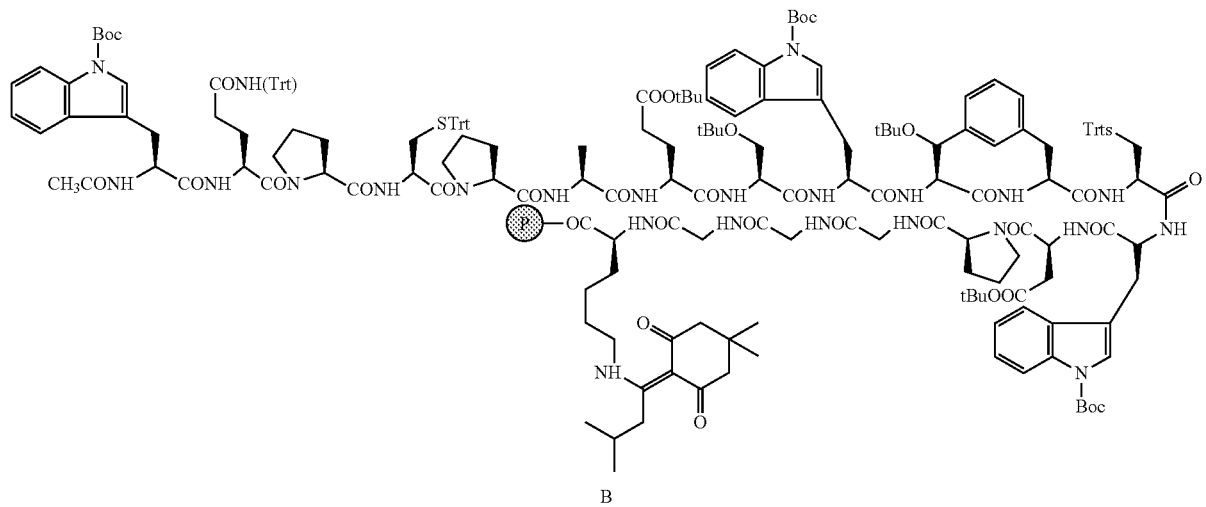

1) 10% Hydrazine in DMF
2) Fmoc-Lys(Fmoc)-OH, DIC, HOBt, DMAC
3) 50% Morpholine in DMAC
4) Fmoc-Lys(Fmoc)-OH, DIC, HOBt, DMAC
5) 50% Morpholine in DMAC
6) DTPA-Glu, DIC, HOBt, DMAC
7) Reagent B, $Et_2O$
8) Air oxidation, purification (prep. HPLC)
9) $GdCl_3$, NaOH, pH = 7
10) Desalting

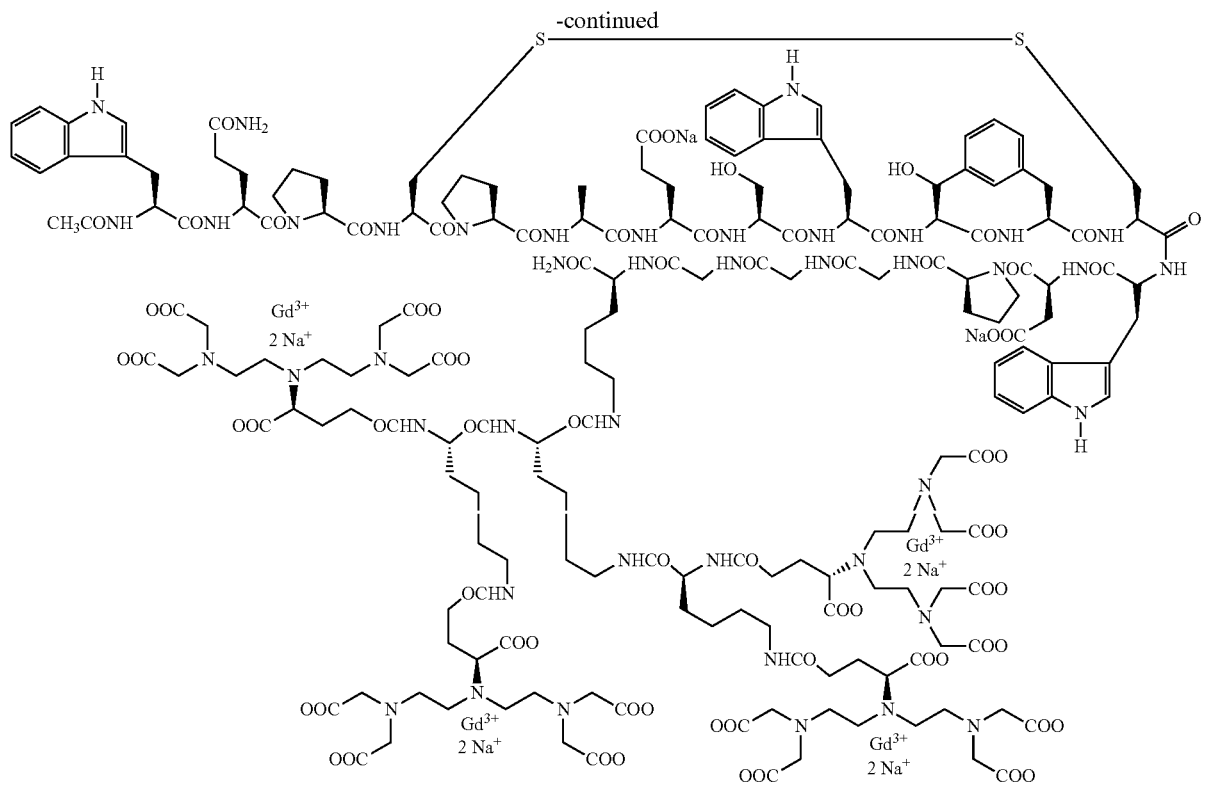

Chelated Complex 2

To Fmoc-PAL-PEG-PS resin supported intermediate B (3.00 g; 0.60 mmol) obtained according to Procedure A, described above, was shaken in a SPPS vessel with DMAC (25 mL) for 1 h to swell the resin. After the solvent was filtered, the resin was washed with DMF (5×25 mL). The resin was then shaken with 10% hydrazine in DMF (25 mL) for 15 min, the solvent filtered and fresh 10% hydrazine in DMF (25 mL) was added.

The suspension was stirred for more 20 min then the mixture was filtered and the resin washed with DMF (5×25 mL) and then DMAC (5×25 mL). Fmoc-Lys(Fmoc)-OH (1.42 g; 2.40 mmol), HOBt (0.36 g; 2.40 mmol), DIC (0.37 mL; 2.40 mmol) and DMAC (25 mL) were added to the resin, the suspension shaken for 24 h at room temperature, filtered and the resin washed with DMAC (5×25 mL). The resin was then shaken with 50% morpholine in DMAC (25 mL) for 10 min, the mixture filtered and fresh 50% morpholine in DMAC (25 mL) was added. The suspension was stirred for 20 min then the mixture was filtered and the resin washed with DMAC (5×25 mL). Fmoc-Lys(Fmoc)-OH (2.84 g; 4.80 mmol), HOBt (0.73 g; 4.80 mmol), DIC (0.75 mL; 4.80 mmol) and DMAC (25 mL) were added to the resin, the suspension shaken for 24 h at room temperature, filtered and the resin washed with DMAC (5×25 mL). The resin was then shaken with 50% morpholine in DMAC (25 mL) for 10 min, the mixture filtered and fresh 50% morpholine in DMAC (25 mL) was added. The suspension was stirred for 20 min then the mixture was filtered and the resin washed with DMAC (5×25 mL). DTPA-Glu (7.17 g; 9.60 mmol), HOBt (1.47 g; 9.60 mmol), DIC (1.50 mL; 9.60 mmol), DIEA (3.26 mL; 9.60 mmol) and DMAC (25 mL) were added to the resin. The suspension was shaken for 24 h at room temperature, filtered and the resin washed with DMAC (5×25 mL), $CH_2Cl_2$ (5×25 mL) and then vacuum dried. The resin was shaken in a flask with "Reagent B" (100 mL) for 4.5 h. The resin was filtered and the solution was evaporated under reduced pressure to afford an oily crude that, after treatment with $Et_2O$ (40 mL), gave a precipitate. The precipitate was centrifuged, decanted and washed with $Et_2O$ (4×40 mL) to give a white solid (1.60 g). This product (1.60 g) was dissolved in a mixture of DMSO (27 mL) and $H_2O$ (3.0 mL) and the pH adjusted to 8 with D-(−)-N-methyl glucamine (0.94 g). The solution was stirred for 96 hours at room temperature and then purified by preparative HPLC. The fractions containing the product were lyophilized to afford the desired chelating ligand (0.260 g; 0.060 mmol) as a white solid. The ligand (0.220 g; 0.050 mmol) was suspended in $H_2O$ (80 mL) and dissolved by addiction of 0.1 N NaOH (7.40 mL; 0.74 mmol) up to pH 6.5. 6.21 mM aq. $GdCl_3$ (32.60 mL; 0.202 mmol) was added maintaining pH 6.5 by means of 0.1 N NaOH (6.10 mL; 0.61 mmol). The solution was adjusted to pH 7.0 with 0.1 N NaOH and then loaded onto a XAD 1600 column and eluted with a gradient $H_2O$/ACN (the desired product elutes with a percentage of ACN=30) to give, after evaporation, the Chelated complex 2, sodium salt, (0.174 g; 0.033 mmol) as a white solid. Yield 6.6%.

Analytical Data

Mr: 5202.26 ($C_{187}H_{245}Gd_4N_{43}Na_{10}O_{74}S_2$)

CE: 87.8% (Area %)

MS: Obtained data consistent with Chelated Complex 2 structure

Example 24

Preparation of the Chelated Complex 4

By following the synthetic procedure of Scheme 6, and by using the suitable AAZTA ligand instead of the corresponding DTPA ligand the Chelated Complex 4 has been also prepared.

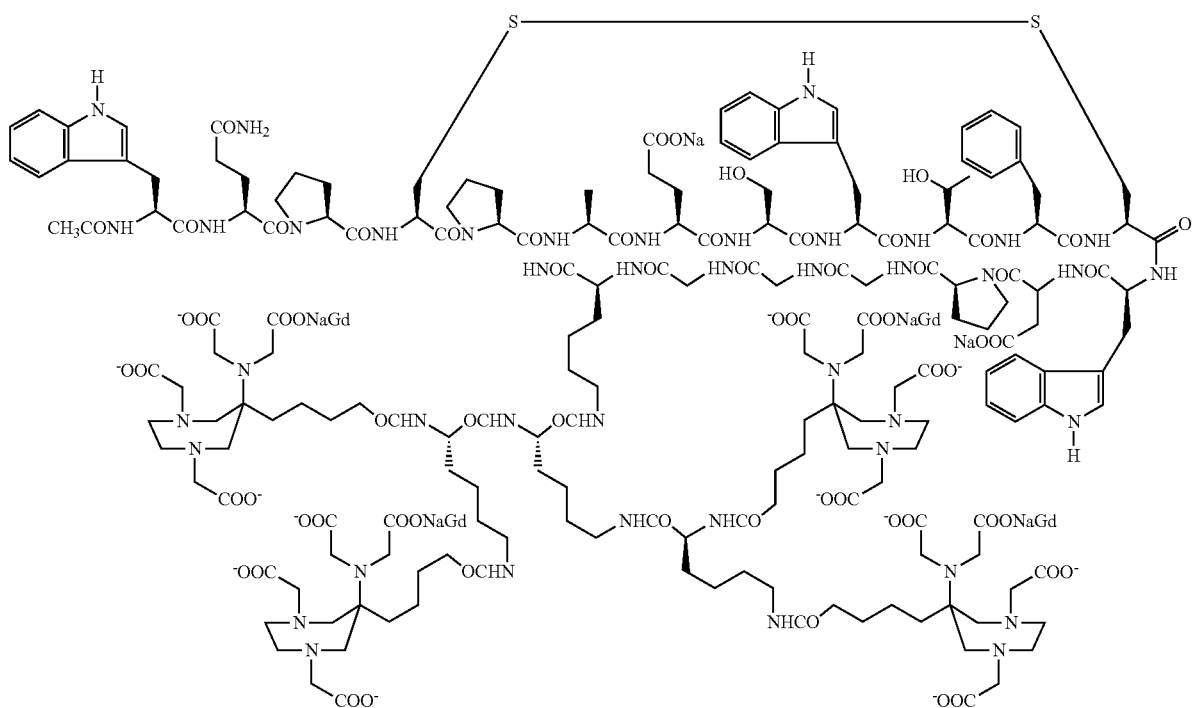

Chelated Complex 4

Reference Complexes

By starting from the previously known peptide Ac-WQPC*PWESWTFC*WDGGGK-NH$_2$ provided by WO02/055544 and by following the synthetic procedures of Schemes 5 and 6, suitably changing the chelating ligand moiety to be conjugated to linker-functionalized peptide intermediate, some chelated compounds have been prepared as Reference Compounds for in vivo and in vitro tests. The following reference compounds have, in particular, been prepared:

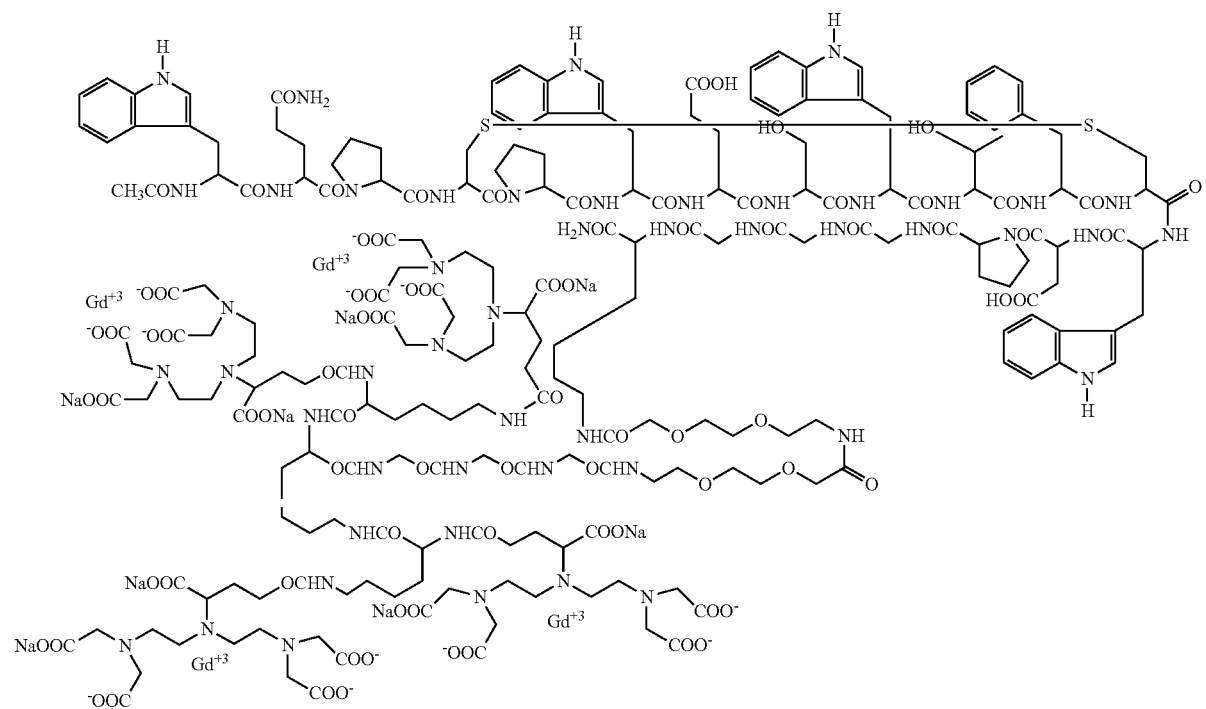

Reference 1

Reference 2
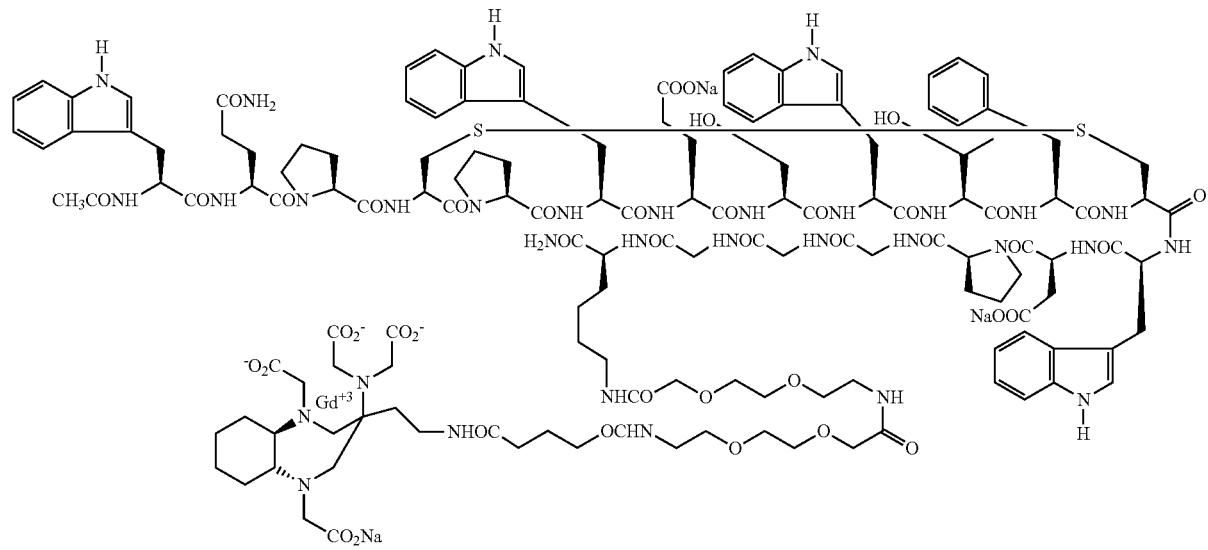
Reference 3
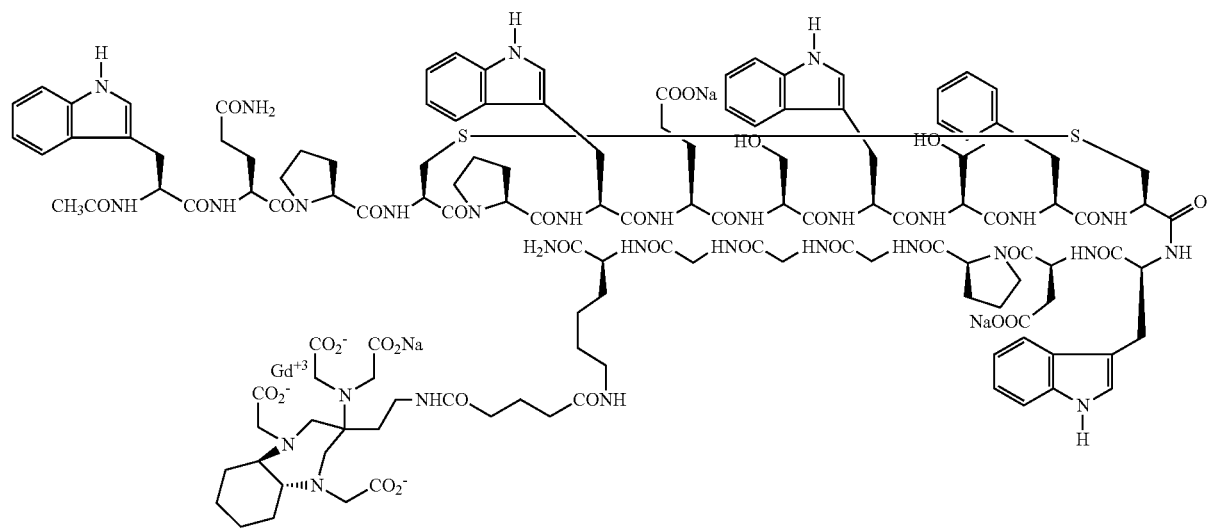

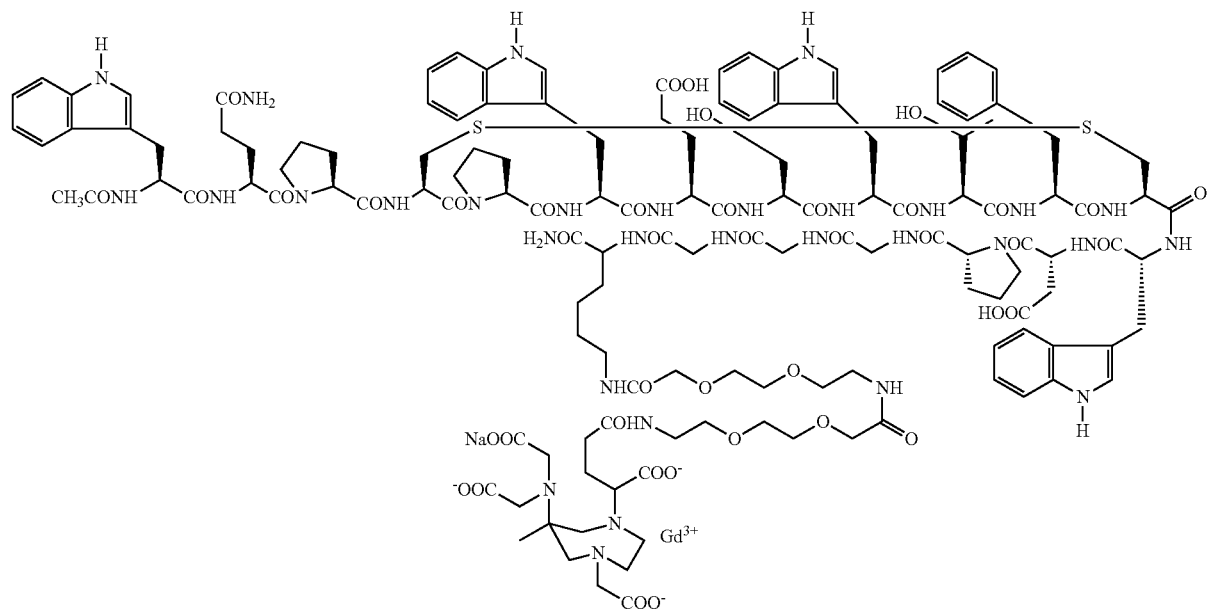

Reference 4

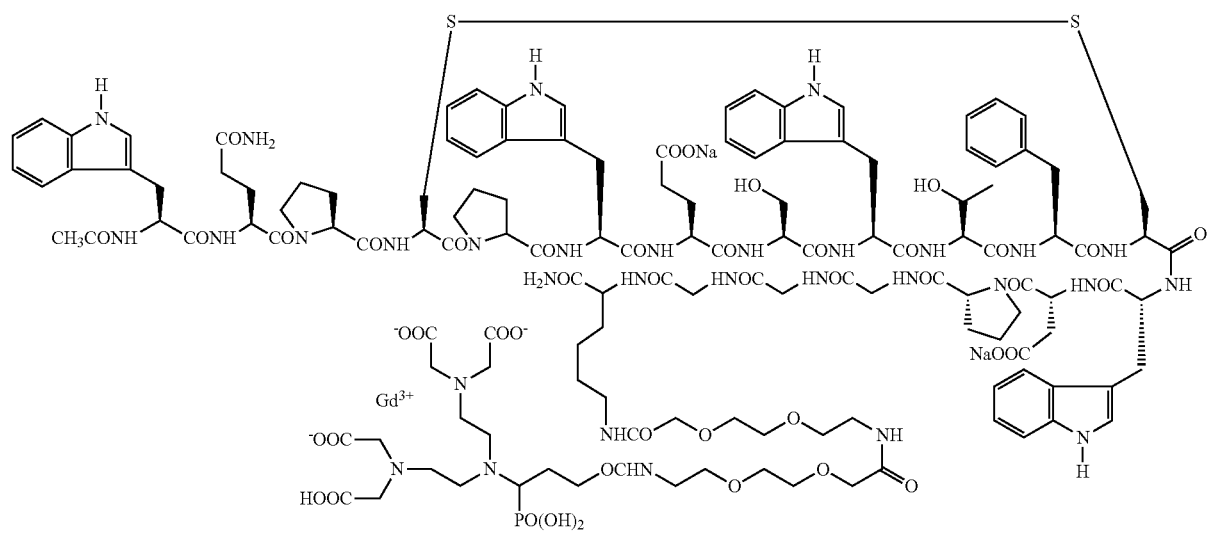

Reference 5

Example 25

Fibrin MRI Imaging in Human/Mouse Clots

In Vitro MRI Tests

Small plasma clots from different species (human, guinea pig and mouse) ranging from 0.5-7 mm in diameter were formed by combining citrate plasma (1:3,v/v) phospholipids (Reagent Pathromtin) and $CaCl_2$ 0.008 M (Dade Behring, Germany) into small 2 ml vials at 37° C. Clots were washed 3 times with TBS 1× and incubated with contrast agents at 100 μM for 30 minutes at 37° C. Two clots were prepared for each solution of incubation. After the incubation clots were washed 4 times with TBS 1× and placed into small vials filled with TBS 1× for MRI analysis. T1-weighted 2D Spin-Echo (SE) images were acquired with the following parameters: TR/TE=400/8 ms, spatial resolution=344 μm and slice thickness=2 mm. Maximum signal intensity was measured in each image containing clot and compared to the signal from a clots incubated in TBS. After MRI, clots were prepared for ICP analysis.

The Chelated Complex 1 of the invention, Reference compound 1, Reference compound 2, Reference compound 4, and Reference compound 5 were tested on human clots by MRI at different concentrations in the incubation medium (25, 100 and 400 μM of complex).

Results

By comparing the signal enhancement in clots registered after incubation with the compounds at 100 μM concentration, tested compounds could be classified in term of performance as follows:

TABLE 10

| Compound | Max signal Enhancement at 100 μM | Comparison to Chelate Complex 1 |
| --- | --- | --- |
| Chelated Complex 1 | 100% | |
| Reference Compound 2 | 68% | −32% |
| Reference Compound 1 | 44% | −66% |
| Reference Compound 5 | 41% | −69% |
| Reference Compound 4 | 23% | −77% |

The results indicate that the compound of the invention, Chelated Complex 1, has the maximum signal enhancement.

Example 26

Fibrin MRI Imaging in Tumor Models

In Vivo MRI Tests:

Three groups of 5 mice each, inoculated with $2 \cdot 10^6$ neuroblastoma cells with PBS, were formed and tested as follows:
 Group a: Reference compound 2,
 Group b: Chelate Complex 1
 Group c: ProHance® (see Protocol)

At day-10 post tumor cells inoculation, at least 4 mice per group with similar tumor size (5-10 mm in diameter) were selected for the in vivo MRI tests. After pre-contrast MRI acquisition (T1 and T2 high resolution 2D spin-echo and 3D gradient echo images), the test compounds were administered (25 μmol/kg iv.) and MRI was performed at 4 h and 24 h post injection. Maximum signal intensity was measured in the entire tumor area and in each post contrast image covering the whole tumor and the signal was compared to the pre-contrast images. At the end of MRI exams, all animals were sacrificed and the tumor, blood, liver, kidneys and femoral bone were removed and prepared for Gd assay by ICP-AES. (Inductively Coupled Plasma Atomic Emission Spectroscopy).

Results

The size of the tumors in all groups was similar (volume of about 500 mm$^3$).

Figure 8:
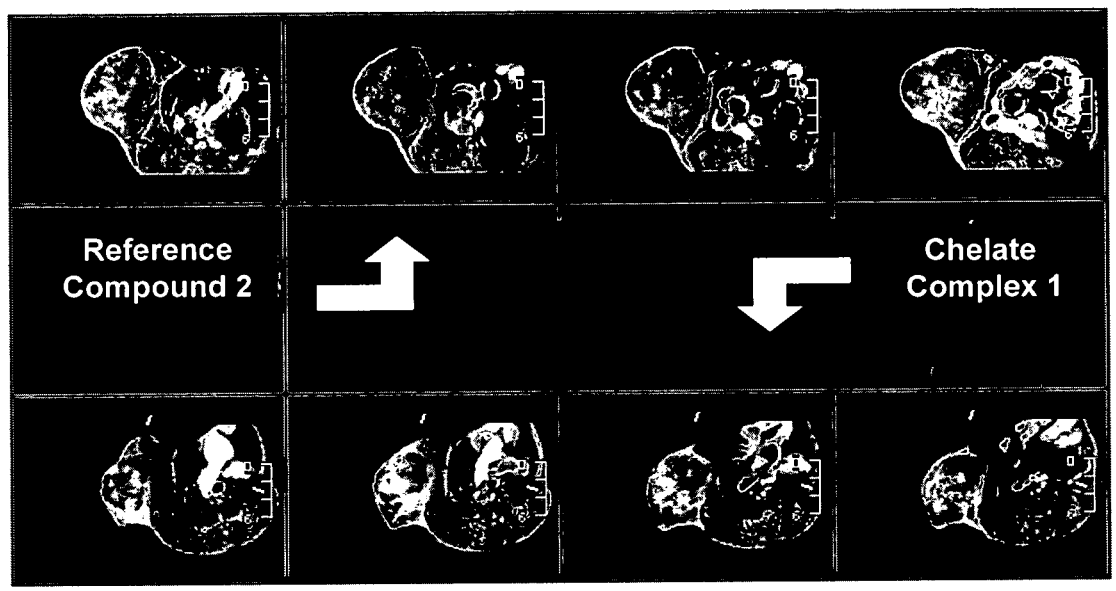
FIG. 8 relates to T1 weighted MRI images (Successive slices) acquired 4 h post injection (25 µmol/kg of complex) of chelate complex 1 (bottom) and Reference Compound 2 (top) as described in Example 26.

A significant tumor signal enhancement was observed 4 h post Chelated Complex 1 injection whereas with the Reference Compound 2 the enhancement was low and did not cover the whole tumor (<3 slices over 9, ~30% of slices covering the tumor). FIG. 8 shows obtained T1 weighted MRI images, registered at 2T, after injection of 25 μmol/kg of the complex. For the ProHance® injection signal distribution was only on the border and no signal enhancement was observed inside the tumors.

In vitro and in vivo tests described in Examples 25 and 26 were performed by following the protocols below.

Protocols

Screening of Fibrin Targeted Compounds of the Invention.

With the aim to test the specificity and efficiency of the compounds of the invention the following two protocols have been developed and used. One is dedicated to the in vitro MRI tests on clots and the other for the in vivo MRI tests on neuroblastoma mouse model.

In Vitro Tests

This protocol has been developed and used to test the specificity and efficiency of the fibrin targeted contrast agents of the invention for sensitive detection of thrombus by use of MRI. The study was performed on clots generated in vitro from different plasma species. Signal enhancement from each sample incubated with the fibrin targeted contrast agent was evaluated and compared to a standard contrast agent ProHance®.

Materials

Test Article

Compounds: The contrast agents tested were compounds of the present invention comprising a fibrin peptide, an optional linker and at least one chelated complex of gadolinium.

Reagents

Compounds: Biological samples (species, biological fluid and strain):
 guinea pig plasma(Dunkin Hartley)
 mouse plasma CD®-1(ICR)BR IGS
 rabbit plasma (New Zealand White)
 Storage: at −20° C.

Test System

The test system used was clots generated in-vitro from different plasma species (Human, guinea pig, mouse and rabbit), chosen because they are a suitable model and easy to replicate for this study.

Equipment

All MRI experiments were performed on a 2T Oxford magnet (bore=45 cm i.d.), equipped with a self-shielded gradient set (16 cm i.d.) driven by six TECHRON® amplifiers (4:1:1 configuration) with a maximum gradient strength of 110 mT/m and slew rate of 75 μs, and interfaced to an MRRS console (MR Research Systems Ltd, Surrey UK). A bird-cage resonator antenna (7.3 cm i.d.) was used.

Methods

In-Vitro Tests

The delivered Control Plasma N was obtained from pooled plasma collected from healthy blood donors, stabilized with HEPES buffer solution (12 g/L) and lyophilized. Before use, Plasma Control N was reconstituted in distilled water by shaking carefully the suspension to dissolve the lyophilized plasma. Clots were formed, in a 2 mL vial, to which was added 300 μl of reconstituted plasma and 300 μL of Pathromtin**SL (silicon dioxide particles, vegetable phospholipids, sodium chloride 2.4 g/L, Hepes 14.3 g/L, pH 7.6). The mixture was incubated for 2 minutes at 37° C., and then 300 μL of calcium chloride solution, previously incubated at 37° C., was added to obtain a new mixture that was further incubated for 30 minutes at 37° C. The obtained clot was transferred to a 5 mL tube, washed 3 times with 3 mL of TBS and incubated with the test article at the final concentration ranging from 0.0 to 0.2 mM for 30 minutes at 37° C. At the end of incubation, clots were rinsed 4 times with 3 mL of TBS to remove the unbound test article and then placed in 1.5 ml vials for MRI procedure.

High resolution MRI was then performed by using T1-weighted Spin-Echo (SE) sequences. T1 maps were also calculated from the acquisition of 2D gradient echo images or inversion recovery spin echo images.

At the end of experiment the clots were sent at the Analytical Laboratory for ICP-AES analysis.

Assay of Gadolinium in Biological Samples

Apparatus

The assays were carried out on a Jobin-Yvon Mod 24 spectrometer operating with the following instrumental parameters:
 sample flow: 1 mL/min
 plasma flame: 6000 to 10000° C.
 wavelength: 342.247 nm
 Argon flow: nebulizer 0.3 L/min, transport gas 0.2 L/min, cooling gas 12 L/min.

Sample digestion was performed by a microwave system (MDS-2000 CEM Corporation).

Sample preparation and analytical conditions

Different preparation for each biological matrix was adopted.

Clot solutions were prepared by suspending the clot in 1.5 mL of nitric acid (65% v/v).

1.5 mL of nitric acid (65% v/v) was added to solutions of incubation (before and after incubation) and to washing solutions.

The destruction of the organic matrix was performed by subjecting the samples to a wet ashing process with a microwave oven system.

Finally, the dried residues were dissolved with 3.0 mL of HCL 5% (v/v) and then analysed by ICP-AES.

Data Processing.

Briefly, linearity was evaluated for two standards, low and high, ranging from 0.00 to 20 mg(Gd)/L in HCl 5% (v/v), respectively. The total content of gadolinium in the test sample was calculated by using the instrumental calibration straight line and express as µg(Gd)/mL.

MRI Data Analysis

The mean signal intensity was measured within a region of interest (ROI) including a clot, drawn by an operator on each MR image using dedicated software (MR Research Systems Ltd, Surrey UK). Signal intensity enhancement (Enh %) was determined as:

$$Enh\% = 100*(SI_x - SI_0)/SI_0$$

where $SI_0$ and $SI_x$ are the mean signal intensity of clots incubated without and with test articles, respectively.

Protocol for In Vivo Tests

The study aim was to evaluate the specificity and efficiency of fibrin targeted agents of the invention as contrast agents for sensitive detection of fibrin within solid tumor.

The study was performed on a mouse model of neuroblastoma induced by Neuro-2a cells subcutaneously injected in the right flank of a A/J mouse (see for instance: Y. Chen. Effects of irradiated tumor vaccine and continuous localized infusion of granulocyte-macrophage colony-stimulating factor on neuroblastomas in mice. J. Pediatr Surg. 2003. 37(9), 1298-1304; Anthony D. Sandler, Hiroshi Chihara and Gen Kobayashi. CpG Oligonucleotides Enhance the Tumor Antigen-specific Immune Response of a Granulocyte Macrophage Colony-stimulating Factor-based Vaccine Strategy in Neuroblastoma Cancer Research 2003, 63, 394-399)

Signal enhancement kinetic within tumors was evaluated after injection of a fibrin targeted contrast agent of the invention and compared to a standard agent, ProHance®.

Materials

Test Article

Compound: The contrast agents tested comprise a fibrin targeted peptide, an optional linker and at least one chelated complex of gadolinium.

Reference Article

Compound: ProHance®

Concentration: 0.5 M

Batch: T2059

Storage: at RT, protected from light

Reagents

Compound: Penicillin/Streptomycin (10000 µg/mL), supplier: Biochrom KG, Berlin, Germany Compound: L-Glutamine (200 mM), supplier: SIGMA-ALDRICH, Steinheim, Germany Compound: Foetal bovine serum, supplier: HyClone®, Logan, Utah, USA Compound: Minimum Essential Medium Eagle, supplier: SIGMA-ALDRICH, Steinheim, Germany Compound: Dulbecco's Phosphate Buffered Saline (PBS, supplier: SIGMA Chemicals, St. Louis, Mo., U.S.A.

Compound: Zoletil 100, supplier: Virbac, Carros, France

Compound: Rompun®, supplier: Bayer AG, Layerkusen, Germany

Test System

Animals

Species and strain: mouse A/J (chosen as it is a suitable model for pharmaco-toxicological and imaging studies on neuroblastoma tumor).

Number and sex of animals: 10 males (5 males/group); 5 animals for possible replacements Weight and age at arrival: 20-25 g; 5-6 weeks old Supplier: Harlan Italy, S. Pietro al Natisone (UD), Italy Equipment All the experiments were performed on a MRRS console (MR Research Systems Ltd, Surrey UK) interfaced to a 2T Oxford magnet (bore=45 cm i.d.), equipped with a 16 cm i.d. self-shielded gradient set, driven by six TECHRON® amplifiers (4:1:1 configuration) with a maximum gradient strength of 110 mT/m and slew rate of 75 µs. As R.F. coil, a quadrature resonator optimized to the mouse size was used.

Methods

Experimental Design

Mouse neuroblastoma cell line (BS TCL 128 Neuro-2a) was supplied by the Istituto Zooprofilattico Sperimentale della Lombardia e dell'Emilia, Brescia. The cells were grown in 90% MEM medium and 10% fetal bovine serum, collected, washed two times with physiological saline and resuspended in PBS ($10^6$ cells/0.2 mL). $10^6$ cells were injected subcutaneously in the right flank of each animal.

The tumor development was followed every other day after inoculation by measuring the tumor diameter until the day of the MRI experiment. Animals with a tumor diameter ranging from 300 to 700 mm were selected for in vivo imaging. Signal enhancement of the tumor was followed by MRI up to 24 h after the administration of the test article and it was compared with that of the reference article. Animals were anaesthetized and during the experimental phase the anesthesia was maintained.

The test articles and ProHance® (reference article) were administered at doses in the range of 0.025-0.1 mmol/kg.

High resolution T1-weighted Spin-Echo and Gradient Echo sequences were used to achieve images with a suitable contrast to detect tumors and to follow the contrastographic effects of test and reference articles.

At the end of the experiment, animals were sacrificed. Tumor, blood, kidneys, liver and femoral bones were then taken, weighed and stored at about 4° C. until analyzed by ICP-AES.

Assay of Gadolinium in Biological Samples

Apparatus

The assays was carried out on a Jobin-Yvon Mod 24 spectrometer operating with the following instrumental parameters:

sample flow: 1 mL/min plasma flame: 6000 to 10000° C.

wavelength: 342.247 nm

Argon flow: nebulizer 0.3 L/min, transport gas 0.2 L/min, cooling gas 12 L/min.

Sample digestion was performed by a microwave system (MDS-2000 CEM Corporation).

Sample Preparation and Analytical Conditions

Different preparation for each biological matrix was adopted:

Tumor solutions were prepared by suspending the tumor, accurately weighed, in 1.5 mL of nitric acid (65% v/v).

Liver was prepared by measuring the liver, accurately weighed, in 1.5 mL of nitric acid (65% v/v).

Kidney solutions were prepared by suspending each kidney, accurately weighed, in 1.5 mL of nitric acid (65% v/v).

Blood solutions were prepared by mixing 1 mL of blood in 1.5 mL of nitric acid (65% v/v).

Bone solutions were prepared by suspending each femur, accurately weighed, in 1.5 mL of nitric acid (65% v/v).

The destruction of the organic matrix was performed by subjecting the samples to a wet ashing process with a microwave oven system.

Finally the dried residues were dissolved with 3.0 mL of HCL 5% (v/v) and then analysed by ICP-AES.

Data Processing.

Briefly, linearity was evaluated for two standards, low and high, ranging from 0.00 to 20 mg(Gd)/L in HCl 5% (v/v), respectively. The total content of gadolinium in the test sample was calculated by using the instrumental calibration straight line and express as μg(Gd)/mL.

MRI Data Analysis

The mean signal intensity was measured within a region of interest (ROI) including the entire tumor, drawn by an operator on each MR image using dedicated software (MR Research Systems Ltd, Surrey UK). Signal intensity enhancement (Enh %) was determined as:

$$Enh\% = 100 * (SI_x(t) - SI_0)/SI_0$$

where $SI_0$ and $SI_x(t)$ are the mean signal intensity of tumor pre and post injection of the contrast agent (test articles or reference), respectively.

Data collected (bodyweight, clinical signs, gross pathology examination) were subjected to qualitative analysis.

Representative Embodiments

The following non-limiting, enumerated embodiments further describe the present invention:

1. An isolated fibrin-binding peptide having an amino acid sequence selected from the group consisting of the sequences provided in Table 1 or Table 2.
2. A diagnostic imaging agent comprising a fibrin-binding peptide according to embodiment 1, wherein said fibrin-binding peptide is linked to a detectable label.
3. The imaging agent of embodiment 2, wherein said fibrin-binding peptide is linked to at least one paramagnetic metal atom suitable for magnetic resonance imaging, optionally via a chelator.
4. The imaging agent of embodiment 2, wherein said fibrin-binding peptide is linked to an echogenic label suitable for ultrasound imaging.
5. The imaging agent of embodiment 2, wherein the fibrin binding peptide is linked to a diagnostic radionuclide, optionally via a chelator.
6. The imaging agent of embodiment 5, wherein the diagnostic radionuclide is selected from the group consisting of $^{64}$Cu, $^{67}$Ga, $^{68}$Ga, $^{99m}$Tc, and $^{111}$In.
7. The imaging agent of embodiment 2, wherein said fibrin-binding peptide is fluoresceinated.
8. A therapeutic agent comprising a fibrin-binding peptide according to embodiment 1, wherein said fibrin-binding peptide is linked to a therapeutic agent.
9. The therapeutic agent of embodiment 8, wherein the fibrin-binding peptide is linked to a therapeutic radionuclide, optionally via a chelator.
10. The therapeutic agent of embodiment 9, wherein the therapeutic radionuclide is selected from the group consisting of $^{64}$Cu, $^{90}$Y, $^{105}$Rh, $^{111}$In, $^{117m}$Sn, $^{149}$Pm, $^{153}$Sm, $^{161}$Tb, $^{166}$Dy, $^{166}$Ho, $^{175}$Yb, $^{177}$Lu, $^{186-188}$Re, and $^{199}$Au.
11. The imaging agent of embodiment 3, wherein the chelator is selected from the group consisting of DTPA, DTPA-GLU, DTPA-Lys, DOTA, AAZTA, and the following derivatives thereof:

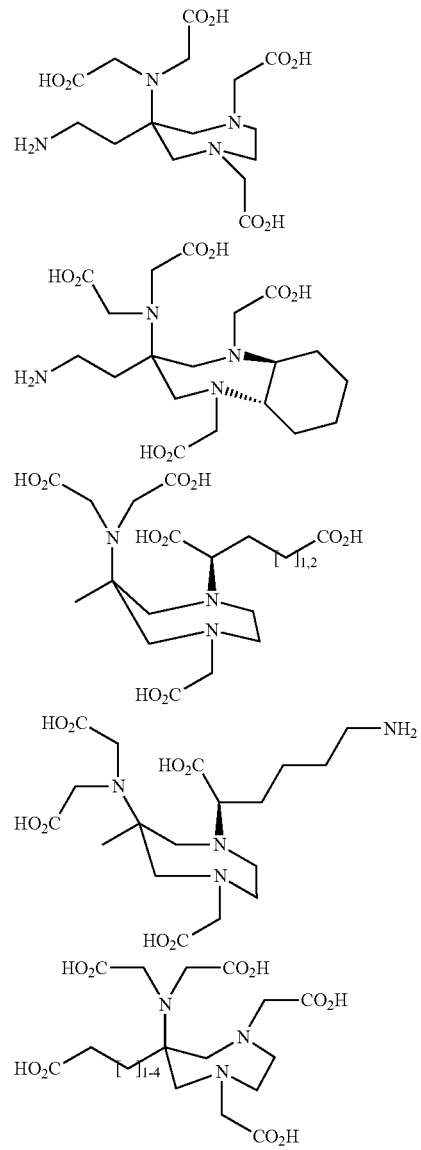

12. The imaging agent of embodiment 3, selected from the group consisting of:

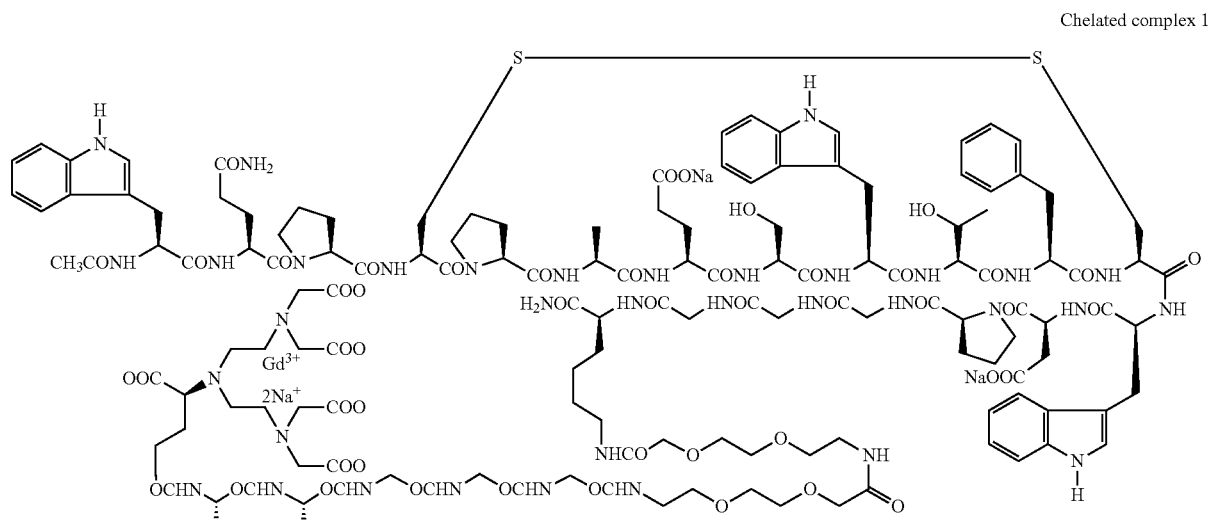
Chelated complex 1
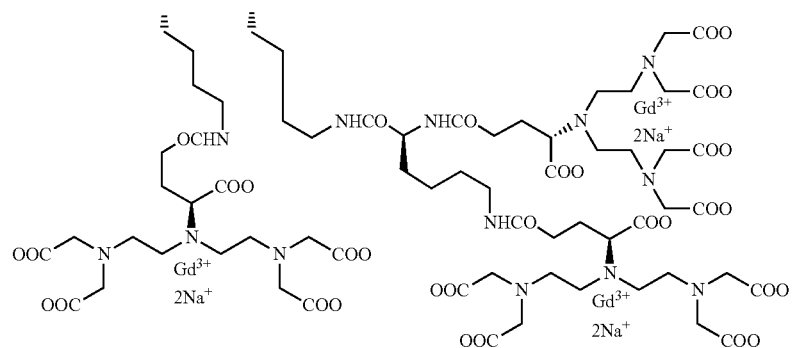
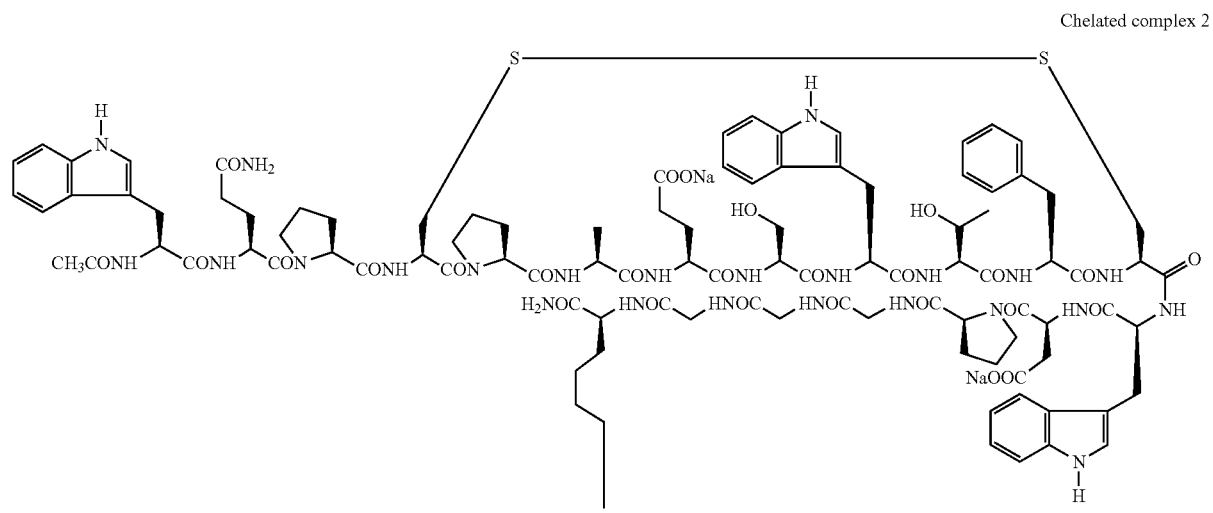
Chelated complex 2

149
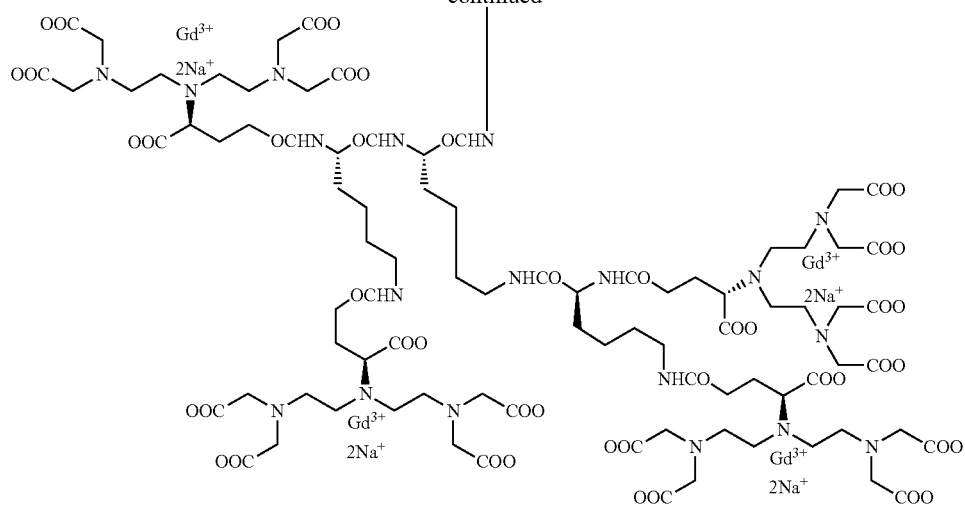
150
-continued
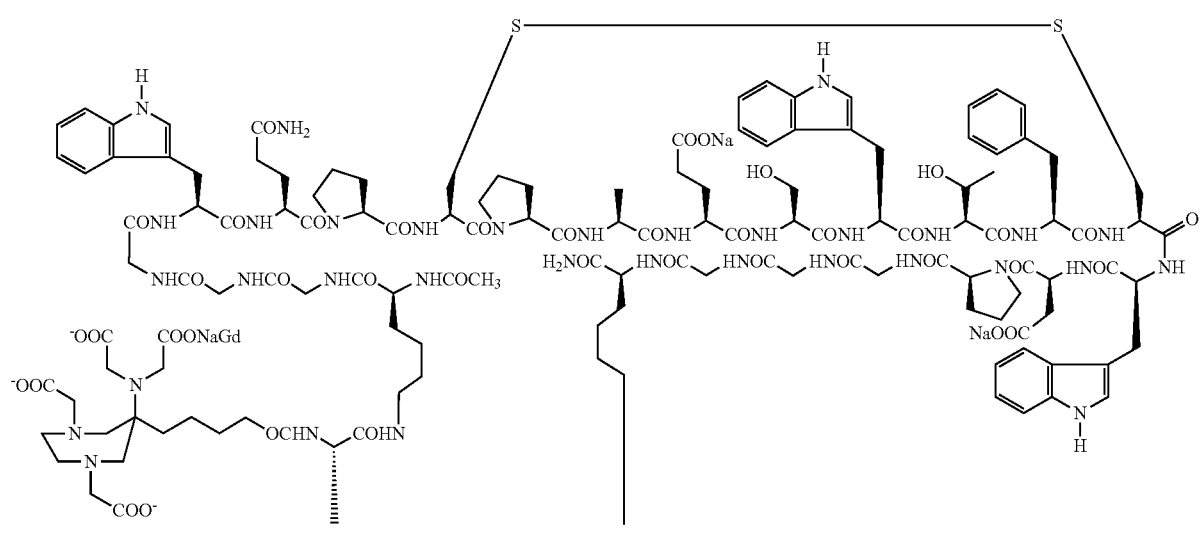
Chelated complex 3
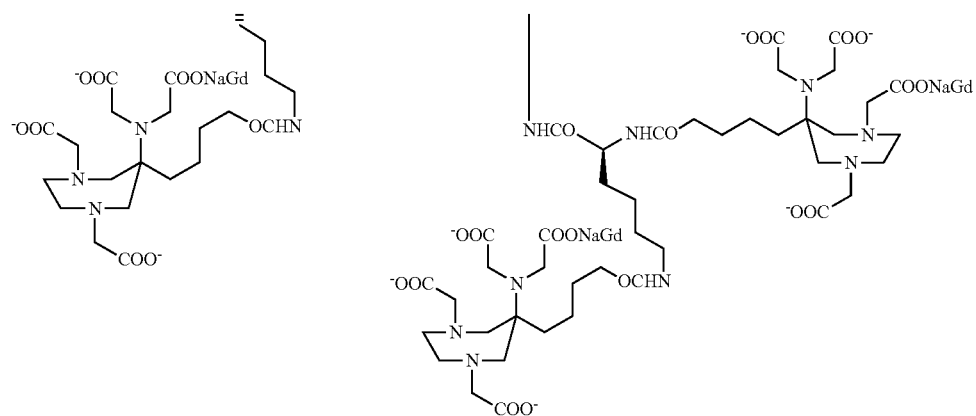

-continued
Chelated complex 4
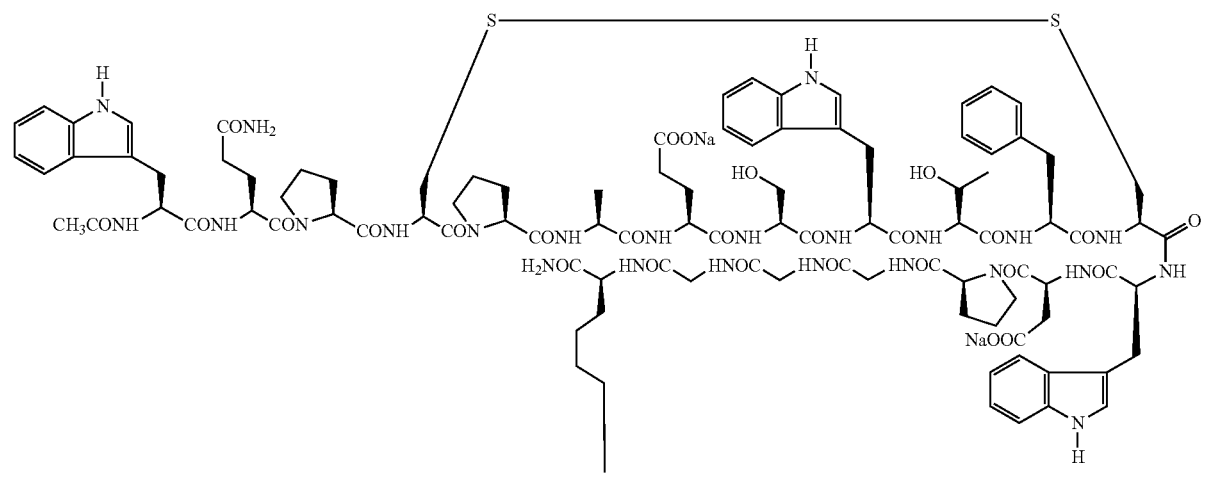
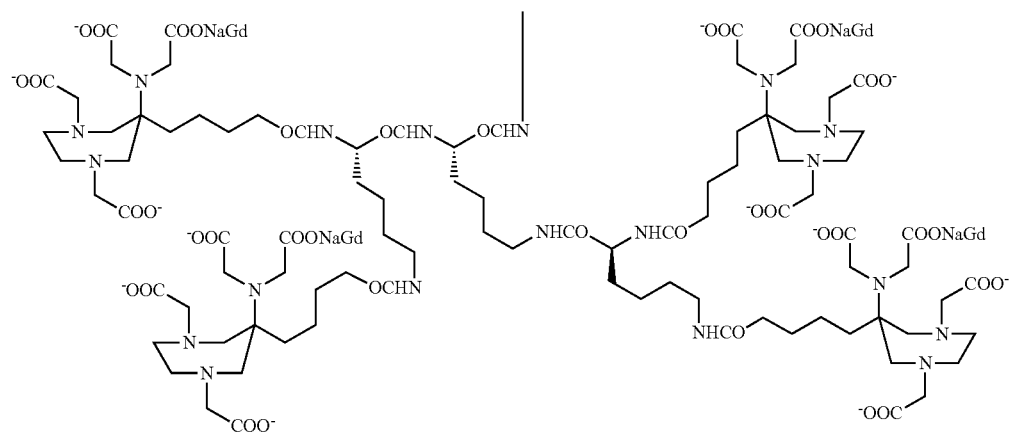
Chelated complex 5
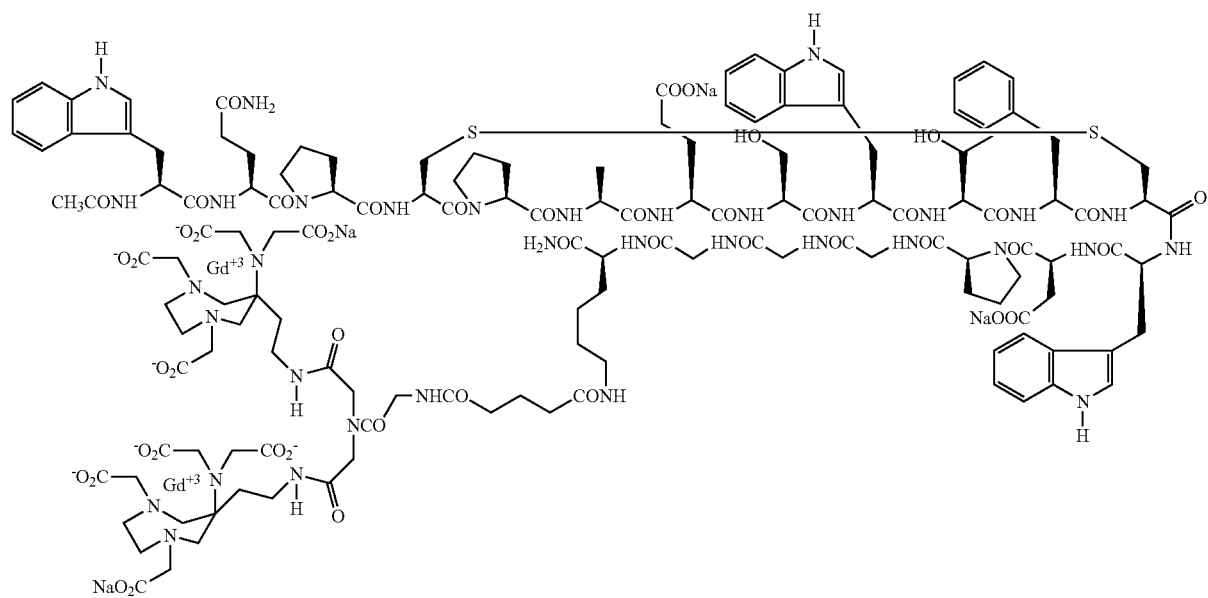

Chelated complex 6
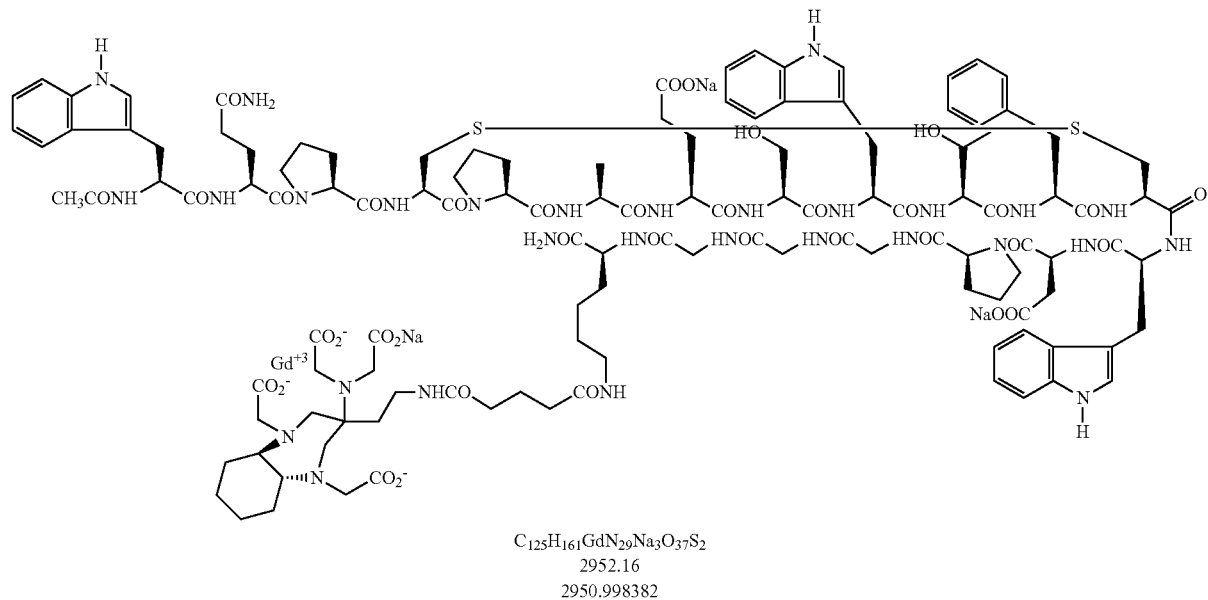
$C_{125}H_{161}GdN_{29}Na_3O_{37}S_2$
2952.16
2950.998382
Chelated complex 7
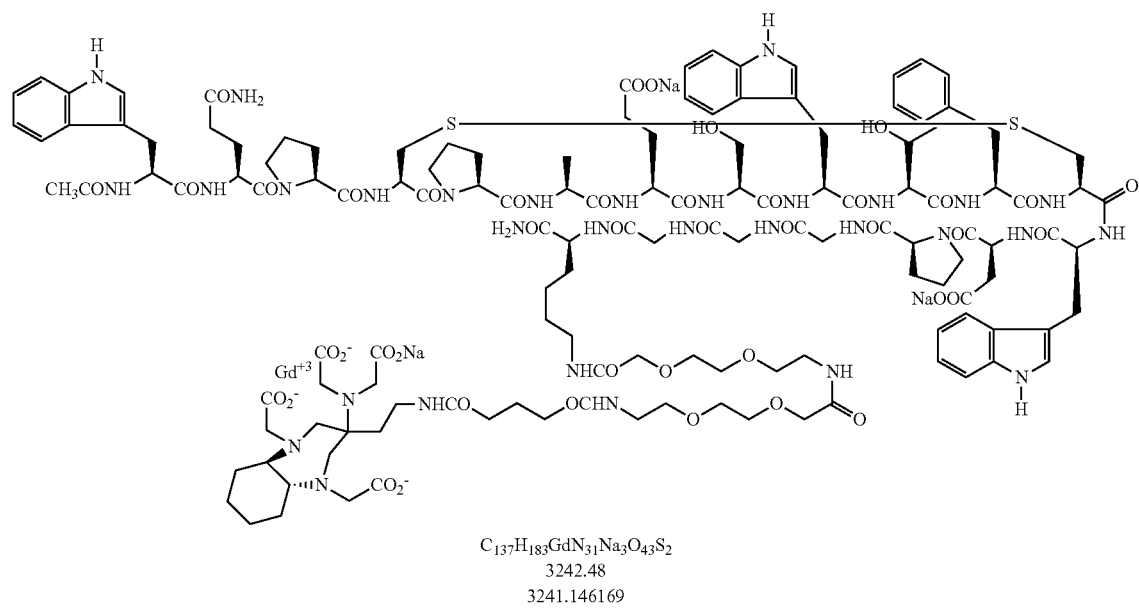
$C_{137}H_{183}GdN_{31}Na_3O_{43}S_2$
3242.48
3241.146169

Chelated complex 8
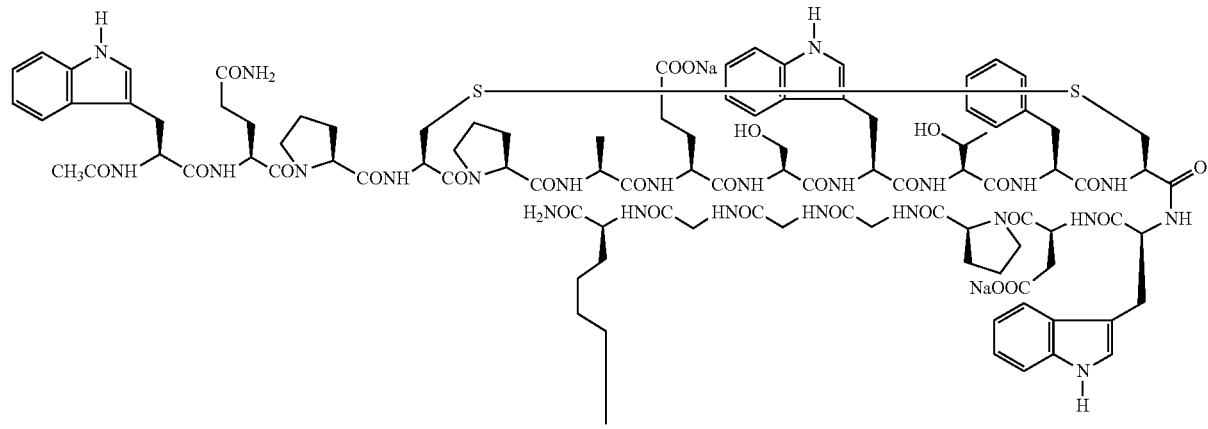
C$_{146}$H$_{192}$Gd$_2$N$_{34}$Na$_4$O$_{47}$S$_2$
3645.90
3645.119355
Chelated complex 9
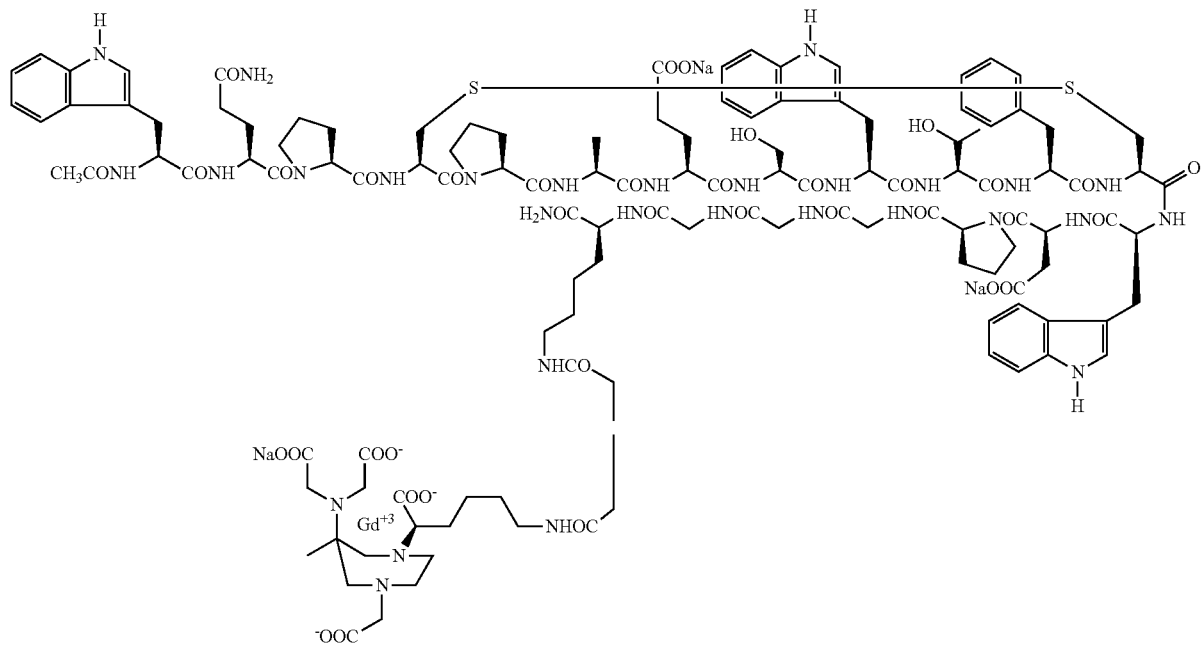
C$_{123}$H$_{159}$GdN$_{29}$Na$_3$O$_{37}$S$_2$
2926.12
2924.982732

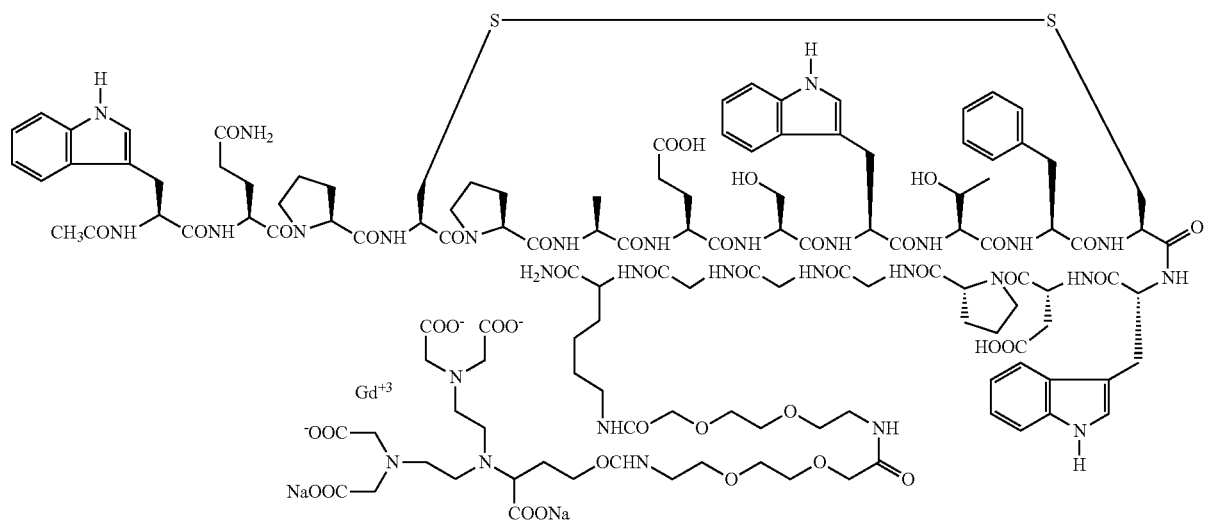

Chelated complex 10

13. The imaging agent of embodiment 4, wherein the echogenic label suitable for ultrasound imaging comprises a microballoon comprising a gas.
14. The imaging agent of embodiment 4, wherein the echogenic label suitable for ultrasound imaging comprises a microbubble comprising a gas.
15. The imaging agent of embodiment 14, wherein the microbubble comprises a mixture of two or more selected form the group consisting of DSPC, DPPG, DPPA, DSPE-PEG1000, DSPE-PEG2000, DSPE-PEG3400, DPPE-PEG3400, palmitic acid and stearic acid.
16. An ultrasound contrast agent comprising a microbubble comprising a gas, wherein the microbubble comprises a lipopeptide comprising a fibrin-binding peptide of embodiment 1 linked to a phospholipid.
17. The ultrasound contrast agent of embodiment 16 comprising a lipopeptide selected from the group consisting of: Seq000-PL1, Seq005-PL1, Seq016-PL1, Seq017-PL1, Seq023-PL1 and Seq024-PL1.
18. The ultrasound contrast agent of embodiment 17, wherein the microbubble further comprises DSPC and DPPG.
19. The ultrasound contrast agent of embodiment 17, wherein the microbubble further comprises DSPE-PEG1000, DPPE and DPPG.
20. The ultrasound contrast agent of embodiment 17, wherein the microbubble further comprises DSPE-PEG1000, DSPC and DSPG.
21. The ultrasound contrast agent of embodiment 17, wherein the gas comprises $SF_6$ or a perfluorocarbon, optionally in admixture with air, nitrogen, oxygen or carbon dioxide.
22. The ultrasound contrast agent of any one of embodiments 18 to 20, wherein the gas comprises $C_4F_{10}$, optionally in admixture with air, nitrogen, oxygen or carbon dioxide.
23. The ultrasound contrast agent of embodiment 16, further comprising a lyophilization additive and/or a bulking agent.
24. An isolated fibrin-binding peptide having an amino acid sequence Ac-WQPC*PWESWTFC*WDPGGGK-NH$_2$ (SEQ ID NO. 2), in which one or more of the following modifications have been made:
   (a) replacement of Trp$^6$ with Ala;
   (b) replacement of Phe$^{11}$ with Cha; and
   (c) addition of one or more polar amino acids at the N terminus.
25. A diagnostic imaging agent comprising a fibrin-binding peptide of embodiment 24, wherein said fibrin-binding peptide is linked to a detectable label.
26. A therapeutic agent comprising a fibrin-binding peptide of embodiment 24, wherein said fibrin-binding peptide is linked to a therapeutic agent.
27. A compound of general Formula (I)

$$A[-Y(-T)_r]_s \qquad (I)$$

wherein
A is a fibrin-binding peptide moiety comprising an amino acid sequence selected from the group consisting of the sequences provided in Table 1 or Table 2;
Y is a suitable linking moiety connecting A with at least one T; when s is 2, the units Y may be the same or different from each other;
T is, independently in each occurrence, a diagnostically or therapeutically active moiety;
s is 1 or 2, and
r is, independently in each occurrence, an integer from 1 to 8;
or a physiologically acceptable salt thereof
28. A compound of embodiment 27, wherein T is a diagnostically active moiety.
29. A compound of embodiment 28, wherein the diagnostically active moiety is selected from the group consisting of a chelated gamma ray or positron emitting radionuclide, a paramagnetic metal ion in the form of a chelated or poly-chelated complex, an X-ray absorbing agent including an atom of atomic number higher than 20, a dye molecule, a fluorescent molecule, a phosphorescent molecule, a molecule absorbing in the UV spectrum, a quantum dot, a molecule capable of absorption within near or far infrared radiations, and a moiety detectable by ultrasound.
30. A compound of embodiment 27, wherein T is a therapeutically active moiety.
31. A compound of embodiment 30, wherein the therapeutically active moiety is selected from the group consisting of a thrombolytic agent, a fibrinolytic agent, a cytotoxic agent, an agent for selective killing and/or inhibiting the growth of tumor cells and a radiotherapeutic agent.
32. A compound of embodiment 27, wherein Y is selected from the group consisting of a linear or branched divalent linking moiety and a linear or branched polyfunctional linking moiety.

33. A compound of embodiment 32, wherein the divalent linking moiety comprises -GGGK.

34. A compound of embodiment 27 wherein A comprises Seq005 as shown in Table 1.

35. An intermediate compound comprising a peptide moiety A conjugated with an optionally protected Y moiety or with an optionally protected, sub-unit of a Y moiety, wherein A is a fibrin-binding peptide having an amino acid sequence selected from the group consisting of the sequences provided in Table 1 or Table 2 and Y is a linking moiety.

What is claimed is:

1. An ultrasound contrast agent comprising a gas-filled microvesicle comprising at least one fibrin-binding peptide comprising an amino acid sequence selected from the group consisting of SEQ ID NOS: 1, 2, 3, 4, 5, 6, 9, 10, 11, 12, 13, 14, 15, 16, 19, 20, 21, 22, 23, 24, 25, 26, 27, 28, 29, 30, 31, 32, 33, 34, 37, 38, 39, 40, 41, 42, 47, 48, 49, 50, 51, 52, 55, 56, 61, 62, 63, 64, 67, 68, 69, 70, 71, 72, 73, 74, 75, 76, 77, 78, 79, 80, 81, 82, 83, 84, 85, 86, 88, 89, 91, 92, 93, 94, 96, 97, 98, 99, 100, 101, 102, 103, 104, 105, 106, 107, 108, 109, 110, 111, 112, 113, 114, 115, 116, 117, 118, 119, 120, 121, 134, and 135.

2. The ultrasound contrast agent of claim 1, wherein the microvesicle comprises a peptide-phospholipid conjugate comprising the fibrin-binding peptide and a phospholipid.

3. The ultrasound contrast agent of claim 2, wherein the phospholipid comprises distearoyl phosphatidyl-ethanolamine (DSPE) or dipalmitoyl phospatidylethanolamine (DPPE).

4. The ultrasound contrast agent of claim 3, wherein the phospholipid is pegylated.

5. The ultrasound contrast agent of claim 4, wherein the pegylated phospholipid is selected from the group consisting of: distearoyl phosphatidyl-ethanolamine-polyethyleneglycol 2000 (DSPE-PEG2000 and dipalmitoyl phospatidylethanolamine-polyethyleneglycol 2000 (DPPE-PEG2000).

6. The ultrasound contrast agent of claim 2, wherein the peptide and phospholipid are attached by a linking group.

7. The ultrasound contrast agent of claim 6, wherein the linking group comprises a moiety selected from the group consisting of: hydrophilic polymers and an amino acid chain.

8. The ultrasound contrast agent of claim 7, wherein the hydrophilic polymer is polyethylenglycol.

9. The ultrasound contrast agent of claim 7, wherein the amino acid chain comprises proline.

10. The ultrasound contrast agent of claim 1, wherein the gas filled microvesicle comprises a phospholipid.

11. The ultrasound contrast agent of claim 10, wherein the phospholipid is selected from the group consisting of: distearoyl-phosphatidylcholine (DSPC), dipalmitoyl-phophatidylglycerol (DPPG), DPPE, distearoylphosphatidylglycerol (DSPG), and distearoyl phosphatidic acid (DSPA).

12. The ultrasound contrast agent of claim 1, wherein the gas-filled microvesicle comprises two or more components selected form the group consisting of: DSPC, DPPG, dipalmitoyl phophatidic acid (DPPA), DSPA, DPPE, DSPG, DSPE-PEG1000, DSPE-PEG2000, palmitic acid and stearic acid.

13. The ultrasound contrast agent of claim 1, wherein the gas is selected from the group consisting of: air, nitrogen, oxygen, $CO_2$, hydrogen, nitrous oxide, a noble or inert gas, a radioactive gas, a hyperpolarized noble gas, a fluorinated gas, a low molecular weight hydrocarbon, a cycloalkane, an alkene, an alkyne, an ether, a ketone, an ester, a halogenated gas and/or mixtures thereof.

14. The ultrasound contrast agent of claim 13, wherein the gas comprises a fluorinated gas.

15. The ultrasound contrast agent of claim 14, wherein the gas is a mixture of $C_4F_{10}$ and nitrogen.

16. The ultrasound contrast agent of claim 10 further comprising a therapeutic agent.

17. The ultrasound contrast agent of claim 10, wherein the phospholipid is selected from the group consisting of dilauryloyl-phosphatidylcholine ("DLPC"), dimyristoylphosphatidylcholine ("DMPC"), dipalmitoyl-phosphatidylcholine ("DPPC"), diarachidoylphosphatidylcholine ("DAPC"), distearoyl-phosphatidylcholine ("DSPC"), 1-myristoyl-2-palmitoylphosphatidylcholine ("MPPC"), 1-palmitoyl-2-myristoylphosphatidylcholine ("PMPC"), 1-palmitoyl-2-stearoylphosphatidylcholine ("PSPC"), 1-stearoyl-2-palmitoyl-phosphatidylcholine ("SPPC"), dioleoylphosphatidylycholine ("DOPC"), 1,2 Distearoyl-sn-glycero-3-Ethylphosphocholine (Ethyl-DSPC), dilauryloyl-phosphatidylglycerol ("DLPG") and its alkali metal salts, diarachidoylphosphatidylglycerol ("DAPG") and its alkali metal salts, dimyristoylphosphatidylglycerol ("DMPG") and its alkali metal salts, dipalmitoyl-phosphatidylglycerol ("DPPG") and its alkali metal salts, distearolyphosphatidylglycerol ("DSPG") and its alkali metal salts, dioleoylphosphatidylglycerol ("DOPG") and its alkali metal salts, dimyristoyl phosphatidic acid ("DMPA") and its alkali metal salts, dipalmitoyl phosphatidic acid ("DPPA") and its alkali metal salts, distearoyl phosphatidic acid ("DSPA"), diarachidoyl phosphatidic acid ("DAPA") and its alkali metal salts, dimyristoyl phosphatidyl-ethanolamin-e ("DMPE"), dipalmitoyl phosphatidylethanolamine ("DPPE"), distearoyl phosphatidyl-ethanolamine ("DSPE"), dimyristoyl phosphatidylserine ("DMPS"), diarachidoyl phosphatidylserine ("DAPS"), dipalmitoyl phosphatidylserine ("DPPS"), distearoylphosphatidylserine ("DSPS"), dioleoylphosphatidylserine ("DOPS"), dipalmitoyl sphingomyelin ("DPSP"), and distearoyl sphingomyelin ("DSSP").

18. The ultrasound contrast agent of claim 17, wherein the phospholipid is selected form the group consisting of: DSPC, DPPG, DPPE, DSPG, and DSPA.

19. The ultrasound contrast agent of claim 12, wherein the gas is selected from the group consisting of air, nitrogen, oxygen, $CO_2$, hydrogen, nitrous oxide, a noble or inert gas, a radioactive gas, a hyperpolarized noble gas, a fluorinated gas, a low molecular weight hydrocarbon, a cycloalkane, an alkene, an alkyne, an ether, a ketone, an ester, a halogenated gas and/or mixtures thereof.

20. The ultrasound contrast agent of claim 12, wherein the gas comprises a fluorinated gas.

21. The ultrasound contrast agent of claim 20, wherein the gas is a mixture of $C_4F_{10}$ and nitrogen.

22. The ultrasound contrast agent of claim 12, further comprising a therapeutic agent.

23. A method for diagnosing or treating a clot or thromboembolic disease comprising administering to a mammal a composition according to claim 1.

24. The method of claim 23, wherein the composition further comprises a therapeutic agent.

25. The diagnostic or treatment method of claim 24, wherein the therapeutic agent comprises an anticoagulant-thrombolytic or fibrinolytic agents capable of clots lysis.

26. A method for imaging fibrin-containing tissue in a mammal comprising administering an effective amount of a composition of claim 1 to the mammal and imaging the mammal.

27. A method for imaging fibrin-containing tissue in a mammal comprising administering an effective amount of a composition of claim 22 to the mammal and subjecting the mammal to ultrasound scanning to image said fibrin-containing tissue.

* * * * *